(12) United States Patent
Kossmann et al.

(10) Patent No.: US 7,402,420 B2
(45) Date of Patent: Jul. 22, 2008

(54) NUCLEIC ACID MOLECULES ENCODING ALTERNANSUCRASE

(75) Inventors: Jens Kossmann, Berlin (DE); Thomas Welsh, Berlin (DE); Martin Quanz, Berlin (DE); Karola Knuth, Berlin (DE)

(73) Assignee: Bayer Bioscience GmbH, Potsdam (DE)

( * ) Notice: Subject to any disclaimer, the term of this patent is extended or adjusted under 35 U.S.C. 154(b) by 259 days.

(21) Appl. No.: 10/417,280

(22) Filed: Apr. 15, 2003

(65) Prior Publication Data

US 2003/0229923 A1 Dec. 11, 2003

Related U.S. Application Data

(62) Division of application No. 09/499,203, filed on Feb. 8, 2000, now Pat. No. 6,570,065.

(30) Foreign Application Priority Data

Feb. 8, 1999 (DE) ................................. 199 05 069

(51) Int. Cl.
*C12N 9/10* (2006.01)
(52) U.S. Cl. ..................................... 435/193; 536/23.2
(58) Field of Classification Search ................. 435/193; 536/23.2
See application file for complete search history.

(56) References Cited

U.S. PATENT DOCUMENTS 6,127,602 A 10/2000 Nichols

FOREIGN PATENT DOCUMENTS

| WO | WO 95/13389 A1 | 5/1995 |
| WO | WO 96/04365 A1 | 2/1996 |

OTHER PUBLICATIONS

Cote, Gregory L. et al., "Production, isolation, and immobilization of alternansucrase," Am. Chem. Soc. Meeting, 1994, 207(1). XP002066232.
Raemaekers, Marc H.M. et al., "Production of Aleternansucrase by Leuconostoc mesenteroides . . . ," Journal of Chem. Tech. Biotechnol., 1997, 69(4), pp. 470-478.
Cote, Gregory L. et al., "Alternan and highly branched limit dextrans . . . ," Spanier/Chemistry of Novel Foods, Chapter 8, (1997), pp. 95-110.
Smith, Michael R. et al.,"*Leuconostoc mesenteroides* B-155 Mutants Producing Alternansucrases . . . ," Applied and Environmental Microbiology, Feb. 1997, vol. 63, No. 2, pp. 581-586.
Monchois, Vincent et al., "Cloning and sequencing of a gene coding for a novel dextransucrase . . . ," Gene, 182, (1996), pp. 23-32.
IUBMB Enzyme Nomenclature EC 2.4.1.140.
Promega Brochure (1998) on "pGEM®-T and pGEM®- T Easy Vector Systems", Technical Manual No. 042, p. 1 and 6.
Old, R.W. et al., "Principles of Gene Manipulation," Blackwell Sceintific Publications, 4th Edition, (1989), vol. 2, pp. 32-35 and 108-142.
Tsumori, Hideaki et al., "Purification of Exracellular Glucosyltransferase . . . ," Journal of General Microbiology, (1985), 131, pp. 3347-3353.
Cote G., et al., Microbial Polysaccharides, Kirk-Othmer Encyclopedia of Chemical Technology, 1995, pp. 1-28.
Journal of Gerneral Microbiology (1989) 2055-63 Mukasa et al.
Eur. J. Biochem. (1994) 226, 633-39 Biely et al. "Purification . . . ".
Carbohydrate Research (1982) 101, 57-74 Cote et al. "Isolation and partial . . . ".
Journal of Industrial Microbiology & Biotechnology (1997) 18, 278-83 Leathers.
Enzyme Microb. Technol. (1993) Jan. 15 77-85 Lopez-Munguia et al.
Carbohydrate Polymers (1992) 19: 249-52, Cote, "Low-viscosity . . . ".
Carbohydrate Research (1979) 74: 41-62, Seymour et al., "Structural . . . ".
Sciences des Aliments (1991) 11: 465-76, Pelenc et al., "Enzymatic . . . ".
Applied and Environmental Microbiology (Mar. 1995) 1120-23, Zahnley et al., vol. 61 (3).
Applied New York Academy of Sciences vol. 613: 717-722, Lopez Munguia et al., "Production . . . " (1990).
Enzyme Microb. Technol. (Aug. 1994) 16: 659-64, Kim et al., "Production . . . ".
GenBank, Accession No. AJ250173 (Jan. 2000).
FEMS Microbiol Lett 182(1) (2000) 81-85 Arguello-Morales et al "Sequence analysis of the gene encoding alternansucrase, a sucrose . . . ".
Hanada et al., "Infection and Immunity" 57(7): 2079-2085 (Jul. 1989).
Shiroza et al. J.Bacteriology 169(9): 4263-4270 (1987).
Fuchs, A Biochem. Soc. Trans. 19: 555-560 (1991).
Smeekens et al. Biochem. Soc. Trans. 19: 565-569 (1991).
Turk et al. New Phytol. 136(1): 29-38 (1997).

*Primary Examiner*—Rebecca Prouty
(74) *Attorney, Agent, or Firm*—Birch Stewart Kolasch & Birch LLP

(57) ABSTRACT

Nucleic acid molecules encoding an alternansucrase are provided. Moreover, vectors, host cells and plant cells transformed by the herein-described nucleic acid molecules and plants containing them are provided. Furthermore, methods are described for preparing transgenic plants which synthesize the carbohydrate alternan, because of the insertion of nucleic acid molecules encoding an alternansucrase. Moreover, methods for preparing alternan and products resulting from them are provided.

5 Claims, 12 Drawing Sheets

SEQUENCE LISTING

<160> NUMBER OF SEQ ID NOS: 54
<210> SEQ ID NO 1
<211> LENGTH: 9321
<212> TYPE: DNA
<213> ORGANISM: Leuconostoc mesenteroides
<220> FEATURE:
<221> NAME/KEY: CDS
<222> LOCATION: (678)..(6848)

<400> SEQUENCE: 1

```
gatcaaatag atgctaccgt tatacgagac gttaaggatt atcccaatct agtcgttttg      60
cgtaccttgt cgaaagctta tggtctggca aacctgagaa tcggctatgg cgtcatgcag     120
gaaccacttt atcaggttat gcaggccgta cgtttaccat ataatttaaa tacctatcaa     180
atcacaggtg cagtagctgc ccttagtgat caactttatc tgcaatcagt tgttgctaag     240
gtgaagtctg aacgtgaaaa atttgaacaa ttttttgacga aacaccagtt taagtattat     300
caatcacaaa ccaactttct ctggattaaa gttggtgatg cgaaacgtgt tggtgaggct     360
cttctgtcag aagggtatca aattaatgac cgcctaaatg ccgaatggat tcgcattgca     420
ttaggaactg tgtctgataa tgaggggatg cagcgcattt tattgaattg ttaaaaaata     480
gctaagagag tatgttcttc tcttacctat ttttatttgt aattcctatt atttaatttt     540
gcatgacaat attaatagcg tgttacgatt ctactattta atgttaataa aattaataaa     600
tatggtatta tcttatatgg gtgatagatg caccaaatac tgtatcatgt ctggtcacat     660
```

```
gaaagggaga ataatta atg aaa caa caa gaa aca gtt acc cgt aaa aaa          710
                    Met Lys Gln Gln Glu Thr Val Thr Arg Lys Lys
                     1               5                  10 ctt tat aaa tcc ggt aag gtt tgg gtt gca gca gct act gca ttt gcg          758
Leu Tyr Lys Ser Gly Lys Val Trp Val Ala Ala Ala Thr Ala Phe Ala
         15                  20                  25 gta ttg ggg gtt tca act gta aca aca gtc cat gcg gat aca aat tcg          806
Val Leu Gly Val Ser Thr Val Thr Thr Val His Ala Asp Thr Asn Ser
             30                  35                  40 aat gtc gct gtt aag caa ata aat aat aca gga acc aat gat tct ggc          854
Asn Val Ala Val Lys Gln Ile Asn Asn Thr Gly Thr Asn Asp Ser Gly
 45                  50                  55 gaa aaa aag gta ccg gtt cca tca act aat aat gat agt ttg aag caa          902
Glu Lys Lys Val Pro Val Pro Ser Thr Asn Asn Asp Ser Leu Lys Gln
 60                  65                  70                  75 gga aca gat ggt ttt tgg tat gat tca gac ggc aat cgt gtc gat cag          950
Gly Thr Asp Gly Phe Trp Tyr Asp Ser Asp Gly Asn Arg Val Asp Gln
                 80                  85                  90 aag acc aat cag att ctg ctt act gcg gaa caa ctt aaa aaa aat aac          998
Lys Thr Asn Gln Ile Leu Leu Thr Ala Glu Gln Leu Lys Lys Asn Asn
             95                 100                 105 gaa aaa aat tta tca gta atc agt gat gat aca tca aaa aaa gat gat         1046
Glu Lys Asn Leu Ser Val Ile Ser Asp Asp Thr Ser Lys Lys Asp Asp
         110                 115                 120 gaa aat att tct aag cag acc aaa att gct aat caa caa aca gta gat         1094
Glu Asn Ile Ser Lys Gln Thr Lys Ile Ala Asn Gln Gln Thr Val Asp
 125                 130                 135 act gct aaa ggc ctg act acc agt aat tta tct gat ccc atc act ggg         1142
Thr Ala Lys Gly Leu Thr Thr Ser Asn Leu Ser Asp Pro Ile Thr Gly
 140                 145                 150                 155 ggt cac tat gaa aat cac aat ggc tac ttt gtt tat ata gat gct tca         1190
Gly His Tyr Glu Asn His Asn Gly Tyr Phe Val Tyr Ile Asp Ala Ser
                 160                 165                 170 gga aaa caa gta aca ggt ttg caa aat att gat ggt aat tta caa tat         1238
Gly Lys Gln Val Thr Gly Leu Gln Asn Ile Asp Gly Asn Leu Gln Tyr
             175                 180                 185 ttt gat gac aat gga tat caa gtc aag gga tcc ttc cga gat gtc aac         1286
Phe Asp Asp Asn Gly Tyr Gln Val Lys Gly Ser Phe Arg Asp Val Asn
         190                 195                 200 ggc aag cat atc tat ttt gat tca gta aca ggg aaa gct agt tca aat         1334
Gly Lys His Ile Tyr Phe Asp Ser Val Thr Gly Lys Ala Ser Ser Asn
 205                 210                 215 gtt gat att gtt aac ggt aaa gct caa gga tat gat gcg caa ggc aac         1382
Val Asp Ile Val Asn Gly Lys Ala Gln Gly Tyr Asp Ala Gln Gly Asn
 220                 225                 230                 235 caa tta aag aaa agt tat gtc gcc gat agt tct ggg caa act tac tat         1430
Gln Leu Lys Lys Ser Tyr Val Ala Asp Ser Ser Gly Gln Thr Tyr Tyr
                 240                 245                 250 ttt gat ggt aat ggc caa ccg tta atc ggc ttg caa aca att gat ggg         1478
Phe Asp Gly Asn Gly Gln Pro Leu Ile Gly Leu Gln Thr Ile Asp Gly
             255                 260                 265 aac cta caa tat ttt aac caa caa ggg gtt caa ata aag ggt ggt ttc         1526
Asn Leu Gln Tyr Phe Asn Gln Gln Gly Val Gln Ile Lys Gly Gly Phe
         270                 275                 280 caa gat gtt aac aat aaa cgt att tat ttt gca cca aac aca ggt aat         1574
Gln Asp Val Asn Asn Lys Arg Ile Tyr Phe Ala Pro Asn Thr Gly Asn
 285                 290                 295 gcc gtt gcc aat act gaa ata att aac ggt aaa tta cag ggg cgt gac         1622
Ala Val Ala Asn Thr Glu Ile Ile Asn Gly Lys Leu Gln Gly Arg Asp
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| | | 300 | | | | 305 | | | | 310 | | | | 315 | | |

```
gca aat ggt aac cag gta aag aat gca ttt agt aaa gat gtt gca gga      1670
Ala Asn Gly Asn Gln Val Lys Asn Ala Phe Ser Lys Asp Val Ala Gly
            320                 325                 330 aat aca ttt tat ttt gac gca aac ggt gtg atg tta aca ggg ttg caa      1718
Asn Thr Phe Tyr Phe Asp Ala Asn Gly Val Met Leu Thr Gly Leu Gln
        335                 340                 345 act att tca gga aag aca tat tat ctt gat gaa caa gga cac ctg aga      1766
Thr Ile Ser Gly Lys Thr Tyr Tyr Leu Asp Glu Gln Gly His Leu Arg
    350                 355                 360 aaa aat tac gcg gga aca ttc aat aat cag ttt atg tac ttc gat gct      1814
Lys Asn Tyr Ala Gly Thr Phe Asn Asn Gln Phe Met Tyr Phe Asp Ala
365                 370                 375 gat aca ggt gcg ggt aaa aca gcg att gaa tat caa ttt gat caa gga      1862
Asp Thr Gly Ala Gly Lys Thr Ala Ile Glu Tyr Gln Phe Asp Gln Gly
380                 385                 390                 395 ttg gta tca caa agt aat gaa aat act cct cac aat gcc gca aag tct      1910
Leu Val Ser Gln Ser Asn Glu Asn Thr Pro His Asn Ala Ala Lys Ser
        400                 405                 410 tat gat aaa agt agt ttt gaa aat gtt gat ggt tac tta aca gca gat      1958
Tyr Asp Lys Ser Ser Phe Glu Asn Val Asp Gly Tyr Leu Thr Ala Asp
    415                 420                 425 aca tgg tat cgt cca acc gat att tta aaa aat gga gat act tgg acg      2006
Thr Trp Tyr Arg Pro Thr Asp Ile Leu Lys Asn Gly Asp Thr Trp Thr
430                 435                 440 gca tct acc gaa act gat atg cgt ccg ctt tta atg aca tgg tgg cct      2054
Ala Ser Thr Glu Thr Asp Met Arg Pro Leu Leu Met Thr Trp Trp Pro
        445                 450                 455 gac aaa caa aca caa gca aat tac ttg aat ttt atg tct agt aaa gga      2102
Asp Lys Gln Thr Gln Ala Asn Tyr Leu Asn Phe Met Ser Ser Lys Gly
460                 465                 470                 475 ctt ggt ata acg acc act tat aca gca gct acg tca caa aaa aca cta      2150
Leu Gly Ile Thr Thr Thr Tyr Thr Ala Ala Thr Ser Gln Lys Thr Leu
        480                 485                 490 aat gac gca gcc ttt gtt att caa aca gca att gaa caa caa ata tct      2198
Asn Asp Ala Ala Phe Val Ile Gln Thr Ala Ile Glu Gln Gln Ile Ser
    495                 500                 505 ttg aaa aaa agt act gag tgg tta cgt gat gca att gat agt ttt gtg      2246
Leu Lys Lys Ser Thr Glu Trp Leu Arg Asp Ala Ile Asp Ser Phe Val
510                 515                 520 aag acg caa gct aat tgg aat aag caa aca gaa gat gaa gct ttc gat      2294
Lys Thr Gln Ala Asn Trp Asn Lys Gln Thr Glu Asp Glu Ala Phe Asp
        525                 530                 535 ggt ttg cag tgg ctt caa ggg gga ttc cta gct tat caa gat gat tca      2342
Gly Leu Gln Trp Leu Gln Gly Gly Phe Leu Ala Tyr Gln Asp Asp Ser
540                 545                 550                 555 cat cgg acg ccg aat act gat tca gga aat aac aga aaa cta gga cgt      2390
His Arg Thr Pro Asn Thr Asp Ser Gly Asn Asn Arg Lys Leu Gly Arg
            560                 565                 570 caa cca att aat atc gat ggt tcg aaa gat aca act gat ggt aaa ggc      2438
Gln Pro Ile Asn Ile Asp Gly Ser Lys Asp Thr Thr Asp Gly Lys Gly
        575                 580                 585 tct gaa ttc tta tta gct aac gat att gac aac tca aat ccg att gtt      2486
Ser Glu Phe Leu Leu Ala Asn Asp Ile Asp Asn Ser Asn Pro Ile Val
    590                 595                 600 caa gct gag caa tta aac tgg cta cac tat tta atg aat ttt ggt agt      2534
Gln Ala Glu Gln Leu Asn Trp Leu His Tyr Leu Met Asn Phe Gly Ser
605                 610                 615 att aca ggt aat aat gac aat gcg aat ttt gat ggc att cgt gta gat      2582
```

-continued

```
Ile Thr Gly Asn Asn Asp Asn Ala Asn Phe Asp Gly Ile Arg Val Asp
620                 625                 630                 635 gct gtt gat aat gtt gat gct gat tta cta aaa ata gct ggc gat tat    2630
Ala Val Asp Asn Val Asp Ala Asp Leu Leu Lys Ile Ala Gly Asp Tyr
                640                 645                 650 ttt aaa gct cta tat ggt aca gat aaa agc gac gcc aat gcc aat aag    2678
Phe Lys Ala Leu Tyr Gly Thr Asp Lys Ser Asp Ala Asn Ala Asn Lys
            655                 660                 665 cat ttg tct att tta gaa gac tgg aac ggt aaa gat cct cag tat gtt    2726
His Leu Ser Ile Leu Glu Asp Trp Asn Gly Lys Asp Pro Gln Tyr Val
        670                 675                 680 aat caa cag ggc aat gcg caa tta aca atg gat tac aca gtt act tca    2774
Asn Gln Gln Gly Asn Ala Gln Leu Thr Met Asp Tyr Thr Val Thr Ser
    685                 690                 695 cag ttt ggc aat tct cta aca cat ggc gcc aac aac agg agt aac atg    2822
Gln Phe Gly Asn Ser Leu Thr His Gly Ala Asn Asn Arg Ser Asn Met
700                 705                 710                 715 tgg tat ttc tta gat act ggc tat tat ctt aat gga gat ctt aat aag    2870
Trp Tyr Phe Leu Asp Thr Gly Tyr Tyr Leu Asn Gly Asp Leu Asn Lys
                720                 725                 730 aag ata gta gat aag aac cgt cca aat tct ggc act ttg gtt aac aga    2918
Lys Ile Val Asp Lys Asn Arg Pro Asn Ser Gly Thr Leu Val Asn Arg
            735                 740                 745 att gct aat tca ggt gat aca aaa gtt att cca aat tat agt ttt gtt    2966
Ile Ala Asn Ser Gly Asp Thr Lys Val Ile Pro Asn Tyr Ser Phe Val
        750                 755                 760 aga gca cat gat tac gat gct caa gat cca att aga aaa gcc atg att    3014
Arg Ala His Asp Tyr Asp Ala Gln Asp Pro Ile Arg Lys Ala Met Ile
    765                 770                 775 gat cat ggt att att aaa aac atg cag gat act ttc act ttt gac caa    3062
Asp His Gly Ile Ile Lys Asn Met Gln Asp Thr Phe Thr Phe Asp Gln
780                 785                 790                 795 ctg gct cag gga atg gaa ttc tac tat aaa gat caa gag aat ccg tct    3110
Leu Ala Gln Gly Met Glu Phe Tyr Tyr Lys Asp Gln Glu Asn Pro Ser
                800                 805                 810 ggt ttc aaa aag tat aac gat tat aac tta cct agt gct tat gca atg    3158
Gly Phe Lys Lys Tyr Asn Asp Tyr Asn Leu Pro Ser Ala Tyr Ala Met
            815                 820                 825 ttg ttg act aat aag gat act gta cct cgt gtc tat tat gga gat atg    3206
Leu Leu Thr Asn Lys Asp Thr Val Pro Arg Val Tyr Tyr Gly Asp Met
        830                 835                 840 tac ctc gaa ggc ggg caa tat atg gaa aaa ggg acg att tac aat cct    3254
Tyr Leu Glu Gly Gly Gln Tyr Met Glu Lys Gly Thr Ile Tyr Asn Pro
    845                 850                 855 gtc att tca gcg ttg ctc aaa gct aga ata aaa tat gtt tct ggt ggg    3302
Val Ile Ser Ala Leu Leu Lys Ala Arg Ile Lys Tyr Val Ser Gly Gly
860                 865                 870                 875 caa aca atg gct acc gat agt tct gga aaa gac ctt aaa gat ggc gaa    3350
Gln Thr Met Ala Thr Asp Ser Ser Gly Lys Asp Leu Lys Asp Gly Glu
                880                 885                 890 act gat ttg tta aca agt gtt cga ttt ggt aaa gga att atg aca tca    3398
Thr Asp Leu Leu Thr Ser Val Arg Phe Gly Lys Gly Ile Met Thr Ser
            895                 900                 905 gat caa acc aca aca caa gac aat agc caa gat tat aaa aat caa ggc    3446
Asp Gln Thr Thr Thr Gln Asp Asn Ser Gln Asp Tyr Lys Asn Gln Gly
        910                 915                 920 atc ggt gtc att gtt ggt aat aac cct gac ctt aag ttg aac aat gat    3494
Ile Gly Val Ile Val Gly Asn Asn Pro Asp Leu Lys Leu Asn Asn Asp
    925                 930                 935
```

-continued

| | |
|---|---|
| aag acc att acc ttg cat atg gga aag gcg cat aag aat caa ctt tac<br>Lys Thr Ile Thr Leu His Met Gly Lys Ala His Lys Asn Gln Leu Tyr<br>940                      945                    950                        955 | 3542 |
| cgt gcc tta gta tta tca aat gac tca gga att gat gtt tat gat agt<br>Arg Ala Leu Val Leu Ser Asn Asp Ser Gly Ile Asp Val Tyr Asp Ser<br>                      960                    965                        970 | 3590 |
| gat gat aaa gca cca act ttg aga aca aat gac aac ggt gac ttg att<br>Asp Asp Lys Ala Pro Thr Leu Arg Thr Asn Asp Asn Gly Asp Leu Ile<br>              975                    980                        985 | 3638 |
| ttc cat aag aca aat acg ttt gtg aag caa gat gga act att ata aat<br>Phe His Lys Thr Asn Thr Phe Val Lys Gln Asp Gly Thr Ile Ile Asn<br>        990                    995                    1000 | 3686 |
| tac gaa atg aag gga tca tta aat gct tta att tca ggt tat tta<br>Tyr Glu Met Lys Gly Ser Leu Asn Ala Leu Ile Ser Gly Tyr Leu<br>1005                  1010                  1015 | 3731 |
| ggt gtc tgg gtg cca gtt gga gct agt gat tca caa gat gct cgt<br>Gly Val Trp Val Pro Val Gly Ala Ser Asp Ser Gln Asp Ala Arg<br>1020                  1025                  1030 | 3776 |
| aca gtg gca act gag tca tca tca agt aat gat ggt tct gta ttc<br>Thr Val Ala Thr Glu Ser Ser Ser Ser Asn Asp Gly Ser Val Phe<br>1035                  1040                  1045 | 3821 |
| cat tca aat gct gca tta gat tct aat gtt ata tat gaa ggc ttt<br>His Ser Asn Ala Ala Leu Asp Ser Asn Val Ile Tyr Glu Gly Phe<br>1050                  1055                  1060 | 3866 |
| tca aac ttt caa gcg atg ccg act tct cct gag caa agt aca aat<br>Ser Asn Phe Gln Ala Met Pro Thr Ser Pro Glu Gln Ser Thr Asn<br>1065                  1070                  1075 | 3911 |
| gtt gtt att gca aca aag gct aac tta ttt aaa gaa tta ggt att<br>Val Val Ile Ala Thr Lys Ala Asn Leu Phe Lys Glu Leu Gly Ile<br>1080                  1085                  1090 | 3956 |
| act agt ttt gag tta gca cct caa tat agg tct agt ggt gac act<br>Thr Ser Phe Glu Leu Ala Pro Gln Tyr Arg Ser Ser Gly Asp Thr<br>1095                  1100                  1105 | 4001 |
| aat tac ggt ggc atg tca ttc tta gat tct ttc tta aat aat ggt<br>Asn Tyr Gly Gly Met Ser Phe Leu Asp Ser Phe Leu Asn Asn Gly<br>1110                  1115                  1120 | 4046 |
| tat gca ttt acc gat aga tat gat tta ggc ttt aac aaa gca gac<br>Tyr Ala Phe Thr Asp Arg Tyr Asp Leu Gly Phe Asn Lys Ala Asp<br>1125                  1130                  1135 | 4091 |
| ggg aat cct aac cca aca aag tat gga aca gat caa gat tta cgt<br>Gly Asn Pro Asn Pro Thr Lys Tyr Gly Thr Asp Gln Asp Leu Arg<br>1140                  1145                  1150 | 4136 |
| aat gca ata gag gca tta cac aaa aac ggc atg cag gct ata gct<br>Asn Ala Ile Glu Ala Leu His Lys Asn Gly Met Gln Ala Ile Ala<br>1155                  1160                  1165 | 4181 |
| gat tgg gtt cct gac caa ata tat gct tta cca gga aag gaa gtt<br>Asp Trp Val Pro Asp Gln Ile Tyr Ala Leu Pro Gly Lys Glu Val<br>1170                  1175                  1180 | 4226 |
| gtt acc gct act aga gta gac gaa cgg gga aat caa cta aaa gac<br>Val Thr Ala Thr Arg Val Asp Glu Arg Gly Asn Gln Leu Lys Asp<br>1185                  1190                  1195 | 4271 |
| aca gat ttt gtc aac tta ctc tat gtt gct aat act aaa agt agt<br>Thr Asp Phe Val Asn Leu Leu Tyr Val Ala Asn Thr Lys Ser Ser<br>1200                  1205                  1210 | 4316 |
| ggt gtg gat tat cag gca aag tat ggc ggc gaa ttt tta gat aaa<br>Gly Val Asp Tyr Gln Ala Lys Tyr Gly Gly Glu Phe Leu Asp Lys<br>1215                  1220                  1225 | 4361 |
| tta aga gaa gag tac cca tcg tta ttc aaa cag aac caa gta tcg<br>Leu Arg Glu Glu Tyr Pro Ser Leu Phe Lys Gln Asn Gln Val Ser<br>1230                  1235                  1240 | 4406 |

| | | |
|---|---|---|
| aca ggt cag cca att gat gct tct aca aaa att aag caa tgg tca<br>Thr Gly Gln Pro Ile Asp Ala Ser Thr Lys Ile Lys Gln Trp Ser<br>1245                        1250                        1255 | 4451 |

| gct aaa tat atg aat ggg acc aat att tta cat cga ggt gct tat<br>Ala Lys Tyr Met Asn Gly Thr Asn Ile Leu His Arg Gly Ala Tyr<br>1260                        1265                        1270 | 4496 |

| tat gtt ttg aaa gac tgg gct act aac cag tat ttt aac att gca<br>Tyr Val Leu Lys Asp Trp Ala Thr Asn Gln Tyr Phe Asn Ile Ala<br>1275                        1280                        1285 | 4541 |

| aaa acg aat gaa gta ttt ttg cca cta cag ttg cag aat aaa gat<br>Lys Thr Asn Glu Val Phe Leu Pro Leu Gln Leu Gln Asn Lys Asp<br>1290                        1295                        1300 | 4586 |

| gcg caa act ggt ttc att agt gat gcc tcc ggt gta aaa tat tac<br>Ala Gln Thr Gly Phe Ile Ser Asp Ala Ser Gly Val Lys Tyr Tyr<br>1305                        1310                        1315 | 4631 |

| tca att agt ggt tat caa gca aaa gat act ttt att gaa gat ggt<br>Ser Ile Ser Gly Tyr Gln Ala Lys Asp Thr Phe Ile Glu Asp Gly<br>1320                        1325                        1330 | 4676 |

| aat ggg aat tgg tat tac ttt gat aaa gat ggt tac atg gtg cgt<br>Asn Gly Asn Trp Tyr Tyr Phe Asp Lys Asp Gly Tyr Met Val Arg<br>1335                        1340                        1345 | 4721 |

| tcg cag caa gga gaa aat cct ata aga aca gtc gaa act agt gtc<br>Ser Gln Gln Gly Glu Asn Pro Ile Arg Thr Val Glu Thr Ser Val<br>1350                        1355                        1360 | 4766 |

| aac aca cga aac ggt aat tat tac ttt atg cca aat ggt gtc gag<br>Asn Thr Arg Asn Gly Asn Tyr Tyr Phe Met Pro Asn Gly Val Glu<br>1365                        1370                        1375 | 4811 |

| ttg cgc aaa ggc ttt gga acg gat aat agt ggt aat gtc tat tat<br>Leu Arg Lys Gly Phe Gly Thr Asp Asn Ser Gly Asn Val Tyr Tyr<br>1380                        1385                        1390 | 4856 |

| ttt gat gat caa ggt aag atg gtg aga gat aaa tac att aac gat<br>Phe Asp Asp Gln Gly Lys Met Val Arg Asp Lys Tyr Ile Asn Asp<br>1395                        1400                        1405 | 4901 |

| gat gct aat aat ttt tat cac tta aat gtt gat ggg act atg tct<br>Asp Ala Asn Asn Phe Tyr His Leu Asn Val Asp Gly Thr Met Ser<br>1410                        1415                        1420 | 4946 |

| cga gga cta ttt aaa ttt gat tct gat act cta cag tat ttt gct<br>Arg Gly Leu Phe Lys Phe Asp Ser Asp Thr Leu Gln Tyr Phe Ala<br>1425                        1430                        1435 | 4991 |

| agt aat ggt gtc caa ata aaa gat agt tat gcg aag gat agt aaa<br>Ser Asn Gly Val Gln Ile Lys Asp Ser Tyr Ala Lys Asp Ser Lys<br>1440                        1445                        1450 | 5036 |

| ggc aat aaa tat tat ttt gac tca gct aca gga aat aac gat act<br>Gly Asn Lys Tyr Tyr Phe Asp Ser Ala Thr Gly Asn Asn Asp Thr<br>1455                        1460                        1465 | 5081 |

| ggg aaa gcc caa act tgg gat ggt aat ggc tac tat att act att<br>Gly Lys Ala Gln Thr Trp Asp Gly Asn Gly Tyr Tyr Ile Thr Ile<br>1470                        1475                        1480 | 5126 |

| gat tct gat gcg aac aat aca att ggg gtt aac aca gac tac act<br>Asp Ser Asp Ala Asn Asn Thr Ile Gly Val Asn Thr Asp Tyr Thr<br>1485                        1490                        1495 | 5171 |

| gcc tac atc act agc tcg ctg cgc gaa gat ggc tta ttt gct aac<br>Ala Tyr Ile Thr Ser Ser Leu Arg Glu Asp Gly Leu Phe Ala Asn<br>1500                        1505                        1510 | 5216 |

| gca cct tac ggt gtt gta aca aaa gac caa aat ggt aac gat ctt<br>Ala Pro Tyr Gly Val Val Thr Lys Asp Gln Asn Gly Asn Asp Leu<br>1515                        1520                        1525 | 5261 |

| aag tgg cag tat att aac cat acg aaa cag tac gaa ggg caa caa<br>Lys Trp Gln Tyr Ile Asn His Thr Lys Gln Tyr Glu Gly Gln Gln | 5306 |

-continued

```
                1530                1535                1540
gtg caa gtc acg cgt caa tac aca gac agt aag gga gtc agc tgg     5351
Val Gln Val Thr Arg Gln Tyr Thr Asp Ser Lys Gly Val Ser Trp
    1545                1550                1555 aac tta att acc ttt gct ggt ggt gat tta caa gga caa agg ctt     5396
Asn Leu Ile Thr Phe Ala Gly Gly Asp Leu Gln Gly Gln Arg Leu
    1560                1565                1570 tgg gtg gat agt cgt gcg tta act atg aca cca ttt aaa acg atg     5441
Trp Val Asp Ser Arg Ala Leu Thr Met Thr Pro Phe Lys Thr Met
    1575                1580                1585 aac caa ata agc ttc att agt tat gct aac cgc aat gat ggg ttg     5486
Asn Gln Ile Ser Phe Ile Ser Tyr Ala Asn Arg Asn Asp Gly Leu
    1590                1595                1600 ttt ttg aat gcg cca tac caa gtc aag ggg tat caa tta gct ggg     5531
Phe Leu Asn Ala Pro Tyr Gln Val Lys Gly Tyr Gln Leu Ala Gly
    1605                1610                1615 atg tcc aac caa tac aag ggc caa caa gtg acc att gct ggg gtg     5576
Met Ser Asn Gln Tyr Lys Gly Gln Gln Val Thr Ile Ala Gly Val
    1620                1625                1630 gcg aac gtt tct gga aaa gac tgg agt ctg att agt ttt aat ggg     5621
Ala Asn Val Ser Gly Lys Asp Trp Ser Leu Ile Ser Phe Asn Gly
    1635                1640                1645 aca cag tac tgg att gat agt cag gca ttg aat acc aat ttc aca     5666
Thr Gln Tyr Trp Ile Asp Ser Gln Ala Leu Asn Thr Asn Phe Thr
    1650                1655                1660 cat gac atg aac caa aag gtc ttt gtc aat aca act agt aat ctt     5711
His Asp Met Asn Gln Lys Val Phe Val Asn Thr Thr Ser Asn Leu
    1665                1670                1675 gat ggg tta ttc tta aat gcg cca tac cgt caa ccg ggt tat aag     5756
Asp Gly Leu Phe Leu Asn Ala Pro Tyr Arg Gln Pro Gly Tyr Lys
    1680                1685                1690 tta gcc ggt ttg gct aaa aat tac aac aac caa acg gtt act gtt     5801
Leu Ala Gly Leu Ala Lys Asn Tyr Asn Asn Gln Thr Val Thr Val
    1695                1700                1705 agt caa cag tac ttt gat gat caa ggc acg gtc tgg agt cag gtt     5846
Ser Gln Gln Tyr Phe Asp Asp Gln Gly Thr Val Trp Ser Gln Val
    1710                1715                1720 gtc ctt ggg ggt cag acg gtc tgg gtt gat aac cat gca ttg gca     5891
Val Leu Gly Gly Gln Thr Val Trp Val Asp Asn His Ala Leu Ala
    1725                1730                1735 cag atg caa gtt agt gat aca gac caa cag ctc tat gtg aat agc     5936
Gln Met Gln Val Ser Asp Thr Asp Gln Gln Leu Tyr Val Asn Ser
    1740                1745                1750 aat ggt cgg aat gat ggg tta ttc ttg aat gcg cca tat cgt ggt     5981
Asn Gly Arg Asn Asp Gly Leu Phe Leu Asn Ala Pro Tyr Arg Gly
    1755                1760                1765 caa ggg tca caa ctg ata ggc atg acg gca gat tat aat ggg caa     6026
Gln Gly Ser Gln Leu Ile Gly Met Thr Ala Asp Tyr Asn Gly Gln
    1770                1775                1780 cat gta caa gtg acc aag caa ggg caa gat gcc tat ggt gca caa     6071
His Val Gln Val Thr Lys Gln Gly Gln Asp Ala Tyr Gly Ala Gln
    1785                1790                1795 tgg cgt ctt att acg cta aat aat caa cag gtc tgg gtt gat agt     6116
Trp Arg Leu Ile Thr Leu Asn Asn Gln Gln Val Trp Val Asp Ser
    1800                1805                1810 cgc gct ttg agc aca aca atc atg caa gcc atg aat gat aat atg     6161
Arg Ala Leu Ser Thr Thr Ile Met Gln Ala Met Asn Asp Asn Met
    1815                1820                1825 tat gta aat agc agc caa cgg aca gat ggc ttg tgg tta aac gca     6206
```

```
            Tyr Val Asn Ser Ser Gln Arg Thr Asp Gly Leu Trp Leu Asn Ala
                1830                1835                1840 cct tat acg atg agt ggg gct aaa tgg gct ggt gat aca cgt tca        6251
Pro Tyr Thr Met Ser Gly Ala Lys Trp Ala Gly Asp Thr Arg Ser
    1845                1850                1855 gct aat ggg cgc tat gtc cat att tca aaa gct tat tca aac gaa        6296
Ala Asn Gly Arg Tyr Val His Ile Ser Lys Ala Tyr Ser Asn Glu
    1860                1865                1870 gtc ggc aat aca tat tac ttg acg aat ttg aat ggt caa agc aca        6341
Val Gly Asn Thr Tyr Tyr Leu Thr Asn Leu Asn Gly Gln Ser Thr
    1875                1880                1885 tgg att gac aag cgg gcg ttt act gtg acc ttc gat cag gtg gtg        6386
Trp Ile Asp Lys Arg Ala Phe Thr Val Thr Phe Asp Gln Val Val
    1890                1895                1900 gca tta aat gca acg att gtg gca cgc caa cga cca gat ggg atg        6431
Ala Leu Asn Ala Thr Ile Val Ala Arg Gln Arg Pro Asp Gly Met
    1905                1910                1915 ttt aag aca gca cca tat ggt gaa gcg ggg gcg cag ttt gtc gat        6476
Phe Lys Thr Ala Pro Tyr Gly Glu Ala Gly Ala Gln Phe Val Asp
    1920                1925                1930 tat gtg aca aac tat aac cag caa acc gtg cca gta aca aag caa        6521
Tyr Val Thr Asn Tyr Asn Gln Gln Thr Val Pro Val Thr Lys Gln
    1935                1940                1945 cat tca gat gct cag ggg aat caa tgg tac tta gcg aca gtg aat        6566
His Ser Asp Ala Gln Gly Asn Gln Trp Tyr Leu Ala Thr Val Asn
    1950                1955                1960 ggg aca caa tac tgg att gat caa cgg tca ttt tca cca gta gta        6611
Gly Thr Gln Tyr Trp Ile Asp Gln Arg Ser Phe Ser Pro Val Val
    1965                1970                1975 acg aag gtg gtt gat tat caa gct aag att gtg cca cgg aca aca        6656
Thr Lys Val Val Asp Tyr Gln Ala Lys Ile Val Pro Arg Thr Thr
    1980                1985                1990 cgt gat ggt gtg ttt agt ggc gca ccc tat ggg gaa gtg aat gct        6701
Arg Asp Gly Val Phe Ser Gly Ala Pro Tyr Gly Glu Val Asn Ala
    1995                2000                2005 aag cta gtt aac atg gca act gcg tat caa aat caa gtt gtc cat        6746
Lys Leu Val Asn Met Ala Thr Ala Tyr Gln Asn Gln Val Val His
    2010                2015                2020 gcg aca ggg gaa tat acg aat gct tca ggg atc aca tgg agt cag        6791
Ala Thr Gly Glu Tyr Thr Asn Ala Ser Gly Ile Thr Trp Ser Gln
    2025                2030                2035 ttc gcg tta agc ggg caa gaa gac aag cta tgg att gat aag cgt        6836
Phe Ala Leu Ser Gly Gln Glu Asp Lys Leu Trp Ile Asp Lys Arg
    2040                2045                2050 gct ttg caa gct taagggaagg attcgacaaa ggagggtaac attatcagcg        6888
Ala Leu Gln Ala
    2055 gatggtgtta tcctcctttc ctgtactcag tatttcccaa ataattgaga cagtttcatg    6948 acaaatcaac aaaactagtg tcaatgcctc ggttatgggg taaactacta ttagttaaag    7008 ggttgttgca taataatatc acattcaata tattatgtat ttttatctga ttatgtgatt    7068 ttttgagatt tggagcgaaa atgaataaag taataattaa taaaagtttc tgtgttttgg    7128 taatgagttt gttgtcgata tttctattct cattaagagt agacgctcgt tccaatagtg    7188 gctacaatca aatatctttt aatcaacatg aaattgctta tgcgcctttt agtcaagtac    7248 cttggtatgc aactgtgaat gtcggaatgt ctgcagacaa aaataatatc tatacagcta    7308 ttgatatggg gccatagtat caaggaactt ctttttttcc gtggtggtat caacatgata    7368
```

```
attatgatta tcatgatggt tatcaacttg cgattgacaa tcaatcgctt ttcatagaaa    7428
tggttgatac aggaaggtcg tcgtttgatg ttattgagtt gtatacaggt aaaaaagttg    7488
gttatggaaa attcacagcc tataactata acaagacttc atggcagttt caaatatctt    7548
taaaggcgat aaagaaaatt ttaaataata acatatcaga aaatgcgaca attagtttgt    7608
acaatggtta tctattcaaa caagccgaaa gtatcacgta tgctggttca ccaacagggc    7668
catggttact tgccggtatt ggtttggttt ttgctggtgg gggctattac ctgcaaaatc    7728
agcgccgaaa aacgattacg gcatcatcaa caaacgaggt aacccatgct taataatgct    7788
gttattattg gtctaattat tatttgggtc tatgtattat ctgttctgaa gcgtgctaaa    7848
acggatgcgt tttatttttt ggctggcagc gcaggcttgt tcgtcattct tcttttatgg    7908
agtaaacctt atggtgtttg gttgttttcg accattctca cttggtcggc cggggttgtt    7968
ggtcatctca ctggcttatt tgatactttc tatgcgtcac atgttattca ggttgtggcg    8028
aatcatcata ccagcatttt attggttgat tatgaatgtt caggcattat tgaaacaacg    8088 gcatttggg gattaattgc ctttatcct gtgtatgatg cacaaaagcg gttaatgttg    8148
gcgcttattg gggcattatg gtttttcctt gcaaatacgt tacgactatc ttttgttgca    8208
gttgtaattt attattttgg cgatggcgct ttttatgttg ctcattcaat tatcggacgc    8268
ctgttgttct attcaattgt aatcttgctt tattatctag tcttcataaa ggggcaactt    8328
gttaatcaaa tgctcaaaaa acagggataa actatgtcat tttatttaca tcaatttact    8388
tatcagttag gttttttggtt cacttggttg ctcattccgt ttgttgtgga aattttccca    8448
gctattattt caatctagtt ttgataaaaa catcaaaaaa gcatcaagtg atgcaagaac    8508
cattgaaatt accaatggta tctattgtat tacctatata taattcagga caaacattat    8568
accagtgtat tcagtcgatt agtcaatcaa cctatccaaa acaattaatc caaattattg    8628
ccgtgaataa tcaaagcact gataacagtt ttacagtgtt taatcaggct caagctgatt    8688
tcccaatact tagaatgcag tggatgaaca cagatcaagg taaagcgcgt gcactaaatg    8748 ctgctatta taatagtatg gggcaatata ttattaattt ggatactgat ggttggttag    8808
aacccaatgc cttaaaacgg tttgtgcttt attttgaaaa tcactcagaa attgatgtag    8868
caactggtac gattctgaca caaaaaaaaa tgattcaaaa aacgcaaagt aaatggctta    8928
aattgctaca gttaaacgaa tattttgagt atgcacaatc attcttatca ggccgtagta    8988
ttgaaaaccg tggtaatcgt tgttcacaa tgtcaggtgc attttcagcg tttagacgtg    9048
atgtattagt tcagacatt atgtataatg ttgacacggt tggtgaagat actgatatga    9108
catttcaact gcgattccgc ctaggcaagc gtattggttt ctgtgatgat gccatgtttt    9168
atgttgaacc aatatcaggt tatagtgaac tttatttaca acggcagcgt tggcagcgtg    9228
ggcaaattga agtcgcacaa aatttcatgc agaataagtt gagtgtccgt cagattttta    9288
ctaactttat gattagtcga ttaatgattg atc                                9321
```

<210> SEQ ID NO 2
<211> LENGTH: 2057
<212> TYPE: PRT
<213> ORGANISM: Leuconostoc mesenteroides

<400> SEQUENCE: 2

Met Lys Gln Gln Glu Thr Val Thr Arg Lys Lys Leu Tyr Lys Ser Gly
1               5                   10                  15

Lys Val Trp Val Ala Ala Ala Thr Ala Phe Ala Val Leu Gly Val Ser
            20                  25                  30

-continued

```
Thr Val Thr Thr Val His Ala Asp Thr Asn Ser Asn Val Ala Val Lys
            35                  40                  45

Gln Ile Asn Asn Thr Gly Thr Asn Asp Ser Gly Glu Lys Lys Val Pro
 50                  55                  60

Val Pro Ser Thr Asn Asn Asp Ser Leu Lys Gln Gly Thr Asp Gly Phe
 65                  70                  75                  80

Trp Tyr Asp Ser Asp Gly Asn Arg Val Asp Gln Lys Thr Asn Gln Ile
                85                  90                  95

Leu Leu Thr Ala Glu Gln Leu Lys Lys Asn Asn Glu Lys Asn Leu Ser
            100                 105                 110

Val Ile Ser Asp Asp Thr Ser Lys Lys Asp Glu Asn Ile Ser Lys
            115                 120                 125

Gln Thr Lys Ile Ala Asn Gln Gln Thr Val Asp Thr Ala Lys Gly Leu
            130                 135                 140

Thr Thr Ser Asn Leu Ser Asp Pro Ile Thr Gly Gly His Tyr Glu Asn
145                 150                 155                 160

His Asn Gly Tyr Phe Val Tyr Ile Asp Ala Ser Gly Lys Gln Val Thr
                165                 170                 175

Gly Leu Gln Asn Ile Asp Gly Asn Leu Gln Tyr Phe Asp Asp Asn Gly
            180                 185                 190

Tyr Gln Val Lys Gly Ser Phe Arg Asp Val Asn Gly Lys His Ile Tyr
            195                 200                 205

Phe Asp Ser Val Thr Gly Lys Ala Ser Ser Asn Val Asp Ile Val Asn
            210                 215                 220

Gly Lys Ala Gln Gly Tyr Asp Ala Gln Gly Asn Gln Leu Lys Lys Ser
225                 230                 235                 240

Tyr Val Ala Asp Ser Ser Gly Gln Thr Tyr Tyr Phe Asp Gly Asn Gly
                245                 250                 255

Gln Pro Leu Ile Gly Leu Gln Thr Ile Asp Gly Asn Leu Gln Tyr Phe
            260                 265                 270

Asn Gln Gln Gly Val Gln Ile Lys Gly Gly Phe Gln Asp Val Asn Asn
            275                 280                 285

Lys Arg Ile Tyr Phe Ala Pro Asn Thr Gly Asn Ala Val Ala Asn Thr
            290                 295                 300

Glu Ile Ile Asn Gly Lys Leu Gln Gly Arg Asp Ala Asn Gly Asn Gln
305                 310                 315                 320

Val Lys Asn Ala Phe Ser Lys Asp Val Ala Gly Asn Thr Phe Tyr Phe
                325                 330                 335

Asp Ala Asn Gly Val Met Leu Thr Gly Leu Gln Thr Ile Ser Gly Lys
            340                 345                 350

Thr Tyr Tyr Leu Asp Glu Gln Gly His Leu Arg Lys Asn Tyr Ala Gly
            355                 360                 365

Thr Phe Asn Asn Gln Phe Met Tyr Phe Asp Ala Asp Thr Gly Ala Gly
            370                 375                 380

Lys Thr Ala Ile Glu Tyr Gln Phe Asp Gln Gly Leu Val Ser Gln Ser
385                 390                 395                 400

Asn Glu Asn Thr Pro His Asn Ala Ala Lys Ser Tyr Asp Lys Ser Ser
                405                 410                 415

Phe Glu Asn Val Asp Gly Tyr Leu Thr Ala Asp Thr Trp Tyr Arg Pro
            420                 425                 430

Thr Asp Ile Leu Lys Asn Gly Asp Thr Trp Thr Ala Ser Thr Glu Thr
            435                 440                 445
```

```
Asp Met Arg Pro Leu Leu Met Thr Trp Trp Pro Asp Lys Gln Thr Gln
450                 455                 460

Ala Asn Tyr Leu Asn Phe Met Ser Ser Lys Gly Leu Gly Ile Thr Thr
465                 470                 475                 480

Thr Tyr Thr Ala Ala Thr Ser Gln Lys Thr Leu Asn Asp Ala Ala Phe
                485                 490                 495

Val Ile Gln Thr Ala Ile Glu Gln Gln Ile Ser Leu Lys Lys Ser Thr
            500                 505                 510

Glu Trp Leu Arg Asp Ala Ile Asp Ser Phe Val Lys Thr Gln Ala Asn
            515                 520                 525

Trp Asn Lys Gln Thr Glu Asp Glu Ala Phe Asp Gly Leu Gln Trp Leu
530                 535                 540

Gln Gly Gly Phe Leu Ala Tyr Gln Asp Ser His Arg Thr Pro Asn
545                 550                 555                 560

Thr Asp Ser Gly Asn Asn Arg Lys Leu Gly Arg Gln Pro Ile Asn Ile
                565                 570                 575

Asp Gly Ser Lys Asp Thr Thr Asp Gly Lys Gly Ser Glu Phe Leu Leu
                580                 585                 590

Ala Asn Asp Ile Asp Asn Ser Asn Pro Ile Val Gln Ala Glu Gln Leu
                595                 600                 605

Asn Trp Leu His Tyr Leu Met Asn Phe Gly Ser Ile Thr Gly Asn Asn
610                 615                 620

Asp Asn Ala Asn Phe Asp Gly Ile Arg Val Asp Ala Val Asp Asn Val
625                 630                 635                 640

Asp Ala Asp Leu Leu Lys Ile Ala Gly Asp Tyr Phe Lys Ala Leu Tyr
                645                 650                 655

Gly Thr Asp Lys Ser Asp Ala Asn Ala Asn Lys His Leu Ser Ile Leu
                660                 665                 670

Glu Asp Trp Asn Gly Lys Asp Pro Gln Tyr Val Asn Gln Gln Gly Asn
            675                 680                 685

Ala Gln Leu Thr Met Asp Tyr Thr Val Thr Ser Gln Phe Gly Asn Ser
690                 695                 700

Leu Thr His Gly Ala Asn Asn Arg Ser Asn Met Trp Tyr Phe Leu Asp
705                 710                 715                 720

Thr Gly Tyr Tyr Leu Asn Gly Asp Leu Asn Lys Lys Ile Val Asp Lys
                725                 730                 735

Asn Arg Pro Asn Ser Gly Thr Leu Val Asn Arg Ile Ala Asn Ser Gly
            740                 745                 750

Asp Thr Lys Val Ile Pro Asn Tyr Ser Phe Val Arg Ala His Asp Tyr
            755                 760                 765

Asp Ala Gln Asp Pro Ile Arg Lys Ala Met Ile Asp His Gly Ile Ile
            770                 775                 780

Lys Asn Met Gln Asp Thr Phe Thr Phe Asp Gln Leu Ala Gln Gly Met
785                 790                 795                 800

Glu Phe Tyr Tyr Lys Asp Gln Glu Asn Pro Ser Gly Phe Lys Lys Tyr
                805                 810                 815

Asn Asp Tyr Asn Leu Pro Ser Ala Tyr Ala Met Leu Leu Thr Asn Lys
                820                 825                 830

Asp Thr Val Pro Arg Val Tyr Tyr Gly Asp Met Tyr Leu Glu Gly Gly
                835                 840                 845

Gln Tyr Met Glu Lys Gly Thr Ile Tyr Asn Pro Val Ile Ser Ala Leu
850                 855                 860

Leu Lys Ala Arg Ile Lys Tyr Val Ser Gly Gly Gln Thr Met Ala Thr
```

-continued

```
            865                 870                 875                 880
        Asp Ser Ser Gly Lys Asp Leu Lys Asp Gly Glu Thr Asp Leu Leu Thr
                        885                 890                 895
        Ser Val Arg Phe Gly Lys Gly Ile Met Thr Ser Asp Gln Thr Thr Thr
                        900                 905                 910
        Gln Asp Asn Ser Gln Asp Tyr Lys Asn Gln Gly Ile Gly Val Ile Val
                        915                 920                 925
        Gly Asn Asn Pro Asp Leu Lys Leu Asn Asn Asp Lys Thr Ile Thr Leu
                        930                 935                 940
        His Met Gly Lys Ala His Lys Asn Gln Leu Tyr Arg Ala Leu Val Leu
        945                 950                 955                 960
        Ser Asn Asp Ser Gly Ile Asp Val Tyr Asp Ser Asp Lys Ala Pro
                        965                 970                 975
        Thr Leu Arg Thr Asn Asp Asn Gly Asp Leu Ile Phe His Lys Thr Asn
                        980                 985                 990
        Thr Phe Val Lys Gln Asp Gly Thr Ile Ile Asn Tyr Glu Met Lys Gly
                        995                 1000                1005
        Ser Leu Asn Ala Leu Ile Ser Gly Tyr Leu Gly Val Trp Val Pro
                1010                1015                1020
        Val Gly Ala Ser Asp Ser Gln Asp Ala Arg Thr Val Ala Thr Glu
                1025                1030                1035
        Ser Ser Ser Asn Asp Gly Ser Val Phe His Ser Asn Ala Ala
                1040                1045                1050
        Leu Asp Ser Asn Val Ile Tyr Glu Gly Phe Ser Asn Phe Gln Ala
                1055                1060                1065
        Met Pro Thr Ser Pro Glu Gln Ser Thr Asn Val Val Ile Ala Thr
                1070                1075                1080
        Lys Ala Asn Leu Phe Lys Glu Leu Gly Ile Thr Ser Phe Glu Leu
                1085                1090                1095
        Ala Pro Gln Tyr Arg Ser Ser Gly Asp Thr Asn Tyr Gly Gly Met
                1100                1105                1110
        Ser Phe Leu Asp Ser Phe Leu Asn Asn Gly Tyr Ala Phe Thr Asp
                1115                1120                1125
        Arg Tyr Asp Leu Gly Phe Asn Lys Ala Asp Gly Asn Pro Asn Pro
                1130                1135                1140
        Thr Lys Tyr Gly Thr Asp Gln Asp Leu Arg Asn Ala Ile Glu Ala
                1145                1150                1155
        Leu His Lys Asn Gly Met Gln Ala Ile Ala Asp Trp Val Pro Asp
                1160                1165                1170
        Gln Ile Tyr Ala Leu Pro Gly Lys Glu Val Val Thr Ala Thr Arg
                1175                1180                1185
        Val Asp Glu Arg Gly Asn Gln Leu Lys Asp Thr Asp Phe Val Asn
                1190                1195                1200
        Leu Leu Tyr Val Ala Asn Thr Lys Ser Ser Gly Val Asp Tyr Gln
                1205                1210                1215
        Ala Lys Tyr Gly Gly Glu Phe Leu Asp Lys Leu Arg Glu Glu Tyr
                1220                1225                1230
        Pro Ser Leu Phe Lys Gln Asn Gln Val Ser Thr Gly Gln Pro Ile
                1235                1240                1245
        Asp Ala Ser Thr Lys Ile Lys Gln Trp Ser Ala Lys Tyr Met Asn
                1250                1255                1260
        Gly Thr Asn Ile Leu His Arg Gly Ala Tyr Tyr Val Leu Lys Asp
                1265                1270                1275
```

```
Trp Ala Thr Asn Gln Tyr Phe Asn Ile Ala Lys Thr Asn Glu Val
    1280            1285                1290

Phe Leu Pro Leu Gln Leu Gln Asn Lys Asp Ala Gln Thr Gly Phe
    1295            1300                1305

Ile Ser Asp Ala Ser Gly Val Lys Tyr Tyr Ser Ile Ser Gly Tyr
    1310            1315                1320

Gln Ala Lys Asp Thr Phe Ile Glu Asp Gly Asn Gly Asn Trp Tyr
    1325            1330                1335

Tyr Phe Asp Lys Asp Gly Tyr Met Val Arg Ser Gln Gln Gly Glu
    1340            1345                1350

Asn Pro Ile Arg Thr Val Glu Thr Ser Val Asn Thr Arg Asn Gly
    1355            1360                1365

Asn Tyr Tyr Phe Met Pro Asn Gly Val Glu Leu Arg Lys Gly Phe
    1370            1375                1380

Gly Thr Asp Asn Ser Gly Asn Val Tyr Tyr Phe Asp Asp Gln Gly
    1385            1390                1395

Lys Met Val Arg Asp Lys Tyr Ile Asn Asp Asp Ala Asn Asn Phe
    1400            1405                1410

Tyr His Leu Asn Val Asp Gly Thr Met Ser Arg Gly Leu Phe Lys
    1415            1420                1425

Phe Asp Ser Asp Thr Leu Gln Tyr Phe Ala Ser Asn Gly Val Gln
    1430            1435                1440

Ile Lys Asp Ser Tyr Ala Lys Asp Ser Lys Gly Asn Lys Tyr Tyr
    1445            1450                1455

Phe Asp Ser Ala Thr Gly Asn Asn Asp Thr Gly Lys Ala Gln Thr
    1460            1465                1470

Trp Asp Gly Asn Gly Tyr Tyr Ile Thr Ile Asp Ser Asp Ala Asn
    1475            1480                1485

Asn Thr Ile Gly Val Asn Thr Asp Tyr Thr Ala Tyr Ile Thr Ser
    1490            1495                1500

Ser Leu Arg Glu Asp Gly Leu Phe Ala Asn Ala Pro Tyr Gly Val
    1505            1510                1515

Val Thr Lys Asp Gln Asn Gly Asn Asp Leu Lys Trp Gln Tyr Ile
    1520            1525                1530

Asn His Thr Lys Gln Tyr Glu Gly Gln Gln Val Gln Val Thr Arg
    1535            1540                1545

Gln Tyr Thr Asp Ser Lys Gly Val Ser Trp Asn Leu Ile Thr Phe
    1550            1555                1560

Ala Gly Gly Asp Leu Gln Gly Gln Arg Leu Trp Val Asp Ser Arg
    1565            1570                1575

Ala Leu Thr Met Thr Pro Phe Lys Thr Met Asn Gln Ile Ser Phe
    1580            1585                1590

Ile Ser Tyr Ala Asn Arg Asn Asp Gly Leu Phe Leu Asn Ala Pro
    1595            1600                1605

Tyr Gln Val Lys Gly Tyr Gln Leu Ala Gly Met Ser Asn Gln Tyr
    1610            1615                1620

Lys Gly Gln Gln Val Thr Ile Ala Gly Val Ala Asn Val Ser Gly
    1625            1630                1635

Lys Asp Trp Ser Leu Ile Ser Phe Asn Gly Thr Gln Tyr Trp Ile
    1640            1645                1650

Asp Ser Gln Ala Leu Asn Thr Asn Phe Thr His Asp Met Asn Gln
    1655            1660                1665
```

```
Lys Val Phe Val Asn Thr Thr Ser Asn Leu Asp Gly Leu Phe Leu
    1670            1675            1680

Asn Ala Pro Tyr Arg Gln Pro Gly Tyr Lys Leu Ala Gly Leu Ala
    1685            1690            1695

Lys Asn Tyr Asn Asn Gln Thr Val Thr Val Ser Gln Gln Tyr Phe
    1700            1705            1710

Asp Asp Gln Gly Thr Val Trp Ser Gln Val Val Leu Gly Gly Gln
    1715            1720            1725

Thr Val Trp Val Asp Asn His Ala Leu Ala Gln Met Gln Val Ser
    1730            1735            1740

Asp Thr Asp Gln Gln Leu Tyr Val Asn Ser Asn Gly Arg Asn Asp
    1745            1750            1755

Gly Leu Phe Leu Asn Ala Pro Tyr Arg Gly Gln Gly Ser Gln Leu
    1760            1765            1770

Ile Gly Met Thr Ala Asp Tyr Asn Gly Gln His Val Gln Val Thr
    1775            1780            1785

Lys Gln Gly Gln Asp Ala Tyr Gly Ala Gln Trp Arg Leu Ile Thr
    1790            1795            1800

Leu Asn Asn Gln Gln Val Trp Val Asp Ser Arg Ala Leu Ser Thr
    1805            1810            1815

Thr Ile Met Gln Ala Met Asn Asp Asn Met Tyr Val Asn Ser Ser
    1820            1825            1830

Gln Arg Thr Asp Gly Leu Trp Leu Asn Ala Pro Tyr Thr Met Ser
    1835            1840            1845

Gly Ala Lys Trp Ala Gly Asp Thr Arg Ser Ala Asn Gly Arg Tyr
    1850            1855            1860

Val His Ile Ser Lys Ala Tyr Ser Asn Glu Val Gly Asn Thr Tyr
    1865            1870            1875

Tyr Leu Thr Asn Leu Asn Gly Gln Ser Thr Trp Ile Asp Lys Arg
    1880            1885            1890

Ala Phe Thr Val Thr Phe Asp Gln Val Val Ala Leu Asn Ala Thr
    1895            1900            1905

Ile Val Ala Arg Gln Arg Pro Asp Gly Met Phe Lys Thr Ala Pro
    1910            1915            1920

Tyr Gly Glu Ala Gly Ala Gln Phe Val Asp Tyr Val Thr Asn Tyr
    1925            1930            1935

Asn Gln Gln Thr Val Pro Val Thr Lys Gln His Ser Asp Ala Gln
    1940            1945            1950

Gly Asn Gln Trp Tyr Leu Ala Thr Val Asn Gly Thr Gln Tyr Trp
    1955            1960            1965

Ile Asp Gln Arg Ser Phe Ser Pro Val Val Thr Lys Val Val Asp
    1970            1975            1980

Tyr Gln Ala Lys Ile Val Pro Arg Thr Thr Arg Asp Gly Val Phe
    1985            1990            1995

Ser Gly Ala Pro Tyr Gly Glu Val Asn Ala Lys Leu Val Asn Met
    2000            2005            2010

Ala Thr Ala Tyr Gln Asn Gln Val Val His Ala Thr Gly Glu Tyr
    2015            2020            2025

Thr Asn Ala Ser Gly Ile Thr Trp Ser Gln Phe Ala Leu Ser Gly
    2030            2035            2040

Gln Glu Asp Lys Leu Trp Ile Asp Lys Arg Ala Leu Gln Ala
    2045            2050            2055
```

```
<210> SEQ ID NO 3
<211> LENGTH: 30
<212> TYPE: DNA
<213> ORGANISM: Artificial Sequence
<220> FEATURE:
<223> OTHER INFORMATION: 5'b512-1 PCR primer directed to the sequences
      encoding the dextransucrase.

<400> SEQUENCE: 3
actgcggccg catgccattt acagaaaaag                                     30

<210> SEQ ID NO 4
<211> LENGTH: 30
<212> TYPE: DNA
<213> ORGANISM: Artificial Sequence
<220> FEATURE:
<223> OTHER INFORMATION: 3'b512 PCR primer directed to the sequences
      encoding the dextransucrase.

<400> SEQUENCE: 4
actgctcgag ttatgctgac acagcatttc                                     30

<210> SEQ ID NO 5
<211> LENGTH: 7
<212> TYPE: PRT
<213> ORGANISM: Leuconostoc mesenteroides

<400> SEQUENCE: 5

Lys Thr Asn Glu Val Phe Leu
1               5

<210> SEQ ID NO 6
<211> LENGTH: 7
<212> TYPE: PRT
<213> ORGANISM: Leuconostoc mesenteroides

<400> SEQUENCE: 6

Lys Phe Asp Ser Asp Arg Leu
1               5

<210> SEQ ID NO 7
<211> LENGTH: 19
<212> TYPE: PRT
<213> ORGANISM: Leuconostoc mesenteroides

<400> SEQUENCE: 7

Lys Asn Met Gln Asp Thr Phe Thr Phe Asp Gln Leu Ala Gln Gly Met
1               5                   10                  15

Glu Phe Tyr

<210> SEQ ID NO 8
<211> LENGTH: 15
<212> TYPE: PRT
<213> ORGANISM: Leuconostoc mesenteroides

<400> SEQUENCE: 8

Lys Ser Thr Glu Trp Leu Arg Asp Ala Ile Asp Leu Phe Val Lys
1               5                   10                  15

<210> SEQ ID NO 9
<211> LENGTH: 22
<212> TYPE: PRT
<213> ORGANISM: Leuconostoc mesenteroides

<400> SEQUENCE: 9
```

Lys Gly Ser Glu Phe Leu Leu Ala Asn Asp Ile Asp Asn Ser Asn Pro
1               5                   10                  15

Ile Val Gln Ala Glu Gln
            20

<210> SEQ ID NO 10
<211> LENGTH: 33
<212> TYPE: DNA
<213> ORGANISM: Artificial Sequence
<220> FEATURE:
<223> OTHER INFORMATION: Oligonucleotide primer directed to genomic DNA
      of NRRL-B1355.
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 10
ytgrtcraan gtraangtrt cytgcatrtt ytt                                 33

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide primer directed to genomic
      DNA of NRRL-B1355.
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 11
gaygcnathg ayytnttygt naar                                           24

<210> SEQ ID NO 12
<211> LENGTH: 837
<212> TYPE: DNA
<213> ORGANISM: Leuconostoc mesenteroides

<400> SEQUENCE: 12
gatgcaattg atagttttgt gaagacgcaa gctaattgga ataagcaaac agaagatgaa    60
gctttcgatg gtttgcagtg gcttcaaggg ggattcctag cttatcaaga tgattcacat   120
cggacgccga atactgattc aggaaataac agaaaactag gacgtcaacc aattaatatc   180
gatggttcga aagatacaac tgatggtaaa ggctctgaat tcttattagc taacgatatt   240
gacaactcaa atccgattgt tcaagctgag caattaaact ggctacacta tttaatgaat   300
tttggtagta ttacaggtaa taatgacaat gcgaattttg atggcattcg tgtagatgct   360
gttgataatg ttgatgctga tttactaaaa atagctggcg attattttaa agctctatat   420
ggtacagata aaagcgacgc caatgccaat aagcatttgt ctattttaga agactggaac   480
ggtaaagatc ctcagtatgt taatcaacag ggcaatgcgc aattaacaat ggattacaca   540
gttacttcac agtttggcaa ttctctaaca catggcgcca acaacaggag taacatgtgg   600

-continued

```
tatttcttag atactggcta ttatcttaat ggagatctta ataagaagat agtagataag      660
aaccgtccaa attctggcac tttggttaac agaattgcta attcaggtga tacaaaagtt      720
attccaaatt atagttttgt tagagcacat gattacgatg ctcaagatcc aattagaaaa      780
gccatgattg atcatggtat tattaaaaac atgcaggata ctttcacttt tgaccaa        837
```

<210> SEQ ID NO 13
<211> LENGTH: 2862
<212> TYPE: DNA
<213> ORGANISM: Leuconostoc mesenteroides

<400> SEQUENCE: 13

```
gatcaaatag atgctaccgt tatacgagac gttaaggatt atcccaatct agtcgttttg       60
cgtaccttgt cgaaagctta tggtctggca aacctgagaa tcggctatgg cgtcatgcag      120
gaaccacttt atcaggttat gcaggccgta cgtttaccat ataatttaaa tacctatcaa      180
atcacaggtg cagtagctgc ccttagtgat caactttatc tgcaatcagt tgttgctaag      240
gtgaagtctg aacgtgaaaa atttgaacaa ttttttgacga acaccagtt taagtattat      300 caatcacaaa ccaactttct ctggattaaa gttggtgatg cgaaacgtgt tggtgaggct      360
cttctgtcag aagggtatca aattaatgac cgcctaaatg ccgaatggat tcgcattgca      420
ttaggaactg tgtctgataa tgaggggatg cagcgcattt tattgaattg ttaaaaaata      480
gctaagagag tatgttcttc tcttacctat ttttatttgt aattcctatt atttaatttt      540
gcatgacaat attaatagcg tgttacgatt ctactattta atgttaataa aattaataaa      600
tatggtatta tcttatatgg gtgatagatg caccaaatac tgtatcatgt ctggtcacat      660
gaaagggaga ataattaatg aaacaacaag aaacagttac ccgtaaaaaa ctttataaat      720
ccggtaaggt ttgggttgca gcagctactg catttgcggt attgggggtt tcaactgtaa      780
caacagtcca tgcggataca aattcgaatg tcgctgttaa gcaaataaat aatacaggaa      840
ccaatgattc tggcgaaaaa aaggtaccgg ttccatcaac taataatgat agtttgaagc      900
aaggaacaga tggttttttgg tatgattcag acggcaatcg tgtcgatcag aagaccaatc      960
agattctgct tactgcggaa caacttaaaa aaataacga aaaaaattta tcagtaatca     1020
gtgatgatac atcaaaaaaa gatgatgaaa atatttctaa gcagaccaaa attgctaatc     1080
aacaaacagt agatactgct aaaggcctga ctaccagtaa tttatctgat cccatcactg     1140
ggggtcacta tgaaaatcac aatggctact tgttttatat agatgcttca ggaaaacaag     1200
taacaggttt gcaaaatatt gatggtaatt tacaatattt tgatgacaat ggatatcaag     1260
tcaagggatc cttccgagat gtcaacggca agcatatcta ttttgattca gtaacaggga     1320
aagctagttc aaatgttgat attgttaacg gtaaagctca aggatatgat gcgcaaggca     1380
accaattaaa gaaaagttat gtcgccgata gttctgggca aacttactat tttgatggta     1440
atggccaacc gttaatcggc ttgcaaacaa ttgatgggaa cctacaatat tttaaccaac     1500
aaggggttca aataaagggt ggtttccaag atgttaacaa taaacgtatt tattttgcac     1560
caaacacagg taatgccgtt gccaatactg aaataattaa cggtaaatta caggggcgtg     1620
acgcaaatgg taaccaggta aagaatgcat ttagtaaaga tgttgcagga aatacatttt     1680
attttgacgc aaacggtgtg atgttaacag ggttgcaaac tatttcagga aagacatatt     1740
atcttgatga acaaggacac ctgagaaaaa attacgcggg aacattcaat aatcagttta     1800
tgtacttcga tgctgataca ggtgcgggta aaacagcgat tgaatatcaa tttgatcaag     1860
```

```
gattggtatc acaaagtaat gaaaatactc ctcacaatgc cgcaaagtct tatgataaaa    1920
gtagttttga aaatgttgat ggttacttaa cagcagatac atggtatcgt ccaaccgata    1980
ttttaaaaaa tggagatact tggacggcat ctaccgaaac tgatatgcgt ccgcttttaa    2040
tgacatggtg gcctgacaaa caaacacaag caaattactt gaattttatg tctagtaaag    2100
gacttggtat aacgaccact tatacagcag ctacgtcaca aaaaacacta atgacgcag     2160 cctttgttat tcaaacagca attgaacaac aaatatcttt gaaaaaagt actgagtggt     2220 tacgtgatgc aattgatagt tttgtgaaga cgcaagctaa ttggaataag caaacagaag    2280
atgaagcttt cgatggtttg cagtggcttc aagggggatt cctagcttat caagatgatt    2340
cacatcggac gccgaatact gattcaggaa ataacagaaa actaggacgt caaccaatta    2400
atatcgatgg ttcgaaagat acaactgatg gtaaaggctc tgaattctta ttagctaacg    2460
atattgacaa ctcaaatccg attgttcaag ctgagcaatt aaactggcta cactatttaa    2520
tgaattttgg tagtattaca ggtaataatg acaatgcgaa ttttgatggc attcgtgtag    2580
atgctgttga taatgttgat gctgatttac taaaaatagc tggcgattat tttaaagctc    2640
tatatggtac agataaaagc gacgccaatg ccaataagca tttgtctatt ttagaagact    2700
ggaacggtaa agatcctcag tatgttaatc aacagggcaa tgcgcaatta acaatggatt    2760
acacagttac ttcacagttt ggcaattctc taacacatgg cgccaacaac aggagtaaca    2820
tgtggtattt cttagatact ggctattatc ttaatggaga tc                       2862

<210> SEQ ID NO 14
<211> LENGTH: 3970
<212> TYPE: DNA
<213> ORGANISM: Leuconostoc mesenteroides

<400> SEQUENCE: 14
gatcaaggat tggtatcaca agtaatgaaa atactcctc acaatgccgc aaagtcttat       60
gataaaagta gttttgaaaa tgttgatggt tacttaacag cagatacatg gtatcgtcca    120
accgatattt taaaaaatgg agatacttgg acggcatcta ccgaaactga tatgcgtccg    180
cttttaatga catggtggcc tgacaaacaa acacaagcaa attacttgaa ttttatgtct    240
agtaaaggac ttggtataac gaccacttat acagcagcta cgtcacaaaa aacactaaat    300
gacgcagcct ttgttattca acagcaatt gaacaacaaa tatctttgaa aaaagtact     360 gagtggttac gtgatgcaat tgatagtttt gtgaagacgc aagctaattg gaataagcaa    420
acagaagatg aagctttcga tggtttgcag tggcttcaag ggggattcct agcttatcaa    480
gatgattcac atcggacgcc gaatactgat tcaggaaata acagaaaact aggacgtcaa    540
ccaattaata tcgatggttc gaaagataca actgatggta aaggctctga attcttatta    600
gctaacgata ttgacaactc aaatccgatt gttcaagctg agcaattaaa ctggctacac    660
tatttaatga attttggtag tattacaggt aataatgaca atgcgaattt tgatggcatt    720
cgtgtagatg ctgttgataa tgttgatgct gatttactaa aaatagctgg cgattatttt    780
aaagctctat atggtacaga taaaagcgac gccaatgcca ataagcattt gtctatttta    840
gaagactgga acggtaaaga tcctcagtat gttaatcaac agggcaatgc gcaattaaca    900
atggattaca cagttacttc acagtttggc aattctctaa cacatggcgc caacaacagg    960
agtaacatgt ggtatttctt agatactggc tattatctta tgggagatct aataagaag    1020 atagtagata agaaccgtcc aaattctggc actttggtta cagaattgc taattcaggt    1080
```

```
gatacaaaag ttattccaaa ttatagtttt gttagagcac atgattacga tgctcaagat   1140
ccaattagaa aagccatgat tgatcatggt attattaaaa acatgcagga tactttcact   1200
tttgaccaac tggctcaggg aatggaattc tactataaag atcaagagaa tccgtctggt   1260
ttcaaaaagt ataacgatta taacttacct agtgcttatg caatgttgtt gactaataag   1320
gatactgtac ctcgtgtcta ttatggagat atgtacctcg aaggcgggca atatatggaa   1380
aaagggacga tttacaatcc tgtcatttca gcgttgctca aagctagaat aaaatatgtt   1440
tctggtgggc aaacaatggc taccgatagt tctggaaaag accttaaaga tggcgaaact   1500
gatttgttaa caagtgttcg atttggtaaa ggaattatga catcagatca aaccacaaca   1560
caagacaata gccaagatta taaaaatcaa ggcatcggtg tcattgttgg taataaccct   1620
gaccttaagt tgaacaatga taagaccatt accttgcata tgggaaaggc gcataagaat   1680
caactttacc gtgccttagt attatcaaat gactcaggaa ttgatgttta tgatagtgat   1740
gataaagcac caactttgag aacaaatgac aacggtgact tgattttcca taagacaaat   1800
acgtttgtga agcaagatgg aactattata aattacgaaa tgaagggatc attaaatgct   1860
ttaatttcag gttatttagg tgtctgggtg ccagttggag ctagtgattc acaagatgct   1920
cgtacagtgg caactgagtc atcatcaagt aatgatggtt ctgtattcca ttcaaatgct   1980
gcattagatt ctaatgttat atatgaaggc ttttcaaact ttcaagcgat gccgacttct   2040
cctgagcaaa gtacaaatgt tgttattgca acaaaggcta acttatttaa agaattaggt   2100
attactagtt ttgagttagc acctcaatat aggtctagtg gtgacactaa ttacggtggc   2160
atgtcattct tagattcttt cttaaataat ggttatgcat ttaccgatag atatgattta   2220
ggctttaaca aagcagacgg gaatcctaac ccaacaaagt atggaacaga tcaagattta   2280
cgtaatgcaa tagaggcatt acacaaaaac ggcatgcagg ctatagctga ttgggttcct   2340
gaccaaatat atgctttacc aggaaaggaa gttgttaccg ctactagagt agacgaacgg   2400
ggaaatcaac taaaagacac agattttgtc aacttactct atgttgctaa tactaaaagt   2460
agtggtgtgg attatcaggc aaagtatggc ggcgaatttt tagataaatt aagagaagag   2520
tacccatcgt tattcaaaca gaaccaagta tcgacaggtc agccaattga tgcttctaca   2580
aaaattaagc aatggtcagc taaatatatg aatgggacca atattttaca tcgaggtgct   2640
tattatgttt tgaaagactg gctactaac cagtatttta acattgcaaa acgaatgaa   2700 gtattttgc cactacagtt gcagaataaa gatgcgcaaa ctggtttcat tagtgatgcc   2760
tccggtgtaa aatattactc aattagtggt tatcaagcaa aagatacttt tattgaagat   2820
ggtaatggga attggtatta ctttgataaa gatggttaca tggtgcgttc gcagcaagga   2880
gaaaatccta agaacagt cgaaactagt gtcaacacac gaaacggtaa ttattacttt   2940
atgccaaatg tgtcgagtt gcgcaaaggc tttggaacgg ataatagtgg taatgtctat   3000
tattttgatg atcaaggtaa gatggtgaga gataaataca ttaacgatga tgctaataat   3060
ttttatcact taaatgttga tgggactatg tctcgaggac tatttaaatt tgattctgat   3120
actctacagt atttttgctag taatggtgtc caaataaaag atagttatgc gaaggatagt   3180
aaaggcaata atatattttt tgactcagct acaggaaata acgatactgg gaaagcccaa   3240
acttgggatg gtaatggcta ctatattact attgattctg atgcgaacaa tacaattggg   3300
gttaacacag actacactgc ctacatcact agctcgctgc gcgaagatgg cttatttgct   3360
aacgcaccct tacggtgttgt aacaaaagac caaaatggta acgatcttaa gtggcagtat   3420
attaaccata cgaaacagta cgaagggcaa caagtgcaag tcacgcgtca atacacagac   3480
```

```
agtaagggag tcagctggaa cttaattacc tttgctggtg gtgatttaca aggacaaagg    3540 cttttgggtgg atagtcgtgc gttaactatg acaccattta aaacgatgaa ccaaataagc   3600
ttcattagtt atgctaaccg caatgatggg ttgttttttga atgcgccata ccaagtcaag   3660
gggtatcaat tagctgggat gtccaaccaa tacaagggcc aacaagtgac cattgctggg    3720
gtggcgaacg tttctggaaa agactggagt ctgattagtt ttaatgggac acagtactgg    3780
attgatagtc aggcattgaa taccaatttc acacatgaca tgaaccaaaa ggtctttgtc    3840
aatacaacta gtaatcttga tgggttattc ttaaatgcgc cataccgtca accgggttat    3900
aagttagccg gtttggctaa aaattacaac aaccaaacgg ttactgttag tcaacagtac    3960
tttgatgatc                                                           3970

<210> SEQ ID NO 15
<211> LENGTH: 1917
<212> TYPE: DNA
<213> ORGANISM: Leuconostoc mesenteroides

<400> SEQUENCE: 15
gatcaaggta agatggtgag agataaatac attaacgatg atgctaataa tttttatcac      60
ttaaatgttg atgggactat gtctcgagga ctatttaaat ttgattctga tactctacag     120
tattttgcta gtaatggtgt ccaaataaaa gatagttatg cgaaggatag taaaggcaat     180
aaatattatt ttgactcagc tacaggaaat aacgatactg ggaaagccca aacttgggat     240
ggtaatggct actatattac tattgattct gatgcgaaca atacaattgg ggttaacaca     300
gactacactg cctacatcac tagctcgctg cgcgaagatg gcttatttgc taacgcacct     360
tacggtgttg taacaaaaga ccaaaatggt aacgatctta gtggcagta tattaaccat      420 acgaaacagt acgaagggca acaagtgcaa gtcacgcgtc aatacacaga cagtaaggga     480
gtcagctgga acttaattac ctttgctggt ggtgatttac aaggacaaag gctttgggtg     540
gatagtcgtg cgttaactat gacaccattt aaaacgatga accaaataag cttcattagt     600
tatgctaacc gcaatgatgg gttgttttg aatgcgccat accaagtcaa ggggtatcaa     660
ttagctggga tgtccaacca atacaagggc caacaagtga ccattgctgg ggtggcgaac     720
gtttctggaa aagactggag tctgattagt tttaatggga cacagtactg gattgatagt     780
caggcattga ataccaattt cacacatgac atgaaccaaa aggtctttgt caatacaact     840
agtaatcttg atgggttatt cttaaatgcg ccataccgtc aaccgggtta taagttagcc     900
ggtttggcta aaaattacaa caaccaaacg gttactgtta gtcaacagta ctttgatgat     960
caaggcacgt tctggagtca ggttgtcctt gggggtcaga cggtctgggt tgataaccat    1020
gcattggcac agatgcaagt tagtgataca gaccaacagc tctatgtgaa tagcaatggt    1080
cggaatgatg ggttattctt gaatgcgcca tatcgtggtc aagggtcaca actgataggc    1140
atgacggcag attataatgg gcaacatgta caagtgacca gcaagggca agatgcctat    1200 ggtgcacaat ggcgtcttat tacgctaaat aatcaacagg tctgggttga tagtcgcgct    1260
ttgagcacaa caatcatgca agccatgaat gataatatgt atgtaaatag cagccaacgg    1320
acagatggct tgtggttaaa cgcacccttat acgatgagtg gggctaaatg gctggtgat    1380 acacgttcag ctaatgggcg ctatgtccat atttcaaaag cttattcaaa cgaagtcggc    1440
aatacatatt acttgacgaa tttgaatggt caaagcacat ggattgacaa gcgggcgttt    1500
actgtgacct tcgatcaggt ggtggcatta aatgcaacga ttgtggcacg ccaacgacca    1560
```

-continued

```
gatgggatgt ttaagacagc accatatggt gaagcggggg cgcagtttgt cgattatgtg    1620
acaaactata accagcaaac cgtgccagta acaaagcaac attcagatgc tcagggggaat   1680 caatggtact tagcgacagt gaatgggaca caatactgga ttgatcaacg gtcattttca    1740
ccagtagtaa cgaaggtggt tgattatcaa gctaagattg tgccacggac aacacgtgat    1800
ggtgtgttta gtggcgcacc ctatggggaa gtgaatgcta agctagttaa catggcaact    1860
gcgtatcaaa atcaagttgt ccatgcgaca ggggaatata cgaatgcttc agggatc      1917
```

<210> SEQ ID NO 16
<211> LENGTH: 4066
<212> TYPE: DNA
<213> ORGANISM: Leuconostoc mesenteroides

<400> SEQUENCE: 16

```
gatcttaagt ggcagtatat taaccatacg aaacagtacg aagggcaaca agtgcaagtc     60
acgcgtcaat acacagacag taagggagtc agctggaact taattacctt tgctggtggt    120
gatttacaag gacaaaggct ttgggtggat agtcgtgcgt taactatgac accatttaaa    180
acgatgaacc aaataagctt cattagttat gctaaccgca atgatgggtt gttttttgaat   240 gcgccatacc aagtcaaggg gtatcaatta gctgggatgt ccaaccaata caagggccaa    300
caagtgacca ttgctggggt ggcgaacgtt tctggaaaag actggagtct gattagtttt    360
aatgggacac agtactggat tgatagtcag gcattgaata ccaatttcac acatgacatg    420
aaccaaaagg tctttgtcaa tacaactagt aatcttgatg ggttattctt aaatgcgcca    480
taccgtcaac cgggttataa gttagccggt ttggctaaaa attacaacaa ccaaacggtt    540
actgttagtc aacagtactt tgatgatcaa ggcacggtct ggagtcaggt tgtccttggg    600
ggtcagacgg tctgggttga taccatgca ttggcacaga tgcaagttag tgatacagac     660
caacagctct atgtgaatag caatggtcgg aatgatgggt tattcttgaa tgcgccatat    720
cgtggtcaag ggtcacaact gataggcatg acggcagatt ataatgggca acatgtacaa    780
gtgaccaagc aagggcaaga tgcctatggt gcacaatggc gtcttattac gctaaataat    840
caacaggtct gggttgatag tcgcgctttg agcacaacaa tcatgcaagc catgaatgat    900
aatatgtatg taaatagcag ccaacggaca gatggcttgt ggttaaacgc accttatacg    960
atgagtgggg ctaaatgggc tggtgataca cgttcagcta atgggcgcta tgtccatatt   1020
tcaaaagctt attcaaacga agtcggcaat acatattact tgacgaattt gaatggtcaa   1080
agcacatgga ttgacaagcg ggcgtttact gtgaccttcg atcaggtggt ggcattaaat   1140
gcaacgattg tggcacgcca acgaccagat gggatgttta agacagcacc atatggtgaa   1200
gcgggggcgc agtttgtcga ttatgtgaca aactataacc agcaaaccgt gccagtaaca   1260
aagcaacatt cagatgctca ggggaatcaa tggtacttag cgacagtgaa tgggacacaa   1320
tactggattg atcaacggtc attttcacca gtagtaacga aggtggttga ttatcaagct   1380
aagattgtgc cacggacaac acgtgatggt gtgtttagtg gcgcacccta tggggaagtg   1440
aatgctaagc tagttaacat ggcaactgcg tatcaaaatc aagttgtcca tgcgacaggg   1500
gaatatacga atgcttcagg gatcacatgg agtcagttcg cgttaagcgg gcaagaagac   1560
aagctatgga ttgataagcg tgctttgcaa gcttaaggga aggattcgac aaaggagggt   1620
aacattatca gcggatggtg ttatcctcct ttcctgtact cagtatttcc caaataattg   1680
agacagtttc atgacaaatc aacaaaacta gtgtcaatgc ctcggttatg ggtaaaacta   1740
ctattagtta aagggttgtt gcataataat atcacattca atatattatg tatttttatc   1800
```

-continued

```
tgattatgtg attttttgag atttggagcg aaaatgaata agtaataat taataaaagt    1860
ttctgtgttt tggtaatgag tttgttgtcg atatttctat tctcattaag agtagacgct    1920
cgttccaata gtggctacaa tcaaatatct tttaatcaac atgaaattgc ttatgcgcct    1980
tttagtcaag taccttggta tgcaactgtg aatgtcggaa tgtctgcaga caaaaataat    2040
atctatacag ctattgatat ggggccatag tatcaaggaa cttctttttt tccgtggtgg    2100
tatcaacatg ataattatga ttatcatgat ggttatcaac ttgcgattga caatcaatcg    2160
cttttcatag aaatggttga tacaggaagg tcgtcgtttg atgttattga gttgtataca    2220
ggtaaaaaag ttggttatgg aaaattcaca gcctataact ataacaagac ttcatggcag    2280
tttcaaatat ctttaaaggc gataaagaaa attttaaata ataacatatc agaaaatgcg    2340
acaattagtt tgtacaatgg ttatctattc aaacaagccg aaagtatcac gtatgctggt    2400
tcaccaacag ggccatggtt acttgccggt attggtttgg tttttgctgg tgggggctat    2460
tacctgcaaa atcagcgccg aaaaacgatt acggcatcat caacaaacga ggtaacccat    2520
gcttaataat gctgttatta ttggtctaat tattatttgg gtctatgtat tatctgttct    2580
gaagcgtgct aaaacggatg cgttttattt tttggctggc agcgcaggct tgttcgtcat    2640
tcttctttta tggagtaaac cttatggtgt ttggttgttt tcgaccattc tcacttggtc    2700
ggccggggtt gttggtcatc tcactggctt atttgatact ttctatgcgt cacatgttat    2760
tcaggttgtg gcgaatcatc ataccagcat tttattggtt gattatgaat gttcaggcat    2820
tattgaaaca acggcatttt ggggattaat tgccttttat cctgtgtatg atgcacaaaa    2880
gcggttaatg ttggcgctta ttggggcatt atggtttttc cttgcaaata cgttacgact    2940
atcttttgtt gcagttgtaa tttattattt tggcgatggc gcttttttatg ttgctcattc    3000
aattatcgga cgcctgttgt tctattcaat tgtaatcttg ctttattatc tagtcttcat    3060
aaaggggcaa cttgttaatc aaatgctcaa aaaacaggga taaactatgt catttttattt   3120
acatcaattt acttatcagt taggttttg gttcacttgg ttgctcattc cgtttgttgt    3180
ggaaattttc ccagctatta tttcaatcta gttttgataa aaacatcaaa aaagcatcaa    3240
gtgatgcaag aaccattgaa attaccaatg gtatctattg tattacctat atataattca    3300
ggacaaacat tataccagtg tattcagtcg attagtcaat caacctatcc aaaacaatta    3360
atccaaatta ttgccgtgaa taatcaaagc actgataaca gttttacagt gtttaatcag    3420
gctcaagctc atttcccaat acttagaatg cagtggatga acacagatca aggtaaagcg    3480
cgtgcactaa atgctgctat ttataatagt atggggcaat atattattaa tttggatact    3540
gatggttggt tagaacccaa tgccttaaaa cggtttgtgc tttatttga aaatcactca     3600
gaaattgatg tagcaactgg tacgattctg acacaaaaaa aaatgattca aaaaacgcaa    3660
agtaaatggc ttaaattgct acagttaaac gaatattttg agtatgcaca atcattctta    3720
tcaggccgta gtattgaaaa ccgtggtaat cgtttgttca caatgtcagg tgcattttca    3780
gcgtttagac gtgatgtatt agttcagaca tttatgtata atgttgacac ggttggtgaa    3840
gatactgata tgacatttca actgcgattc cgcctaggca agcgtattgg tttctgtgat    3900
gatgccatgt tttatgttga accaatatca ggttatagtg aactttattt acaacgcag    3960
cgttggcagc gtgggcaaat tgaagtcgca caaaatttca tgcagaataa gttgagtgtc    4020
cgtcagattt ttactaactt tatgattagt cgattaatga ttgatc                  4066
```

<210> SEQ ID NO 17

<211> LENGTH: 7387
<212> TYPE: DNA
<213> ORGANISM: Leuconostoc mesenteroides

<400> SEQUENCE: 17

```
gatcaaatag atgctaccgt tatacgagac gttaaggatt atcccaatct agtcgttttg        60
cgtaccttgt cgaaagctta tggtctggca aacctgagaa tcggctatgg cgtcatgcag       120
gaaccacttt atcaggttat gcaggccgta cgtttaccat ataatttaaa tacctatcaa       180
atcacaggtg cagtagctgc ccttagtgat caactttatc tgcaatcagt tgttgctaag       240
gtgaagtctg aacgtgaaaa atttgaacaa tttttgacga acaccagtt taagtattat       300
caatcacaaa ccaactttct ctggattaaa gttggtgatg cgaaacgtgt tggtgaggct       360
cttctgtcag aagggtatca aattaatgac cgcctaaatg ccgaatggat tcgcattgca       420
ttaggaactg tgtctgataa tgaggggatg cagcgcattt tattgaattg ttaaaaaata       480
gctaagagag tatgttcttc tcttacctat ttttatttgt aattcctatt atttaatttt       540
gcatgacaat attaatagcg tgttacgatt ctactattta atgttaataa aattaataaa       600
tatggtatta tcttatatgg gtgatagatg caccaaatac tgtatcatgt ctggtcacat       660
gaaagggaga ataattaatg aaacaacaag aaacagttac ccgtaaaaaa ctttataaat       720
ccggtaaggt ttgggttgca gcagctactg catttgcggt attggggggtt tcaactgtaa       780
caacagtcca tgcggataca aattcgaatg tcgctgttaa gcaaataaat aatacaggaa       840
ccaatgattc tggcgaaaaa aaggtaccgg ttccatcaac taataatgat agtttgaagc       900
aaggaacaga tggttttttgg tatgattcag acggcaatcg tgtcgatcag aagaccaatc       960
agattctgct tactgcggaa caacttaaaa aaaataacga aaaaaattta tcagtaatca      1020
gtgatgatac atcaaaaaaa gatgatgaaa atatttctaa gcagaccaaa attgctaatc      1080
aacaaacagt agatactgct aaaggcctga ctaccagtaa tttatctgat cccatcactg      1140
ggggtcacta tgaaaatcac aatggctact tgttttatat agatgcttca ggaaaacaag      1200
taacaggttt gcaaaatatt gatggtaatt tacaatattt tgatgacaat ggatatcaag      1260
tcaagggatc cttccgagat gtcaacggca agcatatcta tttttgattca gtaacaggga      1320
aagctagttc aaatgttgat attgttaacg gtaaagctca aggatatgat gcgcaaggca      1380
accaattaaa gaaaagttat gtcgccgata gttctgggca aacttactat tttgatggta      1440
atggccaacc gttaatcggc ttgcaaacaa ttgatgggaa cctacaatat tttaaccaac      1500
aagggggttca aataaagggt ggtttccaag atgttaacaa taaacgtatt tattttgcac      1560
caaacacagg taatgccgtt gccaatactg aaataattaa cggtaaatta caggggcgtg      1620
acgcaaatgg taaccaggta aagaatgcat ttagtaaaga tgttgcagga atacattttt      1680
attttgacgc aaacggtgtg atgttaacag ggttgcaaac tatttcagga aagacatatt      1740
atcttgatga acaaggacac ctgagaaaaa attacgcggg aacattcaat aatcagttta      1800
tgtacttcga tgctgataca ggtgcgggta aacagcgat tgaatatcaa tttgatcaag      1860
gattggtatc acaaagtaat gaaaatactc ctcacaatgc cgcaaagtct tatgataaaa      1920
gtagttttga aaatgttgat ggttacttaa cagcagatac atggtatcgt ccaaccgata      1980
ttttaaaaaa tggagatact tggacggcat ctaccgaaac tgatatgcgt ccgcttttaa      2040
tgacatggtg gcctgacaaa caaacacaag caaattactt gaattttatg tctagtaaag      2100
gacttggtat aacgaccact tatacagcag ctacgtcaca aaaaacacta aatgacgcag      2160
cctttgttat tcaaacagca attgaacaac aaatatcttt gaaaaaaagt actgagtggt      2220
```

```
tacgtgatgc aattgatagt tttgtgaaga cgcaagctaa ttggaataag caaacagaag   2280
atgaagcttt cgatggtttg cagtggcttc aagggggatt cctagcttat caagatgatt   2340
cacatcggac gccgaatact gattcaggaa ataacagaaa actaggacgt caaccaatta   2400
atatcgatgg ttcgaaagat acaactgatg gtaaaggctc tgaattctta ttagctaacg   2460
atattgacaa ctcaaatccg attgttcaag ctgagcaatt aaactggcta cactatttaa   2520
tgaattttgg tagtattaca ggtaataatg acaatgcgaa ttttgatggc attcgtgtag   2580
atgctgttga taatgttgat gctgatttac taaaaatagc tggcgattat tttaaagctc   2640
tatatggtac agataaaagc gacgccaatg ccaataagca tttgtctatt ttagaagact   2700
ggaacggtaa agatcctcag tatgttaatc aacagggcaa tgcgcaatta caatggatt    2760 acacagttac ttcacagttt ggcaattctc taacacatgg cgccaacaac aggagtaaca   2820
tgtggtattt cttagatact ggctattatc ttaatggaga tcttaataag aagatagtag   2880
ataagaaccg tccaaattct ggcactttgg ttaacagaat tgctaattca ggtgatacaa   2940
aagttattcc aaattatagt tttgttagag cacatgatta cgatgctcaa gatccaatta   3000
gaaaagccat gattgatcat ggtattatta aaaacatgca ggatactttc acttttgacc   3060
aactggctca gggaatggaa ttctactata agatcaaga gaatccgtct ggtttcaaaa    3120
agtataacga ttataactta cctagtgctt atgcaatgtt gttgactaat aaggatactg   3180
tacctcgtgt ctattatgga gatatgtacc tcgaaggcgg gcaatatatg gaaaaaggga   3240
cgatttacaa tcctgtcatt tcagcgttgc tcaaagctag aataaaatat gtttctggtg   3300
ggcaaacaat ggctaccgat agttctggaa aagaccttaa agatggcgaa actgatttgt   3360
taacaagtgt tcgatttggt aaaggaatta tgacatcaga tcaaaccaca acacaagaca   3420
atagccaaga ttataaaaat caaggcatcg gtgtcattgt tggtaataac cctgacctta   3480
agttgaacaa tgataagacc attaccttgc atatgggaaa ggcgcataag aatcaacttt   3540
accgtgcctt agtattatca aatgactcag gaattgatgt ttatgatagt gatgataaag   3600
caccaacttt gagaacaaat gacaacggtg acttgatttt ccataagaca aatacgtttg   3660
tgaagcaaga tggaactatt ataaattacg aaatgaaggg atcattaaat gctttaattt   3720
caggttattt aggtgtctgg gtgccagttg gagctagtga ttcacaagat gctcgtacag   3780
tggcaactga gtcatcatca agtaatgatg gttctgtatt ccattcaaat gctgcattag   3840
attctaatgt tatatatgaa ggcttttcaa actttcaagc gatgccgact tctcctgagc   3900
aaagtacaaa tgttgttatt gcaacaaagg ctaacttatt taaagaatta ggtattacta   3960
gttttgagtt agcacctcaa tataggtcta gtggtgacac taattacggt ggcatgtcat   4020
tcttagattc tttcttaaat aatggttatg catttaccga tagatatgat ttaggcttta   4080
acaaagcaga cgggaatcct aacccaacaa gtatggaac agatcaagat ttacgtaatg    4140
caatagaggc attacacaaa aacggcatgc aggctatagc tgattgggtt cctgaccaaa   4200
tatatgcttt accaggaaag gaagttgtta ccgctactag agtagacgaa cggggaaatc   4260
aactaaaaga cacagatttt gtcaacttac tctatgttgc taatactaaa agtagtggtg   4320
tggattatca ggcaaagtat ggcggcgaat tttagataa attaagagaa gagtacccat    4380
cgttattcaa acagaaccaa gtatcgacag gtcagccaat tgatgcttct acaaaaatta   4440
agcaatggtc agctaaatat atgaatggga ccaatatttt acatcgaggt gcttattatg   4500
ttttgaaaga ctgggctact aaccagtatt ttaacattgc aaaaacgaat gaagtatttt   4560
```

```
tgccactaca gttgcagaat aaagatgcgc aaactggttt cattagtgat gcctccggtg    4620
taaaatatta ctcaattagt ggttatcaag caaaagatac ttttattgaa gatggtaatg    4680
ggaattggta ttactttgat aaagatggtt acatggtgcg ttcgcagcaa ggagaaaatc    4740
ctataagaac agtcgaaact agtgtcaaca cacgaaacgg taattattac tttatgccaa    4800
atggtgtcga gttgcgcaaa ggctttggaa cggataatag tggtaatgtc tattattttg    4860
atgatcaagg taagatggtg agagataaat acattaacga tgatgctaat aattttatc     4920 acttaaatgt tgatgggact atgtctcgag gactatttaa atttgattct gatactctac    4980
agtattttgc tagtaatggt gtccaaataa agatagtta tgcgaaggat agtaaaggca     5040
ataaatatta ttttgactca gctacaggaa ataacgatac tgggaaagcc caaacttggg    5100
atggtaatgg ctactatatt actattgatt ctgatgcgaa caatacaatt ggggttaaca    5160
cagactacac tgcctacatc actagctcgc tgcgcgaaga tggcttattt gctaacgcac    5220
cttacggtgt tgtaacaaaa gaccaaaatg gtaacgatct taagtggcag tatattaacc    5280
atacgaaaca gtacgaaggg caacaagtgc aagtcacgcg tcaatacaca gacagtaagg    5340
gagtcagctg gaacttaatt accttttgctg gtggtgattt acaaggacaa aggctttggg    5400
tggatagtcg tgcgttaact atgacaccat ttaaaacgat gaaccaaata agcttcatta    5460
gttatgctaa ccgcaatgat gggttgtttt tgaatgcgcc ataccaagtc aaggggtatc    5520
aattagctgg gatgtccaac caatacaagg gccaacaagt gaccattgct ggggtggcga    5580
acgtttctgg aaaagactgg agtctgatta gttttaatgg gacacagtac tggattgata    5640
gtcaggcatt gaataccaat ttcacacatg acatgaacca aaaggtcttt gtcaatacaa    5700
ctagtaatct tgatgggtta ttcttaaatg cgccataccg tcaaccgggt tataagttag    5760
ccggtttggc taaaaattac aacaaccaaa cggttactgt tagtcaacag tactttgatg    5820
atcaaggcac ggtctggagt caggttgtcc ttggggtca gacggtctgg gttgataacc      5880
atgcattggc acagatgcaa gttagtgata cagaccaaca gctctatgtg aatagcaatg    5940
gtcggaatga tgggttattc ttgaatgcgc catatcgtgg tcaagggtca caactgatag    6000
gcatgacggc agattataat gggcaacatg tacaagtgac caagcaaggg caagatgcct    6060
atggtgcaca atggcgtctt attacgctaa ataatcaaca ggtctgggtt gatagtcgcg    6120 cttttgagcac aacaatcatg caagccatga atgataatat gtatgtaaat agcagccaac    6180
ggacagatgg cttgtggtta aacgcaccct tatacgatgag tggggctaaa tgggctggtg    6240
atacacgttc agctaatggg cgctatgtcc atatttcaaa agcttattca aacgaagtcg    6300
gcaatacata ttacttgacg aatttgaatg gtcaaagcac atggattgac aagcgggcgt    6360
ttactgtgac cttcgatcag gtggtggcat taaatgcaac gattgtggca cgccaacgac    6420
cagatgggat gtttaagaca gcaccatatg gtgaagcggg ggcgcagttt gtcgattatg    6480
tgacaaacta taaccagcaa accgtgccag taacaaagca acattcagat gctcagggga    6540
atcaatggta cttagcgaca gtgaatggga cacaatactg gattgatcaa cggtcatttt    6600
caccagtagt aacgaaggtg gttgattatc aagctaagat tgtgccacgg acaacacgtg    6660
atggtgtgtt tagtggcgca ccctatgggg aagtgaatgc taagctagtt aacatggcaa    6720
ctgcgtatca aaatcaagtt gtccatgcga caggggaata tacgaatgct tcagggatca    6780
catggagtca gttcgcgtta agcgggcaag aagacaagct atggattgat aagcgtgctt    6840
tgcaagctta agggaaggat tcgacaaagg agggtaacat tatcagcgga tggtgttatc    6900 ctccttttcct gtactcagta tttcccaaat aattgagaca gtttcatgac aaatcaacaa    6960
```

-continued

```
aactagtgtc aatgcctcgg ttatggggta aactactatt agttaaaggg ttgttgcata    7020
ataatatcac attcaatata ttatgtattt ttatctgatt atgtgatttt ttgagatttg    7080
gagcgaaaat gaataaagta ataattaata aaagtttctg tgttttggta atgagtttgt    7140
tgtcgatatt tctattctca ttaagagtag acgctcgttc caatagtggc tacaatcaaa    7200
tatcttttaa tcaacatgaa attgcttatg cgccttttag tcaagtacct tggtatgcaa    7260
ctgtgaatgt cggaatgtct gcagacaaaa ataatatcta tacagctatt gatatggggc    7320
catagtatca aggaacttct ttttttccgt ggtggtatca acatgataat tatgattatc    7380
atgatgg                                                              7387
```

<210> SEQ ID NO 18
<211> LENGTH: 32
<212> TYPE: DNA
<213> ORGANISM: Artificial Sequence
<220> FEATURE:
<223> OTHER INFORMATION: A1-4 primer directed to NheI restriction site.

<400> SEQUENCE: 18

```
gggcccgcta gcatgaaaca acaagaaaca gt                                  32
```

<210> SEQ ID NO 19
<211> LENGTH: 30
<212> TYPE: DNA
<213> ORGANISM: Artificial Sequence
<220> FEATURE:
<223> OTHER INFORMATION: A1-5 primer directed to SalI restriction site.

<400> SEQUENCE: 19

```
cccggggtcg acctttgtcg aatccttccc                                     30
```

<210> SEQ ID NO 20
<211> LENGTH: 6204
<212> TYPE: DNA
<213> ORGANISM: Leuconostoc mesenteroides

<400> SEQUENCE: 20

```
gctagcatga acaacaaga aacagttacc cgtaaaaaac tttataaatc cggtaaggtt    60
tgggttgcag cagctactgc atttgcggta ttggggggttt caactgtaac aacagtccat   120
gcggatacaa attcgaatgt cgctgttaag caaataaata atacaggaac caatgattct   180
ggcgaaaaaa aggtaccggt tccatcaact aataatgata gtttgaagca aggaacagat   240 ggttttttggt atgattcaga cggcaatcgt gtcgatcaga agaccaatca gattctgctt   300
actgcggaac aacttaaaaa aaataacgaa aaaaatttat cagtaatcag tgatgataca   360
tcaaaaaaag atgatgaaaa tatttctaag cagaccaaaa ttgctaatca acaaacagta   420
gatactgcta aaggcctgac taccagtaat ttatctgatc ccatcactgg gggtcactat   480
gaaaatcaca atggctactt tgtttatata gatgcttcag gaaaacaagt aacaggtttg   540
caaaatattg atggtaattt acaatatttt gatgacaatg gatatcaagt caagggatcc   600
ttccgagatg tcaacggcaa gcatatctat tttgattcag taacagggaa agctagttca   660
aatgttgata ttgttaacgg taaagctcaa ggatatgatg cgcaaggcaa ccaattaaag   720
aaaagttatg tcgccgatag ttctgggcaa acttactatt ttgatggtaa tggccaaccg   780
ttaatcggct tgcaaacaat tgatgggaac ctacaatatt ttaaccaaca aggggttcaa   840
ataaagggtg gtttccaaga tgttaacaat aaacgtattt attttgcacc aaacacaggt   900
```

```
aatgccgttg ccaatactga ataattaac ggtaaattac aggggcgtga cgcaaatggt      960
aaccaggtaa agaatgcatt tagtaaagat gttgcaggaa atacatttta ttttgacgca     1020
aacggtgtga tgttaacagg gttgcaaact atttcaggaa agacatatta tcttgatgaa     1080
caaggacacc tgagaaaaaa ttacgcggga acattcaata atcagtttat gtacttcgat     1140
gctgatacag gtgcgggtaa aacagcgatt gaatatcaat ttgatcaagg attggtatca     1200
caaagtaatg aaaatactcc tcacaatgcc gcaaagtctt atgataaaag tagttttgaa     1260
aatgttgatg gttacttaac agcagataca tggtatcgtc caaccgatat tttaaaaaat     1320
ggagatactt ggacggcatc taccgaaact gatatgcgtc cgcttttaat gacatggtgg     1380
cctgacaaac aaacacaagc aaattacttg aattttatgt ctagtaaagg acttggtata     1440
acgaccactt atacagcagc tacgtcacaa aaaacactaa atgacgcagc ctttgttatt     1500
caaacagcaa ttgaacaaca atatctttg aaaaaagta ctgagtggtt acgtgatgca      1560
attgatagtt ttgtgaagac gcaagctaat tggaataagc aaacagaaga tgaagctttc     1620
gatggtttgc agtggcttca aggggattc ctagcttatc aagatgattc acatcggacg      1680
ccgaatactg attcaggaaa taacagaaaa ctaggacgtc aaccaattaa tatcgatggt     1740
tcgaaagata caactgatgg taaaggctct gaattcttat tagctaacga tattgacaac     1800
tcaaatccga ttgttcaagc tgagcaatta aactggctac actatttaat gaattttggt     1860
agtattacag gtaataatga caatgcgaat tttgatggca ttcgtgtaga tgctgttgat     1920
aatgttgatg ctgatttact aaaaatagct ggcgattatt ttaaagctct atatggtaca     1980
gataaaagcg acgccaatgc caataagcat ttgtctattt tagaagactg gaacggtaaa     2040
gatcctcagt atgttaatca acagggcaat gcgcaattaa caatggatta cacagttact     2100
tcacagtttg gcaattctct aacacatggc gccaacaaca ggagtaacat gtggtatttc     2160
ttagatactg gctattatct taatggagat cttaataaga agatagtaga taagaaccgt     2220
ccaaattctg gcactttggt taacagaatt gctaattcag gtgatacaaa agttattcca     2280
aattatagtt ttgttagagc acatgattac gatgctcaag atccaattag aaaagccatg     2340
attgatcatg gtattattaa aaacatgcag gatactttca cttttgacca actggctcag     2400
ggaatggaat tctactataa agatcaagag aatccgtctg gtttcaaaaa gtataacgat     2460
tataacttac ctagtgctta tgcaatgttg ttgactaata aggatactgt acctcgtgtc     2520
tattatggag atatgtacct cgaaggcggg caatatatgg aaaaagggac gatttacaat     2580
cctgtcattt cagcgttgct caaagctaga ataaaatatg tttctggtgg gcaaacaatg     2640
gctaccgata gttctggaaa agaccttaaa gatggcgaaa ctgatttgtt aacaagtgtt     2700
cgatttggta aggaattat gacatcgat caaaccacac acaagacaa tagccaagat        2760 tataaaaatc aaggcatcgg tgtcattgtt ggtaataacc ctgaccttaa gttgaacaat     2820
gataagacca ttaccttgca tatgggaaag gcgcataaga atcaacttta ccgtgcctta     2880
gtattatcaa atgactcagg aattgatgtt tatgatagtg atgataaagc accaactttg     2940
agaacaaatg acaacggtga cttgattttc ataagacaa atacgtttgt gaagcaagat      3000
ggaactatta taaattacga aatgaaggga tcattaaatg ctttaatttc aggttattta     3060
ggtgtctggg tgccagttgg agctagtgat tcacaagatg ctcgtacagt ggcaactgag     3120
tcatcatcaa gtaatgatgg ttctgtattc cattcaaatg ctgcattaga ttctaatgtt     3180
atatatgaag cttttcaaa cttttcaagcg atgccgactt ctcctgagca agtacaaat      3240 gttgttattg caacaaaggc taacttattt aaagaattag gtattactag ttttgagtta     3300
```

```
gcacctcaat ataggtctag tggtgacact aattacggtg gcatgtcatt cttagattct   3360
ttcttaaata atggttatgc atttaccgat agatatgatt taggctttaa caaagcagac   3420
gggaatccta acccaacaaa gtatggaaca gatcaagatt tacgtaatgc aatagaggca   3480
ttacacaaaa acggcatgca ggctatagct gattgggttc ctgaccaaat atatgcttta   3540
ccaggaaagg aagttgttac cgctactaga gtagacgaac ggggaaatca actaaaagac   3600
acagattttg tcaacttact ctatgttgct aatactaaaa gtagtggtgt ggattatcag   3660
gcaaagtatg cggcgaatt tttagataaa ttaagagaag agtacccatc gttattcaaa   3720
cagaaccaag tatcgacagg tcagccaatt gatgcttcta caaaaattaa gcaatggtca   3780
gctaaatata tgaatgggac caatatttta catcgaggtg cttattatgt tttgaaagac   3840
tgggctacta accagtattt taacattgca aaaacgaatg aagtattttt gccactacag   3900
ttgcagaata aagatgcgca aactggtttc attagtgatg cctccggtgt aaaatattac   3960
tcaattagtg gttatcaagc aaaagatact tttattgaag atggtaatgg aattggtat   4020 tactttgata agatggtta catggtgcgt tcgcagcaag gagaaaatcc tataagaaca   4080
gtcgaaacta gtgtcaacac acgaaacggt aattattact ttatgccaaa tggtgtcgag   4140
ttgcgcaaag gctttggaac ggataatagt ggtaatgtct attattttga tgatcaaggt   4200
aagatggtga gagataaata cattaacgat gatgctaata atttttatca cttaaatgtt   4260
gatgggacta tgtctcgagg actatttaaa tttgattctg atactctaca gtattttgct   4320
agtaatggtg tccaaataaa agatagttat gcgaaggata gtaaaggcaa taaatattat   4380
tttgactcag ctacaggaaa taacgatact gggaaagccc aaacttggga tggtaatggc   4440
tactatatta ctattgattc tgatgcgaac aatacaattg gggttaacac agactacact   4500
gcctacatca ctagctcgct gcgcgaagat ggcttatttg ctaacgcacc ttacggtgtt   4560
gtaacaaaag accaaaatgg taacgatctt aagtggcagt atattaacca tacgaaacag   4620
tacgaagggc aacaagtgca agtcacgcgt caatacacag acagtaaggg agtcagctgg   4680
aacttaatta cctttgctgg tggtgattta caaggacaaa ggctttgggt ggatagtcgt   4740
gcgttaacta tgacaccatt taaaacgatg aaccaaataa gcttcattag ttatgctaac   4800
cgcaatgatg ggttgttttt gaatgcgcca taccaagtca agggggtatca attagctggg   4860 atgtccaacc aatacaaggg ccaacaagtg accattgctg gggtggcgaa cgtttctgga   4920
aaagactgga gtctgattag ttttaatggg acacagtact ggattgatag tcaggcattg   4980
aataccaatt tcacacatga catgaaccaa aaggtctttg tcaatacaac tagtaatctt   5040
gatgggttat tcttaaatgc gccataccgt caaccgggtt ataagttagc cggtttggct   5100
aaaaattaca acaaccaaac ggttactgtt agtcaacagt actttgatga tcaaggcacg   5160
gtctggagtc aggttgtcct tgggggtcag acggtctggg ttgataacca tgcattggca   5220
cagatgcaag ttagtgatac agaccaacag ctctatgtga atagcaatgg tcggaatgat   5280
gggttattct tgaatgcgcc atatcgtggt caagggtcac aactgatagg catgacggca   5340
gattataatg ggcaacatgt acaagtgacc aagcaagggc aagatgccta tggtgcacaa   5400
tggcgtctta ttacgctaaa taatcaacag gtctgggttg atagtcgcgc tttgagcaca   5460
acaatcatgc aagccatgaa tgataatatg tatgtaaata gcagccaacg gacagatggc   5520
ttgtggttaa acgcacctta tacgatgagt ggggctaaat gggctggtga tacacgttca   5580
gctaatgggc gctatgtcca tatttcaaaa gcttattcaa acgaagtcgg caatacatat   5640
```

-continued

```
tacttgacga atttgaatgg tcaaagcaca tggattgaca agcgggcgtt tactgtgacc    5700
ttcgatcagg tggtggcatt aaatgcaacg attgtggcac gccaacgacc agatgggatg    5760
tttaagacag caccatatgg tgaagcgggg gcgcagtttg tcgattatgt gacaaactat    5820
aaccagcaaa ccgtgccagt aacaaagcaa cattcagatg ctcaggggaa tcaatggtac    5880
ttagcgacag tgaatgggac acaatactgg attgatcaac ggtcattttc accagtagta    5940
acgaaggtgg ttgattatca agctaagatt gtgccacgga caacacgtga tggtgtgttt    6000
agtggcgcac cctatgggga agtgaatgct aagctagtta acatggcaac tgcgtatcaa    6060
aatcaagttg tccatgcgac aggggaatat acgaatgctt cagggatcac atggagtcag    6120
ttcgcgttaa gcgggcaaga agacaagcta tggattgata agcgtgcttt gcaagcttaa    6180
gggaaggatt cgacaaaggt cgac                                            6204
```

<210> SEQ ID NO 21
<211> LENGTH: 7
<212> TYPE: PRT
<213> ORGANISM: Artificial Sequence
<220> FEATURE:
<223> OTHER INFORMATION: N-terminus peptide sequence directed to
      Leuconostoc mesenteriodes NRR1-B1335.

<400> SEQUENCE: 21

Asp Thr Asn Ser Asn Val Ala
1               5

<210> SEQ ID NO 22
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 22

Met Lys Gln Gln Glu
1               5

<210> SEQ ID NO 23
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 23

Lys Lys Val Pro Val
1               5

<210> SEQ ID NO 24
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 24

Lys Asp Asp Glu Asn
1               5

<210> SEQ ID NO 25
<211> LENGTH: 5

```
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 25

Ile Asp Gly Asn Leu
1               5

<210> SEQ ID NO 26
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 26

Tyr Val Ala Asp Ser
1               5

<210> SEQ ID NO 27
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 27

His Leu Arg Lys Asn
1               5

<210> SEQ ID NO 28
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 28

Asn Glu Asn Thr Pro
1               5

<210> SEQ ID NO 29
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 29

Asn Val Asp Gly Tyr
1               5

<210> SEQ ID NO 30
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 30

Asn Pro Asp Leu Lys
```

```
<210> SEQ ID NO 31
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 31

Ser Asn Asp Ser Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 32

Asn Thr Phe Val Lys
1               5

<210> SEQ ID NO 33
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 33

Ile Ser Gly Tyr Leu
1               5

<210> SEQ ID NO 34
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 34

Ser Asn Ala Ala Leu
1               5

<210> SEQ ID NO 35
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 35

Arg Gln Tyr Thr Asp
1               5

<210> SEQ ID NO 36
<211> LENGTH: 5
<212> TYPE: PRT
<213> ORGANISM: Artificial Sequence
<220> FEATURE:
<223> OTHER INFORMATION: Peptide motif directed to Leuconostoc
```

-continued mesenteroides.

<400> SEQUENCE: 36

Gln Leu Tyr Arg Ala
1               5

<210> SEQ ID NO 37
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 37

Asp Asp Lys Ala Pro
1               5

<210> SEQ ID NO 38
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 38

Thr Arg Gln Tyr Thr
1               5

<210> SEQ ID NO 39
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 39

Ile Thr Phe Ala Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 40

Asn Gln Tyr Lys Gly
1               5

<210> SEQ ID NO 41
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 41

Leu Phe Leu Asn Ala
1               5

<210> SEQ ID NO 42

```
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 42

Gln Val Ser Asp Thr
1               5

<210> SEQ ID NO 43
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 43

Leu Ile Thr Leu Asn
1               5

<210> SEQ ID NO 44
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 44

Gly Arg Tyr Val His
1               5

<210> SEQ ID NO 45
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 45

Thr Ala Pro Tyr Gly
1               5

<210> SEQ ID NO 46
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 46

Val Val Asp Tyr Gln
1               5

<210> SEQ ID NO 47
<211> LENGTH: 5
<212> TYPE: PRT
<213> ORGANISM: Artificial Sequence
<220> FEATURE:
<223> OTHER INFORMATION: Peptide motif directed to Leuconostoc
      mesenteroides.

<400> SEQUENCE: 47
```

-continued

```
Leu Ser Gly Gln Glu
1               5
```

<210> SEQ ID NO 48
<211> LENGTH: 26
<212> TYPE: DNA
<213> ORGANISM: Artificial Sequence
<220> FEATURE:
<223> OTHER INFORMATION: Sp-pat-5' oligonucleotide directed to potato.

<400> SEQUENCE: 48
tctagactgc aaaatggcaa ctacta                                          26

<210> SEQ ID NO 49
<211> LENGTH: 26
<212> TYPE: DNA
<213> ORGANISM: Artificial Sequence
<220> FEATURE:
<223> OTHER INFORMATION: Sp-pat-3' oligonucleotide directed to potato.

<400> SEQUENCE: 49
gtcgacggtt tcatttggag tagtta                                          26

<210> SEQ ID NO 50
<211> LENGTH: 276
<212> TYPE: DNA
<213> ORGANISM: Solanum tuberosum

<400> SEQUENCE: 50
atggcaacta ctaaatcttt tttaatttta tttttatga tattagcaac tactagttca      60
acatgtgcta agttggaaga aatggttact gttctaagta ttgatggagg tggaattaag     120
ggaatcattc cagctatcat tctcgaattt cttgaaggac aacttcagga agtggacaat     180
aataaagatg caagacttgc agattacttt gatgtaattg gaggaacaag tacaggaggt     240
ttattgactg ctatgataac tactccaaat gaaacc                               276

<210> SEQ ID NO 51
<211> LENGTH: 31
<212> TYPE: DNA
<213> ORGANISM: Artificial Sequence
<220> FEATURE:
<223> OTHER INFORMATION: Sp-fnr-5' oligonucleotide directed to spinach.

<400> SEQUENCE: 51
gcgtactcta gacgtactcc gccatgacca c                                    31

<210> SEQ ID NO 52
<211> LENGTH: 30
<212> TYPE: DNA
<213> ORGANISM: Artificial Sequence
<220> FEATURE:
<223> OTHER INFORMATION: Sp-fnr-3 oligonucleotide directed to spinach.

<400> SEQUENCE: 52
gcgtacgtcg acggccctga tgggtcccat                                      30

<210> SEQ ID NO 53
<211> LENGTH: 34
<212> TYPE: DNA
<213> ORGANISM: Artificial Sequence
<220> FEATURE:
<223> OTHER INFORMATION: A1-5'-1.2 primer directed to Leuconostoc
      mesenteroides.

<400> SEQUENCE: 53

```
ggccgggtcg acgatacaaa ttcgaatgtc gctg                                    34
```

<210> SEQ ID NO 54
<211> LENGTH: 33
<212> TYPE: DNA
<213> ORGANISM: Artificial Sequence
<220> FEATURE:
<223> OTHER INFORMATION: A1-3'-2.2 primer directed to Leuconostoc
      mesenteroides.

<400> SEQUENCE: 54

```
ggccggctgc aggttaccct cctttgtcga atc                                     33
```

NUCLEIC ACID MOLECULES ENCODING ALTERNANSUCRASE

This application is a divisional of application Ser. No. 09/499,203, filed on Feb. 8, 2000, now U.S. Pat. No. 6,570,065, the entire contents of which are hereby incorporated by reference and for which priority is claimed under 35 U.S.C. § 120; and this application claims priority of Application No. DE 19905069.4 filed in GERMANY on Feb. 8, 1999 under 35 U.S.C. § 119.

The present invention relates to nucleic acid molecules encoding an alternansucrase. Moreover, this invention relates to vectors, host cells and plant cells transformed with the herein-described nucleic acid molecules, and plants containing said cells. Moreover, methods for preparing transgenic plants which due to the insertion of DNA molecules encoding an alternansucrase, synthesize the carbohydrate alternan, are described. Furthermore, methods for preparing alternan are described.

Prior art documents, the disclosure content of which is included into the present application by reference thereto, are cited hereinafter.

Alternan is a polysaccharide composed of glucose units. The glucose units are linked to each other via α-1,3- and α-1,6-glycosidic bonds, and said two types of bonds predominantly appear alternatingly. However, alternan is not a linear polysaccharide, but may contain branches (Seymour et al., Carbohydrate Research 74, (1979), 41-62). Because of its physico-chemical properties, the possibilities of application of alternan both in the pharmaceutical industry, for instance as a carrier of pharmaceutically active ingredients and as an additive in the textile, cosmetics and food industry have been discussed (Lopez-Munguia et al., Enzyme Microb. Technol. 15, (1993), 77-85; Leathers et al., Journal of Industrial Microbiology & Biotechnology 18, (1997), 278-283). Moreover, it can be used as a substitute for gum arabic (Coté, Carbohydrate Polymers 19, (1992), 249-252).

Industry has a high interest in biotechnological methods for preparing oligosaccharides and polysaccharides, and in particular alternan which is hardly or not at all accessible to classical organic synthesis. Compared to the classical approach of organic synthesis chemistry, biotechnological processes offer advantages. For instance, enzymatically catalyzed reactions as a rule show much higher specificities (regio specificity, stereo specificity) and higher reaction speeds, proceed under milder reaction conditions and lead to higher yields. These factors are of outstanding importance in the preparation of new oligosaccharides and polysaccharides.

Alternan is prepared enzymatically with the use of enzymes possessing the biological activity of alternansucrases. Alternansucrases belong to the group of glucosyltransferases, which, starting from saccharose, are able to catalyze the formation of alternan and fructose. So far, alternansucrases have only been found in the bacterium *Streptococcus mutans* (Mukasa et al. (J. Gen. Microbiol. 135 (1989), 2055-2063); Tsumori et al. (J. Gen. Microbiol. 131 (1985), 3347-3353)) and in specific strains of the gram positive bacterium *Leuconostoc mesenteroides* where they are, as a rule, present together with other polysaccharide-forming enzymes, such as for instance dextran-forming dextransucrases, or together with polysaccharide-degrading enzymes, such as alternanases. Hence, the naturally occurring strains also produce dextran in addition to alternan.

So far, alternan has been prepared in a cell-free system using partially purified proteins or by fermentation using alternansucrase-producing strains of *Leuconostoc mesenteroides*.

Various purification methods for the purification of alternansucrases have been described (Lopez-Munguia et al., Enzyme Microb. Technol. 15 (1993), 77-85; Lopez-Munguia et al., Annals New York Academy of Sciences 613 (1990), 717-722; Coté and Robyt, Carbohydrate Research 101 (1982), 57-74). These methods are complex and relatively costly, and, as a rule, lead to low protein yields (Leathers et al., Journal of Industrial Microbiology & Biotechnology 18 (1997), 278-283). None of these methods allows highly pure alternansucrase protein to be produced, and therefore sequencing of the protein and the isolation of the corresponding DNA sequences have not been successful so far. If the alternansucrase protein purified according to these methods is used for in vitro preparation of alternan, then the dextransucrase protein residues contained in the alternansucrase preparation produce dextran impurities in the alternan produced. The separation of alternan and dextran is relatively time-consuming and costly (Leathers et al., Journal of Industrial Microbiology & Biotechnology 18 (1997), 278-283). Another disadvantage of the dextransucrase protein impurities contained in the enzyme preparation of alternansucrase protein is the fact that a part of the saccharose substrate is converted into dextran and not into alternan, which results in a reduction of the alternan yield.

The fermentative preparation by means of *Leuconostoc* also leads to the formation of product mixtures of alternan and dextran. In order to increase the amount of alternansucrase from *Leuconostoc* strains, mutants have been isolated, such as the mutant NRRL B-21138, which secrete the alternansucrase and lead to a higher proportion of the amount of alternansucrase formed relative to dextransucrase. However, if such mutants are fermented with sucrose, the alternan obtained continues to show dextran impurities (Leathers et al., Journal of Industrial Microbiology & Biotechnology 18 (1997), 278-283).

As can be seen from the prior art discussed above, it has not been possible to provide highly purified alternansucrase protein so far.

Hence, the present invention addresses the problem of providing means and methods allowing alternan to be prepared in a time-saving and inexpensive manner.

This problem is solved by the provision of the embodiments characterized in the patent claims.

Consequently, the present invention relates to a nucleic acid molecule encoding a protein possessing the biological activity of an alternansucrase selected from the group consisting of (a) nucleic acid molecules encoding at least the mature form of a protein which comprises the amino acid sequence indicated in SEQ ID NO:2 or the amino acid sequence encoded by the cDNA contained in plasmid DSM 12666;

(b) nucleic acid molecules comprising the nucleotide sequence indicated in SEQ ID NO:1 or the nucleotide sequence of the cDNA contained in plasmid DSM 12666 or a corresponding ribonucleotide sequence;

(c) nucleic acid molecules encoding a protein, the amino acid sequence of which has a homology of at least 40% to the amino acid sequence indicated in SEQ ID NO:2;

(d) nucleic acid molecules, one strand of which hybridizes with the nucleic acid molecules as defined in (a) or (b);

(e) nucleic acid molecules comprising a nucleotide sequence encoding a biologically active fragment of the protein which is encoded by any one of the nucleic acid molecules as defined in (a), (b), (c) or (d); and (f) nucleic acid molecules, the nucleotide sequence of which deviates because of the degeneration of the genetic code from the sequence of the nucleic acid molecules as defined in (a), (b), (c), (d) or (e).

Consequently, the present invention relates to nucleic acid molecules encoding proteins possessing the biological activity of an alternansucrase, said molecules preferably encoding proteins comprising the amino acid sequence indicated in SEQ ID NO:2.

An enzyme possessing the enzymatic or biological activity of an alternansucrase (E.C. 2.4.1.140) is understood to mean an enzyme which is able to catalyze the conversion of saccharose into alternan and fructose. This conversion may occur both in the presence and absence of external acceptors (for instance maltose, isomaltose, isomaltotriose etc.). In the absence of external acceptors, alternansucrases starting from saccharose catalyze the release of fructose and high molecular alternan, a polysaccharide composed of glucose units, the backbone of which consists of glucose units predominantly connected to each other alternatingly by α-1,3- and α-1,6-glycosidic bonds. Concerning the percentage of α-1,3- and α-1,6-linked glucose units the literature displays different values. According to Mukasa et al. (J. Gen. Microbiol. 135 (1989), 2055-2063), alternan consists of 76 mol % α-1,3-linked glucose and 24 mol % α-1,6-linked glucose. Tsumori et al. (J. Gen. Microbiol. 131 (1985), 3347-3353) describe alternan as a polyglucan containing 49.1 mol % α-1,6-linked glucose and 33.9 mol % α-1,3-linked glucose with 13.6 mol % terminal glucose and 3.3 mol % α-1,3,6-branched glucose. In the presence of external acceptors, such as maltose, isomaltose, isomaltotriose and methyl-α-D-glucan, alternansucrase can catalyze the synthesis of α-D-glucan chains, in which the glucose residues are predominantly alternatingly connected by α-1,6- and α-1,3-glycosidic bonds, and the synthesis of fructose at these polysaccharide acceptors. Depending on the acceptor used, the products formed have different structures. The enzymatic activity of an alternansucrase can for instance be detected as described by Lopez-Munguia (Annals New York Academy of Sciences 613 (1990), 717-722) or as described in the examples of the present application.

The invention in particular relates to nucleic acid molecules containing the nucleotide sequence indicated under SEQ ID NO:1 or a part thereof, and preferably to molecules, which comprise the coding region indicated in SEQ ID NO:1 or corresponding ribonucleotide sequences.

Moreover, the present invention -relates to nucleic acid molecules which encode an alternansucrase and the one strand of which hybridizes with one of the above-described molecules.

The present invention also relates to nucleic acid molecules which encode a protein, which has a homology, that is to say an identity of at least 40%, preferably at least 60%, preferably at least 70%, especially preferably at least 80% and in particular at least 90% to the entire amino acid sequence indicated in SEQ ID NO:2, the protein possessing the biological activity of an alternansucrase.

The present invention also relates to nucleic acid molecules, which encode an alternansdcrase and the sequence of which deviates on account of the degeneration of the genetic code from the nucleotide sequences of the above-described nucleic acid molecules.

The invention also relates to nucleic acid molecules possessing a sequence which is complementary to the whole or a part of the above-mentioned sequences.

The nucleic acid sequence indicated in SEQ ID NO:1 for instance encodes an extracellular alternansucrase. Secretion is ensured by a signal sequence which comprises the first approximately 39 N-terminal amino acid groups of the SEQ ID NO:2. In certain circumstances it may be desirable for only the mature protein to be expressed without naturally occurring signal sequences and/or together with other signal sequences. Hence, the above-described nucleic acid molecules encode at least the mature form of a protein possessing the biological activity of an alternansucrase.

Within the present invention the term "hybridization" means hybridization under conventional hybridization conditions, preferably under stringent conditions, as for instance described in Sambrook et al., Molecular Cloning, A Laboratory Manual, $2^{nd}$ edition (1989) Cold Spring Harbour Laboratory Press, Cold Spring Harbour, N.Y. Within an especially preferred meaning the term "hybridization" means that hybridization occurs under the following conditions:

| | |
|---|---|
| Hybridization buffer: | 2 × SSC; 10 × Denhardt solution (Fikoll 400 + PEG + BSA; ratio 1:1:1); 0.1% SDS; 5 mM EDTA; 50 mM $Na_2HPO_4$; 250 µg/ml of herring sperm DNA; 50 µg/ml of tRNA; or 0.25 M of sodium phosphate buffer, pH 7.2; 1 mM EDTA 7% SDS |
| Hybridization temperature T | = 60° C. |
| Washing buffer: | 2 × SSC; 0.1% SDS |
| Washing temperature T | = 60° C. |

Nucleic acid molecules which hybridize with the nucleic acid molecules of the invention can, in principle, encode alternansucrases from any organism expressing such proteins.

Nucleic acid molecules which hybridize with the molecules of the invention can for instance be isolated from genomic libraries of microorganisms. Alternatively, they can be prepared by genetic engineering or chemical synthesis.

Such nucleic acid molecules may be identified and isolated with the use of the molecules of the invention or parts of these molecules or reverse complements of these molecules, for instance by hybridization according to standard methods (see for instance Sambrook et al., 1989, Molecular Cloning. A Laboratory Manual, $2^{nd}$ edition, Cold Spring Harbor Laboratory Press, Cold Spring Harbor, N.Y.).

Nucleic acid molecules possessing the same or substantially the same nucleotide sequence as indicated in SEQ ID NO:1 or parts thereof can, for instance, be used as hybridization probes. The fragments used as hybridization probes can also be synthetic fragments which are prepared by usual synthesis techniques, and the sequence of which substantially coincides with that of an inventive nucleic acid molecule.

The molecules hybridizing with the nucleic acid molecules of the invention also comprise fragments, derivatives and allelic variants of the above-described nucleic acid molecules encoding an alternansucrase of the invention. Herein, fragments are understood to mean parts of the nucleic acid molecules which are long enough to encode one of the described proteins, preferably showing the biological activity of an alternansucrase. In this connection, the term derivative means that the sequences of these molecules also differ from the sequences of the above-described nucleic acid molecules in one or more positions and show a high degree of homology to these sequences. In this context, homology means a sequence identity of at least 40%, in particular an identity of at least 60%, preferably more than 80% and particularly preferably more than 90%. Deviations from the above-described nucleic acid molecules may have been produced by deletion, substitution, insertion and/or recombination.

Preferably, the degree of homology is determined by comparing the respective sequence with the nucleotide sequence of the coding region of SEQ ID NO:1. When the sequences which are compared do not have the same length, the degree of homology preferably refers to the percentage of nucleotide residues in the shorter sequence which are identical to nucleotide residues in the longer sequence. The degree of homology can be determined conventionally using known computer programs such as the ClustalW program (Thompson et al., Nucleic Acids Research 22 (1994), 4673-4680) distributed by Julie Thompson (Thompson@EMBL-Heidelberg.DE) and Toby Gibson (Gibson@EMBL-Heidelberg.DE) at the European Molecular Biology Laboratory, Meyerhofstrasse 1, D 69117 Heidelberg, Germany. ClustalW can also be downloaded from several websites including IGBMC (Institut de Génétique et de Biologie Moléculaire et Cellulaire, B.P.163, 67404 Illkirch Cedex, France; ftp://ftp-igbmc.u-strasbg.fr/pub/) and EBI (ftp://ftp.ebi.ac.uk/pub/software/) and all sites with mirrors to the EBI (European Bioinformatics Institute, Wellcome Trust Genome Campus, Hinxton, Cambridge CB10 1SD, UK).

When using ClustalW program version 1.8 to determine whether a particular sequence is, for instance, 90% identical to a reference sequence according to the present invention, the settings are set in the following way for DNA sequence alignments:

KTUPLE=2, TOPDIAGS=4, PAIRGAP=5, DNAMATRIX:IUB, GAPOPEN=10, GAPEXT=5, MAXDIV=40, TRANSITIONS: unweighted.

For protein sequence alignments using ClustalW program version 1.8 the settings are the following: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

Furthermore, homology means preferably that the encoded protein displays a sequence identity of at least 40%, more preferably of at least 60%, even more preferably of at least 80%, in particular of at least 90% and particularly preferred of at least 95% to the amino acid sequence depicted under SEQ ID NO: 2.

Homology, moreover, means that there is a functional and/or structural equivalence between the corresponding nucleic acid molecules or proteins encoded thereby. Nucleic acid molecules which are homologous to the above-described molecules and represent derivatives of these molecules are, as a rule, variations of these molecules which represent modifications having the same biological function. They may be either naturally occurring variations, for instance sequences from other microorganisms, or mutations, and said mutations may have formed naturally or may have been produced by deliberate mutagenesis. Furthermore, the variations may be synthetically produced sequences. The allelic variants may be naturally occurring variants or synthetically produced variants or variants produced by recombinant DNA techniques.

In a further preferred embodiment the term "derivative" encompasses a nucleic acidmolecule coding for a protein which comprises at least one, more preferably at least three, even more preferably at least five, in particular at least ten and particularly preferred at least twenty of the peptide motifs selected from the group consisting of
a) MKQQE (SEQ ID NO: 22),
b) KKVPV (SEQ ID NO: 23),
c) KDDEN (SEQ ID NO: 24),
d) IDGNL (SEQ ID NO: 25),
e) YVADS (SEQ ID NO: 26),
f) HLRKN (SEQ ID NO: 27),
g) NENTP (SEQ ID NO: 28),
h) NVDGY (SEQ ID NO: 29),
i) NPDLK (SEQ ID NO: 30),
j) SNDSG (SEQ ID NO: 31),
k) NTFVK (SEQ ID NO: 32),
l) ISGYL (SEQ ID NO: 33),
m) SNAAL (SEQ ID NO: 34),
n) RQYTD (SEQ ID NO: 35),
o) QLYRA (SEQ ID NO: 36),
p) DDKAP (SEQ ID NO: 37),
q) TRQYT (SEQ ID NO: 38),
r) ITFAG (SEQ ID NO: 39),
s) NQYKG (SEQ ID NO: 40),
t) LFLNA (SEQ ID NO: 41),
u) QVSDT (SEQ ID NO: 42),
v) LITLN (SEQ ID NO: 43),
w) GRYVH (SEQ ID NO: 44),
x) TAPYG (SEQ ID NO: 45),
y) VVDYQ (SEQ ID NO: 46),
z) LSGQE (SEQ ID NO: 47).

The proteins encoded by the different variants of the nucleic acid molecules of the invention possess certain characteristics they have in common. These include for instance enzymatic activity, molecular weight, immunological reactivity, conformation, etc., and physical properties, such as for instance the migration behavior in gel electrophoreses, chromatographic behavior, sedimentation coefficients, solubility, spectroscopic properties, stability, pH optimum, temperature optimum etc.

Alternansucrase (E.C. 2.4.1.140) is an enzyme belonging to the group of glucosyltransferases. So far, alternansucrase activity has not been found in plants, but only in the bacterium *Streptococcus mutans* (Mukasa et al. (J. Gen. Microbiol. 135 (1989), 2055-2063); Tsumori et al. (J. Gen. Microbiol. 131 (1985), 3347-3353)) and in specific strains of the bacterium *Leuconostoc mesenteroides*, for instance in NRRL B-1355, NRRL B-1498 and NRRL B-1501. As a rule, these strains contain different glucosyltransferases and secrete dextransucrases apart from alternansucrases if they are allowed to grow on saccharose-containing media. As a rule, these two sucrases possess a high binding affinity to the polysaccharides synthesized by them (Lopez-Munguia et al., Annals New York Academy of Sciences 613 (1990), 717-722) with the result that these polysaccharides must be separated from the protein in the purification of the enzymes from *Leuconostoc mesenteroides* strains grown on saccharose-containing medium (Lopez-Munguia et al., Enzyme Microb. Technol. 15 (1993), 77-85; Leathers et al., Journal, of Industrial Microbiology & Biotechnology 18 (1997), 278-283).

In the absence of external acceptors, alternansucrases, starting from saccharose, catalyze the release of fructose and high molecular alternan, a polysaccharide which is composed of glucose units, and the backbone of which consists of glucose units predominantly linked to each other alternatingly by α-1,3- and α-1,6-glycosidic bonds and which according to light scattering measurement data should have a molecular weight of >$10^7$ (Coté, Carbohydrate Polymer 19 (1992), 249-252). To date there has been no report of alternan possessing a terminal fructose residue. Nevertheless, the existence of a terminal fructose unit in alternan can not be completely excluded. Lopez-Munguia et al. (Enzyme Microb. Technol. 15 (1993) 77-85) describe that alternan is resistant to degradation by dextranases. However, it can be degraded by so-called alternanases, whereby ring-shaped oligomers of alternan of different polymerization degree can be produced (Biely et al., Eur. J. Biochem. 226 (1994), 633-639). Ultrasonic treatment of high molecular alternan allows the molecular weight of alternan to be reduced to <10⁶ (Coté, Carbohydrate Polymers 19 (1992), 249-252). If aqueous solutions of this ultrasonically treated alternan are prepared, then these solutions show Theological properties comparable to those of aqueous solutions of gum arabic. So-called "limit alternan" having a molecular weight of about 3500 can be produced by enzymatic degradation using isomaltodextranase from *Arthrobacter globiformis* (NRRL B-4425) (Coté, Carbohydrate Polymers 19 (1992), 249-252). In the presence of external acceptors, such as for instance maltose, isomaltose, isomaltotriose and methyl-α-D-glucan, alternansucrase catalyzes at said saccharide acceptors the synthesis of α-D-glucan chains, in which the glucose moieties are predominantly alternatingly linked by α-1,6- and α-1,3 glycosidic bonds, and the synthesis of fructose. Depending on the acceptor used, the resulting products have different structures and a molecular weight which is lower than that of high molecular alternan and a polymerization degree of <15. Because of the polymerization degree, these products are often also referred to as oligoalternans (Pelenc et al., Sciences Des Aliments 11 (1991), 465-476). However, within the framework of the present invention these low molecular products which can be prepared in the presence of external acceptors are also to be referred to as alternan.

In the preparation of oligoalternans by means of partially purified alternansucrase protein, maltose is an acceptor (Lopez-Munguia et al., Enzyme Microb. Technol. 15 (1993), 77-85) producing high oligoalternan yields. Panose (degree of polymerization (d.p.) of 3) is the first acceptor product which is formed starting from maltose through the formation of an α-1,6-glycosidic bond.

In contrast thereto, isomaltose is a less effective acceptor which leads to lower yields of oligoalternan (Lopez-Munguia et al., Enzyme Microb. Technol. 15 (1993), 77-85).

Alternansucrase is relatively stable and has a half life period of 2 days in 50 mM of acetate buffer, pH 5.4 at 40° C. (Lopez-Munguia et al., Enzyme Microb. Technol. 15 (1993), 77-85). The enzyme shows maximum activity at a temperature of 40° C. and a pH value of 5.6 (Lopez-Munguia et al., Enzyme Microb. Technol. 15 (1993), 77-85).

In the absence of the substrate saccharose, alternansucrase catalyzes disproportionation reactions leading to a (partial) rearrangement of alternan. In particular when partially purified alternansucrase preparations containing dextransucrase contaminations were used to prepare oligoalternans, high disproportionation rates were found which lead to a complete rearrangement of oligoalternan (Lopez-Munguia et al., Enzyme Microb. Technol. 15 (1993), 77-85). For the molecular weight of alternansucrase according to SDS PAGE determination, different numerical values can be found: 135 kDa, 145 kDa, 173 kDa and 196 kDa, respectively (Leathers et al., Journal of Industrial Microbiology & Biotechnology 18 (1997), 278-283; Kim & Robyt, Enzyme Microb. Technol. 16 (1994), 659-664; Zhanley & Smith, Applied and Environmental Microbiology 61(3) (1995), 1120-1123).

The enzymatic activity of an alternansucrase can be shown for instance as described in Lopez-Munguia et al. (Annals New York Academy of Sciences 613 (1990), 717-722) or as described in the examples of the present application. One activity unit (1 u) can be defined as the amount of enzyme leading to the release of 1 μmol of fructose within one minute.

The nucleic acid molecules of the invention can be DNA molecules, in particular genomic molecules. Moreover, the nucleic acid molecules of the invention may be RNA molecules. The nucleic acid molecules of the invention can be obtained for instance from natural sources or may be produced synthetically or by recombinant techniques.

The nucleic acid molecules of the invention allow host cells to be prepared which produce recombinant alternansucrase protein of high purity and/or in sufficient quantities, and genetically engineered plants possessing an activity of these enzymes leading to the formation of alternan in planta. Within the framework of the present invention the term "high purity" means that the protein according to the invention displays a degree of purity of at least 80%, preferably of at least 90%, even more preferably of at least 95%. Moreover, means and methods are provided which may be used for preparing alternan using host cells and/or for preparing recombinant alternansucrase protein. Consequently, the provision of the nucleic acid molecules of the invention permits the preparation of alternan of high purity by methods which are relatively inexpensive and consume relatively little time.

In a preferred embodiment, the nucleic molecules of the invention are derived from microorganisms, preferably from bacteria, more preferably from gram-positive bacteria and in particular preferably from bacteria belonging to the genus *Leuconostoc*. Nucleic acid molecules from bacteria belonging to the species *Leuconostoc mesenteroides* are particularly preferred.

The invention also relates to oligonucleotides specifically hybridizing to a nucleic acid molecule of the invention. Such oligonucleotides have a length of preferably at least 10, in particular at least 15, and particularly preferably of at least 50 nucleotides. They are characterized in that they specifically hybridize to the nucleic acid molecules of the invention, that is to say that they do not or only to a very minor extent hybridize to nucleic acid sequences encoding other proteins, in particular other glucosyltransferases. The oligonucleotides of the invention can be used for instance as primers for amplification techniques such as the PCR reaction or as a hybridization probe to isolate related genes.

Moreover, the invention relates to vectors, in particular plasmids, cosmids, viruses, bacteriophages and other vectors commonly used in gene technology, which contain the above-described nucleic acid molecules of the invention. In a preferred embodiment of the invention, the vectors of the invention lend themselves to the transformation of fungal cells or cells of microorganisms. Preferably, such vectors are suitable to transform plant cells. Particularly preferably, such vectors permit the integration of the nucleic acid molecules of the invention, possibly together with flanking regulatory regions, into the genome of the plant cell. Examples thereof are binary vectors which can be used in the Agrobacteria-mediated gene transfer, and some are already commercially available.

In another preferred embodiment, the nucleic acid molecules contained in the vectors are connected to regulatory elements ensuring the transcription and synthesis of a translatable RNA in prokaryotic or eukaryotic cells.

The expression of the nucleic acid molecules of the invention in prokaryotic or eukaryotic cells, for instance in *Escherichia coli*, is interesting because it permits a more precise characterization of the enzymatic activities of the enzymes encoded by these molecules. Moreover, it is possible to express these enzymes in such prokaryotic or eukaryotic cells which are free from interfering enzymes, such as dextransucrases or other polysaccharide-forming or polysaccharide-degrading enzymes. In addition, it is possible to insert different mutations into the nucleic acid molecules by methods usual in molecular biology (see for instance Sambrook et al., 1989, Molecular Cloning, A Laboratory Manual, 2$^{nd}$ edition, Cold Spring Harbor Laboratory Press, Cold Spring Harbor, NY), leading to the synthesis of proteins possibly having modified biological properties. On the one hand it is possible in this connection to produce deletion mutants in which nucleic acid molecules are produced, by progressive deletions from the 5' or 3' end of the coding DNA sequence, and said nucleic acid molecules lead to the synthesis of correspondingly shortened proteins. Such deletions at the 5' end of the nucleotide sequence for instance allow amino acid sequences to be identified which are responsible for the secretion of the enzyme in microorganisms (transit peptides). This permits the deliberate preparation of enzymes which are no longer secreted by the removal of the corresponding sequences, but remain within the cell of the corresponding host organism or are localized in other compartments, for instance in the plastids, mitochondria, vacuole, on account of the addition of other signal sequences.

On the other hand, the introduction of point mutations is also conceivable at positions at which a modification of the amino acid sequence for instance influences the enzyme activity or the control of the enzyme. In this manner, it is for instance possible to produce mutants which possess a modified stereo and regio selectivity or a modified $K_m$ value or which are no longer subject to the control mechanisms normally existing in the cell and realized via an allosteric control or covalent modification.

Moreover, mutants possessing a modified substrate or product specificity can be prepared. Furthermore, it is possible to prepare mutants having a modified activity-temperature-profile.

Furthermore, in the case of expression in plants, the insertion of mutations into the nucleic acid molecules of the invention allows the gene expression rate and/or the activity of the proteins encoded by the nucleic acid molecules of the invention to be increased.

For genetic engineering in prokaryotic cells, the nucleic acid molecules of the invention or parts of these molecules can be introduced into plasmids which permit mutagenesis or sequence modification by recombination of DNA sequences. Standard methods (see Sambrook et al., 1989, Molecular Cloning: A laboratory manual, $2^{nd}$ edition, Cold Spring Harbor Laboratory Press, NY, USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

Moreover, the invention relates to plasmid pAlsu-pSK (see FIG. 2 and Example 2) which was deposited at Deutsche Sammlung fur Mikroorganismen und Zelikulturen (DSMZ), Braunschweig, under the accession No. DSM 12666 on February 4, 1999, and to the nucleic acid molecules contained in the insert of plasmid DSM 12666 and encoding a protein possessing the enzymatic activity of an alternansucrase. Moreover, the present invention also relates to nucleic acid molecules which hybridize to the insertion of plasmid DSM 12666. Also, the present invention relates to nucleic acid molecules the nucleotide sequence of which deviates from that of the nucleic acid molecules of the plasmid DSM 12666 insert, because of the degeneration of the genetic code. Furthermore, the present invention relates to nucleic acid molecules which have a homology, that is to say a sequence identity of at least 40%, preferably of at least 60%, more preferably of at least 80%, even more preferably of at least 90%, and most preferably of at least 95% to the sequence of the insertion of plasmid DSM 12666.

Another embodiment of the invention relates to host cells, in particular prokaryotic or eukaryotic cells transformed with an above-described nucleic acid molecule of the invention or with a vector of the invention, and to cells descended from such transformed cells and containing a nucleic acid molecule or vector of the invention.

According to another preferred embodiment, the host cells are cells of microorganisms. In the context of the present invention, the term "microorganism" comprises bacteria and all protists (e.g. fungi, in particular yeasts, algae) as defined Schlegel's "Allgemeine Mikrobiologie" (Georg Thieme Verlag, 1985, 1-2). A preferred embodiment of the invention relates to cells of algae and host cells belonging to the genera *Aspergillus, Bacillus, Saccharomyces* or *Pichia* (Rodriguez, Journal of Biotechnology 33 (1994), 135-146, Romanos, Vaccine, Vol. 9 (1991), 901 et seq.). A particularly preferred embodiment of the invention relates to *E. coli* cells. Alternansucrase is especially preferably secreted by the host cell. The preparation of such host cells for the production of recombinant alternansucrase can be carried out by methods known to a man skilled in the art. In a preferred embodiment of the invention, the host cells of the invention show no interfering enzymatic activities, such as those of polysaccharide-forming and/or polysaccharide-degrading enzymes.

An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al, Methods in Molecular Biology.7,5 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters producing a constitutive expression of the gene and inducible promoters which permit a deliberate control of the expression of the postconnected gene. Bacterial and viral promoter sequences possessing these properties are described in detail in the literature. Regulatory sequences for the expression in microorganisms (for instance *E. coli, S. cerevisiae*) are sufficiently described in the literature. Promoters permitting a particularly high expression of the postconnected gene are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, N.Y., (1982), 462-481; DeBoer et al., Proc. Natl. Acad. Sci. USA (1983), 21-25), lp1, rac (Boros et al., Gene 42 (1986), 97-100). As a rule, the protein amounts are highest from the middle up to about the end of the logarithmic phase of the growth cycle of the microorganisms. Therefore, inducible promoters are preferably used for the synthesis of proteins. These promoters often lead to higher protein yields than do constitutive promoters. The use of highly constitutive promoters leads to the continuous transcription and translation of a cloned gene and thus often has the result that energy is lost for other essential cells functions with the effect that cell growth is slowed down (Bernard R. Glick/Jack J. Pasternak, Molekulare Biotechnologie (1995). Spektrum Akademischer Verlag GmbH, Heidelberg, Berlin, Oxford, p. 342). Therefore, in order to obtain an optimum amount of protein, a two-stage process is often used. First, the host cells are cultured under optimum conditions up to a relatively high cell density. In the second step, transcription is then induced depending on the type of promoter used. In this connection, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with DNA encoding an alternansucrase can, as a rule, be carried out by standard methods, as for instance described in Sambrook et al., (Molecular Cloning: A Laboratory Course Manual, $2^{nd}$ edition (1989) Cold Spring Harbor Press, New York; Methods in Yeast Genetics, A Laboratory Course Manual, Cold Spring Harbor Laboratory Press, 1990). The host cell is cultured in nutrient media meeting the requirements of the particular host cell used, in particular in respect of the pH value, temperature, salt concentration, aeration, antibiotics, vitamins, trace elements etc.

Moreover, the invention relates to proteins and biologically active fragments thereof, which are encoded by the nucleic acid molecules of the invention and to methods for their preparation, wherein a host cell according to the invention is cultured under conditions permitting the synthesis of the protein, and the protein is subsequently isolated from the cultured cells and/or the culture medium.

According to a preferred embodiment of the invention, the alternansucrase is a recombinantly produced protein. In the context of the present invention, this is a protein prepared by inserting a DNA sequence encoding the protein into a host cell and expressing it therein. The protein can then be isolated from the host cell and/or the culture medium.

The nucleic acid molecules of the invention now allow host cells to be prepared which produce recombinant alternansucrase protein of high purity and/or in sufficient amounts. Within the framework of the present invention the term "high purity" means that the protein according to the invention displays a degree of purity of at least 80%, preferably of at least 90%, even more preferably of at least 95%. The time-consuming and costly methods already mentioned above, whereby alternansucrase protein which to date can only be obtained from particular Leuconostoc strains can be purified from other components such as for instance dextransucrases, polysaccharides, are dispensed with, because alternansucrase can be produced in host cells not possessing any adverse polysaccharide-synthesizing activities. Moreover, host cells and vectors can also be used, which allow the alternansucrase protein to be produced in the absence of saccharose, with the result that an additional separation of the alternansucrase protein from polysaccharides is no longer necessary. Moreover, the selection of suitable host cells and vectors allows alternansucrase protein to be provided in sufficient amounts, which has not been possible with the systems so far described. Alternansucrase produced by the host cells can be purified by conventional purification methods, such as precipitation, ion exchange chromatography, affinity-chromatography, gel filtration, HPLC Reverse Phase Chromatography etc. The modification of the nucleic acid molecules of the invention encoding an alternansucrase and expressed in the host cells, allows to produce a polypeptide in the host cell which is easier to isolate from the culture medium because of particular properties. Thus, the protein to be expressed can be expressed as a fusion protein with an additional polypeptide sequence, the specific binding properties of which permit the isolation of the fusion protein by affinity chromatography (e.g. Hopp et al., Bio/Technology 6 (1988), 1204-1210; Sassenfeld, Trends Biotechnol. 8 (1990), 88-93).

Another embodiment of the invention relates to proteins possessing the enzymatic activity of an alternansucrase, in particular that from microorganisms, preferably Gram-positive microorganisms, particularly microorganisms of the genus Leuconostoc, and particularly preferably that from Leuconostoc mesenteroides. The molecular weight of the protein indicated in SEQ ID NO:2, as determined by calculation, is 228.96 kDa. The invention also relates to alternansucrases which possess a molecular weight of 229 kDa ± 120 kDa, preferably 229 kDa 50 kDa, and particularly preferably 230 kDa 25 kDa. The molecular weight of the mature protein, as determined by calculation, is 224.77 kDa.

The provision of the nucleic acid molecules of the invention, for the first time, makes it possible to prepare alternansucrase-expressing plant cells by means of genetic engineering, which was not possible so far, because classical culturing methods do not allow bacterial and fungal genes to be expressed in plants.

The invention, therefore, also relates to transgenic plant cells transformed by a nucleic acid molecule of the invention or a vector of the invention or descended from such cells, the nucleic acid molecule which encodes the protein that has the biological activity of an alternansucrase being under the control of regulatory elements permitting the transcription of a translatable mRNA in plant cells.

The introduction of the activity of the proteins of the invention, for instance by expression of corresponding nucleic acid molecules, opens the possibility of producing alternan in plant cells correspondingly modified by genetic engineering. Hence, the expression of the nucleic acid molecules of the invention in plant cells is possible, allowing an additional, corresponding alternansucrase activity not present in the wild type to be introduced. Moreover, it is possible to modify the nucleic acid molecules of the invention according to methods known to a skilled person, in order to obtain alternansucrases of the invention which for instance possess modified temperature dependencies or substrate or product specificities. Such methods have already been described in more detail in a different context above.

A plurality of techniques is available by which DNA can be inserted into a plant host cell. These techniques include the transformation of plant cells by T-DNA using Agrobacterium tumefaciens or Agrobacterium rhizogenes as a transforming agent, the fusion of protoplasts, injection, electroporation of DNA, insertion of DNA by the biolistic approach and other possibilities.

The use of the Agrobacteria-mediated transformation of plant cells has been extensively investigated and sufficiently described in EP 120 516; Hoekema, In: The Binary Plant Vector System, Offsetdrukkerij Kanters B. V., Alblasserdam (1985), Chapter V; Fraley et al, Crit. Rev. Plant Sci. 4 (1993), 1-46 and An et al., EMBO J. 4 (1985), 277-287. Regarding the transformation of potatoes see for instance Rocha-Sosa et al. (EMBO J. 8 (1989), 29-33).

The transformation of monocotyledonous plants by means of Agrobacterium-based vectors has also been described (Chan et al., Plant Mol. Biol. 22 (1993), 491-506; Hiei et al., Plant J. 6 (1994) 271-282; Deng et al, Science in China 33 (1990), 28-34; Wilmink et al, Plant Cell Reports 11 (1992), 76-80; May et al., Bio/Technology 13 (1995), 486-492; Conner and Dormisse, Int. J. Plant Sci. 153 (1992), 550-555; Ritchie et al. Transgenic Res. 2 (1993), 252-265). An alternative system for transforming monocotyledonous plants is the transformation by the biolistic approach (Wan and Lemaux, Plant Physiol. 104 (1994), 37-48; Vasil et al., Bio/Technology 11 (1993), 1553-1558; Ritala et al., Plant Mol. Biol. 24 (1994) 317-325; Spencer et al., Theor. Appl. Genet. 79 (1990), 625-631), protoplast transformation, electroporation of partially permeabilized cells, insertion of DNA via glass fibers. The transformation of maize in particular has been repeatedly described in the literature (see for instance WO 95/06128, EP 0 513 849, EP 0 465 875, EP 29 24 35; Fromm et al, Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726).

The successful transformation of other types of cereals has also been described for instance of barley (Wan and Lemaux, supra; Ritala et al., supra, Krens et al., Nature 296 (1982), 72-74) and wheat (Nehra et al., Plant J. 5 (1994), 285-297). Generally, any promoter active in plant cells is suitable to express the nucleic acid molecules in plant cells. The promoter can be so chosen that the expression in the plants of the invention occurs constitutively or only in a particular tissue, at a particular time of plant development or at a time determined by external influences. The promoter may be homologous or heterologous to the plant.

Suitable promoters are for instance the promoter of 35S RNA of the Cauliflower Mosaic Virus (see for instance U.S. Pat. No. 5,352,605) and the ubiquitin-promoter (see for instance U.S. Pat. No. 5,614,399) which lend themselves to constitutive expression, the patatin gene promoter B33 (Rocha-Sosa et al., EMBO J. 8 (1989), 23-29) which lends itself to a tuber-specific expression in potatoes or a promoter ensuring expression in photosynthetically active tissues only, for instance the ST-LS1 promoter (Stockhaus et al., Proc. Natl. Acad. Sci. USA 84 (1987), 7943-7947; Stockhaus et al., EMBO, J. 8 (1989) 2445-2451), the Ca/b-promoter (see for instance U.S. Pat. No. 5,656,496, U.S. Pat. No. 5,639,952, Bansal et al., Proc. Natl. Acad. Sci. USA 89 (1992), 3654-3658) and the Rubisco SSU promoter (see for instance U.S. Pat. No. 5,034,322; U.S. Pat. No. 4,962,028) or the glutelin promoter from wheat which lends itself to endosperm-specific expression (HMW promoter) (Anderson, Theoretical and Applied Genetics 96, (1998), 568-576, Thomas, Plant Cell 2 (12), (1990), 1171-1180), the glutelin promoter from rice (Takaiwa, Plant Mol. Biol. 30(6) (1996), 1207-1221, Yoshihara, FEBS Lett. 383 (1996), 213-218, Yoshihara, Plant and Cell Physiology 37 (1996), 107-111), the shrunken promoter from maize (Maas, EMBO J. 8 (11) (1990), 3447-3452, Werr, Mol. Gen. Genet. 202(3) (1986), 471-475, Werr, Mol. Gen. Genet. 212(2), (1988), 342-350), the USP promoter, the phaseolin promoter (Sengupta-Gopalan, Proc. Natl. Acad. Sci. USA 82 (1985), 3320-3324, Bustos, Plant Cell 1 (9) (1989), 839-853) or promoters of zein genes from maize (Pedersen et al., Cell 29 (1982), 1015-1026; Quatroccio et al., Plant Mol. Biol. 15 (1990), 81-93). However, promoters which are only activated at a point in time determined by external influences can also be used (see for instance WO 93/07279). In this connection, promoters of heat shock proteins which permit simple induction may be of particular interest. Moreover, seed-specific promoters such as the USP promoter from *Vicia faba* which ensures a seed-specific expression in *Vicia* faba and other plants may be used (Fiedler et al., Plant Mol. Biol. 22 (1993), 669-679; Bäumlein et al., Mol. Gen. Genet. 225 (1991), 459-467). Moreover, fruit-specific promoters, such as described in WO 91/01373 may be used too.

Moreover, a termination sequence may be present, which serves to terminate transcription correctly and to add a poly-A-tail to the transcript, which is believed to have a function in the stabilization of the transcripts. Such elements are described in the literature (see for instance Gielen et al., EMBO J. 8 (1989), 23-29) and can be replaced at will.

Such cells can be distinguished from naturally occurring plant cells inter alia by the fact that they contain a nucleic acid molecule of the invention which does not naturally occur in these cells. Moreover, such transgenic plant cells of the invention can be distinguished from naturally occurring plant cells in that they contain at least one copy of the nucleic acid molecule of the invention stably integrated in their genome.

Moreover, the plant cells of the invention can preferably be distinguished from naturally occurring plant cells by at least one of the following features: If the inserted nucleic acid molecule of the invention is heterologous to the plant cell, then the transgenic plant cells are found to have transcripts of the inserted nucleic acid molecules of the invention. The latter can be detected for instance by Northern blot analysis. The plants cells of the invention preferably contain a protein encoded by an inserted nucleic acid molecule of the invention. This can be shown for instance by immunological methods, in particular by Western blot analysis.

Transgenic plant cells can be regenerated to whole plants according to methods known to a person skilled in the art.

The present invention also relates to the plants obtainable by regeneration of the transgenic plant cells of the invention. Furthermore, it relates to plants containing the above-described transgenic plant cells.

In most plants, the photoassimilates in the form of sugars formed during photosynthesis within a plant, i.e. mainly in the form of saccharose, are transported to the corresponding target organs. As saccharose is the substrate of the polymerization reaction of alternansucrase, all plants, both monocotyledonous and dicotyledonous can, in principle, be modified by the nucleic acid molecule of the invention in respect of alternansucrase expression.

The expression in plants of the nucleic acid molecules of the invention encoding a protein having the enzymatic activity of an alternansucrase can, for instance, be used to achieve a modification of the viscosity of the extracts possibly obtained from the plants, said modification being achieved by the synthesis of alternan. In this connection, for instance tomatoes are of interest. The expression of an alternansucrase in a tomato fruit leads to the synthesis of alternan and results in a modification of the viscosity of extracts obtained from these fruits for instance for the production of tomato puree or tomato ketchup.

The expression of the nucleic acid molecules of the invention is in particular advantageous in those organs of the plant which show a higher saccharose content or store saccharose. Such organs are for instance the beet of sugar beet or the cane of sugar cane. As these plants normally do not store any appreciable amounts of starch, the alternans synthesized by the alternansucrase from these plants could be isolated in the pure form.

The site where the biosynthesis of the saccharose in the plant cell occurs is the cytosol. The storage site, however, is the vacuole. During its transport into the storage tissue of the sugar beet or the potato or during its transport into the endosperm of seeds, the saccharose must pass the apoplast. Hence, all three compartments, i.e. the cytosol, the vacuole, the apoplast, lend themselves to the expression of the nucleic acid molecules for the synthesis of alternan. In addition, the plastids also lend themselves thereto, as could for instance be shown by the expression of bacterial fructosyl transferases in amyloplasts. Said fructosyl transferases which likewise require saccharose as a substrate, were able to mediate the formation of "amylofructan" in amyloplasts (Smeekens, Trends in Plant Science, Vol. 2, No. 8 (1997), 286-288).

In the case of starch-producing plants, such as potatoes and maize, where the starch biosynthesis and starch storage normally take place in the amyloplasts, an expression of the alternansucrase in apoplasts, in the cytosol or in the vacuole would lead to an additional synthesis of oligosaccharides and/or polysaccharides in these compartments, which can mean an overall increase in the yield.

As in the case of potatoes the starch synthesized in the amyloplasts can be separated from the alternan synthesized in the apoplast, in the cytosol or in the vacuole, the very same plant can be used to recover starch and alternan.

Moreover, transgenic potato-and maize plants are known, the starch synthesis of which in the tubers and grains, respectively, is completely inhibited due to the inhibition of ADP-glucose-pyrophosphorylase by an antisense construct. In the case of potatoes, soluble sugars, in particular saccharose and glucose, accumulate instead, for instance in the tubers (Müller-Röber et al., EMBO J. 11 (1992), 1229-1238). Alternan can be prepared in the cytosol, the vacuole or apoplast of these plants by the expression of an alternansucrase which uses saccharose as a substrate.

Therefore in another embodiment of the invention the plant cells of the invention are further characterized by a reduced ADP glucose pyrophosphorylase (AGPase) activity compared to corresponding cells from wild-type plants.

DNA molecules encoding AGPase are well known to the person skilled in the art and described for example in Müller-Röber et al. (Mol. Gen. Genet. 224 (1) (1990), 136-146). By using DNA molecules encoding an AGPase it is possible to produce plants by means of recombinant DNA techniques (for example by an antisense, a ribozyme or a cosuppression approach) showing a reduced AGPase activity. Furthermore AGPase mutants, for example from maize (brittle-2 and shrunken-2), with reduced AGPase activity are known to the person skilled in the art.

The term "reduced" means preferably a reduction of AGPase activity of at least 10%, more preferably of at least 50% and even more preferably of at least 80% in comparison to corresponding wild-type cells.

The activity of an AGPase can be determined according to Müller-Röber et al. (Mol. Gen. Genet. 224 (1) (1990), 136-146) or to methods known to a person skilled in the art.

The reaction which is catalyzed by alternansucrase is distinguished by the fact that a glucose moiety is transferred directly from saccharose to an existing carbohydrate acceptor. By contrast, in the case of plants, the biosynthesis of linear glucans from saccharose, proceeds in such a way that the saccharose is first separated into glucose and fructose, which are then each converted into activated intermediate ADP-glucose. The glucose moiety is transferred by the enzyme starch-synthase from the ADP glucose to an already existing glucan, whereby ADP is released. The conversion of saccharose into two ADP glucose molecules requires several energy consuming reactions. Therefore, the energy consumption of the reaction catalyzed by alternansucrase is substantially lower than the energy consumption in the synthesis of polysaccharides from saccharose in plant cells, which can lead to an increased yield of synthesized oligo and/or polysaccharides in plants containing the nucleic acid molecules of the invention.

In the expression of the nucleic acid molecules in plants there exists in principle the possibility that the synthesized protein can be localized in any compartment of the plant cell (e.g. in the cytosol, plastids, vacuole, mitochondria) or the plant (e.g. in the apoplast). In order to achieve the localization in a particular compartment, the coding region must, where necessary, be linked to DNA sequences ensuring localization in the corresponding compartment. The signal sequences used must each be arranged in the same reading frame as the DNA sequence encoding the enzyme.

In order to ensure the location in the plastids it is conceivable to use one of the following transit peptides: of the plastidic Ferredoxin: NADP+ oxidoreductase (FNR) of spinach which is enclosed in Jansen et al. (Current Genetics 13 (1988), 517-522). In particular, the sequence ranging from the nucleotides −171 to 165 of the cDNA Sequence disclosed therein can be used, which comprises the 5' non-translated region as well as the sequence encoding the transit peptide. Another example is the transit peptide of the waxy protein of maize including the first 34 amino acid residues of the mature waxy protein (Klösgen et al., Mol. Gen. Genet. 217 (1989), 155-161). It is also possible to use this transit peptide without the first 34 amino acids of the mature protein. Furthermore, the signal peptides of the ribulose bisposphate carboxylase small subunit (Wolter et al., Proc. Natl. Acad. Sci. USA 85 (1988), 846-850; Nawrath et al., Proc. Natl. Acad. Sci. USA 91 (1994), 12760-12764), of the NADP malat dehydrogenase (Gallardo et al., Planta 197 (1995), 324-332), of the glutathione reductase (Creissen et al., Plant J. 8 (1995), 167-175) or of the R1 protein Lorberth et al. (Nature Biotechnology 16, (1998), 473-477) can be used.

In order to ensure the location in the vacuole it is conceivable to use one of the following transit peptides: the N-terminal sequence (146 amino acids) of the patatin protein (Sonnewald et al., Plant J. 1 (1991), 95-106) or the signal sequences described by Matsuoka und Neuhaus, Journal of Experimental Botany 50 (1999), 165-174; Chrispeels und Raikhel, Cell 68 (1992), 613-616; Matsuoka und Nakamura, Proc. Natl. Acad. Sci. USA 88 (1991), 834-838; Bednarek und Raikhel, Plant Cell 3 (1991), 1195-1206; Nakamura und Matsuoka, Plant Phys. 101 (1993), 1-5 .

In order to ensure the location in the mitochondria it is for example conceivable to use the transit peptide described by Braun et al. (EMBO J. 11, (1992), 3219-3227).

In order to ensure the location in the apoplast it is conceivable to use one of the following transit peptides: signal sequence of the proteinase inhibitor II-gene (Keil et al., Nucleic Acid Res. 14 (1986), 5641-5650; von Schaewen et al., EMBO J. 9 (1990), 30-33), of the levansucrase gene from *Erwinia amylovora* (Geier and Geider, Phys. Mol. Plant Pathol. 42 (1993), 387-404), of a fragment of the patatin gene B33 from *Solanum tuberosum*, which encodes the first 33 amino acids (Rosahl et al., Mol Gen. Genet. 203 (1986), 214-220) or of the one described by Oshima et al. (Nucleic Acid Res. 18 (1990),181).

The nucleic acid sequence indicated in SEQ ID NO:1 encodes an extracellular alternansucrase. Secretion is ensured by a signal sequence comprising the first approximately 39 N-terminal amino acid residues of the SEQ ID NO:2.

The transgenic plants may, in principle, be plants of any plant species, that is to say they may be monocotyledonous and dicotyledonous plants. Preferably, the plants are useful plants cultivated by man for nutrition or for technical, in particular industrial, purposes. They are preferably starch-storing plants, for instance cereal species (rye, barley, oat, wheat, millet, sago etc.), rice, pea, marrow pea, cassava and potato, tomato, rape, soybean, hemp, flax, sunflower, cow pea or arrowroot, fiber-forming plants (e.g. flax, hemp, cotton), oil-storing plants (e.g. rape, sunflower, soybean) and protein-storing plants (e.g. legumes, cereals, soybeans). The invention also relates to fruit trees and palms. Moreover, the invention relates to forage plants (e.g. forage and pasture grasses, such as alfalfa, clover, ryegrass) and vegetable plants (e.g. tomato, lettuce, chicory) and ornamental plants (e.g. tulips, hyacinths). Sugar-storing and/or starch-storing plants are preferred. Sugar cane and sugar beet, and potato plants, maize, rice, wheat and tomato plants are particularly preferred.

A further subject of the invention is a method for the production of transgenic plant cells and transgenic plants which in comparison to non-transformed wildtype cells/non-transformed wildtype plants synthesize alternan. In this method the expression and/or the activity of proteins encoded by the nucleic acid molecules of the invention is increased in comparison to corresponding wild-type cells/wildtype plants which do not show any alternansucrase expression a In particular, such a method comprises the expression of a nucleic acid molecule according to the invention in plant cells. The nucleic acid molecule according to the invention is preferably linked to a promoter ensuring expression in plant cells. In a particularly preferred embodiment the method comprises the introduction of a nucleic acid molecule according to the invention into a plant cell and regeneration of a plant from this cell.

Such an increase in expression may, e.g., be detected by Northern blot analysis. The increase in activity may be detected by testing protein extracts for their alternansucrase activity derived from plant cells. The enzymatic activity of an alternansucrase can be measured, for instance, as described in Lopez-Munguia et al. (Annals New York Academy of Sciences 613, (1990), 717-722) or as described in the examples of the present application.

The invention also relates to propagation material of the plants of the invention. The term "propagation material" comprises those components of the plant which are suitable to produce offspring vegetatively or generatively. Suitable means for vegetative propagation are for instance cuttings, callus cultures, rhizomes or tubers. Other propagation material includes for instance fruits, seeds, seedlings, protoplasts, cell cultures etc. The preferred propagation materials are tubers and seeds. The invention also relates to harvestable parts of the plants of the invention such as, for instance, fruits, seeds, tubers or rootstocks.

Another embodiment of the invention relates to methods for preparing alternan which comprise the step of extracting and isolating alternan from a plant of the invention.

The extraction and isolation of alternan from a plant of the invention may be carried out by standard methods, such as precipitation, extraction and chromatographic methods.

Moreover, the present invention relates to alternan obtainable from a plant of the invention or from propagation material of the invention.

Moreover, the present invention relates to a method for preparing alternan and/or fructose, wherein a host cell of the invention secretes an alternansucrase into a saccharose-containing culture medium and alternan and/or fructose is/are isolated from the culture medium.

A preferred embodiment of the method of the, invention uses an alternansucrase recombinantly produced and secreted by the host cell into the culture medium, thus avoiding the necessity of breaking up the cells and purifying the protein further, because the secreted protein can be obtained from the supernatant. The residual components of the culture medium can be removed by methods usual in processing technology, such as dialysis, reverse osmosis, chromatographic methods, etc. The same applies to the concentration of the protein secreted into the culture medium. The secretion of proteins by microorganisms is normally mediated by N-terminal signal peptides (signal sequence, leader-peptide, transit peptide). Proteins possessing this signal sequence are able to penetrate the cell membrane of the microorganism. A secretion of proteins can be achieved by adding the DNA sequence encoding this signal peptide to the corresponding region encoding the alternansucrase.

The natural signal peptide of the expressed alternansucrase is preferred, that of the alternansucrase from *Leuconostoc mesenteroides* NRRL B 1355 (see the first approximately 25 to 45 N-terminal amino acid residues of SEQ ID NO:2) is particularly preferred.

The signal peptide of α-CGTase from *Klebsiella oxytoca* M5A1 (Fiedler et al., J. Mol. Biol. 256 (1996), 279-291) or a signal peptide as encoded by the nucleotides 11529-11618 of the sequence available under the GenBank accession number X86014 is most preferred.

The preparation of alternan and/or fructose requires neither activated glucose derivatives nor co-factors, as are necessary in most synthesis reactions for polysaccharides occurring within the cells. Hence, alternansucrase-secreting microorganisms can be cultured in saccharose-containing medium, the secreted alternansucrase leading to a synthesis of alternan and fructose in the culture medium.

Contrary to host cells from *Leuconostoc mesenteroides*, which secrete alternansucrase by nature, the host cells used according to the invention have the advantage that they do not secrete proteins possessing adverse polysaccharide-synthesizing side reactions, such as dextransucrase, with the result that outside the host cell, apart from alternan, no other polysaccharides can be formed which, as a rule, can be separated from alternan only by costly and time-consuming procedures. Moreover, the host cells according to a preferred embodiment of the invention do not have any adverse polysaccharide-degrading side activities, which would otherwise lead to losses in the yield of the alternan produced.

The method of the invention yields fructose apart from alternan. Fructose can be used for the inexpensive isolation of so-called "high-fructose-containing syrups" (HFCS). Conventional methods for preparing fructose on the one hand provide for the enzymatic break down of saccharose by means of an invertase or for the break down of starch into glucose units, mostly brought about by acid hydrolysis, and for subsequent enzymatic conversion of the glucose into fructose by glucose isomerases. However, both methods lead to mixtures of glucose and-fructose. The two components must subsequently be separated from each other by chromatographic methods.

The separation of the two reaction products of the method of the invention, or the separation of the reaction products from the substrate saccharose can be achieved for example with the use of membranes permitting the penetration of fructose, but not the penetration of saccharose and/or alternans. If continuous removal of fructose via such a membrane is provided for, a more or less complete conversion of saccharose occurs.

The isolation of alternan and fructose can be carried out by standard methods or can be carried out as for instance described in the working examples.

According to one embodiment of the method, the host cells originate from microorganisms, preferably from *Escherichia coli*.

In another embodiment, the method of the invention works with fungal host cells, in particular cells of yeasts, such as *Saccharomyces cerevisiae*. Yeast cells producing alternan in saccharose-containing medium because of the enzymatic activity of an alternansucrase, cannot be readily used, as yeasts secrete an invertase which breaks down the extracellular saccharose. The yeasts take up the resulting hexoses via a hexose transporter. However, one yeast strain has been described (Riesmeier et al. EMBO J. 11 (1992), 4705-4713) which carriesa defective suc2 gene, and therefore cannot secrete invertase. Moreover, these yeast cells do not contain a transportation system able to import saccharose into the cells. If such a strain is so modified by means of the nucleic acid molecules of the invention that it secretes an alternansucrase into the culture medium, then fructose and alternan will be synthesized in saccharose-containing medium. The resulting fructose can subsequently be taken up by the yeast cells.

In another preferred embodiment of this method the host cell of the invention is present in an immobilized form.

As a rule, host cells are immobilized by inclusion of the cells in a suitable material, such as alginate, polyacrylamide, gelatin, cellulose or chitosan. However, adsorption or covalent binding of the cells to a carrier material is also possible (Brodelius and Mosbach, Methods in Enzymology Vol. 135 (1987), 222-230) An advantage of the immobilization of cells is that it allows substantially higher cell densities to be achieved than does culturing in liquid culture. This results in a higher productivity. Moreover, the costs for agitation and aeration of the culture decrease as do the costs for measures to maintain sterility. Another important aspect is the possibility of a continuous alternan production with the result that unproductive phases regularly occurring in fermentation processes can be avoided or at least greatly reduced.

Another embodiment of the invention relates to a method for preparing alternan and/or fructose, wherein
a) a saccharose-containing solution is contacted with a protein of the invention under conditions permitting the conversion of saccharose into alternan and/or fructose; and
b) alternan and/or fructose is/are isolated from the solution.

In this embodiment, the invention thus relates to a method for preparing alternan and/or fructose in vitro by means of a cell-free enzyme preparation. In this case, microorganisms which for instance secrete alternansucrase are cultured up to the stationary phase in a saccharose-free medium permitting the formation of alternansucrase protein. After removing the cells from the culture medium by centrifugation, the secreted enzyme can be recovered from the supernatant. The enzyme can subsequently be added to saccharose-containing solutions in order to synthesize alternan and/or fructose. Compared to the above-described synthesis of alternan in a system not freed from cells, this method offers the advantage that the reaction conditions can be controlled better and the reaction products are substantially purer and easier to purify. The purification of the protein can be carried out as already described above.

A preferred embodiment of the method of the invention uses a purified alternansucrase. Purified alternansucrase is understood to mean an enzyme which is largely free from cell components of the cells in which the protein is synthesized and shows no contamination with proteins possessing polysaccharide-synthesizing activities (e.g. dextransucrases) or degrading activities, and/or no contamination with (polysaccharide) acceptors. The term "purified alternansucrase" preferably means an alternansucrase possessing a degree of purity of at least 70%, preferably at least 85%, and particularly preferably at least 95%.

The use of a purified protein for preparing alternan and/or fructose offers various advantages. Compared to methods working with partially purified protein extracts, the reaction medium of the method of the invention does not contain any residues of the production strain (microorganism) which is used for the purification of the protein or for its preparation by genetic engineering.

Moreover, the use of the purified protein is advantageous for food and pharmaceutical industry applications. Thanks to the fact that the reaction medium is defined in its composition and freed from all unnecessary components, the product is likewise more precisely defined in respect of its components. In consequence of this, the procedure for obtaining food and pharmaceutical industry approval of these products produced by genetic engineering requires substantially less documentation, especially since these products should not show any traces of a transgenic microorganism.

Moreover, contrary to the so far described in vitro methods in cell free systems using partially purified alternansucrase preparations, the method of the invention using a purified alternansucrase has the advantage that it allows highly pure alternan to be prepared without the occurrence of dextransucrase and dextran contaminations, because of the high purity of the protein of the invention. Moreover, the method of the invention permits the production of alternan in high yields, without losses caused for instance by adverse side reactions of a dextransucrase, which would convert part of the substrate saccharose into undesired dextran, the separation of which from alternan would only be possible using time-consuming and expensive methods.

The method of the invention produces fructose in addition to alternan. The fructose can be used for the inexpensive recovery of so-called "high-fructose-containing syrups" (HFCS). The method of the invention yields products of high purity, because of the use of a purified alternansucrase. Hence, compared to conventional methods for preparing HFCS from maize starch, which comprise costly process steps for removing the buffer salts by ion exchange, (Crabb and Mitchinson, TIBTECH 15 (1997), 349-352) the method of the invention does not require an expensive purification of the fructose.

Another preferred embodiment of the method of the invention uses a recombinantly prepared alternansucrase.

According to another preferred embodiment, the enzyme possessing the enzymatic activity of an alternansucrase is immobilized on a carrier material. Immobilization of the alternansucrase offers the advantage that the enzyme being the catalyst of the synthesis reaction can be easily recovered from the reaction mixture and reused several times. As the purification of enzymes is normally costly and time consuming, immobilization and reutilization of the enzymes allow for a substantial cost saving. Another advantage is the degree of purity of the reaction products not containing any residual protein.

There are many carrier materials available for the immobilization of proteins, and coupling to the carrier material can be made via covalent or non-covalent bonds (for an overview see: Methods in Enzymology 135, 136, 137). Widely used carrier materials include for instance agarose, alginate, cellulose, polyacrylamide, silica or nylon.

According to another embodiment of the invention, the alternansucrase (immobilized on a carrier material) is present between two membranes, one of which allows fructose, but not saccharose and alternan to penetrate, the other one of which allows saccharose, but not alternan to penetrate. The supply with substrate occurs through the membrane which allows saccharose to penetrate it. The synthesized alternan remainsin the space between the two membranes and the released fructose can be continuously removed from the reaction equilibrium via the membrane which only allows fructose to penetrate it. Such an arrangement permits an efficient separation of the reaction products, and thus the production of pure fructose.

Moreover, the separation of fructose by ion exchange chromatography has been described ("Starch Hydrolysis Products, Worldwide Technology, Production, and Application", Edited by F. W. Schenck, R. E. Hebeda, (1992), VCH Publishers, Inc., New York).

Thus, the use of alternansucrases for preparing pure fructose on the one hand involves the advantage that the relatively inexpensive substrate saccharose can be used as the starting material, and on the other hand the fructose can be isolated easily from the reaction mixture without additional enzymatic conversions or chromatographic methods.

Moreover, the invention relates to methods for preparing alternan and/or fructose, wherein a) a saccharose-containing solution is contacted with a protein of the invention and acceptor molecules under conditions permitting the conversion of saccharose to alternan and/or fructose; and b) alternan and/or fructose is/are isolated from the solution.

Within the framework of the present invention an acceptor molecule is understood to mean a molecule at which an alternansucrase is able to catalyze a chain-extending reaction. The acceptor which can be added to the reaction mixture at the beginning of the reaction is preferably a carbohydrate or a carbohydrate derivative. The use of external acceptors leads to the production of low molecular products which are to be designated alternan in the context of the present invention. The carbohydrate acceptor is preferably an oligo or polysaccharide, in particular a branched polysaccharide, such as dextrin, glycogen or amylopectin, preferably a linear polysaccharide, and particularly preferably a saccharide selected from the group consisting of maltose, isomaltose, isomaltotriose and methyl-α-D-glucan. If an extension of the alternan chain at these acceptors occurs, then products are formed which have a higher molecular weight than the educt. Where maltose, isomaltose, isomaltotriose and methyl-α-D-glucan are used, one obtains products which have a lower molecular weight than the alternan that can be prepared in the absence of external carbohydrate acceptors.

The size of the molecular weight of the oligoalternans prepared depends on the saccharose/acceptor ratio used. For instance the degree of polymerization of the products increases as the saccharose/isomaltose ratio increases.

Moreover, the saccharose/acceptor ratio has an influence on the oligoalternan yield. For instance, the oligoalternan yield increases as the saccharose/isomaltose ratio decreases.

The hitherto described methods for producing oligoalternan with the use of alternansucrases which the, authors claim have been purified (Pelenc et al., Sciences Des Aliments 11 (1991), 465-476) only yielded product mixtures of oligoalternan and oligodextran, in the presence of the carbohydrate acceptor maltose. In this case, the synthesis of oligodextran is presumably attributable to dextransucrase-contaminations of the alternansucrase preparation. Compared to this method, the method of the invention offers the advantage that the use of recombinantly produced alternansucrase protein not containing any dextransucrase contaminants permits the preparation of oligoalternan without the simultaneous formation of oligodextran. Thus, the method of the invention makes it possible to provide oligoalternan, without requiring additional costly purification steps for separating oligodextran.

According to another preferred embodiment, the enzyme possessing the enzymatic activity of an alternansucrase is immobilized on a carrier material.

According to another preferred embodiment of the method of the invention, a recombinantly produced alternansucrase is used.

Moreover, the present invention relates to end products containing alternan. In this context, end products are understood to mean cosmetic products, preferably food products, fodder and particularly preferably pharmaceutical products.

Finally, the present invention relates to a method for preparing the afore-mentioned products comprising one of the above-described alternan manufacturing methods of the invention and the formulation of the thus obtained alternan in a form which is suitable for one of the afore-mentioned applications of the corresponding product.

These and other embodiments are disclosed and obvious to a skilled person and embraced by the description and the examples of the present invention. Additional literature regarding one of the above-mentioned methods, means and applications, which can be used within the meaning of the present invention, can be obtained from the state of the art, for instance from public libraries for instance by the use of electronic means. This purpose can be served inter alia by public databases, such as the "medline", which are accessible via internet. Other databases and addresses are known to a skilled person and can be obtained from the internet. An overview of sources and information regarding patents and patent application in biotechnology is contained in Berks, TIBTECH 12 (1994), 352-364.

DESCRIPTION OF THE FIGURES

FIG. 4:
Plasmid map pAlsu-pET24a

The following protein extracts are used
1+2) *E. coli* BL21(DE3) containing pAlsu-pET24a-3
3+4) *E. coli* BL21(DE3) containing pAlsu-pET24a-7
5+6) *E. coli* BL21 (DE3) containing pAlsu-pET24a-21
7+8) *E. coli* BL21 (DE3) containing pET24a
1, 3, 5, 7) culture before induction with IPTG
2, 4, 6, 8) culture at the end of culturing

HPLC chromatogram of oligoalternan after dextranase digestion.

FIG. 10

Map of the expression cassette including the polylinker of the plasmid pBinAR-N.

FIG. 11

Plasmid map pat-Alsu-Hyg.

FIG. 12

Plasmid map fnr-Alsu-Hyg.

EXAMPLES

Vectors used in the examples:

1. BinAR-N

Figure 10:
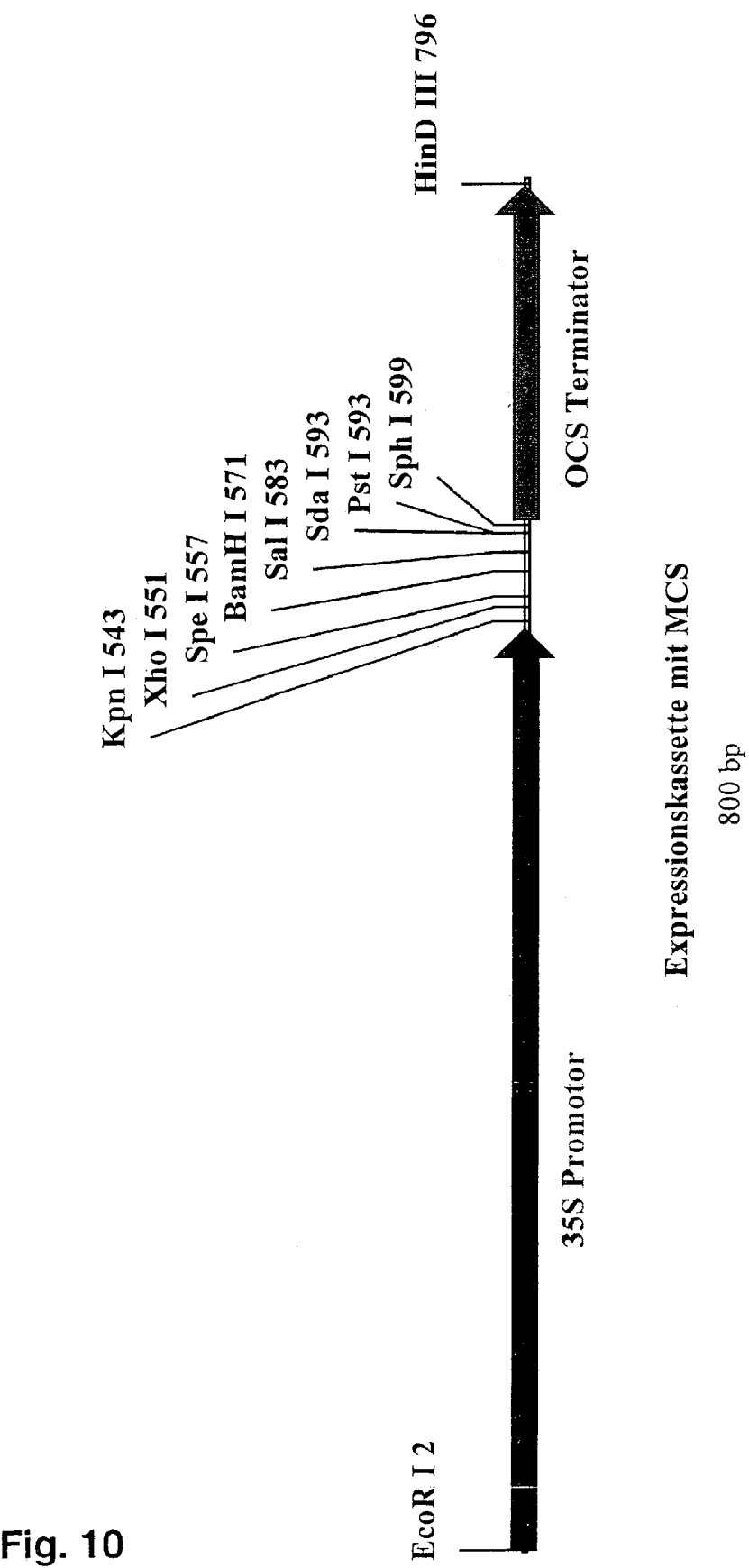

By the use of standard methods (Sambrook et al., Molecular cloning: A laboratory manual, 2nd issue; Cold Spring Harbor Laboratory Press, NY, USA (1989)) we introduced a different polylinker (see FIG. 10) between the 35S Promoter and the OCS-Terminator into the plasmid pBinAR (Höfgen und Willmitzer, Plant Science 66 (1990), 221-230). The resulting plasmid was called pBinAR-N.

2. pBinAR-Hyg-N

Via standard methods (Sambrook et al., Molecular cloning: A laboratory manual, 2nd issue; Cold Spring Harbor Laboratory Press, NY, USA (1989)) we isolated an EcoRI/HinDIII-fragment from pBinAR-N containing the 35S Promoter, the polylinker and the OCS-Terminator. This fragment was then ligated into the same restriction sites of plasmid pBIB-Hyg (Becker, Nucleic Acids Research 18 (1990), 203). The resulting plasmid was called pBinAR-Hyg-N.

3. pBinAR-pat-Hyg

By using the oligonucleotides Sp-pat-5' and Sp-pat-3' (see SEQ ID NO:48 and SEQ ID NO:49, respectively) we amplified DNA molecules coding for the leader peptide of the patatin protein from potato (see SEQ ID NO:50, which differs from the sequence used by Sonnewald et al. Plant J. 1 (1991), 95-106) via a PCR approach using plasmid pgT5 (Rosahl et al., Mol. Gen. Genet. 203 (1986), 214-220; Sonnewald et al., Plant J. 1 (1991), 95-106) as a template. The resulting PCR products were cut by the restriction enzymes XbaI and SalI and then ligated into the plasmid pBinAR-Hyg-N which was linearized before by using the restriction enzymes SpeI and SalI. The resulting plasmid was called pBinAR-pat-Hyg.

PCR Conditions:

Buffer and polymerase from Boehringer Mannheim (Pwo Polymerase No. 1644947)

| DNA | 0.2 ng |
| --- | --- |
| 10 × Buffer + MgSO4 | 5 µl |
| dNTPs (je 10 mM) | 1 µl |
| Primer Sp-pat-5' | 120 nM |
| Primer Sp-pat-3' | 120 nM |
| Pwo Polymerase | 1.0 units |
| distilled water | ad 50 µl |

Reaction Conditions:

| Step 1 | 95° C. | 2:30 min |
| --- | --- | --- |
| Step 2 | 95° C. | 0:30 min |
| Step 3 | 64° C. | 0:30 min |
| Step 4 | 72° C. | 0:30 min |
| | (plus 1 sec per cycle) | |
| Step 5 | 72° C. | 5:00 min. |

The steps 2 to 4 were repeated 35 times in a cyclical manner.

4. pBinAR-FNR-Hyg

By using the oligonucleotides Sp-fnr-5' and Sp-fnr-3 (see SEQ ID NO:51 and SEQ ID NO:52, respectively) we amplified DNA molecules coding for the transit peptide of the FNR protein from spinach via a PCR approach using plasmid p6SocFNR-15 (Jansen et al., Current Genetics 13, (1988), 517-522) as a template. The resulting PCR products were cut by XbaI and SalI and then cloned into the SpeI/SalI-opened pBinAR-Hyg-N. Resulting plasmid was called pBinAR-fhr-Hyg.

PCR Conditions:

Buffer and polymerase from Gibco BRL (Platinum Taq DNA Polymerase High Fidelity No.1304-0.11)

| DNA | 0.2 ng |
| --- | --- |
| 10 × Buffer | 5 µl |
| MgSO4 | 2.0 µl |
| dNTPs (per 10 mM) | 1 µl |
| Primer Sp-fnr-5' | 150 nM |
| Primer Sp-fnr-3' | 150 nM |
| Taq Platinum Hifi Polymerase | 1.5 units |
| distilled water | ad |
| | 50 µl |

Reaction Conditions:

| Step 1 | 95° C. | 2:30 min |
| --- | --- | --- |
| Step 2 | 95° C. | 0:30 min |
| Step 3 | 58° C. | 0:30 min |
| Step 4 | 68° C. | 0:20 min |
| | (plus 1 sec per cycle) | |
| Step 5 | 68° C. | 3:00 min |

The steps 2 to 4 were repeated 35 times in a cyclical manner.

Example 1

Cloning of Alternansucrase from *Leuconostoc mesenteroides* NRRL-B1355

Isolation and Sequencing of Alternansucrase

The strain *Leuconostoc mesenteroides* NRRL-B1355 was cultured in 1 l of Lactobacilli MRS Broth (Difco) complemented with 5% saccharose at 28° C. for two days. After the culture was subjected to centrifugation at 20,000×g for 30 minutes, the supernatant was admixed with the same volume of 10% trichloro acetic acid and stirred at 4° C. for 16 hours. This solution was then subjected to centrifugation at 10,000×g for 30 minutes. The thus obtained precipitate was dissolved in 4.5 ml of 40 mM Tris-HCl, pH 8.8, and subsequently neutralized with (about 0.5 ml) 2 M Tris-base. This protein solution was given to the company Toplab Gesellschaft für angewandte Biotechnologie mbH, Martinsried, Germany, for protein sequencing. At this company, the protein solution was electrophoretically separated in SDS polyacrylamide gel, the gel was stained with Coomassie Blue and the staining was subsequently removed by 10% acetic acid. For the enzymatic digestion of the protein, the protein bands were cut from the gel, pressed through a sieve and fragmented (pores 30 μm×100 μm). The crushed gel was then washed with half concentrated incubation buffer (12.5 mM Tris, 0.5 mM EDTA pH 8.5) for 2 minutes. Subsequently, it was subjected to centrifugation, the buffer was removed and the gel was dried in the "Speedvac" for one hour (about 5% residual water, rubber-like). Subsequently, a solution of endoproteinase LysC in 400 μl 12.5 mM Tris/HCl, pH 8.5 (enzyme: protein=1:10) and 0.1% of laurylmaltosite was prepared. 200 μl of this solution were added to the sample and incubated in the heat block shaker at 37° C. overnight. In order to elute the peptide fragments, a one hour incubation with 1% TFA was carried out, twice, followed by centrifugation, and subsequently by elution with 10% formic acid, 20% isopropanol, 60% acetonitrile for 3 hours. The peptide fragments obtained were then separated from each other by HPLC (column Supersher 60 RP select B (Merck, Darmstadt) 2 mm×125 mm; buffer A 0.1% trifluoro acetic acid, buffer B: 0.085% TFA in acetonitrile; flow rate: 0.2 ml/min; gradient: 5-60% in 60 min; detection at 206 nm. The peptide fragments obtained were then sequenced in an automatic sequencer Procise 492 (Applied Biosystems, PE); the procedure being the stepwise Edman degradation in a modification according to Hunkapiller (Hunkapiller et al., Meth. Enzymol. 91 (1983), 399-413).

Six different peptide sequences (see SEQ ID NOS:5 to 9, SEQ ID NO:21) were identified which were designated lysC-66, lysC-67, lysC-82, lysC-83, lysC-88 and "N-terminus".

Preparation of a Genomic DNA Library from *Leuconostoc mesenteroides* NRRL B1355

*Leuconostoc mesenteroides* NRRL-B1355 (purchased from ATCC) was cultured in 100 ml YT medium (Sambrook et al, loc. cit.) additionally containing 2% (w/v) of glucose and 50 mM sodium phosphate buffer pH 7.0, at 28° C. for 36 hours. After harvesting the cells by centrifugation, genomic DNA was isolated according to Ausubel et al. (Current Protocols in Molecular Biology, Volume 1, Greene and John Wiley & Sons (1994), USA).

100 μg of genomic DNA from *Leuconostoc mesenteroides* NRRL-B1355 were partially digested with 0.001 units of the restriction enzyme Sau3A for 30 minutes, subsequently extracted with phenol:chloroform:isoamyl alcohol (25:24:1) and precipitated with ethanol. 2.5 μg of the partially digested DNA obtained from *Leuconostoc mesenteroides* NRRL-B1355 were ligated with T4 DNA ligase in 1 μg of the BamHI-cut and dephosphorylated vector pBKCMVBamHI (Stratagene) under the conditions indicated by the manufacturer (Stratagene, pBK phagemid vectors instruction manual & T4 DNA ligase ligation kit). 2 μl of the ligation mixture were packaged with Gigapack III Gold (Stratagene) according to the instructions of the manufacturer and stored after, the amount of phage content had been determined.

Preparation of the Probe for Isolating the Alternansucrase Gene

From the peptide sequences lysC-66 (SEQ ID NO:5), lysC-67 (SEQ ID NO:6), lysC-82 (SEQ ID NO:7), lysC-83 (SEQ ID NO:8) and lysC-88 (SEQ ID NO:9) obtained after tryptic digestion of the purified alternansucrase protein (see above) the peptides lysC-82 and lysC-83, after having undergone reverse translation, were selected for the synthesis of degenerated oligonucleotides (SEQ ID NO: 10, SEQ ID NO:11). Said oligonucleotides served as primers in a PCR reaction on genomic DNA of NRRL-B1355. All positions within oligonucleotides depicted as N were replaced by inosin in the primer synthesis.

PCR Reaction Conditions

The reaction mixture was prepared with the buffers supplied for Taq polymerase (Company GibcoBRL).

Reaction Mixture:

| Taq Polymerase (Gibco) | |
|---|---|
| DNA | 100 ng (genomic NRRL-B1355) |
| DNTPs | 2.5 mM for each nucleotide |
| primer | 10 μl of a solution containing 0.2 μMol |
| 10 fold buffer | 5 μl |
| magnesium chloride | 2 mM |
| polymerase | 1 unit |
| water | ad 50 μl |
| Step 1 | 95° C. 3' |
| Step 2 | 95° C. 1' |
| Step 3 | 58° C. 2' |
| Step 4 | 72° C. 2' |
| Step 5 | 72° C. 10' |

40 repetitions of steps 2 to 4

An 837 bp fragment (SEQ ID NO:12) resulting from this PCR reaction, the ends of which were blunted with T4 DNA polymerase, was cloned into the SmaI-cut pBlueSkript vector (Stratagene). The resulting plasmid was designated pAlsu-PCR-lysc82/83. After sequencing of the insert and computer-aided translation into the corresponding protein sequences, a data base comparison was carried out in the Swiss Prot data base. This comparison showed homologies to known glycosyl transferases (P49331, P11001, P68987, P13470, P27470, P29336).

About 5,000 phages of the genomic DNA library of *Leuconostoc mesentetoides* NRRL-B1355 were plated out using the bacterial strains and nutrient solutions indicated by the manufacturer (Stratagene), and after incubation at 37° C. for 12 hours were transferred to nitrocellulose filters. This was followed by denaturation of the phages by immersion of the nitrocellulose filters in 1.5 m sodium chloride, 0.5 M caustic soda solution for 2 minutes and neutralization of the filters by immersion in 1.5 M sodium chloride, 0.5 M Tris-HCl, pH 8.0 for 5 minutes. After rinsing the filters in 0.2 M Tris-HCl, 2×SSC, the phage DNA was bound to the membranes by UV cross link (Stratalinker of the company Stratagene, 120,000 μJ for 30 seconds). The filters were incubated in a prehybridization solution (5×SSC, 0.5% BSA, 5×Denhardt, 1% SDS, 40 mM sodium phosphate buffer, pH 7.2, 100 mg/l herring sperm-DNA, 25% formamide) at 42° C. for 6 hours. 30 ng of the isolated insert from the plasmid pAlsu-PCR-lysc82/83 were radioactivley labeled by means of a multiprime kit (Boebringer Mannheim) using α-$^{32}$P dCTP (ICN Biomedicals). This radioactive probe was added to the prehybridization mixture and the filters were incubated in this hybridization mixture at 42° C. overnight. After removal of the hybridization mixture the filters were washed three times in a washing solution (0.1×SSC, 0.5% SDS) at 55° C. for 15 minutes. An X-ray film (Kodak) was then placed on the filter for 18 hours. Phage colonies, producing hybridization signals, were identified, isolated, resuspended in SM medium and then again plated out in a dissolution such that they could be recognized as single plaques. After these phages were transferred to nitrocellulose filters and subjected to further treatment and hybridization under conditions as described above, hybridizing phages were obtained as individual isolates by means of the radioactive gene probe used. After in vivo excision of the isolated phages in accordance with the manufacturer's instructions (Stratagene) the clones AS-19B1 and AS-19B2 could be isolated as plasmids. After complete sequencing of both clones (Agowa) (SEQ ID NO:13, SEQ ID NO:14) both sequences showed an 1008 bp overlap. The joining of SEQ ID NO:13 with SEQ ID NO:14 followed by computer aided translation of all possible reading frames allowed a continuous reading frame, starting with the codon ATG (corresponding to the bases 678 to 680 in SEQ ID NO:1), to be identified. As no stop codon could be found in this composed reading frame, additional clones were isolated in order to obtain the complete coding sequence of alternansucrase.

Figure 1:
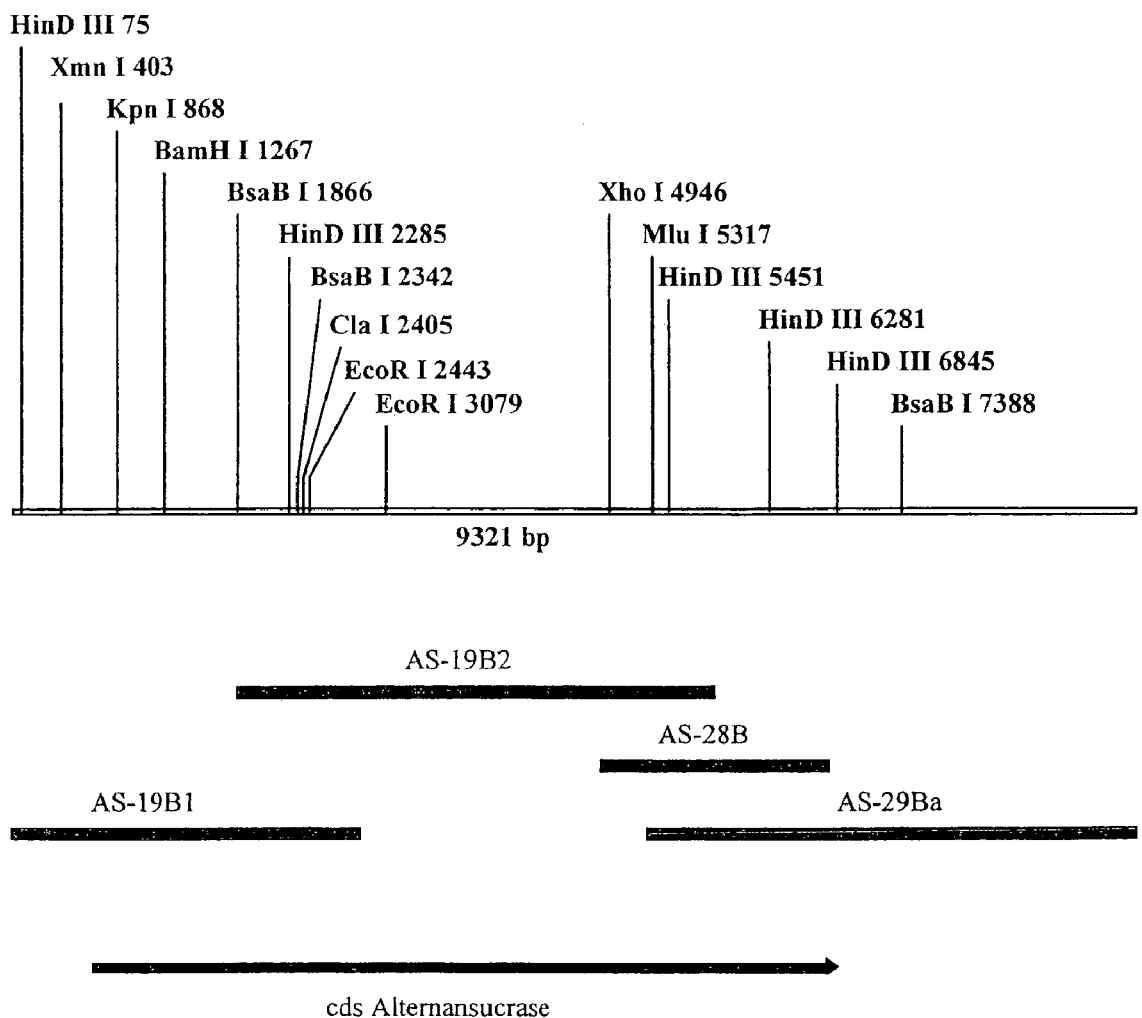
FIG. 1:
Linear map of the entire sequence region which was cloned after the screening of a genomic library of *Leuconostoc mesenteroides* NRRL B 1355 by the corresponding overlapping fragments of the clones AS-19B1, AS-19B2, AS-28B and AS-29Ba.

Therefore, about 5,000 phages of the genomic DNA library of *L. mesentetoides* NRRL-B1355 were again examined for hybridization by means of a clone AS-19B2 subfragment radioactively labeled using the multiprime kit (Boebringer Mannheim), as described above. The hybridization probe was prepared with the use of the Hindill (restriction site in the insert of AS-19B2)/SalI (cuts the pBKCMV phagemid vector in the polylinker)-fragment from AS-19B2. Said fragment contains 372 bases of the 3' end of the sequences encoding the above-described reading frame. The screening of the phage library, singling out, and transformation of the phages into plasmids was carried out under the above-described conditions. After complete sequence analysis of the thus isolated clones AS-28B (see SEQ ID NO:15) and AS-29Ba (SEQ ID NO:16) it was possible to identify an overlap of 960 identical bases (corresponding to bases 4863 to 5823 in SEQ ID NO:1) between clones AS-19B2 (SEQ ID NO:14) and AS-28B and an overlap of 567 identical bases (corresponding to bases 5256 to 5823 in SEQ ID NO:1) between clones AS-19B2 and AS-29Ba (SEQ ID NO:16). Clones AS-28B and AS-29Ba have 1523 identical bases (corresponding to bases 5256 to 6779 in SEQ ID NO:1). After computer-aided joining of clones AS-19B1, AS-19-B2 and AS-28B a continuous reading frame starting with codon ATG (bases 678 to 680 on the complete sequence) appeared. This reading frame also does not contain a stop codon. After the joining of clones AS-19B1, AS-19B2, AS-28B and AS-29Ba it was possible to identify a reading frame starting with the codon "ATG" (corresponding to bases 678 to 680 in SEQ ID NO:1) and ending with "TAA" (corresponding to bases 6849 to 6851 in SEQ ID NO:1) encoding 2057 amino acids. In addition to the coding region, the entire isolated and identified DNA sequence of the composed clones (SEQ ID NOS:13-16) contains 677 bases in the 5' region and 2469 bases in the 3' region which represent sequences not encoding altemansucrase (see FIG. 1).

Example 2

Figure 2:
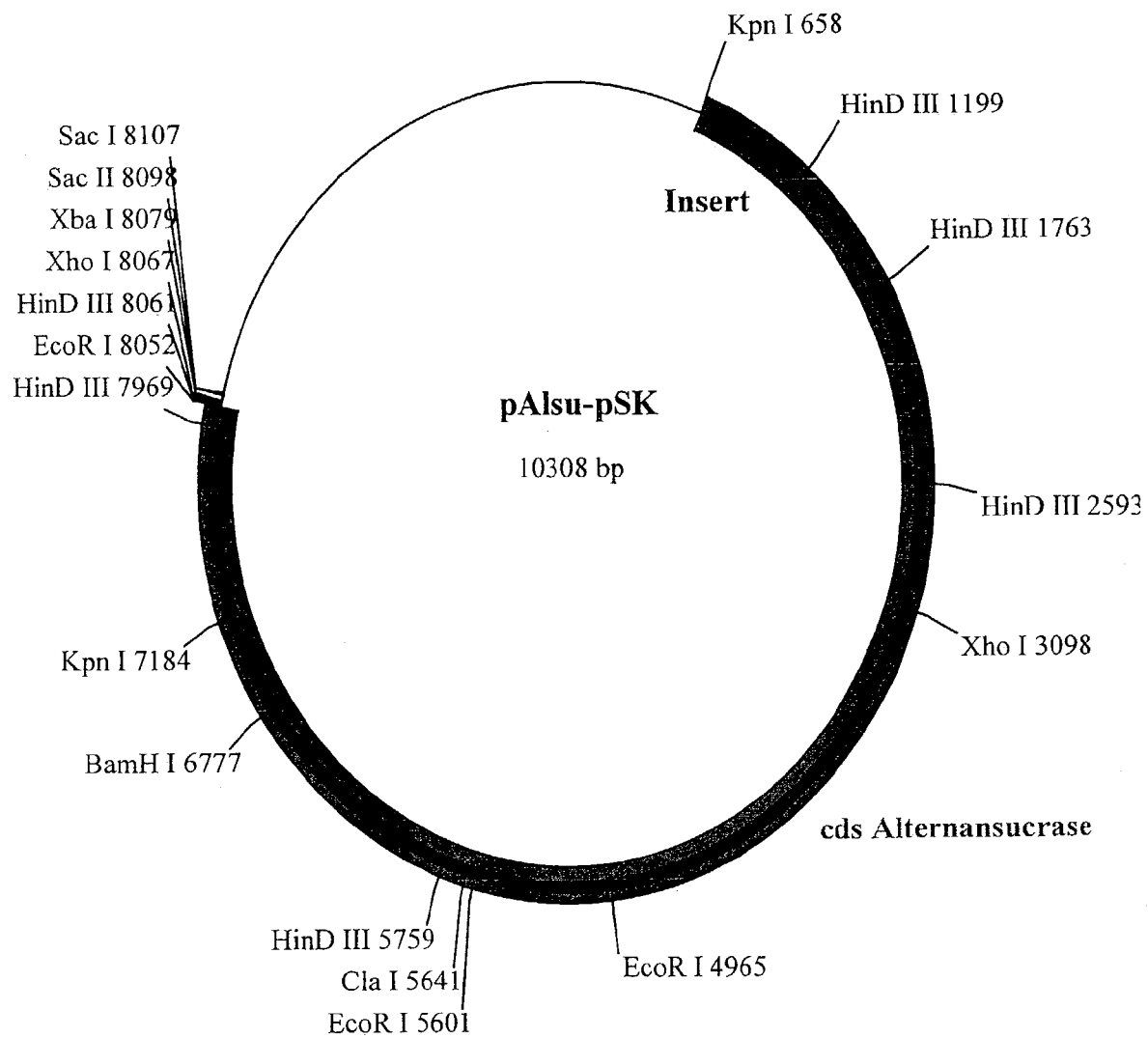
FIG. 2:
Plasmid map pAlsu-pSK

Construction of Plasmid pAlsu-pSK for the Transformation of *E. coli* and Test of the Protein Extracts for Enzymatic Activity Plasmids AS-19B1, AS-19B2, AS-28B and AS-29Ba (see Example 1) were joined in the following manner: A NotI-(restriction site in the polylinker of vector pBK CMV, company Novagen)/ClaI-fragment of clone AS-19B1 was inserted into the vector pBluescript SK (company Stratagene) at the same restriction sites (=first cloning step). Consecutive insertion of the ClaI/XhoI fragment from AS-19B2, XhoI/MluI fragment from AS-28B and MluI/BsaBI (BsaBI-cut fragment cloned into the blunted ApaI restriction site of the vector) fragment of AS-28B into the clone obtained from the first cloning step produced plasmid pAlsu-pSK (see FIG. 2). This plasmid contains the complete coding sequence of the alternansucrase from *Leuconostoc mesenteroides* NRRL-B1355 as well as non-coding sequences of 677 bp (promoter region) in the 5' region and 539 bp in the 3' region (SEQ ID NO:17).

Plasmid pAlsu-pSK was then transformed in *E. coli* (DH5α company Fermentas). The bacteria were then cultured at 27° C. for two days in 50 ml "Terrific broth" (the composition of which is described in Sambrook et al., Molecular Cloning, A Laboratory Manual, $2^{nd}$ edition (1989) Cold Spring Harbor Laboratory Press, Cold Spring Harbor, N.Y. (supplemented with 0.5% glucose) or in a fermentation medium having the following composition: $KH_2PO_4$ 1.5 g/l, $(NH_4)_2SO_4$ 5.0 g/l, NaCl 0.5 g/l, Na-citrate 1.0 g/l, $Fe^{2+}SO_4 \times 7\ H_2O$, 0.075 g/l, yeast extract 0.5 g/l, tryptone 1.0 g/l, glucose 15.0 g/l, $MgSO_4 \times 7$, $H_2O$ 0.3 g/l, $CaCl_2 \times 2\ H_2O$ 0.014 g/l, mineral salts 10 ml/l, $H_3BO_3$ 2.5 g/l, $CoCl_2 \times 6\ H_2O$ 0.7 g/l, $CuSO_4 \times 5\ H_2O$ 0.25 g/l, $MnCl_2 \times 4\ H_2O$, 1.6 g/l, $ZnSO_4 \times 7\ H_2O$ 0.3 g/l, $Na_2MoO_4 \times 2\ H_2O$ 0.15 g/l, vitamin B1 (thiamine) 0.005 g/l.

All cultures contained 100 mg/l ampicillin. The cells were then harvested by centrifugation, resuspended in 2 ml 50 mM Na-phosphate buffer pH 7.2 and crushed by a French Press. Subsequently, they were again subjected to centrifugation to remove solid particles of the crushed cells, and the supernatant (hereinafter referred to as (protein) extract) was used after sterilfiltration (Sterivex GV 0.2 μm, millipore) for further analyses.

In vitro Preparation of Alternan by Means of Protein Extracts

Figure 3:
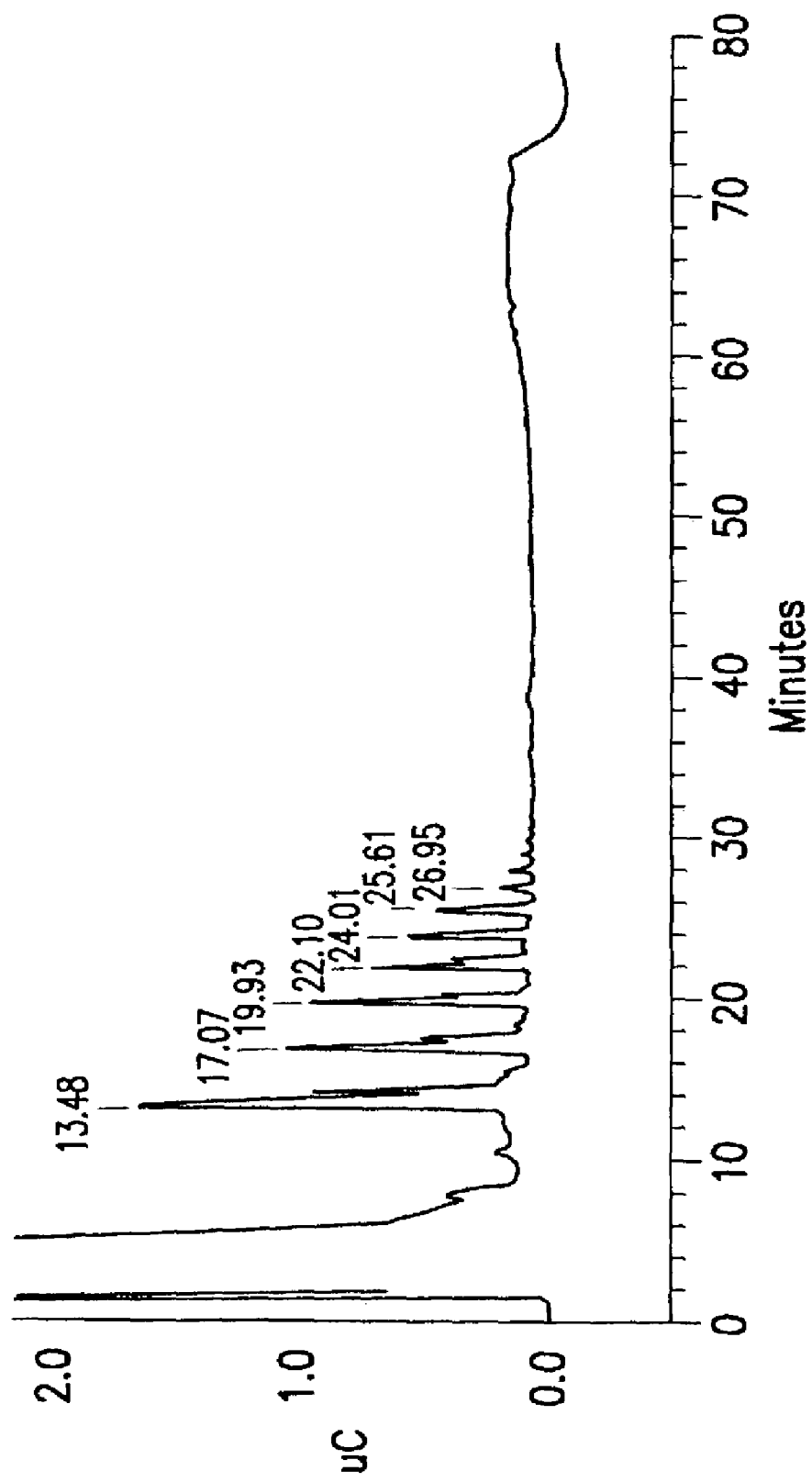
FIG. 3:
HPLC chromatogram: Preparation of oligoalternan in the presence of maltose (Example 2).

For the in vitro preparation of alternan, 200 μl each of the extracts obtained were examined in 2 ml each of 100 mM Na-citrate buffer pH 6.5 and 20% (w/v) saccharose for activity in the presence and absence of 100 μl of 10 mM maltose. The reaction mixture was incubated at 37° C. for 24 hours. In the subsequent precipitation with the same volume of ethanol in the absence of maltose no precipitable polymer was found. In the batch containing maltose, HPLC chromatography (Dionex PA-100 column, running buffer 150 mM NaOH, elution buffer 150 mM NaOH+3 M sodium acetate buffer gradient) showed the formation of oligomers (see FIG. 3).

Activity Gel 20 ml each of the individual protein extracts were applied to a 6% SDS-PAA gel and separated at a current strength of 20 mA per gel. (Before application to the gels, the extracts were not incubated at 95° C.). Subsequently, the extracts were examined for sucrase activity according to the method of Miller and Robyt (Analytical Biochemistry 156 (1986), 357-363).

The control (dextransucrase NRRL-B-512F, see Example 3 for its preparation) showed polymerizing activity. The protein extracts of the above-described *E. coli* cells containing the plasmid pAlsu-pSK, did not show any polymer-forming activity.

Example 3

Cloning and Expression of Dextransucrase from *Leuconostoc mesenteroides* NRRL-B512F Isolation of Genomic DNA

*Leuconostoc mesenteroides* NRRL-B512F (obtained from ATCC) was cultured at 28° C. for 48 hours in YT-medium (Sambrook et al., Molecular Cloning: A Laboratory Course Manual, $2^{nd}$ edition (1989), Cold Spring Harbor Press, New York) additionally containing 1% of saccharose and 50 mM sodium phosphate buffer pH 7.0. After harvesting the cells by centrifugation, genomic DNA was isolated according to Ausubel et al. (Current Protocols in Molecular Biology, Volume 1, Greene and John Wiley & Sons (1994), USA).

PCR Amplification of the Dextransucrase Gene and Cloning in pET24a

For the recombinant expression of dextransucrase in *E. coli*, the gene encoding dextransucrase was cloned in the expression vector pET24a (Novagen) after PCR amplification. For this purpose, an EagI restriction site was introduced at the 5' end of the sequences encoding the dextransucrase and an XhoI restriction site at the 3' end, together with the PCR primers used (5'b512-1: 5'-ACTgCggCCgCATgCCATTTA-CAgAAAAAg-3'; SEQ ID NO:3 and 3'b512: 5'-ACTgCTC-gAgTTATgCTgACACAgCATTTC-3'; SEQ ID NO: 4) derived from the sequence of WO 89/12386. Subsequent cloning into the corresponding restriction sites of the polylinker of pET24a was carried out. The resulting plasmid was designated UL5-20.

PCR Reaction Conditions

Buffer and polymerase of the company Gibco BRL were used.

| DNA: | 100 ng (genomic NRRL-B512F) |
|---|---|
| 10 fold buffer | 5 µl |
| MgCl2 | 4 mM |
| 5' primer | 50 ng |
| 3' primer | 50 ng |
| dNTP | 1 mM of each nucleotide |

| | Pfu polymerase | 0.5 units |
|---|---|---|
| | water | ad 50 µl |
| step 1 | 95° C. | 4 minutes |
| step 2 | 95° C. | 1 minute |
| step 3 | 55° C. | 1 minute |
| step 4 | 72° C. | 5 minutes |
| step 5 | 72° C. | 10 minutes |

40 repetitions were made between steps 2 and 4.

Preparation of Recombinant Dextransucrase

BL21(DE3) *E. coli* cells containing the plasmid UL5-20 were cultured in YT medium (see above) at 37° C. up to an $OD_{600}$=0.8. Subsequently, the cells were subjected to induction with 0.2 mM IPTG and cultured anew at 18° C. for 24 hours. After harvesting the cells by centrifugation and resuspending them in sodium phosphate buffer, pH 5.2, the cells were crushed in a French Press. The solution obtained was freed from insoluble components by centrifugation and the supernatant containing dextransucrase and referred to hereinafter as the extract was obtained.

Example 4

PCR Amplification of the Coding Region of Alternansucrase and Cloning in pET24a

The coding region of alternansucrase was amplified in a PCR reaction (see the reaction conditions below) with genomic DNA from the *Leuconostoc mesenteroides* strain NRRL-B1355 as a template. An NheI restriction site was introduced at the 5' end by means of primers A1-4 (SEQ ID NO:18), and a SalI-restriction site at the 3' end by means of primer A1-5 (SEQ ID No:19). A fragment of about 6200 bp was isolated.

A1-4:
5'-GGG CCC GCT AGC ATG AAA CAA CAA GAA ACA GT

A1-5:
5'-CCC GGG GTC GAC CTT TGT CGA ATC CTT CCC

Reaction conditions of the PCR (kit of the company Gibco BRL):

| DNA | 1 µl |
|---|---|
| 10 × buffer | 5 µl |
| 10 mM per dNTP | 2 µl |
| 50 mM $MgSO_4$ | 2 µl |
| primer per 1 µl | |
| Platinum DNA polymerase | 0.2 µl |
| distilled water | 37.8 µl |
| step 1 | 95° C., 2 minutes |
| step 2 | 95° C., 20 seconds |
| step 3 | 47° C., 20 seconds |
| step 4 | 68° C., 7 minutes (prolonged by 3 seconds per cycle) |
| step 5 | 68° C., 15 minutes |

Steps 2 to 4 were repeated 35 times altogether before step 5 was carried out.

Figure 4:
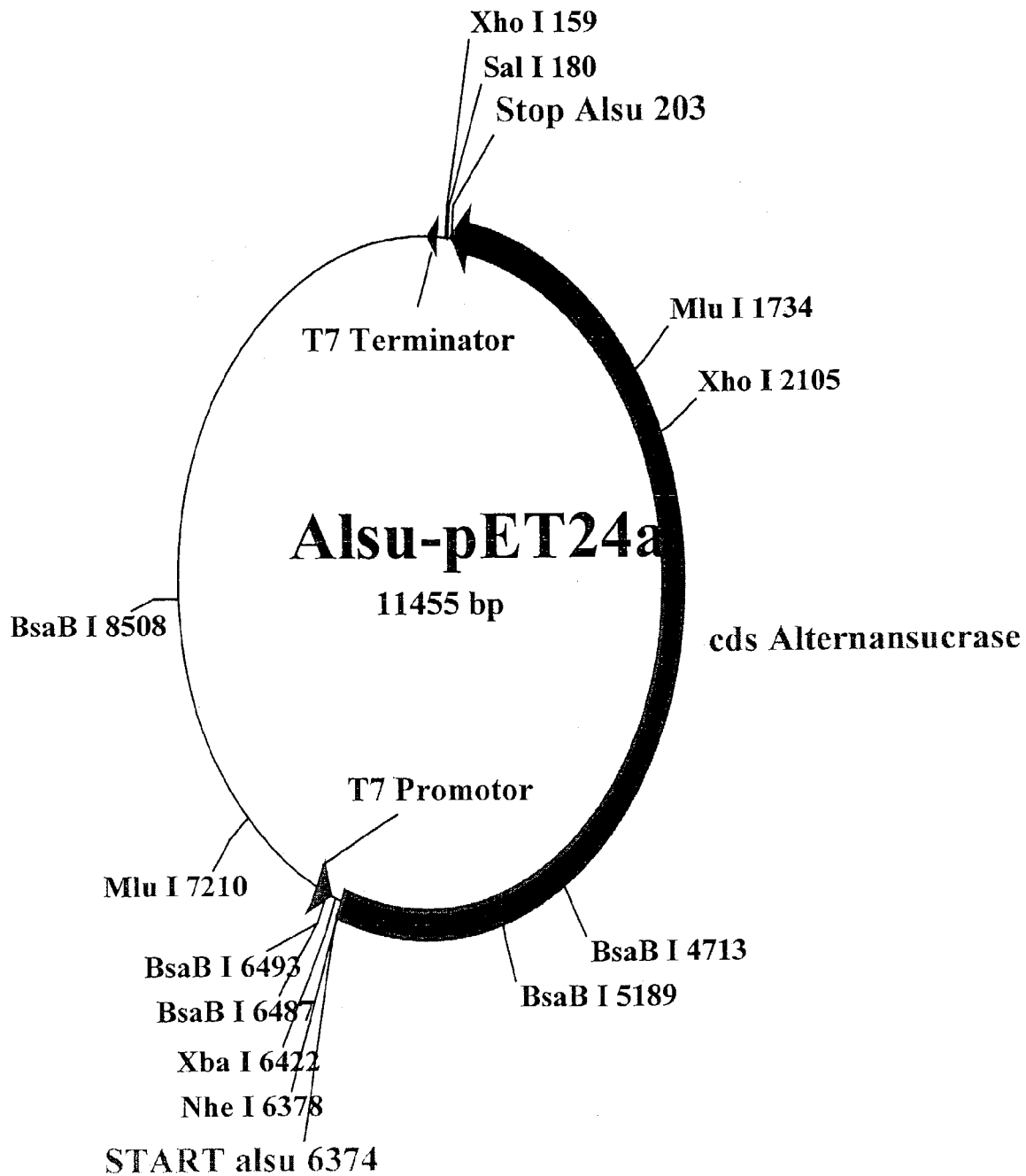

The PCR fragment obtained was purified according to standard methods, treated with the restriction endonucleases NheI and SalI, ligated into vector pET24a (of the company Novagen) which had likewise been cut with these enzymes, and the ligation product was transformed into *E. coli*. After preparation of the plasmid and restriction digestion, three positive clones were selected. They were designated pAlsu-pET24a-3, pAlsu-pET24a-7 and pAlsu-pET24a-21 (see FIG. 4), respectively. All contained the sequence indicated in SEQ ID NO:20 as an insertion.

Example 5

Expression of the Recombinant Alternansucrase in *E. coli* in Shake Flask Cultures and in the Fermenter Shake Flask Culture Plasmids pAlsu-pET24a-3, pAlsu-pET24a-7, pAlsu-pET24a-21 and pET24a were transformed into *E. coli* BL21 (DE3), of the company Novagen, and after initial culturing at 37° C. for 3 hours in 3 ml YT medium (Sambrook et al., Molecular Cloning, A Laboratory Manual, $2^{nd}$ edition (1989), Cold Spring Harbor Laboratory Press, Cold Spring Harbor, N.Y.) they were each cultured in shake flasks in 2 replicas in 50 ml Davis minimal medium (DIFCO Manual, Dehydrated Culture Media and Reagents for Microbiology, $10^{th}$ edition, Detroit Mich., USA (1984)) containing 0.2% glucose instead of dextrose as a carbon source at 37° C. until an $OD_{600}$ of about 0.8 was reached. After centrifugation and resuspension, one of the two replica cultures was cultured in Davis Minimal Medium (DMA) containing 1% lactose as the carbon source and inductor at 27° C. for another 16 hours. The cells of the individual cultures were harvested after centrifugation, resuspended in 50 mM sodium acetate buffer pH 5.3, and a protein extract was prepared as described in Example 2.

Fermenter

Clone pAlsu-pET24a-21 transformed in *E. coli* BL21 (DE3) was cultured in a 2 l fermenter (Biostad B; B.Braun, Melsungen) under the following conditions:

Medium:

Fermentation medium: $KH_2PO_4$ 1.5 g/l, $(NH_4)_2SO_4$ 5.0 g/l, NaCl 0.5 g/l, Na-citrate 1.0 g/l, $Fe^{2+}SO_4 \times 7\ H_2O$ 0.075 g/l, yeast extract 0.5 g/l, tryptone 1.0 g/l, glucose 15.0 g/l, $MgSO_4 \times 7\ H_2O$ 0.3 g/l, $CaCl_2 \times 2\ H_2O$ 0.014 g/l, mineral salts 10 ml/l, $H_3BO_3$ 2.5 g/l, $CoCl_2 \times 6\ H_2O$ 0.7 g/l, $CuSO_4 \times 5\ H_2O$ 0.25 g/l, $MnCl_2 \times 4\ H_2O$ 1.6 g/l, $ZnSO_4 \times 7\ H_2O$ 0.3 g/l, $Na_2MoO_4 \times 2\ H_2O$ 0.15 g/l, vitamin B1 (thiamine) 0.005 g/l.

Carbon source: Glucose (1.5% (w/v)) is present in the medium, 70% (w/v) glucose solution is added.

Automatic pH control by ammonia and phosphoric acid at pH 7.0+/−0.1. A 20% concentration of $pO_2$ is adjusted in the medium via control by the stirrer.

Conditions:

1.5 l of fermentation medium were inoculated with 50 ml of the preculture. The cells were first cultured at 37° C. until the glucose present was consumed. They were then cultured at the same temperature at a feeding rate of 9 g of glucose$\times$l$^{-1} \times$h$^{-1}$ until an $OD_{600}$=40 was reached. At this time, the temperature of the culture broth was lowered to 20° C. and the amount of glucose addition was lowered to 2 g$\times$l$^{-2} \times$h$^{-1}$. At a culture temperature of 20° C., the culture was subjected to induction with 0.2 mM IPTG (isopropyl-β-D-thiogalactopyranoside (Sigma)). After culturing at 20° C. for another 18 hours, the cells were harvested by centrifugation, resuspended in 50 mM sodium phosphate buffer pH 5.3 and an extract was prepared as described in Example 2.

Example 6

SDS PAGE Assay of the Activity of the Recombinant Alternansucrase, Periodic Acid Oxidation and Staining According to Schiff Protein extracts were prepared from *E. coli* shake flask cultures (strain BL21 (DE3)), containing the plasmids pAlsu-pET24a-3, pAlsu-pET24a-7, pAlsu-pET24a-21 and pET24a (control), respectively. Two different extracts were each prepared from the cells transformed with the different extracts, one of said extracts being prepared before induction with IPTG and the other one being prepared after induction with IPTG at the end of culturing. The activity of these extracts of shake flask cultures (see Example 5) was detected by SDS PAGE separation of the proteins, followed by SDS removal by washing with 50 mM sodium acetate buffer pH 5.3 and incubation of the gels in 50 mM sodium acetate pH 5.3, 5% (w/v) saccharose at 37° C. for 16 hours, followed by periodic acid oxidation of the polymer formed and staining by means of acidic Schiff reagent (Miller and Robyt, Analytical Biochemistry 156, (1986), 357-363).

Figure 5:
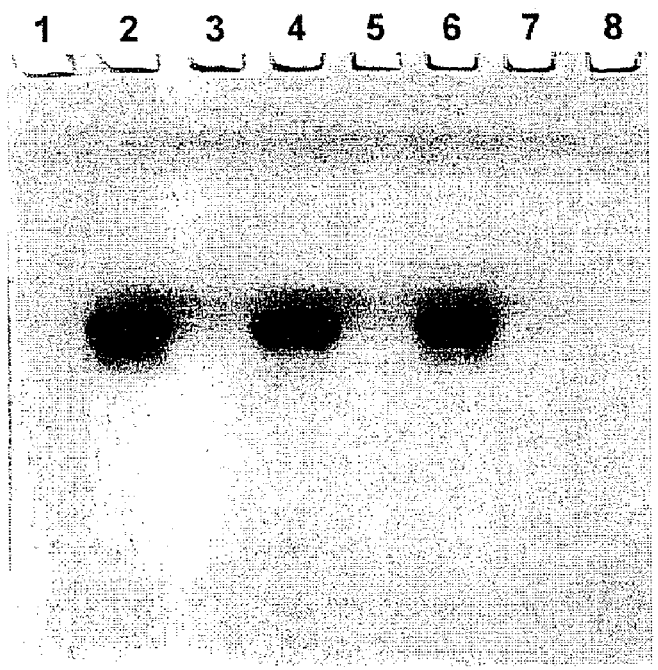
FIG. 5:
SDS PAGE with subsequent assay of sucrase activity (see Example 6)

FIG. 5 shows that sucrase activity has not been found for either one of the extracts (preparation of the extract before and after IPTG-induction) containing the cloning vector pET24a. In the case of strains which had been transformed with the plasmids pAlsu-pET24a-3, pAlsu-pET24a-7 and pAlsu-pET24a-21, respectively, all protein extracts showed sucrase activity at the end of the induction phase (concentrated in one band).

Before induction with IPTG such activity bands were not found.

As the polymer formed in the gel can be stained according to the above-described methods by acidic Schiff reagent, it can be assumed not to be composed of pure α-1,3-linked units which would not lead to any staining.

As the gene contained in vectors pAlsu-pET24a-3, pAlsu-pET24a-7 and pAlsu-pET24a-21, respectively, was isolated from the *Leuconostoc mesenteroides* strain NRRL-B1355 which expresses at least one dextran sucrase apart from alternansucrase, it was not possible to determine unambiguously with this staining method whether the nucleic acid sequence contained in the plasmid actually encodes an alternansucrase. Dextrans and alternans can both be detected by this method because both polymers contain α-1,6 linkages.

Example 7

Tests for the Enzymatic Activity of Recombinantly Prepared Alternansucrases after Heat Treatment and for the Specificity of Alternansucrase In order to prove polymerization activities, extracts from shake flask cultures were used (see Example 5). 100 μl of extract were each added to 2 ml reaction buffer (50 mM sodium acetate pH 5.3, 20% saccharose) and incubated at 37° C. for 24 hours. For comparison, an extract inactivated by a 10 minute treatment at 95° C., and an extract from *E. coli* BL21 (DE3) containing vector pET24a were used. Polymer formation was only found in the batch that had not been inactivated, while the batch treated at 95° C. for 10 minutes and the batch with the extract from BL21(DE3) containing pET24a did not show any polymer formation. After addition of the same volume of absolute ethanol to all batches, polymers could only be precipitated from the batch which had not been inactivated. This finding is a clear indication of the activity of alternansucrase, because the dextransucrase present in NRRL B-1355 is inactivated by a treatment at 45° C. for 30 minutes, while alternansucrase remains active under these conditions (Lopez-Munguia et al., Enzyme Microb. Technol. 15 (1993), 77-85). The enzymatic assay by a coupled enzymatic test of the glucose and fructose released and of the saccharose still contained in the reaction mixture after 24 hours, respectively, revealed that fructose was only present in the extract that was not inactivated.

For carrying out the enzymatic test either purified protein or crude protein extract is added in different dilutions to 1 ml batches containing 5% saccharose and 50 mM acetate, pH 5.5 and subjected to incubation at 37° C. After 5 minutes, 10 minutes, 15 minutes, 20 minutes, 25 minutes and 30 minutes, 10 μl each are removed from these batches and the enzymatic activity of alternansucrase is terminated by immediate heating to 95° C. Subsequently, in the coupled photometric test, the portions of fructose and glucose released by alternansucrase and the portion of used-up saccharose, respectively, are determined. For this purpose, 1 μl to 10 μl of the inactivated sample are placed into 1 ml of 50 mM imidazole buffer, pH 6.9, 2 mM $MgCl_2$, 1 mM ATP, 0.4 mM NAD and 0.5 U/ml hexokinase. After sequential addition of about 1 u of glucose-6-phosphate dehydrogenase (from *Leuconostoc mesenteroides*), about 1 u of phosphoglucose isomerase and about 5 u of invertase, the alteration of adsorption at 340 nm is measured. Subsequently, the amount of fructose and glucose released and used-up saccharose, respectively, is calculated according to the Lambert-Beer law.

In control batches (inactivation of the extract by treatment with 95° C. and extract from *E. coli* containing pET24a) no significant release of fructose and no decrease of saccharose, respectively, was found in the reaction batch after 24 hours.

These results confirm that the specificity of the sucrase encoded by plasmids pAlsu-pET24a-3, pAlsu-pET24a-7 and pAlsu-pET24a-21, respectively, is that of a glucosyltransferase. The specificity of a fructosyl transferase, the presence of which has been described for some strains of the genus *Leuconostoc* is to be excluded, because otherwise glucose should have been found.

Example 8

Production of Alternan by Means of Alternansucrase Prepared in *E. coli*

100 ml of extract obtained by fermentation of *E. coli* BL21 (DE3) containing plasmid pAlsu-pET24a-3 (see Example 4) were added to 900 ml of reaction buffer (50 mM sodium acetate pH 5.3, 20% saccharose) and incubated at 37° C. for 24 hours. The addition of the same amount of absolute ethanol to the reaction mixture caused the alternan formed to precipitate. After the precipitate was washed twice with 50% ethanol, it was dried by lyophilization. The yield of dried polymer based on the amount of saccharose used in the reaction was 60%.

Example 9

Figure 6:
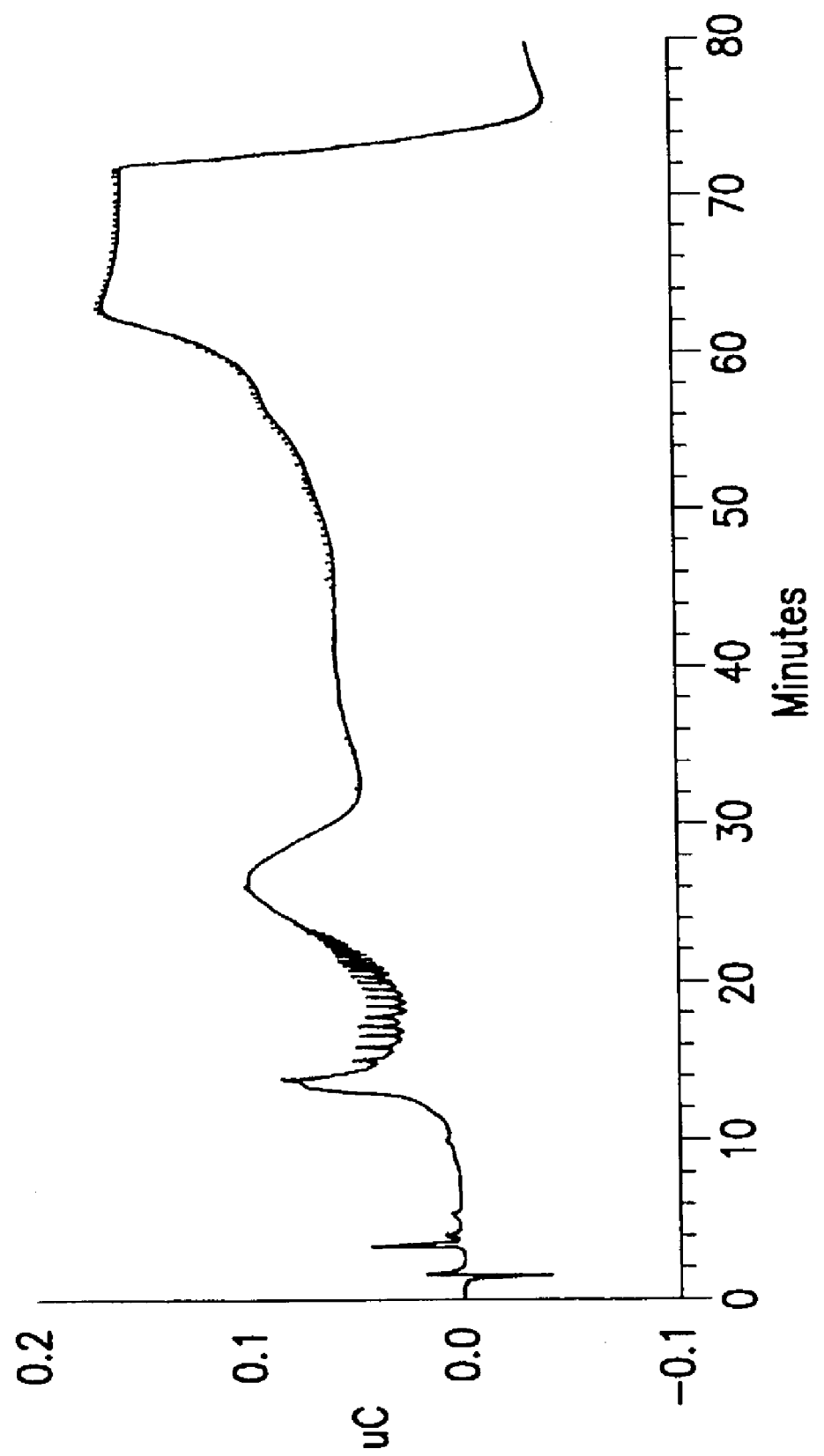
FIG. 6:
HPLC chromatogram of dextran T10
Figure 7:
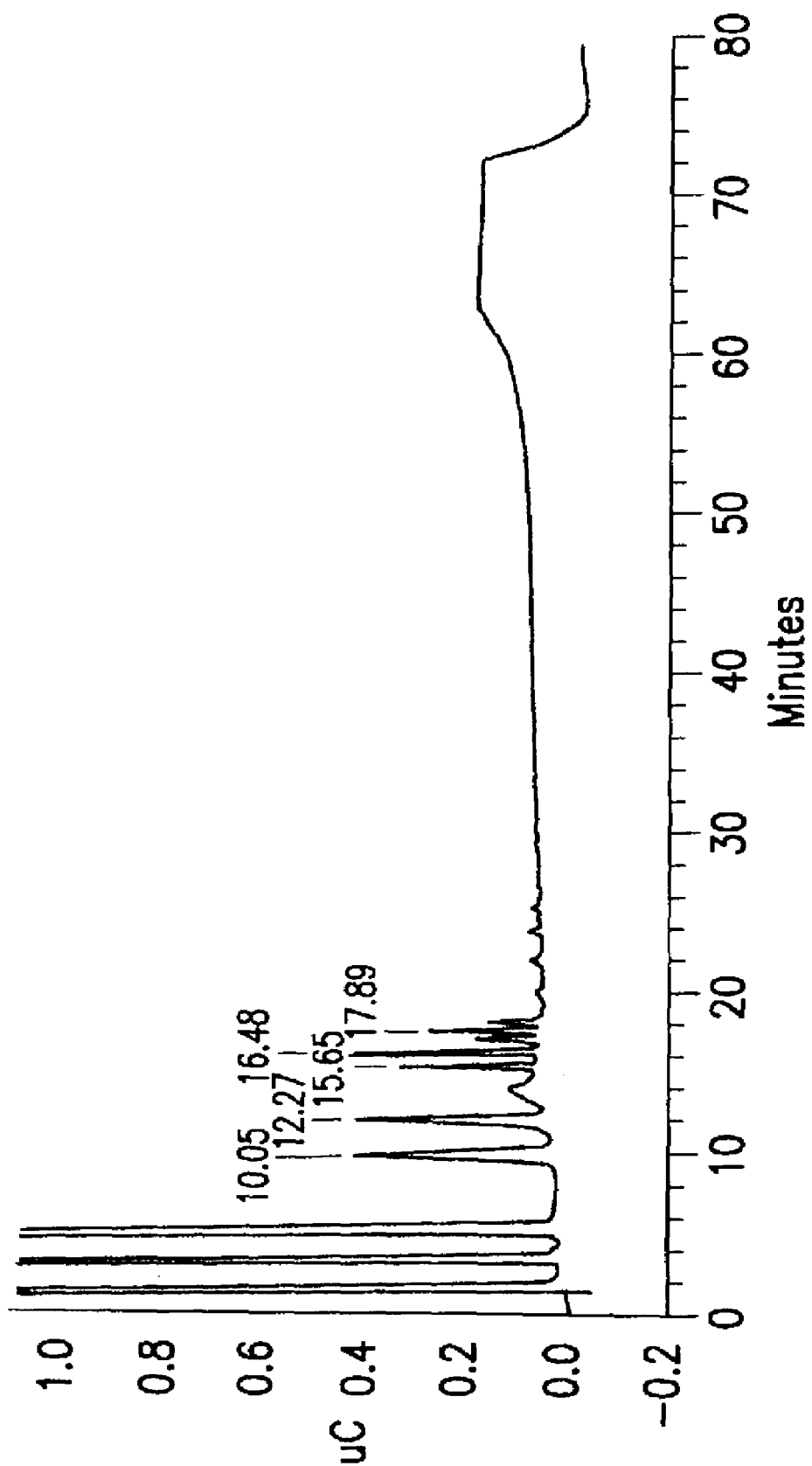
FIG. 7:
HPLC chromatogram of dextran T10 after dextranase digestion

HPLC Analysis of Alternan and Dextran after Dextranase Digestion 100 mg of the polymer prepared in Example 7 and 100 mg of dextran T10 (Pharmacia) were each dissolved in 1 ml of water. 40 µl each of these solutions were added to 700 µl reaction buffer (50 mM potassium phosphate pH 5.7, 8 units of dextranase, ICN Biomedicals Inc. No. 190097), and incubated at 37° C. for 16 hours. 50 µl of the polymer solutions not treated with dextranase (see FIG. 6) and 50 µl of the polymer solutions treated with dextranase (FIG. 7) were analyzed by HPLC (Dionex, column PA-100, NaOH/NaOH-NaAc gradient).

In the case of dextran T10 the cleavage of the polymer into different molecules of lower molecular weights can be clearly seen. -The entire high molecular weight dextran is converted by dextranase into smaller units (mostly isomaltose). By contrast, in the case of alternan, short chained oligosaccharides only appear in small amounts after dextranase incubation. Most of the alternan is not digestible by dextranase. This finding suggests that the product prepared by recombinant alternansucrase is not dextran, but alternan which is known to be hardly accessible to enzymatic digestion by dextranase (Lopez-Mungia et al., Enzyme Microb. Technol. 15, (1993), 77-85).

Example 10

In vitro Preparation of Alternan in the Absence of Dextranase

100 µl extract from shake flask cultures (see Example 5) were added to 2 ml of reaction buffer (50 mM sodium acetate, pH 5.3, 20% saccharose). 50 units of dextranase (Biomedicals Inc. No. 190097) were additionally added to another batch. Two corresponding batches which contained dextransucrase from *Leuconostoc mesenteroides* NRRL-B512F instead of the enzyme extract served as controls; one of these two batches had dextranase additionally admixed to it.

After precipitation with ethanol, the reaction batch with dextransucrase and dextranase did not show any polymer formation. All other batches were found to show polymer formation.

Example 11

In vitro Preparation of Oligoalternan and HPLC Analysis

Figure 8:
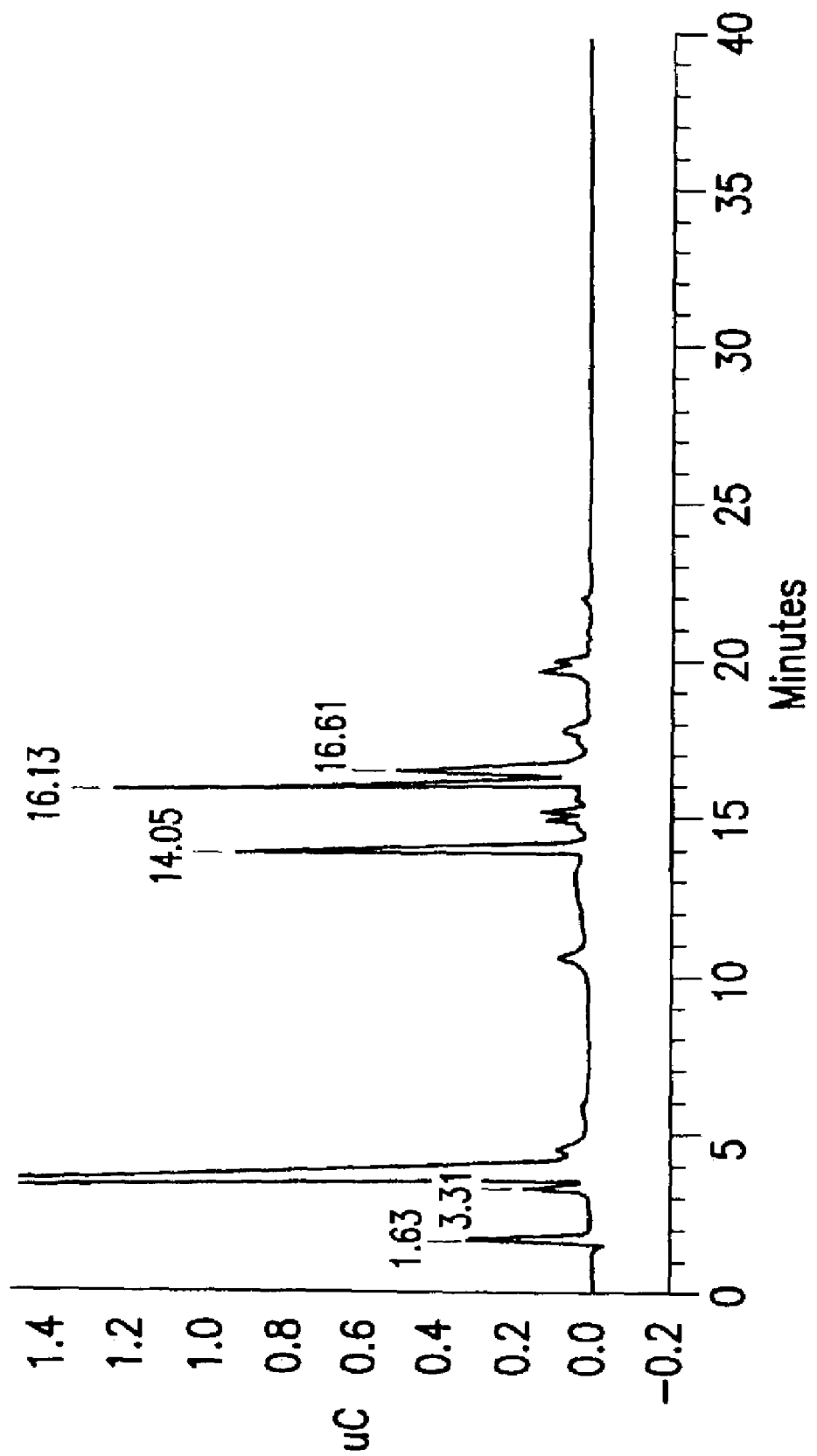
FIG. 8:
HPLC chromatogram of oligoalternan
Figure 9:
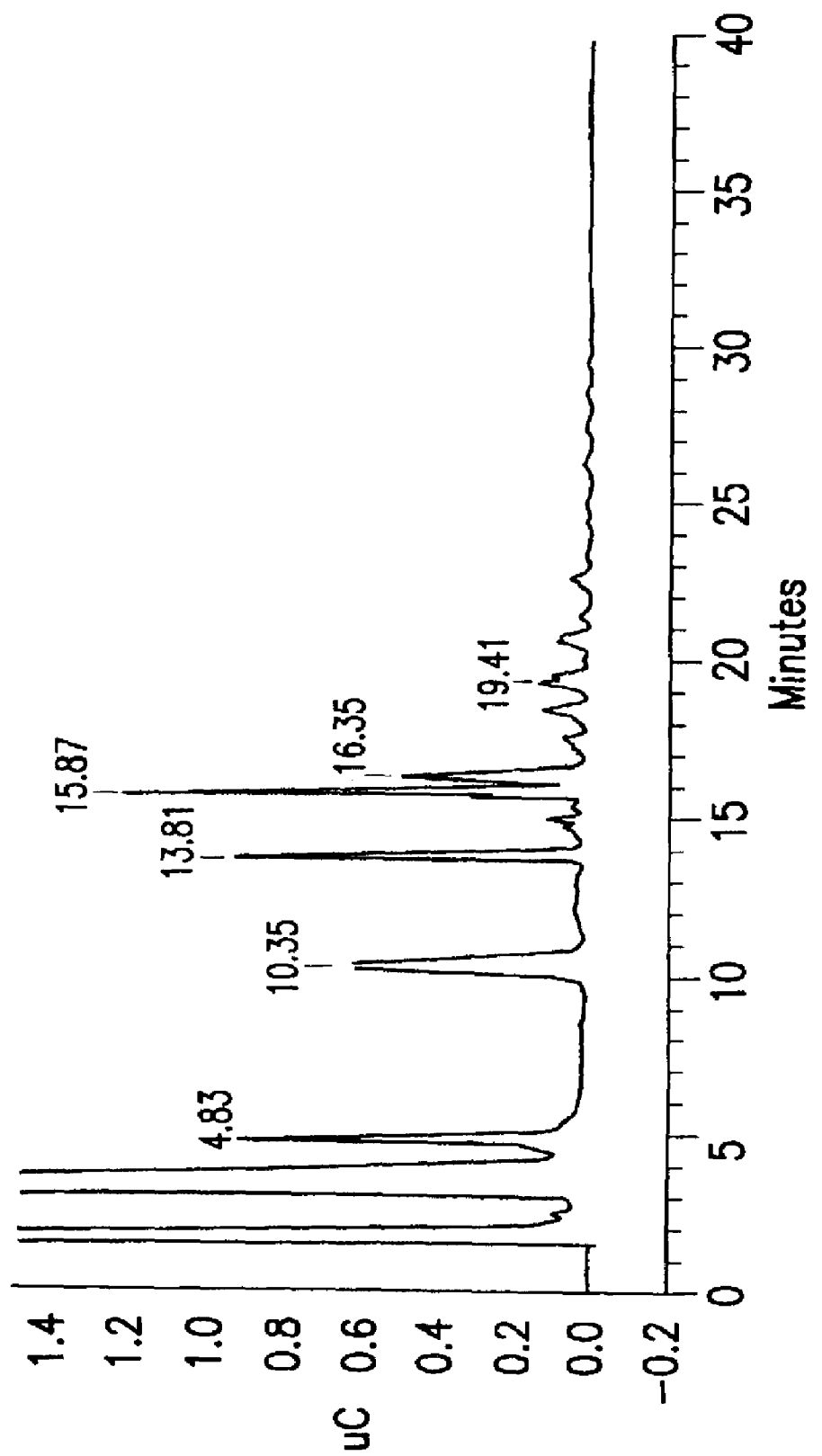
FIG. 9

Oligoalternan was prepared as described in Example 2, with a protein extract in the presence of maltose and was subsequently detected (See FIG. 8) by HPLC-chromatography (see Example 2). For comparison, a portion of this batch was admixed with 50 units of dextranase (Biomedicals Inc. 190097) after preparation of oligoalternan and subsequently separation by HPLC chromatography was carried out as well (see FIG. 9). A comparison of the two chromatograms shows that not only the height of the two peaks which can be allocated to the oligoalternan (α and β-anomer) (retention time between 15.87 and 16.61 minutes) but also the height of all the other peaks, the first signs of which are already visible without dextranase, remain unchanged. This finding suggests that recombinantly prepared alternansucrase allows oligoalternan to be prepared without the simultaneous production of oligodextran. Oligodextran would be liable to digestion by dextranase, which would have to show up in a decrease of the height of the peaks in the HPLC chromatogram, if oligodextran were present.

Example 12

Methylation Analysis of Alternan

In order to further analyze the alternan produced in vitro a methylation analysis was carried out:

Permethylation

The permethylation was performed as described by Ciucanu and Kerek (Carbohydr. Res. 131 (1984), 209-218) by using NaOH/MeI in DMSO or by using a modified method according to Hakomori (Journal of Biochemistry 55 (1964 FEB), 205-208) which relies on the use of freshly prepared Li-Dimsyl/MeI (Dimsyl=methylsulfinyl carbanion) in DMSO at room temperature.

All reactions are performed under a nitrogen atmosphere. The permethylation products are isolated by extracting the excess of methyliodide by the use of dichlormethan. DMSO and salts were washed out at the end.

Degradation into Partially Methylated Sorbitacetates (Methylation Analysis)

The permethylated glucans were hydrolyzed with 2N trifluorine acetic acid at 120° C. for 1-3 hours. After cooling the acid was removed by nitrogen. Then the resulting glucans were co-distilled with a small amount of toluene, afterwards reduced by $NaBD_4$ in 1N ammonia and finally, acetylated by pyridine/acetanhydrid (3 h, 90° C.). The products were extracted by dichlormethan and washed with $NaHCO_3$. The products in the organic phase were analyzed by gas chromatography.

Analysis of the Acetylated Products

The acetylated products were analyzed by gas chromatography which was performed with a chromatograph manufactured by the Carlo-Erba company model GC 6000 Vega equipped with an on-column injector, a 25 m CPSol8CB and a FID-detector. As a carrier gas hydrogen (80 kPa) was used.

The identification and integration of the peaks was performed as described by Sweet et al. (Carbohydr. Res. 40 (1975), 217).

Results

The following main components were identified by gas chromatography:

| Sorbit acetylated in position | Interpretation |
|---|---|
| 1, 5 | Terminal Glucopyranose |
| 1, 3, 5 | 3-linked Glucopyranose |
| 1, 5, 6 | 6-linked Glucopyranose |
| 1, 3, 5, 6 | 3,6-linked Glucopyranose |

Furthermore, small amounts (rel. amount 0.2-0.4 mol %) of the following components were also found: 1, 4, 5- and 1, 3, 4, 5-sorbit and another tetraacetyl component (1,5,x,y). It is supposed that these components are due to incomplete methylation.

The following amounts were found for the above mentioned components in different experiments which were performed by changing the length of hydrolysis (indicated in bold by the number of hours) (MA=methylation analysis1; MA-b=methylation analysis 2):

Values in mol %

| Ac in Pos | MA (1h) | MA (2h) | MA (3h) | MA-b(2h) |
|---|---|---|---|---|
| 1, 5 | 10, 49 | 10, 56 | 9, 17 | 12, 71 |
| 1, 3, 5 | 31, 69 | 34, 70 | 32, 95 | 23, 12 |
| 1, 4, 5 | 0, 70 | 0, 30 | 0, 36 | 0, 33 |
| 1, 5, 6 | 47, 02 | 44, 17 | 47, 23 | 54, 62 |
| 1, 3, 4, 5 | 0, 27 | 0, 22 | 0, 25 | 0, 31 |
| 1, 5, x, y | 0, 19 | 0, 32 | 0, 36 | 0, 24 |
| 1, 3, 5, 6 | 9, 64 | 9, 73 | 9, 68 | 8, 67 |

Example 13

Construction of an Expression Cassette for Plants: Vacuolar and Plastidic Expression of an Alternansucrase.

Figure 11:
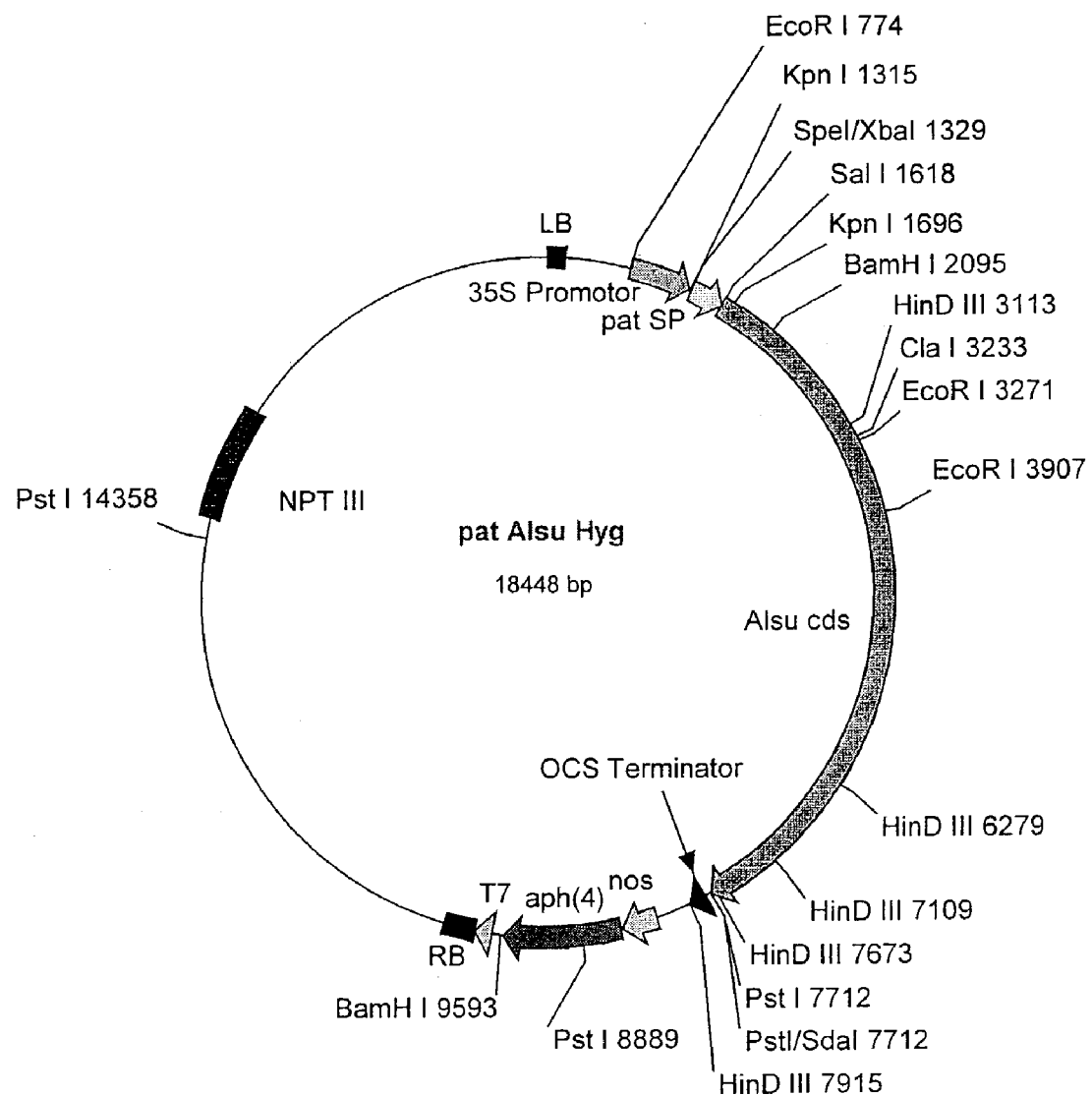
Figure 12:
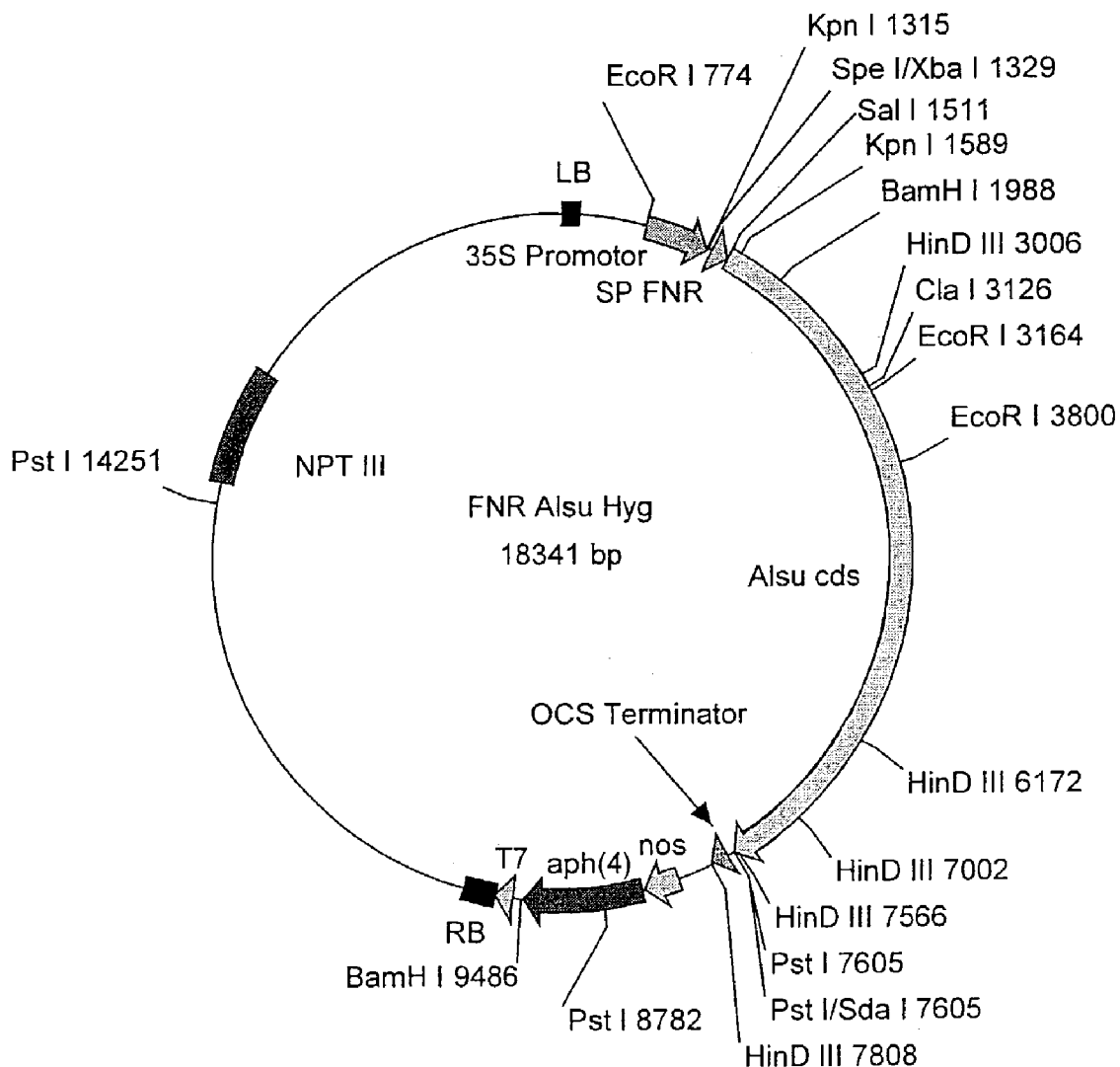

By using plasmid Alsu-pET24a as a template and the PCR primers Al-5'-1.2 and Al-3'-2.2 (see SEQ ID NO:53 and 54) we amplified the coding region of alternansucrase from *Leuconostoc mesenteroides* which was then cut by the restriction enzymes SalI and PstI. Afterwards the resulting fragments were cloned into SalI and SdaI digested plasmids a) pBinAR-pat-Hyg and b) pBinAR-fnr-Hyg. The resulting plasmids were called a) pat-Alsu-Hyg (see FIG. 11) and b) fnr-Alsu-Hyg (see FIG. 12).

Note: The bacterial secretion signal peptide was removed from the cds by choice of the PCR primers.

PCR Conditions:

Buffer and polymerase from Boehringer Mannheim (Pwo Polymerase No. 1644947)

| DNA | 0.5 ng |
|---|---|
| 10x Buffer + MgSO$_4$ | 5 µl |
| dNTPs (je 10 mM) | 2 µl |
| Primer Sp-AS-5' | 100 nM |
| Primer Sp-AS-3' | 100 nM |
| Pwo Polymerase | 1.0 unit |
| distilled water | ad 50 µl |

Reaction Conditions:

| Step 1 | 95° C. | 2:30 min |
|---|---|---|
| Step 2 | 95° C. | 0:30 min |
| Step 3 | 47° C. | 0:30 min |
| Step 4 | 68° C. | 7:00 min |
| | | (plus 3 sec per cycle) |
| Step 5 | 68° C. | 15:00 min |

The steps 2 to 4 were repeated 35 times in a cyclical manner.

Example 14

Northern Blot Analysis for Expression of Alternansucrase in Transgenic Plants

Leaves or tubers from potato plants transformed via agrobacteria with plasmids pat-Alsu-Hyg and fnr-Alsu-Hyg, respectively, were pulverized in a mill, type MM 200, (Retsch GmbH & Co. KG, 42781 Haan, Germany) at 30 Hz for 50 sec. RNA was extracted according to Logemann et al. (Anal. Biochem. 163 (1987), 16-20). 50 µg RNA per sample were loaded on 1% agarose gels containing formaldehyde. After electrophoresis the RNA was transferred to nylon membranes (Hybond N, Amersham, UK) by the capillary transfer method (Sambrook et al., Molecular cloning: A laboratory manual, 2nd issue; Cold Spring Harbor Laboratory Press, NY, USA (1989)). Fixation of nucleic acids at the membrane was achieved by UV crosslinking (Stratalinker by Stratagene).

Membranes were prehybridized at 42° C. in hybridization buffer (25% (v/v) formamide, 250 mM sodium phosphate, pH 7.2, 250 mM sodiumchloride, 1 mM EDTA 7% (w/v) SDS, 25% (w/v) polyethyleneglycol 6000, 0.25 mg/ml sheared salmon sperm DNA) for 6 h. Afterwards hybridization was performed at 42° C. over night in hybridization buffer containing a radiolabelled probe in addition. The radioactive probe was prepared by using the Random Primed DNA Labelling Kit (Boehringer Mannheim, 1004760) and the approx. 4 kb KpnI/XhoI-fragment from plasmid pAlsu-pSK according to the manufacturers manual. Membranes were washed at 50° C. once for 20 min in 3×SSC (Sambrook et al., Molecular cloning: A laboratory manual, 2nd issue; Cold Spring Harbor Laboratory Press, NY, USA (1989)) followed by washing once for 20 min in 0.5×SSC before exposing the membrane to an x-ray-film over night.

Results

| No | Query id | Subject id | % identity | alignment length | mismatches | gap openings | q. start | q. end | s. start | s. end | e-value | bit score |
|---|---|---|---|---|---|---|---|---|---|---|---|---|
| 1. | 1__27810 | gi\|10862851\|emb\|CAB65910.2\| | 100.00 | 2057 | 0 | 0 | 1 | 2057 | 1 | 2057 | 0.0 | 3748.8 |
| 2. | 1__27810 | gi\|11559649\|gb\|AAG38021.1\| | 47.38 | 1258 | 573 | 22 | 238 | 1487 | 137 | 1313 | 0.0 | 941.0 |

-continued

| No | Query id | Subject id | % identity | alignment length | mismatches | gap openings | q. start | q. end | s. start | s. end | e-value | bit score |
|---|---|---|---|---|---|---|---|---|---|---|---|---|
| | | AF294469__1 | | | | | | | | | | |
| 3. | 1__27810 | gi\|11559649\|gb\|AAG38021.1\| AF294469__1 | 29.21 | 315 | 179 | 8 | 4 | 305 | 5 | 288 | 6.1e−21 | 105.5 |
| 4. | 1__27810 | gi\|11559649\|gb\|AAG38021.1\| AF294469__1 | 29.15 | 247 | 133 | 4 | 159 | 403 | 1168 | 1374 | 1.5e−17 | 94.36 |
| 5. | 1__27810 | gi\|11559649\|gb\|AAG38021.1\| AF294469__1 | 31.13 | 212 | 131 | 5 | 159 | 361 | 1298 | 1503 | 4.4e−13 | 79.34 |
| 6. | 1__27810 | gi\|11559649\|gb\|AAG38021.1\| AF294469__1 | 28.32 | 226 | 133 | 6 | 77 | 293 | 1293 | 1498 | 6.3e−05 | 52.37 |
| 7. | 1__27810 | gi\|11559649\|gb\|AAG38021.1\| AF294469__1 | 25.30 | 166 | 113 | 5 | 1308 | 1463 | 1273 | 1437 | 4.2e−04 | 49.68 |
| 8. | 1__27810 | gi\|11559649\|gb\|AAG38021.1\| AF294469__1 | 26.15 | 130 | 84 | 4 | 1355 | 1480 | 133 | 254 | 0.130 | 41.20 |
| 9. | 1__27810 | gi\|7470961\|pir\|\|T31098 | 47.38 | 1258 | 573 | 22 | 238 | 1487 | 137 | 1313 | 0.0 | 939.9 |
| 10. | 1__27810 | gi\|7470961\|pir\|\|T31098 | 29.01 | 324 | 168 | 9 | 4 | 305 | 5 | 288 | 8.4e−21 | 105.1 |
| 11. | 1__27810 | gi\|7470961\|pir\|\|T31098 | 29.15 | 247 | 133 | 4 | 159 | 403 | 1168 | 1374 | 1.9e−17 | 93.97 |
| 12. | 1__27810 | gi\|7470961\|pir\|\|T31098 | 31.13 | 212 | 131 | 5 | 159 | 361 | 1298 | 1503 | 5.1e−13 | 79.34 |
| 13. | 1__27810 | gi\|7470961\|pir\|\|T31098 | 28.32 | 226 | 133 | 6 | 77 | 293 | 1293 | 1498 | 7.7e−05 | 51.99 |
| 14. | 1__27810 | gi\|7470961\|pir\|\|T31098 | 25.30 | 166 | 113 | 5 | 1308 | 1463 | 1273 | 1437 | 4.8e−04 | 49.29 |
| 15. | 1__27810 | gi\|7470961\|pir\|\|T31098 | 26.15 | 130 | 84 | 4 | 1355 | 1480 | 133 | 254 | 0.156 | 41.20 |
| 16. | 1__27810 | gi\|21654700\|gb\|AAG61158.1\| | 44.57 | 1373 | 643 | 26 | 133 | 1482 | 57 | 1334 | 0.0 | 939.5 |
| 17. | 1__27810 | gi\|21654700\|gb\|AAG61158.1\| | 29.62 | 314 | 194 | 8 | 5 | 304 | 5 | 305 | 1.9e−23 | 114.0 |
| 18. | 1__27810 | gi\|21654700\|gb\|AAG61158.1\| | 30.08 | 256 | 153 | 3 | 153 | 382 | 1203 | 1458 | 2.3e−17 | 93.59 |
| 19. | 1__27810 | gi\|21654700\|gb\|AAG61158.1\| | 30.70 | 215 | 133 | 5 | 157 | 361 | 1315 | 1523 | 3.3e−13 | 79.72 |
| 20. | 1__27810 | gi\|21654700\|gb\|AAG61158.1\| | 30.99 | 171 | 90 | 6 | 138 | 302 | 1378 | 1526 | 4.2e−05 | 52.76 |
| 21. | 1__27810 | gi\|21654700\|gb\|AAG61158.1\| | 27.32 | 194 | 106 | 7 | 1301 | 1461 | 1329 | 1520 | 0.122 | 41.59 |
| 22. | 1__27810 | gi\|7161825\|emb\|CAB76565.1\| | 47.46 | 1258 | 572 | 22 | 238 | 1487 | 106 | 1282 | 0.0 | 938.3 |
| 23. | 1__27810 | gi\|7161825\|emb\|CAB76565.1\| | 29.15 | 247 | 133 | 4 | 159 | 403 | 1137 | 1343 | 2.2e−17 | 93.59 |
| 24. | 1__27810 | gi\|7161825\|emb\|CAB76565.1\| | 29.77 | 262 | 167 | 6 | 48 | 305 | 9 | 257 | 4.1e−17 | 92.82 |
| 25. | 1__27810 | gi\|7161825\|emb\|CAB76565.1\| | 31.13 | 212 | 131 | 5 | 159 | 361 | 1267 | 1472 | 5.6e−13 | 78.95 |
| 26. | 1__27810 | gi\|7161825\|emb\|CAB76565.1\| | 28.32 | 226 | 133 | 6 | 77 | 293 | 1262 | 1467 | 8.5e−05 | 51.99 |
| 27. | 1__27810 | gi\|7161825\|emb\|CAB76565.1\| | 25.30 | 166 | 113 | 5 | 1308 | 1463 | 1242 | 1406 | 5.1e−04 | 49.29 |
| 28. | 1__27810 | gi\|7161825\|emb\|CAB76565.1\| | 26.15 | 130 | 84 | 4 | 1355 | 1480 | 102 | 223 | 0.165 | 40.82 |
| 29. | 1__27810 | gi\|4205088\|gb\|AAD10952.1\| | 44.36 | 1373 | 646 | 26 | 133 | 1482 | 57 | 1334 | 0.0 | 925.6 |
| 30. | 1__27810 | gi\|4205088\|gb\|AAD10952.1\| | 28.95 | 304 | 188 | 4 | 153 | 428 | 1203 | 1506 | 3.3e−18 | 96.67 |
| 31. | 1__27810 | gi\|4205088\|gb\|AAD10952.1\| | 31.16 | 215 | 132 | 5 | 157 | 361 | 1315 | 1523 | 1.0e−13 | 81.65 |
| 32. | 1__27810 | gi\|4205088\|gb\|AAD10952.1\| | 30.99 | 171 | 90 | 6 | 138 | 302 | 1378 | 1526 | 3.4e−05 | 53.14 |
| 33. | 1__27810 | gi\|4205088\|gb\|AAD10952.1\| | 27.84 | 194 | 105 | 7 | 1301 | 1461 | 1329 | 1520 | 0.026 | 43.51 |
| 34. | 1__27810 | gi\|3130083\|dbj\|BAA26107.1\| | 46.80 | 1171 | 536 | 20 | 343 | 1495 | 171 | 1272 | 0.0 | 864.0 |
| 35. | 1__27810 | gi\|3130083\|dbj\|BAA26107.1\| | 32.91 | 237 | 117 | 4 | 148 | 382 | 1174 | 1370 | 4.8e−22 | 109.4 |
| 36. | 1__27810 | gi\|3130083\|dbj\|BAA26107.1\| | 29.92 | 244 | 117 | 7 | 192 | 382 | 1064 | 1306 | 8.4e−14 | 81.65 |
| 37. | 1__27810 | gi\|3130083\|dbj\|BAA26107.1\| | 30.98 | 184 | 108 | 6 | 1308 | 1487 | 1226 | 1394 | 3.8e−11 | 73.17 |
| 38. | 1__27810 | gi\|3130083\|dbj\|BAA26107.1\| | 29.35 | 184 | 115 | 4 | 1302 | 1484 | 1285 | 1454 | 3.1e−09 | 66.63 |
| 39. | 1__27810 | gi\|3130083\|dbj\|BAA26107.1\| | 32.67 | 101 | 47 | 2 | 159 | 259 | 1316 | 1395 | 0.014 | 44.67 |
| 40. | 1__27810 | gi\|3130083\|dbj\|BAA26107.1\| | 26.48 | 219 | 142 | 7 | 5 | 214 | 2 | 210 | 0.214 | 40.43 |
| 41. | 1__27810 | gi\|153645\|gb\|AAA26895.1\| | 47.05 | 1171 | 533 | 20 | 343 | 1495 | 171 | 1272 | 0.0 | 862.8 |
| 42. | 1__27810 | gi\|153645\|gb\|AAA26895.1\| | 33.76 | 237 | 115 | 4 | 148 | 382 | 1174 | 1370 | 3.6e−23 | 112.8 |
| 43. | 1__27810 | gi\|153645\|gb\|AAA26895.1\| | 27.81 | 302 | 153 | 8 | 125 | 382 | 1026 | 1306 | 2.0e−17 | 93.97 |
| 44. | 1__27810 | gi\|153645\|gb\|AAA26895.1\| | 29.89 | 184 | 110 | 6 | 1308 | 1487 | 1226 | 1394 | 1.3e−09 | 67.78 |
| 45. | 1__27810 | gi\|153645\|gb\|AAA26895.1\| | 27.44 | 164 | 75 | 2 | 162 | 281 | 1254 | 1417 | 8.4e−07 | 58.54 |
| 46. | 1__27810 | gi\|153645\|gb\|AAA26895.1\| | 27.45 | 153 | 97 | 3 | 1302 | 1453 | 1285 | 1424 | 1.3e−05 | 54.68 |
| 47. | 1__27810 | gi\|153645\|gb\|AAA26895.1\| | 24.66 | 219 | 146 | 6 | 5 | 214 | 2 | 210 | 2.3 | 37.35 |
| 48. | 1__27810 | gi\|6166192\|sp\|P49331\| GTFD__STRMU | 47.05 | 1171 | 533 | 20 | 343 | 1495 | 171 | 1272 | 0.0 | 862.8 |
| 49. | 1__27810 | gi\|6166192\|sp\|P49331\| GTFD__STRMU | 33.76 | 237 | 115 | 4 | 148 | 382 | 1174 | 1370 | 3.6e−23 | 112.8 |
| 50. | 1__27810 | gi\|6166192\|sp\|P49331\| GTFD__STRMU | 27.81 | 302 | 153 | 8 | 125 | 382 | 1026 | 1306 | 2.0e−17 | 93.97 |
| 51. | 1__27810 | gi\|6166192\|sp\|P49331\| GTFD__STRMU | 29.89 | 184 | 110 | 6 | 1308 | 1487 | 1226 | 1394 | 1.3e−09 | 67.78 |
| 52. | 1__27810 | gi\|6166192\|sp\|P49331\| GTFD__STRMU | 28.80 | 184 | 116 | 4 | 1302 | 1484 | 1285 | 1454 | 5.3e−08 | 62.39 |
| 53. | 1__27810 | gi\|6166192\|sp\|P49331\| GTFD__STRMU | 32.67 | 101 | 47 | 2 | 159 | 259 | 1316 | 1395 | 0.015 | 44.28 |
| 54. | 1__27810 | gi\|6166192\|sp\|P49331\| GTFD__STRMU | 24.66 | 219 | 146 | 6 | 5 | 214 | 2 | 210 | 2.3 | 37.35 |
| 55. | 1__27810 | gi\|3130107\|dbj\|BAA26121.1\| | 46.97 | 1171 | 534 | 20 | 343 | 1495 | 171 | 1272 | 0.0 | 862.1 |
| 56. | 1__27810 | gi\|3130107\|dbj\|BAA26121.1\| | 32.91 | 237 | 117 | 4 | 148 | 382 | 1174 | 1370 | 1.3e−21 | 107.8 |
| 57. | 1__27810 | gi\|3130107\|dbj\|BAA26121.1\| | 30.06 | 316 | 161 | 9 | 84 | 382 | 1034 | 1306 | 1.4e−20 | 104.4 |
| 58. | 1__27810 | gi\|3130107\|dbj\|BAA26121.1\| | 29.35 | 184 | 111 | 6 | 1308 | 1487 | 1226 | 1394 | 5.0e−09 | 65.86 |
| 59. | 1__27810 | gi\|3130107\|dbj\|BAA26121.1\| | 29.35 | 184 | 115 | 4 | 1302 | 1484 | 1285 | 1454 | 6.7e−09 | 65.47 |
| 60. | 1__27810 | gi\|3130107\|dbj\|BAA26121.1\| | 32.67 | 101 | 47 | 2 | 159 | 259 | 1316 | 1395 | 0.014 | 44.67 |
| 61. | 1__27810 | gi\|3130107\|dbj\|BAA26121.1\| | 23.74 | 219 | 148 | 6 | 5 | 214 | 2 | 210 | 3.6 | 36.58 |
| 62. | 1__27810 | gi\|3130076\|dbj\|BAA26103.1\| | 46.97 | 1171 | 534 | 20 | 343 | 1495 | 171 | 1272 | 0.0 | 861.7 |
| 63. | 1__27810 | gi\|3130076\|dbj\|BAA26103.1\| | 33.76 | 237 | 115 | 4 | 148 | 382 | 1174 | 1370 | 3.3e−23 | 113.2 |

-continued

| No | Query id | Subject id | % identity | alignment length | mismatches | gap openings | q. start | q. end | s. start | s. end | e-value | bit score |
|---|---|---|---|---|---|---|---|---|---|---|---|---|
| 64. | 1__27810 | gi|3130076|dbj|BAA26103.1| | 27.81 | 302 | 153 | 8 | 125 | 382 | 1026 | 1306 | 2.0e−17 | 93.97 |
| 65. | 1__27810 | gi|3130076|dbj|BAA26103.1| | 29.89 | 184 | 110 | 6 | 1308 | 1487 | 1226 | 1394 | 1.3e−09 | 67.78 |
| 66. | 1__27810 | gi|3130076|dbj|BAA26103.1| | 28.80 | 184 | 116 | 4 | 1302 | 1484 | 1285 | 1454 | 1.1e−08 | 64.70 |
| 67. | 1__27810 | gi|3130076|dbj|BAA26103.1| | 32.67 | 101 | 47 | 2 | 159 | 259 | 1316 | 1395 | 0.015 | 44.67 |
| 68. | 1__27810 | gi|3130076|dbj|BAA26103.1| | 24.89 | 221 | 143 | 8 | 5 | 214 | 2 | 210 | 4.6 | 36.19 |
| 69. | 1__27810 | gi|419649|pir||A45866 | 47.05 | 1171 | 533 | 20 | 343 | 1495 | 171 | 1272 | 0.0 | 861.7 |
| 70. | 1__27810 | gi|419649|pir||A45866 | 33.76 | 237 | 115 | 4 | 148 | 382 | 1174 | 1370 | 4.0e−23 | 112.8 |
| 71. | 1__27810 | gi|419649|pir||A45866 | 27.81 | 302 | 153 | 8 | 125 | 382 | 1026 | 1306 | 2.3e−17 | 93.59 |
| 72. | 1__27810 | gi|419649|pir||A45866 | 29.89 | 184 | 110 | 6 | 1308 | 1487 | 1226 | 1394 | 1.4e−09 | 67.78 |
| 73. | 1__27810 | gi|419649|pir||A45866 | 28.12 | 160 | 101 | 3 | 1302 | 1460 | 1285 | 1431 | 4.5e−07 | 59.31 |
| 74. | 1__27810 | gi|419649|pir||A45866 | 27.44 | 164 | 75 | 2 | 162 | 281 | 1254 | 1417 | 8.8e−07 | 58.54 |
| 75. | 1__27810 | gi|419649|pir||A45866 | 39.34 | 61 | 36 | 1 | 159 | 219 | 1316 | 1375 | 0.644 | 38.89 |
| 76. | 1__27810 | gi|419649|pir||A45866 | 24.66 | 219 | 146 | 6 | 5 | 214 | 2 | 210 | 2.4 | 36.97 |
| 77. | 1__27810 | gi|3130090|dbj|BAA26111.1| | 46.80 | 1171 | 536 | 20 | 343 | 1495 | 171 | 1272 | 0.0 | 860.5 |
| 78. | 1__27810 | gi|3130090|dbj|BAA26111.1| | 33.33 | 237 | 116 | 4 | 148 | 382 | 1174 | 1370 | 8.4e−23 | 111.7 |
| 79. | 1__27810 | gi|3130090|dbj|BAA26111.1| | 27.48 | 302 | 154 | 8 | 125 | 382 | 1026 | 1306 | 7.6e−18 | 95.13 |
| 80. | 1__27810 | gi|3130090|dbj|BAA26111.1| | 29.89 | 184 | 110 | 6 | 1308 | 1487 | 1226 | 1394 | 1.3e−09 | 67.78 |
| 81. | 1__27810 | gi|3130090|dbj|BAA26111.1| | 28.80 | 184 | 116 | 4 | 1302 | 1484 | 1285 | 1454 | 1.1e−08 | 64.70 |
| 82. | 1__27810 | gi|3130090|dbj|BAA26111.1| | 32.67 | 101 | 47 | 2 | 159 | 259 | 1316 | 1395 | 0.015 | 44.28 |
| 83. | 1__27810 | gi|3130090|dbj|BAA26111.1| | 26.48 | 219 | 142 | 7 | 5 | 214 | 2 | 210 | 0.221 | 40.43 |
| 84. | 1__27810 | gi|3130097|dbj|BAA26115.1| | 46.46 | 1171 | 540 | 20 | 343 | 1495 | 171 | 1272 | 0.0 | 855.5 |
| 85. | 1__27810 | gi|3130097|dbj|BAA26115.1| | 33.33 | 237 | 116 | 4 | 148 | 382 | 1174 | 1370 | 2.9e−22 | 109.8 |
| 86. | 1__27810 | gi|3130097|dbj|BAA26115.1| | 27.81 | 302 | 153 | 8 | 125 | 382 | 1026 | 1306 | 1.9e−17 | 93.97 |
| 87. | 1__27810 | gi|3130097|dbj|BAA26115.1| | 29.89 | 184 | 110 | 6 | 1308 | 1487 | 1226 | 1394 | 1.1e−09 | 68.17 |
| 88. | 1__27810 | gi|3130097|dbj|BAA26115.1| | 28.80 | 184 | 116 | 4 | 1302 | 1484 | 1285 | 1454 | 9.5e−09 | 65.08 |
| 89. | 1__27810 | gi|3130097|dbj|BAA26115.1| | 32.67 | 101 | 47 | 2 | 159 | 259 | 1316 | 1395 | 0.014 | 44.67 |
| 90. | 1__27810 | gi|3130097|dbj|BAA26115.1| | 24.89 | 221 | 143 | 8 | 5 | 214 | 2 | 210 | 3.0 | 36.97 |
| 91. | 1__27810 | gi|7684297|dbj|BAA95201.1| | 46.41 | 1142 | 527 | 22 | 337 | 1465 | 217 | 1286 | 0.0 | 850.5 |
| 92. | 1__27810 | gi|7684297|dbj|BAA95201.1| | 31.09 | 238 | 122 | 5 | 147 | 382 | 1348 | 1545 | 5.2e−16 | 89.35 |
| 93. | 1__27810 | gi|7684297|dbj|BAA95201.1| | 35.62 | 146 | 73 | 2 | 155 | 299 | 1421 | 1546 | 8.3e−13 | 78.57 |
| 94. | 1__27810 | gi|7684297|dbj|BAA95201.1| | 26.56 | 418 | 207 | 14 | 45 | 382 | 1019 | 1416 | 3.6e−12 | 76.26 |
| 95. | 1__27810 | gi|7684297|dbj|BAA95201.1| | 27.85 | 219 | 131 | 5 | 180 | 395 | 1101 | 1295 | 1.3e−09 | 67.78 |
| 96. | 1__27810 | gi|7684297|dbj|BAA95201.1| | 29.48 | 173 | 108 | 3 | 1309 | 1480 | 1338 | 1497 | 8.0e−07 | 58.54 |
| 97. | 1__27810 | gi|7684297|dbj|BAA95201.1| | 26.34 | 224 | 137 | 7 | 1280 | 1489 | 1362 | 1571 | 9.4e−06 | 55.07 |
| 98. | 1__27810 | gi|7684297|dbj|BAA95201.1| | 25.93 | 189 | 110 | 5 | 74 | 234 | 1381 | 1567 | 0.012 | 44.67 |
| 99. | 1__27810 | gi|3130079|dbj|BAA26105.1| | 44.43 | 1265 | 599 | 28 | 286 | 1527 | 93 | 1276 | 0.0 | 837.0 |
| 100. | 1__27810 | gi|3130079|dbj|BAA26105.1| | 27.53 | 316 | 186 | 6 | 71 | 382 | 1129 | 1405 | 2.5e−20 | 103.6 |
| 101. | 1__27810 | gi|3130079|dbj|BAA26105.1| | 31.02 | 187 | 103 | 7 | 1308 | 1482 | 1259 | 1431 | 1.7e−14 | 83.96 |
| 102. | 1__27810 | gi|3130079|dbj|BAA26105.1| | 27.87 | 244 | 146 | 8 | 167 | 382 | 1099 | 1340 | 2.1e−14 | 83.96 |
| 103. | 1__27810 | gi|3130079|dbj|BAA26105.1| | 30.43 | 161 | 94 | 6 | 1308 | 1464 | 1324 | 1470 | 3.5e−12 | 76.26 |
| 104. | 1__27810 | gi|3130079|dbj|BAA26105.1| | 36.36 | 99 | 46 | 5 | 1308 | 1402 | 1389 | 1474 | 5.9e−05 | 52.37 |
| 105. | 1__27810 | gi|3130079|dbj|BAA26105.1| | 27.27 | 154 | 89 | 5 | 230 | 382 | 1079 | 1210 | 1.1e−04 | 51.60 |
| 106. | 1__27810 | gi|3130079|dbj|BAA26105.1| | 24.02 | 254 | 155 | 9 | 9 | 250 | 6 | 233 | 0.026 | 43.51 |
| 107. | 1__27810 | gi|1054877|gb|AAC43483.1| | 46.74 | 1136 | 522 | 21 | 342 | 1465 | 224 | 1288 | 0.0 | 836.6 |
| 108. | 1__27810 | gi|1054877|gb|AAC43483.1| | 32.75 | 229 | 112 | 6 | 157 | 382 | 1229 | 1418 | 2.5e−16 | 90.12 |
| 109. | 1__27810 | gi|1054877|gb|AAC43483.1| | 30.53 | 226 | 115 | 5 | 159 | 382 | 1362 | 1547 | 2.5e−15 | 87.04 |
| 110. | 1__27810 | gi|1054877|gb|AAC43483.1| | 27.76 | 407 | 223 | 14 | 45 | 414 | 1021 | 1393 | 7.8e−15 | 85.11 |
| 111. | 1__27810 | gi|1054877|gb|AAC43483.1| | 34.93 | 146 | 74 | 3 | 159 | 303 | 1427 | 1552 | 7.9e−11 | 72.02 |
| 112. | 1__27810 | gi|1054877|gb|AAC43483.1| | 26.56 | 192 | 126 | 5 | 1305 | 1495 | 1336 | 1513 | 9.4e−07 | 58.54 |
| 113. | 1__27810 | gi|1054877|gb|AAC43483.1| | 28.76 | 153 | 93 | 6 | 1315 | 1465 | 1410 | 1548 | 5.4e−05 | 52.76 |
| 114. | 1__27810 | gi|1054877|gb|AAC43483.1| | 24.46 | 139 | 81 | 3 | 1280 | 1406 | 1429 | 1555 | 7.9 | 35.42 |
| 115. | 1__27810 | gi|6166191|sp|P08987|GTFB_STRMU | 45.92 | 1200 | 548 | 25 | 286 | 1465 | 93 | 1211 | 0.0 | 836.3 |
| 116. | 1__27810 | gi|6166191|sp|P08987|GTFB_STRMU | 32.91 | 237 | 131 | 9 | 153 | 382 | 1255 | 1470 | 5.8e−21 | 105.5 |
| 117. | 1__27810 | gi|6166191|sp|P08987|GTFB_STRMU | 28.83 | 281 | 126 | 8 | 155 | 382 | 1146 | 1405 | 5.4e−18 | 95.90 |
| 118. | 1__27810 | gi|6166191|sp|P08987|GTFB_STRMU | 29.95 | 187 | 105 | 7 | 1308 | 1482 | 1259 | 1431 | 1.2e−13 | 81.26 |
| 119. | 1__27810 | gi|6166191|sp|P08987|GTFB_STRMU | 27.13 | 247 | 155 | 10 | 157 | 382 | 1098 | 1340 | 6.9e−13 | 78.95 |
| 120. | 1__27810 | gi|6166191|sp|P08987|GTFB_STRMU | 30.43 | 161 | 94 | 6 | 1308 | 1464 | 1324 | 1470 | 3.5e−12 | 76.26 |
| 121. | 1__27810 | gi|6166191|sp|P08987|GTFB_STRMU | 34.62 | 156 | 80 | 3 | 148 | 301 | 1338 | 1473 | 4.1e−12 | 76.26 |
| 122. | 1__27810 | gi|6166191|sp|P08987|GTFB_STRMU | 27.27 | 154 | 89 | 5 | 230 | 382 | 1079 | 1210 | 1.1e−04 | 51.60 |
| 123. | 1__27810 | gi|6166191|sp|P08987|GTFB_STRMU | 23.23 | 254 | 157 | 8 | 9 | 250 | 6 | 233 | 0.020 | 43.90 |
| 124. | 1__27810 | gi|3130103|dbj|BAA26119.1| | 45.92 | 1200 | 548 | 25 | 286 | 1465 | 93 | 1211 | 0.0 | 836.3 |
| 125. | 1__27810 | gi|3130103|dbj|BAA26119.1| | 32.91 | 237 | 131 | 9 | 153 | 382 | 1255 | 1470 | 2.9e−21 | 106.7 |
| 126. | 1__27810 | gi|3130103|dbj|BAA26119.1| | 28.83 | 281 | 126 | 8 | 155 | 382 | 1146 | 1405 | 5.4e−18 | 95.90 |
| 127. | 1__27810 | gi|3130103|dbj|BAA26119.1| | 29.95 | 187 | 105 | 7 | 1308 | 1482 | 1259 | 1431 | 1.2e−13 | 81.26 |
| 128. | 1__27810 | gi|3130103|dbj|BAA26119.1| | 27.13 | 247 | 155 | 10 | 157 | 382 | 1098 | 1340 | 6.9e−13 | 78.95 |
| 129. | 1__27810 | gi|3130103|dbj|BAA26119.1| | 34.62 | 156 | 80 | 3 | 148 | 301 | 1338 | 1473 | 2.1e−12 | 77.03 |

-continued

| No | Query id | Subject id | % identity | alignment length | mis-matches | gap openings | q. start | q. end | s. start | s. end | e-value | bit score |
|---|---|---|---|---|---|---|---|---|---|---|---|---|
| 130. | 1__27810 | gi\|3130103\|dbj\|BAA26119.1\| | 30.43 | 161 | 94 | 6 | 1308 | 1464 | 1324 | 1470 | 2.7e-12 | 77.03 |
| 131. | 1__27810 | gi\|3130103\|dbj\|BAA26119.1\| | 27.27 | 154 | 89 | 5 | 230 | 382 | 1079 | 1210 | 1.1e-04 | 51.60 |
| 132. | 1__27810 | gi\|3130103\|dbj\|BAA26119.1\| | 24.02 | 254 | 155 | 9 | 9 | 250 | 6 | 233 | 0.026 | 43.51 |
| 133. | 1__27810 | gi\|3130072\|dbj\|BAA26101.1\| | 44.51 | 1265 | 598 | 28 | 286 | 1527 | 93 | 1276 | 0.0 | 835.9 |
| 134. | 1__27810 | gi\|3130072\|dbj\|BAA26101.1\| | 26.90 | 316 | 188 | 6 | 71 | 382 | 1129 | 1405 | 7.1e-20 | 102.1 |
| 135. | 1__27810 | gi\|3130072\|dbj\|BAA26101.1\| | 28.28 | 244 | 145 | 8 | 167 | 382 | 1099 | 1340 | 9.1e-15 | 85.11 |
| 136. | 1__27810 | gi\|3130072\|dbj\|BAA26101.1\| | 30.43 | 161 | 94 | 6 | 1308 | 1464 | 1324 | 1470 | 2.9e-12 | 76.64 |
| 137. | 1__27810 | gi\|3130072\|dbj\|BAA26101.1\| | 28.80 | 191 | 110 | 7 | 1304 | 1482 | 1190 | 1366 | 2.6e-11 | 73.56 |
| 138. | 1__27810 | gi\|3130072\|dbj\|BAA26101.1\| | 26.62 | 154 | 90 | 5 | 230 | 382 | 1079 | 1210 | 0.001 | 48.14 |
| 139. | 1__27810 | gi\|3130072\|dbj\|BAA26101.1\| | 24.02 | 254 | 155 | 9 | 9 | 250 | 6 | 233 | 0.026 | 43.51 |
| 140. | 1__27810 | gi\|3130093\|dbj\|BAA26113.1\| | 44.27 | 1265 | 601 | 28 | 286 | 1527 | 93 | 1276 | 0.0 | 832.8 |
| 141. | 1__27810 | gi\|3130093\|dbj\|BAA26113.1\| | 27.53 | 316 | 186 | 6 | 71 | 382 | 1129 | 1405 | 1.6e-20 | 104.0 |
| 142. | 1__27810 | gi\|3130093\|dbj\|BAA26113.1\| | 31.02 | 187 | 103 | 7 | 1308 | 1482 | 1259 | 1431 | 1.7e-14 | 83.96 |
| 143. | 1__27810 | gi\|3130093\|dbj\|BAA26113.1\| | 27.87 | 244 | 146 | 8 | 167 | 382 | 1099 | 1340 | 2.1e-14 | 83.96 |
| 144. | 1__27810 | gi\|3130093\|dbj\|BAA26113.1\| | 30.43 | 161 | 94 | 6 | 1308 | 1464 | 1324 | 1470 | 3.5e-12 | 76.26 |
| 145. | 1__27810 | gi\|3130093\|dbj\|BAA26113.1\| | 27.92 | 154 | 88 | 5 | 230 | 382 | 1079 | 1210 | 3.0e-05 | 53.53 |
| 146. | 1__27810 | gi\|3130093\|dbj\|BAA26113.1\| | 36.36 | 99 | 46 | 5 | 1308 | 1402 | 1389 | 1474 | 5.9e-05 | 52.37 |
| 147. | 1__27810 | gi\|3130093\|dbj\|BAA26113.1\| | 24.41 | 254 | 154 | 9 | 9 | 250 | 6 | 233 | 0.006 | 45.82 |
| 148. | 1__27810 | gi\|3130086\|dbj\|BAA26109.1\| | 45.83 | 1200 | 549 | 25 | 286 | 1465 | 93 | 1211 | 0.0 | 832.8 |
| 149. | 1__27810 | gi\|3130086\|dbj\|BAA26109.1\| | 27.22 | 316 | 187 | 6 | 71 | 382 | 1129 | 1405 | 3.3e-20 | 103.2 |
| 150. | 1__27810 | gi\|3130086\|dbj\|BAA26109.1\| | 26.92 | 286 | 145 | 7 | 142 | 382 | 1074 | 1340 | 6.4e-15 | 85.50 |
| 151. | 1__27810 | gi\|3130086\|dbj\|BAA26109.1\| | 29.13 | 206 | 117 | 7 | 1301 | 1482 | 1166 | 1366 | 5.8e-12 | 75.87 |
| 152. | 1__27810 | gi\|3130086\|dbj\|BAA26109.1\| | 35.35 | 99 | 47 | 5 | 1308 | 1402 | 1389 | 1474 | 1.4e-04 | 51.22 |
| 153. | 1__27810 | gi\|3130086\|dbj\|BAA26109.1\| | 23.92 | 255 | 154 | 9 | 9 | 250 | 6 | 233 | 0.056 | 42.74 |
| 154. | 1__27810 | gi\|121728\|sp\|P13470\|GTFC__STRMU | 45.07 | 1216 | 557 | 26 | 346 | 1537 | 187 | 1315 | 0.0 | 824.7 |
| 155. | 1__27810 | gi\|121728\|sp\|P13470\|GTFC__STRMU | 31.37 | 204 | 91 | 6 | 155 | 351 | 1175 | 1336 | 1.3e-14 | 84.73 |
| 156. | 1__27810 | gi\|121728\|sp\|P13470\|GTFC__STRMU | 26.55 | 226 | 114 | 6 | 202 | 382 | 1085 | 1303 | 4.2e-08 | 62.77 |
| 157. | 1__27810 | gi\|121728\|sp\|P13470\|GTFC__STRMU | 27.86 | 140 | 77 | 3 | 133 | 268 | 1218 | 1337 | 7.7e-04 | 48.91 |
| 158. | 1__27810 | gi\|121728\|sp\|P13470\|GTFC__STRMU | 29.50 | 139 | 89 | 5 | 295 | 425 | 1087 | 1224 | 0.003 | 46.98 |
| 159. | 1__27810 | gi\|3130095\|dbj\|BAA26114.1\| | 46.73 | 1162 | 510 | 26 | 346 | 1482 | 187 | 1264 | 0.0 | 824.3 |
| 160. | 1__27810 | gi\|3130095\|dbj\|BAA26114.1\| | 28.85 | 253 | 133 | 7 | 162 | 387 | 1205 | 1437 | 1.1e-14 | 84.73 |
| 161. | 1__27810 | gi\|3130095\|dbj\|BAA26114.1\| | 30.69 | 202 | 124 | 6 | 1300 | 1487 | 1193 | 1392 | 1.5e-12 | 77.80 |
| 162. | 1__27810 | gi\|3130095\|dbj\|BAA26114.1\| | 26.55 | 226 | 114 | 6 | 202 | 382 | 1085 | 1303 | 8.0e-08 | 62.00 |
| 163. | 1__27810 | gi\|3130095\|dbj\|BAA26114.1\| | 35.16 | 128 | 77 | 5 | 155 | 277 | 1285 | 1411 | 6.7e-07 | 58.92 |
| 164. | 1__27810 | gi\|3130095\|dbj\|BAA26114.1\| | 29.50 | 139 | 89 | 5 | 295 | 425 | 1087 | 1224 | 0.004 | 46.21 |
| 165. | 1__27810 | gi\|3130081\|dbj\|BAA26106.1\| | 46.73 | 1162 | 510 | 26 | 346 | 1482 | 187 | 1264 | 0.0 | 823.9 |
| 166. | 1__27810 | gi\|3130081\|dbj\|BAA26106.1\| | 29.58 | 240 | 120 | 6 | 155 | 387 | 1175 | 1372 | 1.1e-15 | 88.20 |
| 167. | 1__27810 | gi\|3130081\|dbj\|BAA26106.1\| | 30.46 | 174 | 103 | 6 | 1300 | 1460 | 1193 | 1361 | 8.6e-09 | 65.08 |
| 168. | 1__27810 | gi\|3130081\|dbj\|BAA26106.1\| | 26.55 | 226 | 114 | 6 | 202 | 382 | 1085 | 1303 | 8.0e-08 | 62.00 |
| 169. | 1__27810 | gi\|3130081\|dbj\|BAA26106.1\| | 29.50 | 139 | 89 | 5 | 295 | 425 | 1087 | 1224 | 0.004 | 46.21 |
| 170. | 1__27810 | gi\|3130088\|dbj\|BAA26110.1\| | 46.73 | 1162 | 510 | 26 | 346 | 1482 | 187 | 1264 | 0.0 | 822.4 |
| 171. | 1__27810 | gi\|3130088\|dbj\|BAA26110.1\| | 28.85 | 253 | 133 | 7 | 162 | 387 | 1205 | 1437 | 1.1e-14 | 84.73 |
| 172. | 1__27810 | gi\|3130088\|dbj\|BAA26110.1\| | 26.18 | 359 | 212 | 9 | 112 | 421 | 1072 | 1426 | 5.8e-13 | 78.95 |
| 173. | 1__27810 | gi\|3130088\|dbj\|BAA26110.1\| | 30.69 | 202 | 124 | 6 | 1300 | 1487 | 1193 | 1392 | 1.7e-12 | 77.41 |
| 174. | 1__27810 | gi\|3130088\|dbj\|BAA26110.1\| | 28.06 | 139 | 91 | 5 | 295 | 425 | 1087 | 1224 | 0.077 | 41.97 |
| 175. | 1__27810 | gi\|3130074\|dbj\|BAA26102.1\| | 45.20 | 1219 | 551 | 28 | 346 | 1537 | 187 | 1315 | 0.0 | 820.8 |
| 176. | 1__27810 | gi\|3130074\|dbj\|BAA26102.1\| | 29.64 | 253 | 131 | 8 | 162 | 387 | 1205 | 1437 | 3.7e-15 | 86.27 |
| 177. | 1__27810 | gi\|3130074\|dbj\|BAA26102.1\| | 27.04 | 318 | 183 | 7 | 112 | 380 | 1072 | 1389 | 2.8e-13 | 80.11 |
| 178. | 1__27810 | gi\|3130074\|dbj\|BAA26102.1\| | 30.20 | 202 | 125 | 6 | 1300 | 1487 | 1193 | 1392 | 2.9e-12 | 76.64 |
| 179. | 1__27810 | gi\|3130074\|dbj\|BAA26102.1\| | 29.50 | 139 | 89 | 5 | 295 | 425 | 1087 | 1224 | 0.005 | 46.21 |
| 180. | 1__27810 | gi\|3130105\|dbj\|BAA26120.1\| | 45.20 | 1219 | 551 | 28 | 346 | 1537 | 187 | 1315 | 0.0 | 819.7 |
| 181. | 1__27810 | gi\|3130105\|dbj\|BAA26120.1\| | 27.69 | 260 | 143 | 5 | 133 | 387 | 1218 | 1437 | 4.5e-15 | 85.89 |
| 182. | 1__27810 | gi\|3130105\|dbj\|BAA26120.1\| | 27.33 | 300 | 186 | 8 | 112 | 382 | 1072 | 1368 | 4.4e-13 | 79.34 |
| 183. | 1__27810 | gi\|3130105\|dbj\|BAA26120.1\| | 30.69 | 202 | 124 | 6 | 1300 | 1487 | 1193 | 1392 | 2.7e-12 | 76.64 |
| 184. | 1__27810 | gi\|3130105\|dbj\|BAA26120.1\| | 29.50 | 139 | 89 | 5 | 295 | 425 | 1087 | 1224 | 0.004 | 46.59 |
| 185. | 1__27810 | gi\|97988\|pir\|\|B33135 | 45.17 | 1200 | 556 | 25 | 286 | 1465 | 93 | 1210 | 0.0 | 816.6 |
| 186. | 1__27810 | gi\|97988\|pir\|\|B33135 | 27.53 | 316 | 186 | 6 | 71 | 382 | 1128 | 1404 | 5.9e-21 | 105.3 |
| 187. | 1__27810 | gi\|97988\|pir\|\|B33135 | 27.87 | 244 | 146 | 8 | 167 | 382 | 1098 | 1339 | 3.0e-14 | 83.19 |
| 188. | 1__27810 | gi\|97988\|pir\|\|B33135 | 29.21 | 202 | 122 | 6 | 1301 | 1482 | 1165 | 1365 | 3.1e-12 | 76.64 |
| 189. | 1__27810 | gi\|97988\|pir\|\|B33135 | 27.27 | 154 | 89 | 5 | 230 | 382 | 1078 | 1209 | 7.9e-05 | 51.99 |
| 190. | 1__27810 | gi\|97988\|pir\|\|B33135 | 23.23 | 254 | 157 | 8 | 9 | 250 | 6 | 233 | 0.015 | 44.28 |
| 191. | 1__27810 | gi\|1022963\|gb\|AAB40875.1\| | 42.53 | 1225 | 590 | 30 | 343 | 1541 | 1 | 1137 | 0.0 | 791.2 |
| 192. | 1__27810 | gi\|1022963\|gb\|AAB40875.1\| | 29.69 | 229 | 154 | 5 | 162 | 385 | 1060 | 1286 | 5.5e-18 | 95.90 |
| 193. | 1__27810 | gi\|1022963\|gb\|AAB40875.1\| | 29.18 | 257 | 149 | 7 | 158 | 382 | 964 | 1219 | 8.0e-14 | 82.03 |
| 194. | 1__27810 | gi\|1022963\|gb\|AAB40875.1\| | 26.24 | 263 | 137 | 9 | 173 | 382 | 897 | 1155 | 1.0e-07 | 61.62 |
| 195. | 1__27810 | gi\|1022963\|gb\|AAB40875.1\| | 25.63 | 238 | 131 | 9 | 186 | 380 | 855 | 1089 | 5.0e-04 | 49.29 |
| 196. | 1__27810 | gi\|1022963\|gb\|AAB40875.1\| | 25.62 | 160 | 104 | 5 | 1306 | 1464 | 1138 | 1283 | 0.042 | 43.13 |
| 197. | 1__27810 | gi\|7470958\|pir\|\|JC5473 | 42.45 | 1225 | 591 | 30 | 343 | 1541 | 1 | 1137 | 0.0 | 789.3 |
| 198. | 1__27810 | gi\|7470958\|pir\|\|JC5473 | 29.69 | 229 | 154 | 5 | 162 | 385 | 1060 | 1286 | 1.1e-17 | 94.74 |
| 199. | 1__27810 | gi\|7470958\|pir\|\|JC5473 | 29.18 | 257 | 149 | 7 | 158 | 382 | 964 | 1219 | 6.7e-14 | 82.03 |

-continued

| No | Query id | Subject id | % identity | alignment length | mismatches | gap openings | q. start | q. end | s. start | s. end | e-value | bit score |
|---|---|---|---|---|---|---|---|---|---|---|---|---|
| 200. | 1__27810 | gi\|7470958\|pir\|\|JC5473 | 26.24 | 263 | 137 | 9 | 173 | 382 | 897 | 1155 | 1.0e−07 | 61.62 |
| 201. | 1__27810 | gi\|7470958\|pir\|\|JC5473 | 25.63 | 238 | 131 | 9 | 186 | 380 | 855 | 1089 | 5.0e−04 | 49.29 |
| 202. | 1__27810 | gi\|7470958\|pir\|\|JC5473 | 26.25 | 160 | 103 | 5 | 1306 | 1464 | 1138 | 1283 | 0.009 | 45.05 |
| 203. | 1__27810 | gi\|450874\|dbj\|BAA02976.1\| | 39.54 | 1429 | 725 | 32 | 343 | 1729 | 151 | 1482 | 0.0 | 769.6 |
| 204. | 1__27810 | gi\|450874\|dbj\|BAA02976.1\| | 27.78 | 288 | 156 | 9 | 144 | 382 | 1051 | 1335 | 3.1e−12 | 76.64 |
| 205. | 1__27810 | gi\|450874\|dbj\|BAA02976.1\| | 26.03 | 292 | 157 | 8 | 151 | 383 | 1271 | 1562 | 3.6e−10 | 69.71 |
| 206. | 1__27810 | gi\|450874\|dbj\|BAA02976.1\| | 23.16 | 393 | 235 | 9 | 81 | 430 | 1137 | 1505 | 4.4e−10 | 69.32 |
| 207. | 1__27810 | gi\|450874\|dbj\|BAA02976.1\| | 30.00 | 190 | 101 | 7 | 123 | 281 | 1355 | 1543 | 3.0e−06 | 56.61 |
| 208. | 1__27810 | gi\|450874\|dbj\|BAA02976.1\| | 24.12 | 228 | 111 | 6 | 1310 | 1487 | 1257 | 1472 | 0.005 | 45.82 |
| 209. | 1__27810 | gi\|450874\|dbj\|BAA02976.1\| | 32.73 | 110 | 59 | 4 | 270 | 365 | 1017 | 1125 | 0.117 | 41.59 |
| 210. | 1__27810 | gi\|450874\|dbj\|BAA02976.1\| | 23.22 | 211 | 124 | 7 | 1311 | 1484 | 1372 | 1581 | 3.2 | 36.58 |
| 211. | 1__27810 | gi\|940427\|dbj\|BAA09792.1\| | 43.66 | 1175 | 564 | 23 | 336 | 1495 | 144 | 1235 | 0.0 | 768.8 |
| 212. | 1__27810 | gi\|940427\|dbj\|BAA09792.1\| | 27.57 | 243 | 149 | 7 | 144 | 382 | 1051 | 1270 | 8.3e−13 | 78.57 |
| 213. | 1__27810 | gi\|940427\|dbj\|BAA09792.1\| | 28.37 | 215 | 109 | 5 | 172 | 382 | 1162 | 1335 | 3.3e−12 | 76.64 |
| 214. | 1__27810 | gi\|940427\|dbj\|BAA09792.1\| | 25.45 | 334 | 196 | 9 | 81 | 382 | 1137 | 1449 | 1.3e−09 | 67.78 |
| 215. | 1__27810 | gi\|940427\|dbj\|BAA09792.1\| | 25.68 | 292 | 158 | 8 | 151 | 383 | 1271 | 1562 | 4.1e−09 | 66.24 |
| 216. | 1__27810 | gi\|940427\|dbj\|BAA09792.1\| | 22.75 | 233 | 139 | 5 | 1295 | 1487 | 1241 | 1472 | 0.077 | 41.97 |
| 217. | 1__27810 | gi\|940427\|dbj\|BAA09792.1\| | 32.73 | 110 | 59 | 4 | 270 | 365 | 1017 | 1125 | 0.110 | 41.59 |
| 218. | 1__27810 | gi\|121724\|sp\|P11001\|GTF1_STRDO | 42.87 | 1199 | 583 | 24 | 317 | 1495 | 126 | 1242 | 0.0 | 762.3 |
| 219. | 1__27810 | gi\|121724\|sp\|P11001\|GTF1_STRDO | 28.15 | 302 | 149 | 11 | 155 | 434 | 1148 | 1403 | 3.5e−13 | 79.72 |
| 220. | 1__27810 | gi\|121724\|sp\|P11001\|GTF1_STRDO | 31.43 | 175 | 105 | 4 | 1315 | 1487 | 1204 | 1365 | 4.7e−13 | 79.34 |
| 221. | 1__27810 | gi\|121724\|sp\|P11001\|GTF1_STRDO | 24.68 | 393 | 232 | 10 | 81 | 431 | 1143 | 1513 | 3.7e−12 | 76.26 |
| 222. | 1__27810 | gi\|121724\|sp\|P11001\|GTF1_STRDO | 27.40 | 292 | 153 | 9 | 151 | 383 | 1278 | 1569 | 6.9e−11 | 72.02 |
| 223. | 1__27810 | gi\|121724\|sp\|P11001\|GTF1_STRDO | 33.66 | 202 | 108 | 10 | 156 | 340 | 1397 | 1589 | 8.4e−08 | 62.00 |
| 224. | 1__27810 | gi\|121724\|sp\|P11001\|GTF1_STRDO | 23.36 | 244 | 123 | 6 | 1295 | 1487 | 1248 | 1478 | 0.001 | 47.75 |
| 225. | 1__27810 | gi\|121724\|sp\|P11001\|GTF1_STRDO | 22.05 | 195 | 104 | 5 | 234 | 382 | 1085 | 1277 | 0.029 | 43.51 |
| 226. | 1__27810 | gi\|121724\|sp\|P11001\|GTF1_STRDO | 29.48 | 173 | 101 | 6 | 53 | 219 | 1416 | 1573 | 0.079 | 41.97 |
| 227. | 1__27810 | gi\|121724\|sp\|P11001\|GTF1_STRDO | 23.86 | 176 | 118 | 4 | 1317 | 1487 | 1427 | 1591 | 0.365 | 39.66 |
| 228. | 1__27810 | gi\|121725\|sp\|P27470\|GTF2_STRDO | 39.19 | 1429 | 732 | 31 | 343 | 1729 | 151 | 1484 | 0.0 | 760.0 |
| 229. | 1__27810 | gi\|121725\|sp\|P27470\|GTF2_STRDO | 27.08 | 288 | 160 | 8 | 144 | 382 | 1051 | 1337 | 7.2e−12 | 75.48 |
| 230. | 1__27810 | gi\|121725\|sp\|P27470\|GTF2_STRDO | 22.78 | 395 | 236 | 10 | 81 | 430 | 1137 | 1507 | 7.6e−09 | 65.47 |
| 231. | 1__27810 | gi\|121725\|sp\|P27470\|GTF2_STRDO | 30.51 | 236 | 138 | 11 | 123 | 340 | 1357 | 1584 | 4.6e−08 | 62.77 |
| 232. | 1__27810 | gi\|121725\|sp\|P27470\|GTF2_STRDO | 24.89 | 221 | 147 | 3 | 166 | 383 | 1360 | 1564 | 9.0e−06 | 55.07 |
| 233. | 1__27810 | gi\|121725\|sp\|P27470\|GTF2_STRDO | 22.15 | 438 | 250 | 14 | 1176 | 1556 | 1138 | 1541 | 0.306 | 40.05 |
| 234. | 1__27810 | gi\|121725\|sp\|P27470\|GTF2_STRDO | 23.70 | 211 | 123 | 7 | 1311 | 1484 | 1374 | 1583 | 0.633 | 38.89 |
| 235. | 1__27810 | gi\|4691429\|dbj\|BAA77237.1\| | 43.10 | 1167 | 575 | 23 | 337 | 1480 | 159 | 1259 | 0.0 | 756.5 |
| 236. | 1__27810 | gi\|4691429\|dbj\|BAA77237.1\| | 29.69 | 293 | 145 | 9 | 149 | 382 | 1061 | 1351 | 2.3e−13 | 80.49 |
| 237. | 1__27810 | gi\|4691429\|dbj\|BAA77237.1\| | 28.19 | 259 | 152 | 10 | 156 | 382 | 1248 | 1504 | 4.9e−11 | 72.79 |
| 238. | 1__27810 | gi\|4691429\|dbj\|BAA77237.1\| | 26.67 | 195 | 122 | 5 | 1303 | 1487 | 1281 | 1464 | 1.4e−08 | 64.31 |
| 239. | 1__27810 | gi\|4691429\|dbj\|BAA77237.1\| | 30.32 | 221 | 119 | 6 | 197 | 383 | 1067 | 1286 | 2.3e−08 | 63.93 |
| 240. | 1__27810 | gi\|4691429\|dbj\|BAA77237.1\| | 26.90 | 171 | 116 | 6 | 135 | 298 | 1336 | 1504 | 7.9e−05 | 51.99 |
| 241. | 1__27810 | gi\|4691429\|dbj\|BAA77237.1\| | 22.73 | 242 | 161 | 6 | 2 | 218 | 1268 | 1508 | 6.3 | 35.81 |
| 242. | 1__27810 | gi\|7474116\|pir\|\|T30858 | 43.56 | 1157 | 556 | 24 | 344 | 1482 | 269 | 1346 | 0.0 | 753.1 |
| 243. | 1__27810 | gi\|7474116\|pir\|\|T30858 | 29.12 | 261 | 124 | 3 | 162 | 382 | 1332 | 1571 | 6.7e−18 | 95.52 |
| 244. | 1__27810 | gi\|7474116\|pir\|\|T30858 | 32.58 | 221 | 104 | 6 | 167 | 382 | 1204 | 1384 | 2.7e−17 | 93.59 |
| 245. | 1__27810 | gi\|7474116\|pir\|\|T30858 | 33.13 | 166 | 84 | 2 | 133 | 298 | 1433 | 1571 | 1.9e−12 | 77.41 |
| 246. | 1__27810 | gi\|7474116\|pir\|\|T30858 | 23.83 | 277 | 179 | 9 | 1309 | 1573 | 1281 | 1537 | 2.6e−05 | 53.53 |
| 247. | 1__27810 | gi\|7474116\|pir\|\|T30858 | 28.84 | 215 | 101 | 10 | 1283 | 1464 | 1312 | 1507 | 5.5e−05 | 52.37 |
| 248. | 1__27810 | gi\|7474116\|pir\|\|T30858 | 34.18 | 79 | 52 | 0 | 137 | 215 | 1494 | 1572 | 0.005 | 45.82 |
| 249. | 1__27810 | gi\|322084\|pir\|\|A44811 | 41.61 | 1264 | 626 | 29 | 343 | 1558 | 173 | 1372 | 0.0 | 738.4 |
| 250. | 1__27810 | gi\|322084\|pir\|\|A44811 | 27.54 | 276 | 130 | 6 | 165 | 391 | 1244 | 1498 | 3.4e−13 | 79.72 |
| 251. | 1__27810 | gi\|322084\|pir\|\|A44811 | 27.80 | 295 | 186 | 10 | 102 | 371 | 1058 | 1350 | 2.5e−11 | 73.56 |
| 252. | 1__27810 | gi\|322084\|pir\|\|A44811 | 27.75 | 173 | 105 | 7 | 1314 | 1481 | 1283 | 1440 | 2.2e−04 | 50.45 |
| 253. | 1__27810 | gi\|322084\|pir\|\|A44811 | 22.84 | 162 | 107 | 5 | 1307 | 1464 | 1340 | 1487 | 1.8 | 37.74 |
| 254. | 1__27810 | gi\|322084\|pir\|\|A44811 | 22.22 | 117 | 76 | 3 | 1307 | 1420 | 1405 | 1509 | 3.7 | 36.58 |
| 255. | 1__27810 | gi\|22138845\|dbj\|BAC07265.1\| | 41.82 | 1308 | 641 | 34 | 210 | 1491 | 43 | 1256 | 0.0 | 716.8 |
| 256. | 1__27810 | gi\|22138845\|dbj\|BAC07265.1\| | 29.15 | 319 | 161 | 11 | 165 | 430 | 1173 | 1479 | 1.7e−14 | 83.96 |
| 257. | 1__27810 | gi\|22138845\|dbj\|BAC07265.1\| | 29.18 | 233 | 157 | 8 | 159 | 383 | 1319 | 1551 | 5.4e−09 | 65.86 |

-continued

| No | Query id | Subject id | % identity | alignment length | mis-matches | gap openings | q. start | q. end | s. start | s. end | e-value | bit score |
|---|---|---|---|---|---|---|---|---|---|---|---|---|
| 258. | 1__27810 | gi\|22138845\|dbj\|BAC07265.1\| | 29.77 | 262 | 148 | 9 | 156 | 382 | 1072 | 1332 | 1.3e−08 | 64.70 |
| 259. | 1__27810 | gi\|22138845\|dbj\|BAC07265.1\| | 26.32 | 171 | 112 | 5 | 1308 | 1465 | 1360 | 1529 | 6.6e−05 | 52.37 |
| 260. | 1__27810 | gi\|22138845\|dbj\|BAC07265.1\| | 25.36 | 209 | 120 | 8 | 1308 | 1480 | 1271 | 1479 | 1.9e−04 | 50.83 |
| 261. | 1__27810 | gi\|22138845\|dbj\|BAC07265.1\| | 25.40 | 126 | 83 | 2 | 1317 | 1441 | 1434 | 1549 | 0.165 | 40.82 |
| 262. | 1__27810 | gi\|22138845\|dbj\|BAC07265.1\| | 26.45 | 155 | 93 | 4 | 69 | 219 | 1396 | 1533 | 0.245 | 40.43 |
| 263. | 1__27810 | gi\|7474115\|pir\|\|T30857 | 42.30 | 1201 | 565 | 27 | 309 | 1458 | 168 | 1291 | 0.0 | 716.5 |
| 264. | 1__27810 | gi\|7474115\|pir\|\|T30857 | 37.36 | 182 | 106 | 6 | 162 | 339 | 1244 | 1421 | 1.9e−15 | 87.43 |
| 265. | 1__27810 | gi\|7474115\|pir\|\|T30857 | 27.43 | 226 | 142 | 5 | 171 | 382 | 1079 | 1296 | 4.6e−11 | 72.79 |
| 266. | 1__27810 | gi\|7474115\|pir\|\|T30857 | 27.85 | 158 | 96 | 7 | 1309 | 1464 | 1282 | 1423 | 7.1e−04 | 48.91 |
| 267. | 1__27810 | gi\|7474117\|pir\|\|T30552 | 41.78 | 1228 | 585 | 27 | 287 | 1458 | 138 | 1291 | 0.0 | 715.7 |
| 268. | 1__27810 | gi\|7474117\|pir\|\|T30552 | 23.82 | 382 | 209 | 9 | 46 | 382 | 1079 | 1423 | 6.0e−13 | 78.95 |
| 269. | 1__27810 | gi\|7474117\|pir\|\|T30552 | 29.19 | 185 | 88 | 1 | 162 | 303 | 1244 | 1428 | 6.7e−12 | 75.48 |
| 270. | 1__27810 | gi\|7474117\|pir\|\|T30552 | 26.99 | 226 | 143 | 5 | 171 | 382 | 1079 | 1296 | 1.1e−10 | 71.63 |
| 271. | 1__27810 | gi\|7474117\|pir\|\|T30552 | 27.85 | 158 | 96 | 7 | 1309 | 1464 | 1282 | 1423 | 6.6e−04 | 48.91 |
| 272. | 1__27810 | gi\|79931\|pir\|\|S22737 | 43.14 | 1159 | 559 | 30 | 351 | 1480 | 176 | 1263 | 0.0 | 709.9 |
| 273. | 1__27810 | gi\|79931\|pir\|\|S22737 | 27.87 | 305 | 160 | 7 | 130 | 382 | 1275 | 1571 | 1.6e−17 | 94.36 |
| 274. | 1__27810 | gi\|79931\|pir\|\|S22737 | 28.83 | 222 | 131 | 5 | 164 | 379 | 1196 | 1396 | 5.2e−13 | 79.34 |
| 275. | 1__27810 | gi\|79931\|pir\|\|S22737 | 28.09 | 178 | 106 | 3 | 128 | 303 | 1419 | 1576 | 4.1e−08 | 62.77 |
| 276. | 1__27810 | gi\|79931\|pir\|\|S22737 | 25.99 | 177 | 115 | 6 | 1306 | 1481 | 1208 | 1369 | 8.5e−05 | 51.99 |
| 277. | 1__27810 | gi\|79931\|pir\|\|S22737 | 25.86 | 232 | 146 | 8 | 168 | 385 | 1031 | 1250 | 8.3e−04 | 48.52 |
| 278. | 1__27810 | gi\|79931\|pir\|\|S22737 | 21.00 | 300 | 199 | 7 | 1190 | 1464 | 1285 | 1571 | 0.003 | 46.59 |
| 279. | 1__27810 | gi\|79931\|pir\|\|S22737 | 22.95 | 244 | 150 | 8 | 1299 | 1520 | 1337 | 1564 | 0.009 | 45.05 |
| 280. | 1__27810 | gi\|79931\|pir\|\|S22737 | 30.83 | 120 | 76 | 3 | 128 | 244 | 1484 | 1599 | 0.013 | 44.67 |
| 281. | 1__27810 | gi\|79931\|pir\|\|S22737 | 24.39 | 123 | 76 | 4 | 1302 | 1420 | 1484 | 1593 | 0.497 | 39.28 |
| 282. | 1__27810 | gi\|4691428\|dbj\|BAA77236.1\| | 42.00 | 1188 | 580 | 31 | 313 | 1477 | 83 | 1184 | 0.0 | 697.6 |
| 283. | 1__27810 | gi\|4691428\|dbj\|BAA77236.1\| | 26.58 | 237 | 135 | 7 | 177 | 385 | 1026 | 1251 | 6.9e−12 | 68.94 |
| 284. | 1__27810 | gi\|4691428\|dbj\|BAA77236.1\| | 29.03 | 217 | 124 | 6 | 167 | 382 | 1124 | 1311 | 1.5e−07 | 60.85 |
| 285. | 1__27810 | gi\|4691428\|dbj\|BAA77236.1\| | 24.84 | 306 | 188 | 9 | 1210 | 1480 | 1029 | 1327 | 2.3e−06 | 57.00 |
| 286. | 1__27810 | gi\|4691428\|dbj\|BAA77236.1\| | 41.54 | 65 | 37 | 1 | 156 | 219 | 1252 | 1316 | 0.007 | 45.44 |
| 287. | 1__27810 | gi\|4691428\|dbj\|BAA77236.1\| | 38.30 | 47 | 29 | 0 | 178 | 224 | 120 | 166 | 2.8 | 36.97 |
| 288. | 1__27810 | gi\|121729\|sp\|P29336\|GTFS_STRDO | 42.63 | 1140 | 545 | 30 | 346 | 1465 | 150 | 1200 | 0.0 | 690.3 |
| 289. | 1__27810 | gi\|121729\|sp\|P29336\|GTFS_STRDO | 26.83 | 287 | 128 | 6 | 177 | 382 | 1054 | 1339 | 1.2e−11 | 74.71 |
| 290. | 1__27810 | gi\|121729\|sp\|P29336\|GTFS_STRDO | 26.73 | 303 | 186 | 8 | 1210 | 1480 | 1057 | 1355 | 1.5e−09 | 67.78 |
| 291. | 1__27810 | gi\|121729\|sp\|P29336\|GTFS_STRDO | 31.40 | 172 | 75 | 4 | 172 | 341 | 1231 | 1361 | 3.6e−08 | 63.16 |
| 292. | 1__27810 | gi\|121729\|sp\|P29336\|GTFS_STRDO | 46.67 | 60 | 31 | 1 | 156 | 214 | 1280 | 1339 | 6.8e−04 | 48.91 |
| 293. | 1__27810 | gi\|121729\|sp\|P29336\|GTFS_STRDO | 25.94 | 212 | 132 | 5 | 9 | 220 | 6 | 192 | 0.014 | 44.67 |
| 294. | 1__27810 | gi\|6899809\|dbj\|BAA90527.1\| | 49.41 | 844 | 353 | 17 | 346 | 1173 | 230 | 1015 | 5e−177 | 624.0 |
| 295. | 1__27810 | gi\|18253272\|dbj\|BAB83942.1\| | 46.96 | 428 | 186 | 9 | 1068 | 1482 | 1 | 400 | 1.0e−85 | 320.9 |
| 296. | 1__27810 | gi\|18253272\|dbj\|BAB83942.1\| | 29.25 | 253 | 132 | 7 | 162 | 387 | 341 | 573 | 8.7e−15 | 85.11 |
| 297. | 1__27810 | gi\|18253272\|dbj\|BAB83942.1\| | 25.91 | 359 | 213 | 9 | 112 | 421 | 208 | 562 | 6.6e−13 | 78.95 |
| 298. | 1__27810 | gi\|18253272\|dbj\|BAB83942.1\| | 30.69 | 202 | 124 | 6 | 1300 | 1487 | 329 | 528 | 1.5e−12 | 77.80 |
| 299. | 1__27810 | gi\|18253272\|dbj\|BAB83942.1\| | 28.78 | 139 | 90 | 5 | 295 | 425 | 223 | 360 | 0.027 | 43.51 |
| 300. | 1__27810 | gi\|18147721\|dbj\|BAB83121.1\| | 46.75 | 338 | 168 | 7 | 301 | 633 | 184 | 514 | 3.2e−69 | 265.8 |
| 301. | 1__27810 | gi\|16800133\|ref\|NP_470401.1\| | 24.90 | 510 | 338 | 19 | 1574 | 2054 | 276 | 769 | 1.1e−24 | 117.9 |
| 302. | 1__27810 | gi\|16800133\|ref\|NP_470401.1\| | 21.32 | 469 | 336 | 13 | 1608 | 2054 | 231 | 688 | 5.7e−15 | 95.52 |
| 303. | 1__27810 | gi\|16800133\|ref\|NP_470401.1\| | 23.58 | 458 | 296 | 18 | 1470 | 1896 | 337 | 771 | 1.8e−14 | 83.96 |
| 304. | 1__27810 | gi\|16800133\|ref\|NP_470401.1\| | 22.90 | 572 | 361 | 26 | 1202 | 1741 | 251 | 774 | 0.012 | 44.67 |
| 305. | 1__27810 | gi\|16800133\|ref\|NP_470401.1\| | 21.82 | 307 | 183 | 12 | 1769 | 2055 | 94 | 363 | 3.2 | 36.58 |
| 306. | 1__27810 | gi\|15894364\|ref\|NP_347713.1\| | 35.11 | 225 | 119 | 7 | 159 | 380 | 521 | 721 | 1.6e−16 | 90.89 |
| 307. | 1__27810 | gi\|15894364\|ref\|NP_347713.1\| | 31.23 | 253 | 151 | 6 | 145 | 381 | 1438 | 1683 | 2.8e−15 | 86.66 |
| 308. | 1__27810 | gi\|15894364\|ref\|NP_347713.1\| | 30.63 | 222 | 146 | 6 | 159 | 380 | 2151 | 2364 | 2.9e−14 | 83.57 |
| 309. | 1__27810 | gi\|15894364\|ref\|NP_347713.1\| | 29.37 | 252 | 149 | 6 | 162 | 390 | 672 | 917 | 1.3e−13 | 81.26 |
| 310. | 1__27810 | gi\|15894364\|ref\|NP_347713.1\| | 30.14 | 219 | 147 | 4 | 162 | 380 | 2092 | 2304 | 1.5e−13 | 80.88 |
| 311. | 1__27810 | gi\|15894364\|ref\|NP_347713.1\| | 31.23 | 253 | 160 | 8 | 170 | 416 | 2018 | 2262 | 1.7e−13 | 80.88 |
| 312. | 1__27810 | gi\|15894364\|ref\|NP_347713.1\| | 30.61 | 245 | 141 | 7 | 162 | 385 | 2536 | 2772 | 1.1e−12 | 78.18 |
| 313. | 1__27810 | gi\|15894364\|ref\|NP_347713.1\| | 29.25 | 294 | 146 | 9 | 160 | 400 | 1362 | 1646 | 2.4e−12 | 77.03 |
| 314. | 1__27810 | gi\|15894364\|ref\|NP_347713.1\| | 29.64 | 253 | 147 | 7 | 158 | 384 | 1053 | 1300 | 3.6e−12 | 76.26 |
| 315. | 1__27810 | gi\|15894364\|ref\|NP_347713.1\| | 29.53 | 254 | 163 | 8 | 153 | 400 | 2489 | 2732 | 8.5e−12 | 75.10 |
| 316. | 1__27810 | gi\|15894364\|ref\|NP_347713.1\| | 27.94 | 247 | 152 | 6 | 153 | 380 | 2125 | 2364 | 1.1e−11 | 74.71 |
| 317. | 1__27810 | gi\|15894364\|ref\|NP_347713.1\| | 29.47 | 302 | 171 | 10 | 154 | 422 | 806 | 1098 | 1.5e−11 | 74.33 |
| 318. | 1__27810 | gi\|15894364\|ref\|NP_347713.1\| | 32.00 | 225 | 143 | 7 | 154 | 378 | 2208 | 2422 | 2.9e−11 | 73.56 |
| 319. | 1__27810 | gi\|15894364\|ref\|NP_347713.1\| | 30.49 | 246 | 120 | 7 | 160 | 379 | 1075 | 1295 | 3.6e−11 | 73.17 |
| 320. | 1__27810 | gi\|15894364\|ref\|NP_347713.1\| | 31.25 | 224 | 144 | 7 | 137 | 360 | 2313 | 2526 | 1.1e−10 | 71.63 |
| 321. | 1__27810 | gi\|15894364\|ref\|NP_347713.1\| | 30.70 | 215 | 139 | 9 | 167 | 380 | 2300 | 2505 | 1.1e−10 | 71.25 |
| 322. | 1__27810 | gi\|15894364\|ref\|NP_347713.1\| | 30.24 | 205 | 136 | 5 | 156 | 360 | 2571 | 2768 | 1.4e−10 | 71.25 |
| 323. | 1__27810 | gi\|15894364\|ref\|NP_347713.1\| | 29.29 | 239 | 142 | 8 | 167 | 388 | 1818 | 2046 | 3.6e−10 | 69.71 |
| 324. | 1__27810 | gi\|15894364\|ref\|NP_347713.1\| | 26.93 | 401 | 173 | 13 | 41 | 380 | 232 | 573 | 2.4e−09 | 67.01 |
| 325. | 1__27810 | gi\|15894364\|ref\|NP_347713.1\| | 28.70 | 223 | 141 | 9 | 138 | 360 | 1778 | 1982 | 8.1e−08 | 62.00 |
| 326. | 1__27810 | gi\|15894364\|ref\|NP_347713.1\| | 28.87 | 239 | 143 | 9 | 167 | 386 | 1697 | 1927 | 9.4e−08 | 61.62 |

-continued

| No | Query id | Subject id | % identity | alignment length | mismatches | gap openings | q. start | q. end | s. start | s. end | e-value | bit score |
|---|---|---|---|---|---|---|---|---|---|---|---|---|
| 327. | 1__27810 | gi\|15894364\|ref\|NP_347713.1\| | 25.00 | 224 | 161 | 4 | 138 | 361 | 1628 | 1844 | 4.0e−06 | 56.23 |
| 328. | 1__27810 | gi\|15894364\|ref\|NP_347713.1\| | 32.63 | 190 | 109 | 9 | 1300 | 1480 | 2443 | 2622 | 1.0e−04 | 51.60 |
| 329. | 1__27810 | gi\|15894364\|ref\|NP_347713.1\| | 22.91 | 537 | 345 | 24 | 1242 | 1750 | 1944 | 2439 | 0.104 | 41.59 |
| 330. | 1__27810 | gi\|15894364\|ref\|NP_347713.1\| | 27.90 | 233 | 132 | 11 | 1305 | 1510 | 297 | 520 | 0.216 | 40.43 |
| 331. | 1__27810 | gi\|15894364\|ref\|NP_347713.1\| | 29.52 | 166 | 99 | 6 | 1305 | 1461 | 2328 | 2484 | 0.235 | 40.43 |
| 332. | 1__27810 | gi\|15894364\|ref\|NP_347713.1\| | 27.55 | 265 | 128 | 15 | 1260 | 1481 | 455 | 698 | 0.929 | 38.51 |
| 333. | 1__27810 | gi\|15894364\|ref\|NP_347713.1\| | 27.73 | 220 | 125 | 12 | 1301 | 1495 | 1641 | 1851 | 1.9 | 37.35 |
| 334. | 1__27810 | gi\|15894364\|ref\|NP_347713.1\| | 26.25 | 240 | 133 | 11 | 1261 | 1484 | 984 | 1195 | 1.9 | 37.35 |
| 335. | 1__27810 | gi\|15894364\|ref\|NP_347713.1\| | 29.21 | 202 | 101 | 10 | 1261 | 1461 | 1560 | 1720 | 3.7 | 36.58 |
| 336. | 1__27810 | gi\|1351266\|sp\|P16154\|TOXA_CLODI | 25.74 | 303 | 177 | 7 | 127 | 383 | 1910 | 2210 | 3.3e−14 | 83.19 |
| 337. | 1__27810 | gi\|1351266\|sp\|P16154\|TOXA_CLODI | 26.64 | 289 | 162 | 6 | 132 | 377 | 2325 | 2606 | 1.1e−13 | 81.65 |
| 338. | 1__27810 | gi\|1351266\|sp\|P16154\|TOXA_CLODI | 26.50 | 366 | 178 | 11 | 167 | 449 | 1822 | 2179 | 1.1e−13 | 81.65 |
| 339. | 1__27810 | gi\|1351266\|sp\|P16154\|TOXA_CLODI | 27.78 | 234 | 125 | 5 | 162 | 355 | 2446 | 2675 | 6.9e−11 | 72.02 |
| 340. | 1__27810 | gi\|1351266\|sp\|P16154\|TOXA_CLODI | 25.25 | 400 | 235 | 13 | 5 | 383 | 2102 | 2458 | 1.3e−09 | 67.78 |
| 341. | 1__27810 | gi\|1351266\|sp\|P16154\|TOXA_CLODI | 24.44 | 266 | 141 | 6 | 177 | 383 | 1812 | 2076 | 3.1e−09 | 66.63 |
| 342. | 1__27810 | gi\|1351266\|sp\|P16154\|TOXA_CLODI | 28.65 | 171 | 97 | 8 | 1334 | 1485 | 1930 | 2094 | 0.018 | 44.28 |
| 343. | 1__27810 | gi\|1351266\|sp\|P16154\|TOXA_CLODI | 27.61 | 134 | 85 | 4 | 260 | 383 | 1811 | 1942 | 0.034 | 43.13 |
| 344. | 1__27810 | gi\|1351266\|sp\|P16154\|TOXA_CLODI | 27.16 | 232 | 153 | 11 | 1264 | 1493 | 1812 | 2029 | 2.1 | 37.35 |
| 345. | 1__27810 | gi\|1351266\|sp\|P16154\|TOXA_CLODI | 22.62 | 305 | 189 | 9 | 1208 | 1487 | 2042 | 2324 | 6.8 | 35.81 |

Summary all hits having more than 40% identity (ordered by deceding value of identity):

| No | Query id | Subject id | % identity | alignment length | mismatches | gap openings | q. start | q. end | s. start | s. end | e-value | bit score |
|---|---|---|---|---|---|---|---|---|---|---|---|---|
| 1. | 1__27810 | gi\|10862851\|emb\|CAB65910.2\| | 100.00 | 2057 | 0 | 0 | 1 | 2057 | 1 | 2057 | 0 | 3748.8 |
| 294. | 1__27810 | gi\|6899809\|dbj\|BAA90527.1\| | 49.41 | 844 | 353 | 17 | 346 | 1173 | 230 | 1015 | 5.00E−177 | 624 |
| 22. | 1__27810 | gi\|7161825\|emb\|CAB76565.1\| | 47.46 | 1258 | 572 | 22 | 238 | 1487 | 106 | 1282 | 0 | 938.3 |
| 2. | 1__27810 | gi\|11559649\|gb\|AAG38021.1\|AF294469_1 | 47.38 | 1258 | 573 | 22 | 238 | 1487 | 137 | 1313 | 0 | 941 |
| 9. | 1__27810 | gi\|7470961\|pir\|\|T31098 | 47.38 | 1258 | 573 | 22 | 238 | 1487 | 137 | 1313 | 0 | 939.9 |
| 41. | 1__27810 | gi\|153645\|gb\|AAA26895.1\| | 47.05 | 1171 | 533 | 20 | 343 | 1495 | 171 | 1272 | 0 | 862.8 |
| 48. | 1__27810 | gi\|6166192\|sp\|P49331\|GTFD_STRMU | 47.05 | 1171 | 533 | 20 | 343 | 1495 | 171 | 1272 | 0 | 862.8 |
| 69. | 1__27810 | gi\|419649\|pir\|\|A45866 | 47.05 | 1171 | 533 | 20 | 343 | 1495 | 171 | 1272 | 0 | 861.7 |
| 55. | 1__27810 | gi\|3130107\|dbj\|BAA26121.1\| | 46.97 | 1171 | 534 | 20 | 343 | 1495 | 171 | 1272 | 0 | 862.1 |
| 62. | 1__27810 | gi\|3130076\|dbj\|BAA26103.1\| | 46.97 | 1171 | 534 | 20 | 343 | 1495 | 171 | 1272 | 0 | 861.7 |
| 295. | 1__27810 | gi\|18253272\|dbj\|BAB83942.1\| | 46.96 | 428 | 186 | 9 | 1068 | 1482 | 1 | 400 | 1.00E−85 | 320.9 |
| 34. | 1__27810 | gi\|3130083\|dbj\|BAA26107.1\| | 46.80 | 1171 | 536 | 20 | 343 | 1495 | 171 | 1272 | 0 | 864 |
| 77. | 1__27810 | gi\|3130090\|dbj\|BAA26111.1\| | 46.80 | 1171 | 536 | 20 | 343 | 1495 | 171 | 1272 | 0 | 860.5 |
| 300. | 1__27810 | gi\|18147721\|dbj\|BAB83121.1\| | 46.75 | 338 | 168 | 7 | 301 | 633 | 184 | 514 | 3.20E−69 | 265.8 |
| 107. | 1__27810 | gi\|1054877\|gb\|AAC43483.1\| | 46.74 | 1136 | 522 | 21 | 342 | 1465 | 224 | 1288 | 0 | 836.6 |
| 159. | 1__27810 | gi\|3130095\|dbj\|BAA26114.1\| | 46.73 | 1162 | 510 | 26 | 346 | 1482 | 187 | 1264 | 0 | 824.3 |
| 165. | 1__27810 | gi\|3130081\|dbj\|BAA26106.1\| | 46.73 | 1162 | 510 | 26 | 346 | 1482 | 187 | 1264 | 0 | 823.9 |
| 170. | 1__27810 | gi\|3130088\|dbj\|BAA26110.1\| | 46.73 | 1162 | 510 | 26 | 346 | 1482 | 187 | 1264 | 0 | 822.4 |
| 292. | 1__27810 | gi\|121729\|sp\|P29336\|GTFS_STRDO | 46.67 | 60 | 31 | 1 | 156 | 214 | 1280 | 1339 | 6.80E−04 | 48.91 |
| 84. | 1__27810 | gi\|3130097\|dbj\|BAA26115.1\| | 46.46 | 1171 | 540 | 20 | 343 | 1495 | 171 | 1272 | 0 | 855.5 |
| 91. | 1__27810 | gi\|7684297\|dbj\|BAA95201.1\| | 46.41 | 1142 | 527 | 22 | 337 | 1465 | 217 | 1286 | 0 | 850.5 |
| 115. | 1__27810 | gi\|6166191\|sp\|P08987\|GTFB_STRMU | 45.92 | 1200 | 548 | 25 | 286 | 1465 | 93 | 1211 | 0 | 836.3 |
| 124. | 1__27810 | gi\|3130103\|dbj\|BAA26119.1\| | 45.92 | 1200 | 548 | 25 | 286 | 1465 | 93 | 1211 | 0 | 836.3 |
| 148. | 1__27810 | gi\|3130086\|dbj\|BAA26109.1\| | 45.83 | 1200 | 549 | 25 | 286 | 1465 | 93 | 1211 | 0 | 832.8 |
| 175. | 1__27810 | gi\|3130074\|dbj\|BAA26102.1\| | 45.20 | 1219 | 551 | 28 | 346 | 1537 | 187 | 1315 | 0 | 820.8 |
| 180. | 1__27810 | gi\|3130105\|dbj\|BAA26120.1\| | 45.20 | 1219 | 551 | 28 | 346 | 1537 | 187 | 1315 | 0 | 819.7 |
| 185. | 1__27810 | gi\|97988\|pir\|\|B33135 | 45.17 | 1200 | 556 | 25 | 286 | 1465 | 93 | 1210 | 0 | 816.6 |
| 154. | 1__27810 | gi\|121728\|sp\|P13470\|GTFC_STRMU | 45.07 | 1216 | 557 | 26 | 346 | 1537 | 187 | 1315 | 0 | 824.7 |

-continued

| No | Query id | Subject id | % identity | alignment length | mis- matches | gap openings | q. start | q. end | s. start | s. end | e-value | bit score |
|---|---|---|---|---|---|---|---|---|---|---|---|---|
| 16. | 1__27810 | gi\|21654700\|gb\|AAG61158.1\| | 44.57 | 1373 | 643 | 26 | 133 | 1482 | 57 | 1334 | 0 | 939.5 |
| 133. | 1__27810 | gi\|3130072\|dbj\|BAA26101.1\| | 44.51 | 1265 | 598 | 28 | 286 | 1527 | 93 | 1276 | 0 | 835.9 |
| 99. | 1__27810 | gi\|3130079\|dbj\|BAA26105.1\| | 44.43 | 1265 | 599 | 28 | 286 | 1527 | 93 | 1276 | 0 | 837 |
| 29. | 1__27810 | gi\|4205088\|gb\|AAD10952.1\| | 44.36 | 1373 | 646 | 26 | 133 | 1482 | 57 | 1334 | 0 | 925.6 |
| 140. | 1__27810 | gi\|3130093\|dbj\|BAA26113.1\| | 44.27 | 1265 | 601 | 28 | 286 | 1527 | 93 | 1276 | 0 | 832.8 |
| 211. | 1__27810 | gi\|940427\|dbj\|BAA09792.1\| | 43.66 | 1175 | 564 | 23 | 336 | 1495 | 144 | 1235 | 0 | 768.8 |
| 242. | 1__27810 | gi\|7474116\|pir\|\|T30858 | 43.56 | 1157 | 556 | 24 | 344 | 1482 | 269 | 1346 | 0 | 753.1 |
| 272. | 1__27810 | gi\|79931\|pir\|\|S22737 | 43.14 | 1159 | 559 | 30 | 351 | 1480 | 176 | 1263 | 0 | 709.9 |
| 235. | 1__27810 | gi\|4691429\|dbj\|BAA77237.1\| | 43.10 | 1167 | 575 | 23 | 337 | 1480 | 159 | 1259 | 0 | 756.5 |
| 218. | 1__27810 | gi\|121724\|sp\|P11001\| GTF1__STRDO | 42.87 | 1199 | 583 | 24 | 317 | 1495 | 126 | 1242 | 0 | 762.3 |
| 288. | 1__27810 | gi\|121729\|sp\|P29336\| GTFS__STRDO | 42.63 | 1140 | 545 | 30 | 346 | 1465 | 150 | 1200 | 0 | 690.3 |
| 191. | 1__27810 | gi\|1022963\|gb\|AAB40875.1\| | 42.53 | 1225 | 590 | 30 | 343 | 1541 | 1 | 1137 | 0 | 791.2 |
| 197. | 1__27810 | gi\|7470958\|pir\|\|JC5473 | 42.45 | 1225 | 591 | 30 | 343 | 1541 | 1 | 1137 | 0 | 789.3 |
| 263. | 1__27810 | gi\|7474115\|pir\|\|T30857 | 42.30 | 1201 | 565 | 27 | 309 | 1458 | 168 | 1291 | 0 | 716.5 |
| 282. | 1__27810 | gi\|4691428\|dbj\|BAA77236.1\| | 42.00 | 1188 | 580 | 31 | 313 | 1477 | 83 | 1184 | 0 | 697.6 |
| 255. | 1__27810 | gi\|22138845\|dbj\|BAC07265.1\| | 41.82 | 1308 | 641 | 34 | 210 | 1491 | 43 | 1256 | 0 | 716.8 |
| 267. | 1__27810 | gi\|7474117\|pir\|\|T30552 | 41.78 | 1228 | 585 | 27 | 287 | 1458 | 138 | 1291 | 0 | 715.7 |
| 249. | 1__27810 | gi\|322084\|pir\|\|A44811 | 41.61 | 1264 | 626 | 29 | 343 | 1558 | 173 | 1372 | 0 | 738.4 |
| 286. | 1__27810 | gi\|4691428\|dbj\|BAA77236.1\| | 41.54 | 65 | 37 | 1 | 156 | 219 | 1252 | 1316 | 0.007 | 45.44 |

Annex 3

TblastN search
Statistics
Database: All non-redundant GenBank CDS
translations + PDB + SwissProt + PIR + PRF
Posted date: Sep. 4, 2002 12:20 AM
Number of letters in database: 330,426,180
Number of sequences in database: 1,044,513
Lambda   K   H
0.340   0.279   1.74
Gapped
Lambda   K   H
0.294   0.110   0.610
Matrix: PAM30
Gap Penalties: Existence: 9, Extension: 1
Number of Hits to DB: 2,418,339,159
Number of Sequences: 1044513
Number of extensions: 254327666
Number of successful extensions: 178753
Number of sequences better than 20000.0: 9336
Number of HSP's better than 20000.0 without gapping: 4241
Number of HSP's successfully gapped in prelim test: 5096
Number of HSP's that attempted gapping in prelim test: 165746
Number of HSP's gapped (non-prelim): 16949

-continued

Annex 3 length of query: 2057
length of database: 330,426,180
effective HSP length: 35
effective length of query: 2022
effective length of database: 293,868,225
effective search space: 594201550950
effective search space used: 594201550950
T: 11
A: 40
X1: 15 (7.4 bits)
X2: 35 (14.8 bits)
X3: 58 (24.6 bits)
S1: 41 (21.9 bits)
S2: 52 (25.2 bits)
BLASTP 2.2.3 [Apr-24-2002]
Query: # BLASTP 2.2.3 [Apr-24-2002]
Database: nr
Fields: Query id, Subject id, % identity, alignment length,
mismatches, gap openings, q. start, q. end, s. start,
s. end, e-value, bit score
Query:

| No | Query id | Subject id | % identity | align- ment length | mis- matches | gap open- ings | q. start | q. end | s. start | s. end | e-value | bit score |
|---|---|---|---|---|---|---|---|---|---|---|---|---|
| 1. | 1__21287 | gi\|10862850\|emb\|AJ250173.2\| LME250173 | 100.00 | 2057 | 0 | 0 | 1 | 2057 | 195 | 6365 | 0.0 | 4135.5 |
| 2. | 1__21287 | gi\|21654699\|gb\|AY017384.1\| | 44.76 | 1374 | 735 | 28 | 133 | 1482 | 667 | 4500 | 0.0 | 1068.1 |
| 3. | 1__21287 | gi\|21654699\|gb\|AY017384.1\| | 29.97 | 317 | 205 | 9 | 6 | 304 | 511 | 1413 | 2.8e−29 | 136.7 |
| 4. | 1__21287 | gi\|21654699\|gb\|AY017384.1\| | 28.29 | 304 | 190 | 4 | 153 | 428 | 4105 | 5016 | 2.8e−21 | 110.2 |
| 5. | 1__21287 | gi\|21654699\|gb\|AY017384.1\| | 30.70 | 215 | 139 | 5 | 157 | 361 | 4441 | 5067 | 1.6e−16 | 94.36 |
| 6. | 1__21287 | gi\|21654699\|gb\|AY017384.1\| | 30.99 | 171 | 112 | 6 | 138 | 302 | 4630 | 5076 | 2.3e−07 | 63.93 |
| 7. | 1__21287 | gi\|21654699\|gb\|AY017384.1\| | 27.32 | 194 | 108 | 7 | 1301 | 1461 | 4483 | 5058 | 0.001 | 51.60 |
| 8. | 1__21287 | gi\|4205087\|gb\|U81374.1\| LMU81374 | 44.54 | 1374 | 738 | 28 | 133 | 1482 | 397 | 4230 | 0.0 | 1053.9 |
| 9. | 1__21287 | gi\|4205087\|gb\|U81374.1\| LMU81374 | 28.95 | 304 | 188 | 4 | 153 | 428 | 3835 | 4746 | 2.6e−22 | 113.6 |
| 10. | 1__21287 | gi\|4205087\|gb\|U81374.1\| LMU81374 | 31.16 | 215 | 138 | 5 | 157 | 361 | 4171 | 4797 | 4.2e−17 | 96.29 |

-continued

| No | Query id | Subject id | % identity | alignment length | mismatches | gap openings | q. start | q. end | s. start | s. end | e-value | bit score |
|---|---|---|---|---|---|---|---|---|---|---|---|---|
| 11. | 1__21287 | gi\|4205087\|gb\|U81374.1\| LMU81374 | 30.99 | 171 | 112 | 6 | 138 | 302 | 4360 | 4806 | 1.8e−07 | 64.31 |
| 12. | 1__21287 | gi\|4205087\|gb\|U81374.1\| LMU81374 | 27.84 | 194 | 107 | 7 | 1301 | 1461 | 4213 | 4788 | 2.4e−04 | 53.91 |
| 13. | 1__21287 | gi\|7161824\|emb\|AJ250172.1\| LME250172 | 47.46 | 1258 | 653 | 22 | 238 | 1487 | 1126 | 4656 | 0.0 | 1052.3 |
| 14. | 1__21287 | gi\|7161824\|emb\|AJ250172.1\| LME250172 | 29.84 | 315 | 208 | 8 | 4 | 305 | 733 | 1581 | 2.9e−26 | 126.7 |
| 15. | 1__21287 | gi\|7161824\|emb\|AJ250172.1\| LME250172 | 29.15 | 247 | 173 | 4 | 159 | 403 | 4219 | 4839 | 6.3e−21 | 109.0 |
| 16. | 1__21287 | gi\|7161824\|emb\|AJ250172.1\| LME250172 | 31.13 | 212 | 137 | 5 | 159 | 361 | 4609 | 5226 | 9.5e−17 | 95.13 |
| 17. | 1__21287 | gi\|7161824\|emb\|AJ250172.1\| LME250172 | 28.32 | 226 | 153 | 6 | 77 | 293 | 4594 | 5211 | 1.0e−07 | 65.08 |
| 18. | 1__21287 | gi\|7161824\|emb\|AJ250172.1\| LME250172 | 24.59 | 183 | 127 | 6 | 1308 | 1479 | 4534 | 5079 | 2.6e−06 | 60.46 |
| 19. | 1__21287 | gi\|2766611\|gb\|AF030129.1\| AF030129 | 47.38 | 1258 | 654 | 22 | 238 | 1487 | 1107 | 4637 | 0.0 | 1051.2 |
| 20. | 1__21287 | gi\|2766611\|gb\|AF030129.1\| AF030129 | 29.01 | 324 | 208 | 9 | 4 | 305 | 711 | 1562 | 6.5e−26 | 125.6 |
| 21. | 1__21287 | gi\|2766611\|gb\|AF030129.1\| AF030129 | 29.15 | 247 | 173 | 4 | 159 | 403 | 4200 | 4820 | 6.3e−21 | 109.0 |
| 22. | 1__21287 | gi\|2766611\|gb\|AF030129.1\| AF030129 | 31.13 | 212 | 137 | 5 | 159 | 361 | 4590 | 5207 | 9.5e−17 | 95.13 |
| 23. | 1__21287 | gi\|2766611\|gb\|AF030129.1\| AF030129 | 28.32 | 226 | 153 | 6 | 77 | 293 | 4575 | 5192 | 1.0e−07 | 65.08 |
| 24. | 1__21287 | gi\|2766611\|gb\|AF030129.1\| AF030129 | 24.59 | 183 | 127 | 6 | 1308 | 1479 | 4515 | 5060 | 2.6e−06 | 60.46 |
| 25. | 1__21287 | gi\|11559648\|gb\|AF294469.1\| AF294469 | 47.38 | 1258 | 654 | 22 | 238 | 1487 | 1106 | 4636 | 0.0 | 1049.7 |
| 26. | 1__21287 | gi\|11559648\|gb\|AF294469.1\| AF294469 | 30.48 | 315 | 206 | 9 | 4 | 305 | 710 | 1561 | 1.5e−25 | 124.4 |
| 27. | 1__21287 | gi\|11559648\|gb\|AF294469.1\| AF294469 | 29.15 | 247 | 173 | 4 | 159 | 403 | 4199 | 4819 | 6.3e−21 | 109.0 |
| 28. | 1__21287 | gi\|11559648\|gb\|AF294469.1\| AF294469 | 31.13 | 212 | 137 | 5 | 159 | 361 | 4589 | 5206 | 9.5e−17 | 95.13 |
| 29. | 1__21287 | gi\|11559648\|gb\|AF294469.1\| AF294469 | 28.32 | 226 | 153 | 6 | 77 | 293 | 4574 | 5191 | 1.0e−07 | 65.08 |
| 30. | 1__21287 | gi\|11559648\|gb\|AF294469.1\| AF294469 | 24.59 | 183 | 127 | 6 | 1308 | 1479 | 4514 | 5059 | 2.6e−06 | 60.46 |
| 31. | 1__21287 | gi\|153644\|gb\|M29296.1\|STRGTFD | 47.22 | 1171 | 600 | 21 | 343 | 1495 | 945 | 4260 | 0.0 | 961.1 |
| 32. | 1__21287 | gi\|153644\|gb\|M29296.1\|STRGTFD | 33.76 | 237 | 155 | 4 | 148 | 382 | 3954 | 4544 | 2.0e−27 | 130.6 |
| 33. | 1__21287 | gi\|153644\|gb\|M29296.1\|STRGTFD | 27.81 | 302 | 174 | 8 | 125 | 382 | 3510 | 4352 | 2.0e−22 | 114.0 |
| 34. | 1__21287 | gi\|153644\|gb\|M29296.1\|STRGTFD | 29.89 | 184 | 125 | 6 | 1308 | 1487 | 4110 | 4616 | 1.8e−12 | 80.88 |
| 35. | 1__21287 | gi\|153644\|gb\|M29296.1\|STRGTFD | 26.60 | 203 | 103 | 3 | 162 | 318 | 4194 | 4802 | 7.8e−11 | 75.48 |
| 36. | 1__21287 | gi\|153644\|gb\|M29296.1\|STRGTFD | 27.45 | 153 | 110 | 3 | 1302 | 1453 | 4287 | 4706 | 4.0e−07 | 63.16 |
| 37. | 1__21287 | gi\|153644\|gb\|M29296.1\|STRGTFD | 25.11 | 219 | 155 | 7 | 5 | 214 | 438 | 1064 | 0.003 | 50.45 |
| 38. | 1__21287 | gi\|3130082\|dbj\|D88656.1\| | 42.30 | 1402 | 745 | 32 | 343 | 1680 | 752 | 4726 | 0.0 | 960.7 |
| 39. | 1__21287 | gi\|3130082\|dbj\|D88656.1\| | 32.91 | 237 | 157 | 4 | 148 | 382 | 3761 | 4351 | 3.8e−26 | 126.3 |
| 40. | 1__21287 | gi\|3130082\|dbj\|D88656.1\| | 29.92 | 244 | 118 | 7 | 192 | 382 | 3431 | 4159 | 8.6e−18 | 98.60 |
| 41. | 1__21287 | gi\|3130082\|dbj\|D88656.1\| | 26.48 | 219 | 152 | 7 | 5 | 214 | 245 | 871 | 1.9e−04 | 54.30 |
| 42. | 1__21287 | gi\|3130082\|dbj\|D88656.1\| | 27.42 | 124 | 68 | 2 | 159 | 260 | 4187 | 4555 | 0.003 | 50.06 |
| 43. | 1__21287 | gi\|3130075\|dbj\|D88653.1\| | 47.14 | 1171 | 601 | 21 | 343 | 1495 | 751 | 4056 | 0.0 | 959.1 |
| 44. | 1__21287 | gi\|3130075\|dbj\|D88653.1\| | 33.76 | 237 | 155 | 4 | 148 | 382 | 3760 | 4350 | 2.0e−27 | 130.6 |
| 45. | 1__21287 | gi\|3130075\|dbj\|D88653.1\| | 27.81 | 302 | 174 | 8 | 125 | 382 | 3316 | 4158 | 2.0e−22 | 114.0 |
| 46. | 1__21287 | gi\|3130075\|dbj\|D88653.1\| | 29.89 | 184 | 125 | 6 | 1308 | 1487 | 3916 | 4422 | 1.8e−12 | 80.88 |
| 47. | 1__21287 | gi\|3130075\|dbj\|D88653.1\| | 28.80 | 184 | 130 | 4 | 1302 | 1484 | 4093 | 4602 | 7.8e−11 | 75.48 |
| 48. | 1__21287 | gi\|3130075\|dbj\|D88653.1\| | 24.66 | 219 | 156 | 7 | 5 | 214 | 244 | 870 | 0.002 | 51.22 |
| 49. | 1__21287 | gi\|3130075\|dbj\|D88653.1\| | 27.42 | 124 | 68 | 2 | 159 | 260 | 4186 | 4554 | 0.003 | 50.06 |
| 50. | 1__21287 | gi\|3218540\|dbj\|D89979.1\| | 47.14 | 1171 | 601 | 21 | 343 | 1495 | 751 | 4056 | 0.0 | 958.7 |
| 51. | 1__21287 | gi\|3218540\|dbj\|D89979.1\| | 30.06 | 316 | 204 | 9 | 84 | 382 | 3340 | 4158 | 6.5e−26 | 125.6 |
| 52. | 1__21287 | gi\|3218540\|dbj\|D89979.1\| | 32.91 | 237 | 157 | 4 | 148 | 382 | 3760 | 4350 | 1.1e−25 | 124.8 |
| 53. | 1__21287 | gi\|3218540\|dbj\|D89979.1\| | 29.35 | 184 | 126 | 6 | 1308 | 1487 | 3916 | 4422 | 9.2e−12 | 78.57 |
| 54. | 1__21287 | gi\|3218540\|dbj\|D89979.1\| | 29.35 | 184 | 129 | 4 | 1302 | 1484 | 4093 | 4602 | 5.9e−11 | 75.87 |
| 55. | 1__21287 | gi\|3218540\|dbj\|D89979.1\| | 24.42 | 217 | 157 | 7 | 5 | 214 | 244 | 870 | 0.003 | 50.06 |
| 56. | 1__21287 | gi\|3130089\|dbj\|D88659.1\| | 46.97 | 1171 | 603 | 21 | 343 | 1495 | 752 | 4057 | 0.0 | 958.4 |
| 57. | 1__21287 | gi\|3130089\|dbj\|D88659.1\| | 33.33 | 237 | 156 | 4 | 148 | 382 | 3781 | 4351 | 4.5e−27 | 129.4 |
| 58. | 1__21287 | gi\|3130089\|dbj\|D88659.1\| | 27.48 | 302 | 175 | 8 | 125 | 382 | 3317 | 4159 | 1.5e−22 | 114.4 |
| 59. | 1__21287 | gi\|3130089\|dbj\|D88659.1\| | 29.89 | 184 | 125 | 6 | 1308 | 1487 | 3917 | 4423 | 1.8e−12 | 80.88 |
| 60. | 1__21287 | gi\|3130089\|dbj\|D88659.1\| | 28.80 | 184 | 130 | 4 | 1302 | 1484 | 4094 | 4603 | 7.8e−11 | 75.48 |
| 61. | 1__21287 | gi\|3130089\|dbj\|D88659.1\| | 26.48 | 219 | 152 | 7 | 5 | 214 | 245 | 871 | 1.9e−04 | 54.30 |
| 62. | 1__21287 | gi\|3130089\|dbj\|D88659.1\| | 27.42 | 124 | 68 | 2 | 159 | 260 | 4187 | 4555 | 0.003 | 50.06 |
| 63. | 1__21287 | gi\|3130096\|dbj\|D88662.1\| | 46.63 | 1171 | 607 | 21 | 343 | 1495 | 751 | 4056 | 0.0 | 950.3 |
| 64. | 1__21287 | gi\|3130096\|dbj\|D88662.1\| | 33.33 | 237 | 156 | 4 | 148 | 382 | 3760 | 4350 | 2.2e−26 | 127.1 |
| 65. | 1__21287 | gi\|3130096\|dbj\|D88662.1\| | 27.81 | 302 | 174 | 8 | 125 | 382 | 3316 | 4158 | 3.4e−22 | 113.2 |

-continued

| No | Query id | Subject id | % identity | alignment length | mismatches | gap openings | q. start | q. end | s. start | s. end | e-value | bit score |
|---|---|---|---|---|---|---|---|---|---|---|---|---|
| 66. | 1_21287 | gi\|3130096\|dbj\|D88662.1\| | 29.89 | 184 | 125 | 6 | 1308 | 1487 | 3916 | 4422 | 1.8e−12 | 80.88 |
| 67. | 1_21287 | gi\|3130096\|dbj\|D88662.1\| | 28.80 | 184 | 130 | 4 | 1302 | 1484 | 4093 | 4602 | 7.8e−11 | 75.48 |
| 68. | 1_21287 | gi\|3130096\|dbj\|D88662.1\| | 24.66 | 219 | 156 | 7 | 5 | 214 | 244 | 870 | 0.001 | 51.60 |
| 69. | 1_21287 | gi\|3130096\|dbj\|D88662.1\| | 27.42 | 124 | 68 | 2 | 169 | 260 | 4186 | 4554 | 0.003 | 50.06 |
| 70. | 1_21287 | gi\|3130077\|dbj\|D88654.1\| | 41.48 | 1420 | 774 | 34 | 286 | 1648 | 1378 | 5382 | 0.0 | 922.9 |
| 71. | 1_21287 | gi\|3130077\|dbj\|D88654.1\| | 26.24 | 362 | 217 | 7 | 71 | 382 | 4486 | 5511 | 2.7e−24 | 120.2 |
| 72. | 1_21287 | gi\|3130077\|dbj\|D88654.1\| | 27.87 | 244 | 148 | 8 | 167 | 382 | 4396 | 5121 | 1.5e−17 | 97.83 |
| 73. | 1_21287 | gi\|3130077\|dbj\|D88654.1\| | 28.00 | 225 | 150 | 8 | 1308 | 1520 | 4876 | 5490 | 4.2e−17 | 96.29 |
| 74. | 1_21287 | gi\|3130077\|dbj\|D88654.1\| | 30.43 | 161 | 108 | 6 | 1308 | 1464 | 5071 | 5511 | 4.4e−14 | 86.27 |
| 75. | 1_21287 | gi\|3130077\|dbj\|D88654.1\| | 36.36 | 99 | 69 | 5 | 1308 | 1402 | 5266 | 5523 | 3.4e−06 | 60.08 |
| 76. | 1_21287 | gi\|3130077\|dbj\|D88654.1\| | 23.23 | 254 | 183 | 8 | 9 | 250 | 1117 | 1800 | 1.9e−04 | 54.30 |
| 77. | 1_21287 | gi\|3130070\|dbj\|D88651.1\| | 42.73 | 1341 | 744 | 31 | 286 | 1602 | 1378 | 5121 | 0.0 | 921.8 |
| 78. | 1_21287 | gi\|3130070\|dbj\|D88651.1\| | 26.24 | 362 | 217 | 8 | 71 | 382 | 4486 | 5511 | 1.8e−23 | 117.5 |
| 79. | 1_21287 | gi\|3130070\|dbj\|D88651.1\| | 28.05 | 246 | 147 | 8 | 167 | 382 | 4396 | 5121 | 6.5e−18 | 98.98 |
| 80. | 1_21287 | gi\|3130070\|dbj\|D88651.1\| | 30.43 | 161 | 108 | 6 | 1308 | 1464 | 5071 | 5511 | 3.4e−14 | 86.66 |
| 81. | 1_21287 | gi\|3130070\|dbj\|D88651.1\| | 23.32 | 313 | 226 | 12 | 1304 | 1602 | 4669 | 5511 | 5.7e−14 | 85.89 |
| 82. | 1_21287 | gi\|3130070\|dbj\|D88651.1\| | 23.23 | 254 | 183 | 8 | 9 | 250 | 1117 | 1800 | 1.9e−04 | 54.30 |
| 83. | 1_21287 | gi\|3130070\|dbj\|D88651.1\| | 39.13 | 69 | 41 | 1 | 148 | 215 | 5308 | 5514 | 0.017 | 47.75 |
| 84. | 1_21287 | gi\|3130101\|dbj\|D89977.1\| | 42.65 | 1341 | 745 | 31 | 286 | 1602 | 1378 | 5121 | 0.0 | 920.2 |
| 85. | 1_21287 | gi\|3130101\|dbj\|D89977.1\| | 25.69 | 362 | 219 | 8 | 71 | 382 | 4486 | 5511 | 3.6e−24 | 119.8 |
| 86. | 1_21287 | gi\|3130101\|dbj\|D89977.1\| | 27.87 | 244 | 148 | 8 | 167 | 382 | 4396 | 5121 | 4.2e−17 | 86.29 |
| 87. | 1_21287 | gi\|3130101\|dbj\|D89977.1\| | 29.95 | 187 | 119 | 7 | 1308 | 1482 | 4876 | 5394 | 8.0e−16 | 92.05 |
| 88. | 1_21287 | gi\|3130101\|dbj\|D89977.1\| | 36.54 | 156 | 92 | 7 | 153 | 301 | 5059 | 5520 | 8.9e−15 | 88.58 |
| 89. | 1_21287 | gi\|3130101\|dbj\|D89977.1\| | 30.43 | 161 | 108 | 6 | 1308 | 1464 | 5071 | 5511 | 3.4e−14 | 86.66 |
| 90. | 1_21287 | gi\|3130101\|dbj\|D89977.1\| | 23.23 | 254 | 183 | 8 | 9 | 250 | 1117 | 1800 | 1.9e−04 | 54.30 |
| 91. | 1_21287 | gi\|7684295\|dbj\|AB025228.1\| | 46.32 | 1142 | 600 | 22 | 337 | 1465 | 3428 | 6637 | 0.0 | 918.7 |
| 92. | 1_21287 | gi\|7684295\|dbj\|AB025228.1\| | 31.09 | 238 | 162 | 5 | 147 | 382 | 6821 | 7414 | 2.9e−18 | 100.1 |
| 93. | 1_21287 | gi\|7684295\|dbj\|AB025228.1\| | 26.94 | 438 | 232 | 16 | 45 | 394 | 5834 | 7087 | 2.1e−16 | 93.97 |
| 94. | 1_21287 | gi\|7684295\|dbj\|AB025228.1\| | 35.62 | 146 | 93 | 2 | 155 | 299 | 7040 | 7417 | 7.5e−14 | 85.50 |
| 95. | 1_21287 | gi\|7684295\|dbj\|AB025228.1\| | 27.85 | 219 | 155 | 5 | 180 | 395 | 6080 | 6664 | 2.0e−11 | 77.41 |
| 96. | 1_21287 | gi\|7684295\|dbj\|AB025228.1\| | 29.89 | 174 | 120 | 5 | 1309 | 1480 | 6791 | 7270 | 3.6e−08 | 66.63 |
| 97. | 1_21287 | gi\|7684295\|dbj\|AB025228.1\| | 25.93 | 189 | 112 | 5 | 74 | 234 | 6920 | 7480 | 1.4e−04 | 54.68 |
| 98. | 1_21287 | gi\|7684295\|dbj\|AB025228.1\| | 29.82 | 114 | 78 | 5 | 1309 | 1420 | 7181 | 7480 | 0.147 | 44.67 |
| 99. | 1_21287 | gi\|3130091\|dbj\|D88660.1\| | 41.34 | 1420 | 776 | 34 | 286 | 1648 | 1378 | 5382 | 0.0 | 918.7 |
| 100 | 1_21287 | gi\|3130091\|dbj\|D88660.1\| | 26.24 | 362 | 217 | 7 | 71 | 382 | 4486 | 5511 | 1.6e−24 | 120.9 |
| 101 | 1_21287 | gi\|3130091\|dbj\|D88660.1\| | 27.64 | 246 | 148 | 8 | 167 | 382 | 4396 | 5121 | 1.1e−17 | 98.21 |
| 102 | 1_21287 | gi\|3130091\|dbj\|D88660.1\| | 28.00 | 225 | 150 | 8 | 1308 | 1520 | 4876 | 5490 | 4.2e−17 | 96.29 |
| 103 | 1_21287 | gi\|3130091\|dbj\|D88660.1\| | 30.43 | 161 | 108 | 6 | 1308 | 1464 | 5071 | 5511 | 4.4e−14 | 86.27 |
| 104 | 1_21287 | gi\|3130091\|dbj\|D88660.1\| | 36.36 | 99 | 59 | 5 | 1308 | 1402 | 5266 | 5523 | 3.4e−06 | 60.08 |
| 105 | 1_21287 | gi\|3130091\|dbj\|D88660.1\| | 24.71 | 259 | 178 | 9 | 9 | 250 | 1117 | 1800 | 2.2e−05 | 67.38 |
| 106 | 1_21287 | gi\|11178681\|gb\|U12643.2\|SGU12643 | 46.70 | 1137 | 593 | 22 | 342 | 1465 | 736 | 3930 | 0.0 | 916.0 |
| 107 | 1_21287 | gi\|11178681\|gb\|U12643.2\|SGU12643 | 30.53 | 226 | 155 | 5 | 159 | 382 | 4150 | 4707 | 1.1e−17 | 98.21 |
| 108 | 1_21287 | gi\|11178681\|gb\|U12643.2\|SGU12643 | 27.05 | 414 | 258 | 14 | 45 | 414 | 3127 | 4245 | 1.5e−17 | 97.83 |
| 109 | 1_21287 | gi\|11178681\|gb\|U12643.2\|SGU12643 | 28.93 | 280 | 145 | 8 | 157 | 382 | 3751 | 4515 | 3.3e−17 | 96.67 |
| 110 | 1_21287 | gi\|11178681\|gb\|U12643.2\|SGU12643 | 34.93 | 146 | 94 | 3 | 159 | 303 | 4345 | 4722 | 4.1e−12 | 79.72 |
| 111 | 1_21287 | gi\|11178681\|gb\|U12643.2\|SGU12643 | 26.94 | 193 | 139 | 7 | 1305 | 1495 | 4072 | 4605 | 3.6e−08 | 66.63 |
| 112 | 1_21287 | gi\|11178681\|gb\|U12643.2\|SGU12643 | 28.10 | 153 | 108 | 6 | 1315 | 1465 | 4294 | 4710 | 4.4e−06 | 59.69 |
| 113 | 1_21287 | gi\|11178681\|gb\|U12643.2\|SGU12643 | 32.32 | 99 | 67 | 2 | 159 | 257 | 4540 | 4776 | 0.013 | 48.14 |
| 114 | 1_21287 | gi\|3130084\|dbj\|D88657.1\| | 42.51 | 1341 | 747 | 31 | 286 | 1602 | 1380 | 5123 | 0.0 | 915.2 |
| 115 | 1_21287 | gi\|3130084\|dbj\|D88657.1\| | 26.52 | 362 | 216 | 8 | 71 | 382 | 4488 | 5513 | 8.0e−24 | 118.6 |
| 116 | 1_21287 | gi\|3130084\|dbj\|D88657.1\| | 26.83 | 287 | 164 | 7 | 142 | 382 | 4323 | 5123 | 6.5e−18 | 98.98 |
| 117 | 1_21287 | gi\|3130084\|dbj\|D88657.1\| | 23.78 | 328 | 224 | 12 | 1301 | 1602 | 4599 | 5513 | 8.9e−15 | 88.58 |
| 118 | 1_21287 | gi\|3130084\|dbj\|D88657.1\| | 23.62 | 254 | 182 | 7 | 9 | 250 | 1119 | 1802 | 1.9e−04 | 54.30 |
| 119 | 1_21287 | gi\|3130087\|dbj\|D88658.1\| | 45.20 | 1219 | 641 | 28 | 346 | 1537 | 608 | 3994 | 0.0 | 898.7 |
| 120 | 1_21287 | gi\|3130087\|dbj\|D88658.1\| | 28.85 | 253 | 153 | 7 | 162 | 387 | 3662 | 4360 | 5.5e−17 | 95.90 |
| 121 | 1_21287 | gi\|3130087\|dbj\|D88658.1\| | 26.18 | 359 | 216 | 9 | 112 | 421 | 3263 | 4327 | 5.5e−17 | 95.90 |
| 122 | 1_21287 | gi\|3130087\|dbj\|D88658.1\| | 31.34 | 201 | 125 | 6 | 1300 | 1487 | 3626 | 4225 | 4.4e−14 | 86.27 |
| 123 | 1_21287 | gi\|3130087\|dbj\|D88658.1\| | 28.06 | 139 | 92 | 5 | 295 | 425 | 3308 | 3721 | 0.010 | 48.52 |
| 124 | 1_21287 | gi\|3130087\|dbj\|D88658.1\| | 21.48 | 270 | 189 | 7 | 5 | 251 | 53 | 844 | 1.2 | 41.59 |
| 125 | 1_21287 | gi\|3130094\|dbj\|D88661.1\| | 45.20 | 1219 | 641 | 28 | 346 | 1537 | 600 | 3994 | 0.0 | 897.5 |
| 126 | 1_21287 | gi\|3130094\|dbj\|D88661.1\| | 28.85 | 253 | 153 | 7 | 162 | 387 | 3662 | 4360 | 5.5e−17 | 95.90 |
| 127 | 1_21287 | gi\|3130094\|dbj\|D88661.1\| | 31.34 | 201 | 125 | 6 | 1300 | 1487 | 3626 | 4225 | 4.4e−14 | 86.27 |
| 128 | 1_21287 | gi\|3130094\|dbj\|D88661.1\| | 26.55 | 226 | 121 | 6 | 202 | 382 | 3302 | 3958 | 2.3e−10 | 73.94 |
| 129 | 1_21287 | gi\|3130094\|dbj\|D88661.1\| | 35.16 | 128 | 78 | 5 | 155 | 277 | 3902 | 4282 | 3.6e−08 | 66.63 |
| 130 | 1_21287 | gi\|3130094\|dbj\|D88661.1\| | 29.50 | 139 | 90 | 5 | 295 | 425 | 3308 | 3721 | 5.4e−04 | 52.76 |
| 131 | 1_21287 | gi\|3130094\|dbj\|D88661.1\| | 21.48 | 270 | 189 | 7 | 5 | 251 | 53 | 844 | 0.327 | 43.51 |
| 132 | 1_21287 | gi\|3130104\|dbj\|D89978.1\| | 44.18 | 1288 | 688 | 32 | 346 | 1602 | 608 | 4153 | 0.0 | 897.1 |

-continued

| No | Query id | Subject id | % identity | alignment length | mismatches | gap openings | q. start | q. end | s. start | s. end | e-value | bit score |
|---|---|---|---|---|---|---|---|---|---|---|---|---|
| 133 | 1__21287 | gi\|3130104\|dbj\|D89978.1\| | 27.69 | 260 | 183 | 5 | 133 | 387 | 3701 | 4360 | 2.5e−17 | 97.06 |
| 134 | 1__21287 | gi\|3130104\|dbj\|D89978.1\| | 26.18 | 359 | 216 | 9 | 112 | 421 | 3263 | 4327 | 5.5e−17 | 95.90 |
| 135 | 1__21287 | gi\|3130104\|dbj\|D89978.1\| | 31.34 | 201 | 125 | 6 | 1300 | 1487 | 3626 | 4225 | 7.5e−14 | 85.50 |
| 136 | 1__21287 | gi\|3130104\|dbj\|D89978.1\| | 29.50 | 139 | 90 | 5 | 295 | 425 | 3308 | 3721 | 4.1e−04 | 53.14 |
| 137 | 1__21287 | gi\|3130104\|dbj\|D89978.1\| | 21.85 | 270 | 188 | 7 | 5 | 251 | 53 | 844 | 0.250 | 43.90 |
| 138 | 1__21287 | gi\|3130073\|dbj\|D88652.1\| | 44.18 | 1288 | 688 | 32 | 346 | 1602 | 608 | 4153 | 0.0 | 896.3 |
| 139 | 1__21287 | gi\|3130073\|dbj\|D88652.1\| | 29.64 | 253 | 151 | 8 | 162 | 387 | 3662 | 4360 | 1.1e−17 | 98.21 |
| 140 | 1__21287 | gi\|3130073\|dbj\|D88652.1\| | 26.46 | 359 | 215 | 9 | 112 | 421 | 3263 | 4327 | 3.3e−17 | 96.67 |
| 141 | 1__21287 | gi\|3130073\|dbj\|D88652.1\| | 30.85 | 201 | 126 | 6 | 1300 | 1487 | 3626 | 4225 | 7.5e−14 | 85.50 |
| 142 | 1__21287 | gi\|3130073\|dbj\|D88652.1\| | 29.50 | 139 | 90 | 5 | 295 | 425 | 3308 | 3721 | 5.4e−04 | 62.76 |
| 143 | 1__21287 | gi\|3130073\|dbj\|D88652.1\| | 21.48 | 270 | 189 | 7 | 5 | 251 | 53 | 844 | 0.327 | 43.51 |
| 144 | 1__21287 | gi\|153639\|gb\|M17361.1\|STRGTFBC | 42.10 | 1342 | 752 | 32 | 286 | 1602 | 985 | 4725 | 0.0 | 895.6 |
| 145 | 1__21287 | gi\|153639\|gb\|M17361.1\|STRGTFBC | 45.07 | 1216 | 644 | 26 | 346 | 1537 | 5890 | 9276 | 0.0 | 894.0 |
| 146 | 1__21287 | gi\|153639\|gb\|M17361.1\|STRGTFBC | 27.44 | 317 | 225 | 6 | 71 | 382 | 4090 | 4920 | 1.2e−24 | 121.3 |
| 147 | 1__21287 | gi\|153639\|gb\|M17361.1\|STRGTFBC | 27.87 | 244 | 148 | 8 | 167 | 382 | 4000 | 4725 | 3.3e−17 | 96.67 |
| 148 | 1__21287 | gi\|153639\|gb\|M17361.1\|STRGTFBC | 31.37 | 204 | 133 | 6 | 155 | 351 | 8854 | 9339 | 7.2e−17 | 95.52 |
| 149 | 1__21287 | gi\|153639\|gb\|M17361.1\|STRGTFBC | 23.77 | 324 | 225 | 11 | 1301 | 1602 | 4201 | 5115 | 5.2e−15 | 89.35 |
| 150 | 1__21287 | gi\|153639\|gb\|M17361.1\|STRGTFBC | 26.55 | 226 | 121 | 6 | 202 | 382 | 8584 | 9240 | 1.0e−10 | 75.10 |
| 151 | 1__21287 | gi\|153639\|gb\|M17361.1\|STRGTFBC | 23.23 | 254 | 183 | 8 | 9 | 250 | 724 | 1407 | 2.4e−04 | 53.91 |
| 152 | 1__21287 | gi\|153639\|gb\|M17361.1\|STRGTFBC | 29.50 | 139 | 90 | 5 | 295 | 425 | 8590 | 9003 | 4.1e−04 | 53.14 |
| 153 | 1__21287 | gi\|153639\|gb\|M17361.1\|STRGTFBC | 31.52 | 92 | 62 | 3 | 187 | 277 | 9348 | 9563 | 0.008 | 48.91 |
| 154 | 1__21287 | gi\|153639\|gb\|M17361.1\|STRGTFBC | 27.97 | 118 | 84 | 2 | 271 | 387 | 9348 | 9641 | 0.013 | 48.14 |
| 155 | 1__21287 | gi\|153639\|gb\|M17361.1\|STRGTFBC | 28.57 | 91 | 64 | 3 | 1371 | 1460 | 9348 | 9608 | 0.147 | 44.67 |
| 156 | 1__21287 | gi\|153639\|gb\|M17361.1\|STRGTFBC | 22.22 | 270 | 187 | 7 | 5 | 251 | 5335 | 6126 | 0.427 | 43.13 |
| 157 | 1__21287 | gi\|3130080\|dbj\|D88655.1\| | 45.35 | 1215 | 637 | 28 | 346 | 1633 | 608 | 3982 | 0.0 | 895.6 |
| 158 | 1__21287 | gi\|3130080\|dbj\|D88655.1\| | 29.58 | 240 | 162 | 6 | 155 | 387 | 3572 | 4165 | 5.0e−18 | 99.37 |
| 159 | 1__21287 | gi\|3130080\|dbj\|D88655.1\| | 26.55 | 226 | 121 | 6 | 202 | 382 | 3302 | 3958 | 2.3e−10 | 73.94 |
| 160 | 1__21287 | gi\|3130080\|dbj\|D88655.1\| | 29.50 | 139 | 90 | 5 | 295 | 425 | 3308 | 3721 | 5.4e−04 | 52.76 |
| 161 | 1__21287 | gi\|3130080\|dbj\|D88655.1\| | 28.39 | 155 | 71 | 5 | 1300 | 1414 | 3626 | 4090 | 0.017 | 47.75 |
| 162 | 1__21287 | gi\|3130080\|dbj\|D88655.1\| | 21.48 | 270 | 189 | 7 | 5 | 251 | 53 | 844 | 0.327 | 43.51 |
| 163 | 1__21287 | gi\|153642\|gb\|M22054.1\|STRGTFC | 45.07 | 1216 | 644 | 26 | 346 | 1537 | 757 | 4143 | 0.0 | 894.0 |
| 164 | 1__21287 | gi\|153642\|gb\|M22054.1\|STRGTFC | 31.37 | 204 | 133 | 6 | 155 | 351 | 3721 | 4206 | 7.2e−17 | 95.52 |
| 165 | 1__21287 | gi\|153642\|gb\|M22054.1\|STRGTFC | 26.55 | 226 | 121 | 6 | 202 | 382 | 3451 | 4107 | 1.0e−10 | 75.10 |
| 166 | 1__21287 | gi\|153642\|gb\|M22054.1\|STRGTFC | 29.50 | 139 | 90 | 6 | 295 | 425 | 3457 | 3870 | 4.1e−04 | 53.14 |
| 167 | 1__21287 | gi\|153642\|gb\|M22054.1\|STRGTFC | 31.52 | 92 | 62 | 3 | 187 | 277 | 4215 | 4430 | 0.008 | 48.91 |
| 168 | 1__21287 | gi\|153642\|gb\|M22054.1\|STRGTFC | 27.97 | 118 | 84 | 2 | 271 | 387 | 4215 | 4508 | 0.013 | 48.14 |
| 169 | 1__21287 | gi\|153642\|gb\|M22054.1\|STRGTFC | 28.57 | 91 | 64 | 3 | 1371 | 1480 | 4215 | 4475 | 0.147 | 44.67 |
| 170 | 1__21287 | gi\|153642\|gb\|M22054.1\|STRGTFC | 22.22 | 270 | 187 | 7 | 5 | 251 | 202 | 993 | 0.427 | 43.13 |
| 171 | 1__21287 | gi\|1163182\|gb\|U38181.1\|LMU38181 | 42.69 | 1225 | 676 | 30 | 343 | 1541 | 928 | 4338 | 0.0 | 865.9 |
| 172 | 1__21287 | gi\|1163182\|gb\|U38181.1\|LMU38181 | 29.92 | 244 | 166 | 6 | 162 | 400 | 4105 | 4827 | 8.3e−21 | 108.6 |
| 173 | 1__21287 | gi\|1163182\|gb\|U38181.1\|LMU38181 | 29.18 | 257 | 150 | 7 | 158 | 382 | 3817 | 4584 | 9.5e−17 | 95.13 |
| 174 | 1__21287 | gi\|1163182\|gb\|U38181.1\|LMU38181 | 26.62 | 263 | 140 | 10 | 173 | 382 | 3616 | 4392 | 4.5e−11 | 76.26 |
| 175 | 1__21287 | gi\|1163182\|gb\|U38181.1\|LMU38181 | 25.77 | 163 | 120 | 4 | 1303 | 1464 | 4138 | 4584 | 0.001 | 51.99 |
| 176 | 1__21287 | gi\|1163182\|gb\|U38181.1\|LMU38181 | 24.57 | 175 | 117 | 6 | 201 | 360 | 3283 | 3798 | 8.0 | 38.89 |
| 177 | 1__21287 | gi\|450873\|dbj\|D13858.1\|STRGTF1 | 39.90 | 1431 | 816 | 35 | 343 | 1729 | 981 | 4976 | 0.0 | 864.4 |
| 178 | 1__21287 | gi\|450873\|dbj\|D13858.1\|STRGTF1 | 28.03 | 289 | 158 | 10 | 144 | 382 | 3681 | 4535 | 2.0e−16 | 93.59 |
| 179 | 1__21287 | gi\|450873\|dbj\|D13858.1\|STRGTF1 | 26.71 | 292 | 155 | 8 | 151 | 383 | 4341 | 5216 | 5.7e−14 | 85.89 |
| 180 | 1__21287 | gi\|450873\|dbj\|D13858.1\|STRGTF1 | 31.11 | 135 | 90 | 3 | 260 | 391 | 6311 | 5907 | 3.4e−06 | 60.08 |
| 181 | 1__21287 | gi\|450873\|dbj\|D13858.1\|STRGTF1 | 24.25 | 301 | 174 | 10 | 1310 | 1556 | 4299 | 5147 | 4.4e−06 | 59.69 |
| 182 | 1__21287 | gi\|450873\|dbj\|D13858.1\|STRGTF1 | 29.05 | 148 | 101 | 5 | 239 | 382 | 5922 | 5536 | 5.0e−09 | 55.07 |
| 183 | 1__21287 | gi\|450873\|dbj\|D13858.1\|STRGTF1 | 31.48 | 162 | 105 | 7 | 163 | 318 | 5898 | 5473 | 2.4e−04 | 53.91 |
| 184 | 1__21287 | gi\|450873\|dbj\|D13858.1\|STRGTF1 | 27.61 | 134 | 95 | 3 | 167 | 298 | 6275 | 5934 | 5.4e−04 | 52.76 |
| 185 | 1__21287 | gi\|450873\|dbj\|D13858.1\|STRGTF1 | 31.71 | 123 | 68 | 5 | 270 | 376 | 3579 | 3944 | 0.006 | 49.29 |
| 186 | 1__21287 | gi\|450873\|dbj\|D13858.1\|STRGTF1 | 23.22 | 211 | 125 | 7 | 1311 | 1484 | 4644 | 5273 | 0.023 | 47.37 |
| 187 | 1__21287 | gi\|450873\|dbj\|D13858.1\|STRGTF1 | 23.86 | 176 | 125 | 6 | 1329 | 1495 | 5916 | 5494 | 0.066 | 45.82 |
| 188 | 1__21287 | gi\|450873\|dbj\|D13858.1\|STRGTF1 | 23.48 | 132 | 100 | 3 | 1329 | 1459 | 6305 | 5946 | 0.147 | 44.67 |

-continued

| No | Query id | Subject id | % identity | alignment length | mismatches | gap openings | q. start | q. end | s. start | s. end | e-value | bit score |
|---|---|---|---|---|---|---|---|---|---|---|---|---|
| 189 | 1__21287 | gi\|450873\|dbj\|D13858.1\|STRGTF1 | 28.83 | 111 | 76 | 4 | 1317 | 1424 | 5751 | 5461 | 0.557 | 42.74 |
| 190 | 1__21287 | gi\|450873\|dbj\|D13858.1\|STRGTF1 | 24.14 | 116 | 77 | 2 | 116 | 220 | 6263 | 5918 | 5.0e−09 | 34.27 |
| 191 | 1__21287 | gi\|940426\|dbj\|D63570.1\| | 39.80 | 1427 | 815 | 35 | 336 | 1718 | 1462 | 5446 | 0.0 | 857.8 |
| 192 | 1__21287 | gi\|940426\|dbj\|D63570.1\| | 27.57 | 243 | 172 | 7 | 144 | 382 | 4183 | 4842 | 2.1e−16 | 93.97 |
| 193 | 1__21287 | gi\|940426\|dbj\|D63570.1\| | 29.63 | 216 | 147 | 6 | 172 | 382 | 4516 | 5037 | 1.2e−14 | 88.20 |
| 194 | 1__21287 | gi\|940426\|dbj\|D63570.1\| | 28.10 | 274 | 186 | 12 | 120 | 382 | 6776 | 6039 | 6.3e−13 | 82.42 |
| 195 | 1__21287 | gi\|940426\|dbj\|D63570.1\| | 25.56 | 223 | 161 | 5 | 166 | 383 | 5104 | 5718 | 1.8e−07 | 64.31 |
| 196 | 1__21287 | gi\|940426\|dbj\|D63570.1\| | 23.68 | 190 | 142 | 3 | 1306 | 1492 | 6488 | 5955 | 6.8e−07 | 62.39 |
| 197 | 1__21287 | gi\|940426\|dbj\|D63570.1\| | 28.72 | 188 | 129 | 6 | 232 | 414 | 6836 | 6336 | 2.0e−06 | 60.85 |
| 198 | 1__21287 | gi\|940426\|dbj\|D63570.1\| | 25.82 | 182 | 128 | 5 | 1329 | 1503 | 6614 | 6108 | 1.1e−04 | 55.07 |
| 199 | 1__21287 | gi\|940426\|dbj\|D63570.1\| | 24.03 | 233 | 164 | 8 | 1329 | 1548 | 6809 | 6150 | 0.001 | 51.99 |
| 200 | 1__21287 | gi\|940426\|dbj\|D63570.1\| | 22.93 | 314 | 190 | 10 | 1295 | 1556 | 4753 | 5649 | 0.001 | 51.99 |
| 201 | 1__21287 | gi\|940426\|dbj\|D63570.1\| | 31.71 | 123 | 68 | 5 | 270 | 376 | 4081 | 4448 | 0.006 | 49.29 |
| 202 | 1__21287 | gi\|940426\|dbj\|D63570.1\| | 24.58 | 240 | 141 | 11 | 1311 | 1510 | 5146 | 5847 | 0.086 | 45.44 |
| 203 | 1__21287 | gi\|217032\|dbj\|D90213.1\|STRGTFIA | 39.69 | 1431 | 819 | 36 | 343 | 1729 | 631 | 4532 | 0.0 | 857.1 |
| 204 | 1__21287 | gi\|217032\|dbj\|D90213.1\|STRGTFIA | 27.34 | 289 | 160 | 9 | 144 | 382 | 3331 | 4191 | 1.0e−15 | 91.66 |
| 205 | 1__21287 | gi\|217032\|dbj\|D90213.1\|STRGTFIA | 31.67 | 240 | 145 | 14 | 123 | 343 | 4249 | 4941 | 7.0e−12 | 78.95 |
| 206 | 1__21287 | gi\|217032\|dbj\|D90213.1\|STRGTFIA | 25.56 | 223 | 161 | 5 | 166 | 383 | 4258 | 4872 | 2.1e−08 | 67.40 |
| 207 | 1__21287 | gi\|217032\|dbj\|D90213.1\|STRGTFIA | 22.60 | 438 | 282 | 14 | 1176 | 1556 | 3592 | 4803 | 1.2e−06 | 61.62 |
| 208 | 1__21287 | gi\|217032\|dbj\|D90213.1\|STRGTFIA | 23.70 | 211 | 124 | 7 | 1311 | 1484 | 4300 | 4929 | 0.003 | 50.06 |
| 209 | 1__21287 | gi\|153646\|gb\|M17391.1\|STRGTFI | 42.95 | 1199 | 664 | 25 | 317 | 1495 | 535 | 3885 | 0.0 | 848.2 |
| 210 | 1__21287 | gi\|153646\|gb\|M17391.1\|STRGTFI | 26.01 | 396 | 248 | 13 | 81 | 431 | 3586 | 4698 | 6.5e−18 | 98.98 |
| 211 | 1__21287 | gi\|153646\|gb\|M17391.1\|STRGTFI | 28.62 | 304 | 193 | 12 | 155 | 434 | 3601 | 4368 | 2.5e−17 | 97.06 |
| 212 | 1__21287 | gi\|153646\|gb\|M17391.1\|STRGTFI | 31.43 | 175 | 118 | 4 | 1315 | 1487 | 3769 | 4254 | 1.4e−15 | 91.28 |
| 213 | 1__21287 | gi\|153646\|gb\|M17391.1\|STRGTFI | 28.14 | 295 | 150 | 10 | 151 | 383 | 3991 | 4866 | 4.0e−15 | 89.74 |
| 214 | 1__21287 | gi\|153646\|gb\|M17391.1\|STRGTFI | 32.40 | 179 | 90 | 7 | 156 | 303 | 4348 | 4878 | 8.6e−10 | 72.02 |
| 215 | 1__21287 | gi\|153646\|gb\|M17391.1\|STRGTFI | 23.77 | 244 | 135 | 7 | 1295 | 1487 | 3901 | 4593 | 5.8e−06 | 59.31 |
| 216 | 1__21267 | gi\|153646\|gb\|M17391.1\|STRGTFI | 28.57 | 210 | 144 | 8 | 53 | 256 | 4405 | 4926 | 7.0e−04 | 52.37 |
| 217 | 1__21287 | gi\|153646\|gb\|M17391.1\|STRGTFI | 23.86 | 176 | 129 | 4 | 1317 | 1487 | 4438 | 4932 | 0.017 | 47.75 |
| 218 | 1__21287 | gi\|22138844\|dbj\|AB089438.1\| | 40.96 | 1377 | 768 | 39 | 210 | 1541 | 127 | 3939 | 0.0 | 835.9 |
| 219 | 1__21287 | gi\|22138844\|dbj\|AB089438.1\| | 29.15 | 319 | 173 | 11 | 165 | 430 | 3517 | 4437 | 3.1e−20 | 106.7 |
| 220 | 1__21287 | gi\|22138844\|dbj\|AB089438.1\| | 29.92 | 264 | 148 | 10 | 156 | 382 | 3214 | 3996 | 1.7e−13 | 84.34 |
| 221 | 1__21287 | gi\|22138844\|dbj\|AB089438.1\| | 29.79 | 235 | 155 | 10 | 159 | 383 | 3955 | 4653 | 2.2e−13 | 83.96 |
| 222 | 1__21287 | gi\|22138844\|dbj\|AB089438.1\| | 30.77 | 195 | 130 | 8 | 151 | 340 | 4129 | 4647 | 1.6e−11 | 77.80 |
| 223 | 1__21287 | gi\|22138844\|dbj\|AB089438.1\| | 25.36 | 209 | 120 | 8 | 1308 | 1480 | 3811 | 4437 | 1.8e−07 | 64.31 |
| 224 | 1__21287 | gi\|22138844\|dbj\|AB089438.1\| | 26.20 | 187 | 133 | 6 | 1308 | 1489 | 4078 | 4587 | 2.2e−05 | 57.38 |
| 225 | 1__21287 | gi\|22138844\|dbj\|AB089438.1\| | 26.19 | 126 | 92 | 3 | 1317 | 1441 | 4300 | 4647 | 0.002 | 50.83 |
| 226 | 1__21287 | gi\|22138844\|dbj\|AB089438.1\| | 25.23 | 214 | 154 | 6 | 11 | 218 | 22 | 621 | 0.003 | 50.06 |
| 227 | 1__21287 | gi\|1438117\|dbj\|D13928.1\|STRGTFT | 38.49 | 1447 | 831 | 36 | 316 | 1703 | 717 | 4742 | 0.0 | 828.2 |
| 228 | 1__21287 | gi\|1438117\|dbj\|D13928.1\|STRGTFT | 31.45 | 248 | 140 | 9 | 165 | 382 | 3873 | 4550 | 4.2e−17 | 96.29 |
| 229 | 1__21287 | gi\|1438117\|dbj\|D13928.1\|STRGTFT | 25.48 | 416 | 261 | 12 | 61 | 427 | 3369 | 4580 | 4.0e−15 | 89.74 |
| 230 | 1__21287 | gi\|1438117\|dbj\|D13928.1\|STRGTFT | 28.10 | 242 | 166 | 9 | 150 | 383 | 4020 | 4622 | 3.6e−08 | 66.63 |
| 231 | 1__21287 | gi\|4691427\|dbj\|AB026123.1\| | 43.48 | 1173 | 634 | 25 | 337 | 1480 | 5784 | 9086 | 0.0 | 827.0 |
| 232 | 1__21287 | gi\|4691427\|dbj\|AB026123.1\| | 42.00 | 1188 | 666 | 31 | 313 | 1477 | 1235 | 4540 | 0.0 | 778.5 |
| 233 | 1__21287 | gi\|4691427\|dbj\|AB026123.1\| | 27.90 | 276 | 164 | 8 | 142 | 382 | 8601 | 9362 | 4.0e−15 | 89.74 |
| 234 | 1__21287 | gi\|4691427\|dbj\|AB026123.1\| | 25.50 | 302 | 181 | 10 | 177 | 434 | 4064 | 4957 | 2.0e−14 | 87.43 |
| 235 | 1__21287 | gi\|4691427\|dbj\|AB026123.1\| | 28.84 | 267 | 158 | 12 | 156 | 390 | 9051 | 9842 | 3.4e−14 | 86.66 |
| 236 | 1__21287 | gi\|4691427\|dbj\|AB026123.1\| | 29.03 | 217 | 153 | 6 | 167 | 382 | 4358 | 4921 | 2.9e−10 | 73.56 |
| 237 | 1__21287 | gi\|4691427\|dbj\|AB026123.1\| | 25.16 | 306 | 194 | 9 | 1210 | 1480 | 4073 | 4969 | 1.1e−09 | 71.63 |
| 238 | 1__21287 | gi\|4691427\|dbj\|AB026123.1\| | 22.33 | 300 | 201 | 11 | 1307 | 1574 | 8922 | 9740 | 1.6e−00 | 67.78 |
| 239 | 1__21287 | gi\|4691427\|dbj\|AB026123.1\| | 26.90 | 171 | 118 | 6 | 135 | 298 | 9315 | 9821 | 2.6e−06 | 60.46 |
| 240 | 1__21287 | gi\|4691427\|dbj\|AB026123.1\| | 26.35 | 167 | 119 | 8 | 1302 | 1464 | 9363 | 9821 | 5.4e−04 | 52.76 |
| 241 | 1__21287 | gi\|4691427\|dbj\|AB026123.1\| | 41.54 | 65 | 37 | 1 | 156 | 219 | 4742 | 4936 | 0.002 | 50.83 |
| 242 | 1__21287 | gi\|4691427\|dbj\|AB026123.1\| | 22.73 | 242 | 162 | 6 | 2 | 218 | 9111 | 9833 | 0.147 | 44.67 |
| 243 | 1__21287 | gi\|4691427\|dbj\|AB026123.1\| | 38.30 | 47 | 29 | 0 | 178 | 224 | 1346 | 1486 | 0.950 | 41.97 |
| 244 | 1__21287 | gi\|4691427\|dbj\|AB026123.1\| | 24.70 | 166 | 115 | 7 | 222 | 377 | 8283 | 8741 | 8.0 | 38.89 |
| 245 | 1__21287 | gi\|662380\|gb\|L35928.1\|STRGTFM | 43.65 | 1157 | 634 | 24 | 344 | 1482 | 904 | 4137 | 0.0 | 816.6 |
| 246 | 1__21287 | gi\|662380\|gb\|L35928.1\|STRGTFM | 29.12 | 261 | 145 | 3 | 162 | 382 | 4093 | 4812 | 2.4e−20 | 107.1 |
| 247 | 1__21287 | gi\|662380\|gb\|L35928.1\|STRGTFM | 32.27 | 220 | 145 | 5 | 167 | 382 | 3709 | 4251 | 1.6e−19 | 104.4 |
| 248 | 1__21287 | gi\|662380\|gb\|L35928.1\|STRGTFM | 33.13 | 166 | 111 | 2 | 133 | 298 | 4396 | 4812 | 7.5e−14 | 85.50 |
| 249 | 1__21287 | gi\|662380\|gb\|L35928.1\|STRGTFM | 28.12 | 256 | 133 | 13 | 1260 | 1464 | 3904 | 4620 | 8.9e−07 | 62.00 |
| 250 | 1__21287 | gi\|662380\|gb\|L35928.1\|STRGTFM | 25.49 | 153 | 114 | 3 | 1312 | 1464 | 4396 | 4812 | 0.001 | 51.60 |
| 251 | 1__21287 | gi\|662380\|gb\|L35928.1\|STRGTFM | 34.18 | 79 | 52 | 0 | 137 | 215 | 4579 | 4815 | 0.001 | 51.60 |
| 252 | 1__21287 | gi\|662378\|gb\|L35495.1\|STRGTFL | 41.41 | 1287 | 700 | 32 | 309 | 1541 | 633 | 4247 | 0.0 | 816.2 |
| 253 | 1__21287 | gi\|662378\|gb\|L35495.1\|STRGTFL | 35.92 | 206 | 125 | 8 | 162 | 360 | 3861 | 4466 | 1.7e−18 | 100.9 |

| No | Query id | Subject id | % identity | alignment length | mismatches | gap openings | q. start | q. end | s. start | s. end | e-value | bit score |
|---|---|---|---|---|---|---|---|---|---|---|---|---|
| 254 | 1__21287 | gi|662378|gb|L35495.1|STRGTFL | 24.02 | 383 | 245 | 10 | 46 | 382 | 3366 | 4400 | 4.2e−17 | 96.29 |
| 255 | 1__21287 | gi|662378|gb|L35495.1|STRGTFL | 27.85 | 158 | 112 | 7 | 1309 | 1464 | 3975 | 4400 | 1.7e−05 | 57.77 |
| 256 | 1__21287 | gi|662378|gb|L35495.1|STRGTFL | 21.86 | 494 | 345 | 24 | 11 | 463 | 153 | 1460 | 0.950 | 41.97 |
| 257 | 1__21287 | gi|662378|gb|L35495.1|STRGTFL | 26.61 | 109 | 78 | 4 | 1300 | 1406 | 4137 | 4424 | 4.7 | 39.66 |
| 258 | 1__21287 | gi|153648|gb|M64111.1| STRGTFJA | 41.41 | 1292 | 700 | 33 | 343 | 1577 | 540 | 4214 | 0.0 | 813.9 |
| 259 | 1__21287 | gi|153648|gb|M64111.1| STRGTFJA | 27.90 | 276 | 150 | 5 | 165 | 391 | 3753 | 4517 | 4.7e−16 | 92.82 |
| 260 | 1__21287 | gi|153648|gb|M64111.1| STRGTFJA | 27.80 | 295 | 188 | 10 | 102 | 371 | 3195 | 4073 | 1.4e−15 | 91.28 |
| 261 | 1__21287 | gi|153648|gb|M64111.1| STRGTFJA | 24.14 | 174 | 126 | 8 | 1307 | 1474 | 4041 | 4505 | 0.039 | 46.59 |
| 262 | 1__21287 | gi|153648|gb|M64111.1| STRGTFJA | 22.22 | 117 | 88 | 3 | 1307 | 1420 | 4236 | 4550 | 0.950 | 41.97 |
| 263 | 1__21287 | gi|47526|emb|Z11873.1| SSGTFJKG | 41.41 | 1292 | 700 | 33 | 343 | 1577 | 540 | 4214 | 0.0 | 813.9 |
| 264 | 1__21287 | gi|47526|emb|Z11873.1| SSGTFJKG | 42.86 | 1155 | 635 | 27 | 351 | 1480 | 5315 | 8578 | 0.0 | 776.9 |
| 265 | 1__21287 | gi|47526|emb|Z11873.1| SSGTFJKG | 27.87 | 305 | 168 | 7 | 130 | 382 | 8612 | 9502 | 1.7e−21 | 110.9 |
| 266 | 1__21287 | gi|47526|emb|Z11873.1| SSGTFJKG | 28.83 | 222 | 152 | 5 | 164 | 379 | 8375 | 8977 | 3.6e−16 | 93.20 |
| 267 | 1__21287 | gi|47526|emb|Z11873.1| SSGTFJKG | 27.90 | 276 | 150 | 5 | 165 | 391 | 3753 | 4517 | 4.7e−16 | 92.82 |
| 268 | 1__21287 | gi|47526|emb|Z11873.1| SSGTFJKG | 27.80 | 295 | 188 | 10 | 102 | 371 | 3195 | 4073 | 1.4e−15 | 91.28 |
| 269 | 1__21287 | gi|47526|emb|Z11873.1| SSGTFJKG | 25.70 | 214 | 158 | 4 | 128 | 340 | 9044 | 9568 | 1.1e−09 | 71.63 |
| 270 | 1__21287 | gi|47526|emb|Z11873.1| SSGTFJKG | 26.69 | 236 | 155 | 9 | 168 | 385 | 7880 | 8539 | 1.2e−06 | 61.62 |
| 271 | 1__21287 | gi|47526|emb|Z11873.1| SSGTFJKG | 25.99 | 177 | 130 | 6 | 1306 | 1481 | 8411 | 8896 | 2.6e−06 | 60.46 |
| 272 | 1__21287 | gi|47526|emb|Z11873.1| SSGTFJKG | 21.67 | 300 | 210 | 9 | 1190 | 1464 | 8642 | 9502 | 1.7e−05 | 57.77 |
| 273 | 1__21287 | gi|47526|emb|Z11873.1| SSGTFJKG | 22.95 | 244 | 166 | 8 | 1299 | 1520 | 8798 | 9481 | 3.7e−05 | 56.61 |
| 274 | 1__21287 | gi|47526|emb|Z11873.1| SSGTFJKG | 30.83 | 120 | 80 | 3 | 128 | 244 | 9239 | 9586 | 0.003 | 50.06 |
| 275 | 1__21287 | gi|47526|emb|Z11873.1| SSGTFJKG | 24.14 | 174 | 126 | 8 | 1307 | 1474 | 4041 | 4505 | 0.039 | 46.59 |
| 276 | 1__21287 | gi|47526|emb|Z11873.1| SSGTFJKG | 22.22 | 117 | 88 | 3 | 1307 | 1420 | 4236 | 4550 | 0.960 | 41.97 |
| 277 | 1__21287 | gi|2935545|gb|AF049609.1| AF049609 | 41.08 | 1317 | 714 | 34 | 287 | 1541 | 412 | 4116 | 0.0 | 813.1 |
| 278 | 1__21287 | gi|2935545|gb|AF049609.1| AF049609 | 23.82 | 382 | 246 | 9 | 46 | 382 | 3235 | 4269 | 6.5e−18 | 98.98 |
| 279 | 1__21287 | gi|2935545|gb|AF049609.1| AF049609 | 35.44 | 206 | 126 | 8 | 162 | 360 | 3730 | 4335 | 8.6e−18 | 98.60 |
| 280 | 1__21287 | gi|2935545|gb|AF049609.1| AF049609 | 27.85 | 158 | 112 | 7 | 1309 | 1464 | 3844 | 4269 | 1.7e−05 | 57.77 |
| 281 | 1__21287 | gi|2935545|gb|AF049609.1| AF049609 | 22.26 | 274 | 180 | 11 | 11 | 251 | 22 | 840 | 1.2 | 41.59 |
| 282 | 1__21287 | gi|2935545|gb|AF049609.1| AF049609 | 26.61 | 109 | 78 | 4 | 1300 | 1406 | 4006 | 4293 | 4.7 | 39.66 |
| 283 | 1__21287 | gi|153652|gb|M30943.1|STRGTFS | 42.84 | 1146 | 629 | 33 | 346 | 1465 | 694 | 3846 | 0.0 | 778.5 |
| 284 | 1__21287 | gi|153652|gb|M30943.1|STRGTFS | 26.83 | 287 | 129 | 6 | 177 | 382 | 3406 | 4263 | 3.6e−16 | 93.20 |
| 285 | 1__21287 | gi|153652|gb|M30943.1|STRGTFS | 26.73 | 303 | 190 | 8 | 1210 | 1480 | 3415 | 4311 | 1.3e−13 | 84.73 |
| 286 | 1__21287 | gi|153652|gb|M30943.1|STRGTFS | 32.56 | 172 | 114 | 5 | 172 | 341 | 3937 | 4329 | 7.8e−11 | 75.48 |
| 287 | 1__21287 | gi|153652|gb|M30943.1|STRGTFS | 25.94 | 212 | 157 | 5 | 9 | 220 | 262 | 822 | 4.9e−05 | 56.23 |
| 288 | 1__21287 | gi|153652|gb|M30943.1|STRGTFS | 35.29 | 102 | 65 | 3 | 156 | 256 | 4084 | 4326 | 6.4e−05 | 55.84 |
| 289 | 1__21287 | gi|47530|emb|Z11872.1|SSGTFKG | 42.86 | 1155 | 635 | 27 | 351 | 1480 | 545 | 3808 | 0.0 | 776.9 |
| 290 | 1__21287 | gi|47530|emb|Z11872.1|SSGTFKG | 27.87 | 305 | 168 | 7 | 130 | 382 | 3842 | 4732 | 1.7e−21 | 110.9 |
| 291 | 1__21287 | gi|47530|emb|Z11872.1|SSGTFKG | 28.83 | 222 | 152 | 5 | 164 | 379 | 3605 | 4207 | 3.6e−16 | 93.20 |
| 292 | 1__21287 | gi|47530|emb|Z11872.1|SSGTFKG | 25.70 | 214 | 158 | 4 | 128 | 340 | 4274 | 4798 | 1.1e−09 | 71.63 |
| 293 | 1__21287 | gi|47530|emb|Z11872.1|SSGTFKG | 26.69 | 236 | 155 | 9 | 168 | 385 | 3110 | 3769 | 1.2e−06 | 61.62 |
| 294 | 1__21287 | gi|47530|emb|Z11872.1|SSGTFKG | 25.99 | 177 | 130 | 6 | 1306 | 1481 | 3641 | 4126 | 2.6e−06 | 60.46 |
| 295 | 1__21287 | gi|47530|emb|Z11872.1|SSGTFKG | 21.67 | 300 | 210 | 9 | 1190 | 1464 | 3872 | 4732 | 1.7e−05 | 57.77 |
| 296 | 1__21287 | gi|47530|emb|Z11872.1|SSGTFKG | 22.95 | 244 | 166 | 8 | 1299 | 1520 | 4028 | 4711 | 3.7e−05 | 56.61 |
| 297 | 1__21287 | gi|47530|emb|Z11872.1|SSGTFKG | 30.83 | 120 | 80 | 3 | 128 | 244 | 4469 | 4816 | 0.003 | 50.06 |
| 298 | 1__21287 | gi|940396|dbj|D63569.1| | 45.92 | 967 | 509 | 17 | 336 | 1288 | 1462 | 4167 | 0.0 | 765.4 |
| 299 | 1__21287 | gi|940396|dbj|D63569.1| | 27.57 | 243 | 172 | 7 | 144 | 382 | 4960 | 5619 | 2.1e−18 | 93.97 |
| 300 | 1__21287 | gi|940396|dbj|D63569.1| | 29.63 | 216 | 147 | 6 | 172 | 382 | 5293 | 5814 | 1.2e−14 | 88.20 |
| 301 | 1__21287 | gi|940396|dbj|D63569.1| | 30.25 | 238 | 157 | 10 | 1315 | 1543 | 5398 | 6048 | 2.8e−13 | 83.57 |
| 302 | 1__21287 | gi|940396|dbj|D63569.1| | 28.10 | 274 | 186 | 12 | 120 | 382 | 7553 | 6816 | 6.3e−13 | 82.42 |
| 303 | 1__21287 | gi|940396|dbj|D63569.1| | 25.56 | 223 | 161 | 6 | 166 | 383 | 5081 | 6495 | 1.8e−07 | 64.31 |

-continued

| No | Query id | Subject id | % identity | alignment length | mismatches | gap openings | q. start | q. end | s. start | s. end | e-value | bit score |
|---|---|---|---|---|---|---|---|---|---|---|---|---|
| 304 | 1__21287 | gi|940396|dbj|D63569.1| | 23.68 | 190 | 142 | 3 | 1306 | 1492 | 7265 | 6732 | 6.8e−07 | 62.39 |
| 305 | 1__21287 | gi|940396|dbj|D63569.1| | 28.72 | 188 | 129 | 6 | 232 | 414 | 7613 | 7113 | 2.0e−06 | 60.85 |
| 306 | 1__21287 | gi|940396|dbj|D63569.1| | 25.82 | 182 | 128 | 5 | 1329 | 1503 | 7391 | 6885 | 1.1e−04 | 55.07 |
| 307 | 1__21287 | gi|940396|dbj|D63569.1| | 22.93 | 314 | 190 | 10 | 1295 | 1556 | 5530 | 6426 | 0.001 | 51.99 |
| 308 | 1__21287 | gi|940396|dbj|D63569.1| | 24.03 | 233 | 164 | 8 | 1329 | 1548 | 7586 | 6927 | 0.001 | 51.99 |
| 309 | 1__21287 | gi|940396|dbj|D63569.1| | 24.58 | 240 | 141 | 11 | 1311 | 1510 | 5923 | 6624 | 0.086 | 45.44 |
| 310 | 1__21287 | gi|6899808|dbj|AB020020.1| | 49.53 | 850 | 407 | 19 | 346 | 1173 | 1741 | 4098 | 0.0 | 703.4 |
| 311 | 1__21287 | gi|6899808|dbj|AB020020.1| | 45.32 | 342 | 179 | 7 | 1154 | 1487 | 4031 | 5017 | 7.1e−73 | 281.6 |
| 312 | 1__21287 | gi|6899808|dbj|AB020020.1| | 34.35 | 262 | 137 | 12 | 156 | 382 | 4751 | 5530 | 1.8e−23 | 117.5 |
| 313 | 1__21287 | gi|6899808|dbj|AB020020.1| | 31.79 | 195 | 127 | 5 | 151 | 339 | 4946 | 5524 | 2.3e−15 | 90.51 |
| 314 | 1__21287 | gi|6899808|dbj|AB020020.1| | 29.87 | 231 | 152 | 9 | 162 | 382 | 4511 | 5140 | 9.8e−14 | 85.11 |
| 315 | 1__21287 | gi|6899808|dbj|AB020020.1| | 24.71 | 263 | 166 | 9 | 30 | 260 | 4817 | 5539 | 7.5e−06 | 58.92 |
| 316 | 1__21287 | gi|6899808|dbj|AB020020.1| | 26.90 | 171 | 121 | 7 | 1298 | 1464 | 5075 | 5530 | 1.3e−05 | 58.15 |
| 317 | 1__21287 | gi|6899808|dbj|AB020020.1| | 24.27 | 206 | 117 | 6 | 1315 | 1481 | 4853 | 5470 | 3.7e−05 | 56.61 |
| 318 | 1__21287 | gi|6899808|dbj|AB020020.1| | 21.93 | 269 | 189 | 6 | 6 | 253 | 1036 | 1839 | 0.039 | 46.59 |
| 319 | 1__21287 | gi|18253271|dbj|AB078507.1| | 43.09 | 485 | 261 | 11 | 1068 | 1537 | 3 | 1355 | 2.1e−93 | 349.7 |
| 320 | 1__21287 | gi|18253271|dbj|AB078507.1| | 29.25 | 253 | 152 | 7 | 162 | 387 | 1023 | 1721 | 4.2e−17 | 96.29 |
| 321 | 1__21287 | gi|18253271|dbj|AB078507.1| | 25.91 | 359 | 217 | 9 | 112 | 421 | 624 | 1688 | 7.2e−17 | 95.52 |
| 322 | 1__21287 | gi|18253271|dbj|AB078507.1| | 31.34 | 201 | 125 | 6 | 1300 | 1487 | 987 | 1586 | 4.4e−14 | 86.27 |
| 323 | 1__21287 | gi|18253271|dbj|AB078507.1| | 28.78 | 139 | 91 | 5 | 295 | 425 | 669 | 1082 | 0.003 | 60.06 |
| 324 | 1__21287 | gi|18147720|dbj|AB056712.1| | 46.75 | 338 | 175 | 7 | 301 | 633 | 648 | 1640 | 4.2e−73 | 282.3 |
| 325 | 1__21287 | gi|16413394|emb|AL596167.1| | 25.34 | 513 | 351 | 23 | 1574 | 2054 | 119871 | 121352 | 2.2e−29 | 137.1 |
| 326 | 1__21287 | gi|16413394|emb|AL596167.1| | 21.70 | 470 | 345 | 15 | 1608 | 2054 | 119736 | 121109 | 2.6e−22 | 113.6 |
| 327 | 1__21287 | gi|16413394|emb|AL596167.1| | 23.58 | 458 | 319 | 18 | 1470 | 1896 | 120054 | 121358 | 2.3e−18 | 100.5 |
| 328 | 1__21287 | gi|15023989|gb|AE007623.1| AE007623 | 31.50 | 273 | 171 | 8 | 145 | 401 | 6559 | 5792 | 5.0e−26 | 125.9 |
| 329 | 1__21287 | gi|15023989|gb|AE007623.1| AE007623 | 35.11 | 225 | 143 | 7 | 159 | 380 | 9310 | 8708 | 5.7e−22 | 112.5 |
| 330 | 1__21287 | gi|15023989|gb|AE007623.1| AE007623 | 27.75 | 382 | 234 | 13 | 41 | 380 | 10177 | 9152 | 5.4e−20 | 105.9 |
| 331 | 1__21287 | gi|15023989|gb|AE007623.1| AE007623 | 29.78 | 319 | 205 | 12 | 170 | 469 | 4819 | 3905 | 9.1e−20 | 105.1 |
| 332 | 1__21287 | gi|15023989|gb|AE007623.1| AE007623 | 29.37 | 262 | 155 | 6 | 162 | 390 | 8857 | 8120 | 1.6e−19 | 104.4 |
| 333 | 1__21287 | gi|15023989|gb|AE007623.1| AE007623 | 28.57 | 357 | 218 | 15 | 154 | 473 | 8455 | 7427 | 4.5e−19 | 102.6 |
| 334 | 1__21287 | gi|15023989|gb|AE007623.1| AE007623 | 28.66 | 307 | 166 | 9 | 160 | 413 | 6787 | 5894 | 5.9e−19 | 102.4 |
| 335 | 1__21287 | gi|15023989|gb|AE007623.1| AE007623 | 28.21 | 273 | 169 | 7 | 162 | 407 | 4597 | 3803 | 7.7e−19 | 102.1 |
| 336 | 1__21287 | gi|15023989|gb|AE007623.1| AE007623 | 28.14 | 263 | 171 | 7 | 159 | 403 | 4420 | 3859 | 2.9e−18 | 100.1 |
| 337 | 1__21287 | gi|15023989|gb|AE007623.1| AE007623 | 30.61 | 245 | 149 | 7 | 162 | 385 | 3265 | 2555 | 6.5e−18 | 98.98 |
| 338 | 1__21287 | gi|15023989|gb|AE007623.1| AE007623 | 30.20 | 255 | 150 | 8 | 158 | 384 | 7714 | 6971 | 1.1e−17 | 98.21 |
| 339 | 1__21287 | gi|15023989|gb|AE007623.1| AE007623 | 30.31 | 254 | 171 | 9 | 153 | 400 | 3406 | 2675 | 1.9e−17 | 97.44 |
| 340 | 1__21287 | gi|15023989|gb|AE007623.1| AE007623 | 27.94 | 247 | 159 | 6 | 153 | 380 | 4498 | 3779 | 7.2e−17 | 95.52 |
| 341 | 1__21287 | gi|15023989|gb|AE007623.1| AE007623 | 31.63 | 215 | 146 | 9 | 167 | 380 | 3973 | 3356 | 2.8e−16 | 93.59 |
| 342 | 1__21287 | gi|15023989|gb|AE007623.1| AE007623 | 28.07 | 228 | 146 | 5 | 156 | 365 | 3160 | 2492 | 1.4e−15 | 91.28 |
| 343 | 1__21287 | gi|15023989|gb|AE007623.1| AE007623 | 29.37 | 252 | 178 | 8 | 137 | 388 | 3934 | 3275 | 1 2e−14 | 88.20 |
| 344 | 1__21287 | gi|15023989|gb|AE007623.1| AE007623 | 31.28 | 243 | 146 | 11 | 167 | 388 | 5419 | 4733 | 2.6e−14 | 87.04 |
| 345 | 1__21287 | gi|15023989|gb|AE007623.1| AE007623 | 29.29 | 239 | 150 | 9 | 167 | 386 | 5782 | 5090 | 1.3e−13 | 84.73 |
| 346 | 1__21287 | gi|15023989|gb|AE007623.1| AE007623 | 28.57 | 245 | 175 | 10 | 138 | 382 | 5539 | 4922 | 2.8e−13 | 83.57 |
| 347 | 1__21287 | gi|15023989|gb|AE007623.1| AE007623 | 24.41 | 635 | 437 | 36 | 1242 | 1833 | 5041 | 3296 | 1.8e−12 | 80.88 |
| 348 | 1__21287 | gi|15023989|gb|AE007623.1| AE007623 | 23.31 | 635 | 426 | 32 | 1305 | 1878 | 9982 | 8243 | 4.1e−12 | 79.72 |
| 349 | 1__21287 | gi|15023989|gb|AE007623.1| AE007623 | 25.90 | 278 | 168 | 8 | 138 | 377 | 5989 | 5174 | 4.5e−11 | 76.26 |
| 350 | 1__21287 | gi|15023989|gb|AE007623.1| AE007623 | 25.95 | 289 | 148 | 9 | 160 | 382 | 7648 | 6794 | 7.8e−11 | 75.48 |
| 351 | 1__21287 | gi|15023989|gb|AE007623.1| AE007623 | 23.37 | 719 | 411 | 36 | 1307 | 1885 | 6526 | 4505 | 2.3e−10 | 73.94 |
| 352 | 1__21287 | gi|15023989|gb|AE007623.1| AE007623 | 21.57 | 765 | 512 | 37 | 1260 | 1936 | 9508 | 7526 | 6.6e−10 | 72.40 |

-continued

| No | Query id | Subject id | % identity | alignment length | mis-matches | gap openings | q. start | q. end | s. start | s. end | e-value | bit score |
|---|---|---|---|---|---|---|---|---|---|---|---|---|
| 353 | 1_21287 | gi\|15023989\|gb\|AE007623.1\| AE007623 | 29.96 | 257 | 163 | 13 | 1300 | 1539 | 3544 | 2825 | 2.5e−09 | 70.48 |
| 354 | 1_21287 | gi\|15023989\|gb\|AE007623.1\| AE007623 | 24.08 | 623 | 439 | 32 | 1304 | 1892 | 7402 | 5798 | 3.3e−09 | 70.09 |
| 355 | 1_21287 | gi\|15023989\|gb\|AE007623.1\| AE007623 | 31.01 | 129 | 81 | 6 | 1301 | 1421 | 2815 | 2441 | 3.6 | 40.05 |
| 356 | 1_21287 | gi\|16410252\|emb\|AL591977.1\| | 24.73 | 465 | 328 | 20 | 1614 | 2056 | 216446 | 217753 | 4.5e−19 | 102.8 |
| 357 | 1_21287 | gi\|40444\|emb\|X17194.1\| CDTOXINA | 25.00 | 488 | 302 | 16 | 5 | 428 | 547 | 1917 | 4.5e−19 | 102.8 |
| 358 | 1_21287 | gi\|40444\|emb\|X17194.1\| CDTOXINA | 26.87 | 454 | 316 | 19 | 5 | 442 | 226 | 1362 | 4.2e−17 | 96.29 |
| 359 | 1_21287 | gi\|40444\|emb\|X17194.1\| CDTOXINA | 27.47 | 233 | 132 | 4 | 162 | 357 | 1249 | 1935 | 2.0e−14 | 87.43 |
| 360 | 1_21287 | gi\|40444\|emb\|X17194.1\| CDTOXINA | 26.01 | 296 | 204 | 11 | 162 | 442 | 112 | 966 | 8.3e−13 | 82.03 |
| 361 | 1_21287 | gi\|40444\|emb\|X17194.1\| CDTOXINA | 26.06 | 330 | 213 | 8 | 106 | 404 | 136 | 1071 | 3.1e−12 | 80.11 |
| 362 | 1_21287 | gi\|40444\|emb\|X17194.1\| CDTOXINA | 27.60 | 221 | 145 | 8 | 246 | 451 | 112 | 741 | 7.3e−09 | 68.94 |
| 363 | 1_21287 | gi\|40444\|emb\|X17194.1\| CDTOXINA | 21.61 | 509 | 386 | 25 | 1334 | 1829 | 700 | 1926 | 0.017 | 47.75 |
| 364 | 1_21287 | gi\|40444\|emb\|X17194.1\| CDTOXINA | 26.19 | 210 | 128 | 11 | 1303 | 1485 | 1345 | 1944 | 0.147 | 44.67 |
| 365 | 1_21287 | gi\|2462135\|emb\|Y12616.1\| CDTCDA | 28.38 | 303 | 146 | 10 | 124 | 355 | 217 | 1125 | 1.1e−17 | 98.21 |
| 366 | 1_21287 | gi\|2462135\|emb\|Y12616.1\| CDTCDA | 26.63 | 184 | 131 | 5 | 1313 | 1492 | 493 | 1011 | 0.327 | 43.51 |

Summary: all hits having 40% or higher identity (ordered by descending value of identity)

| No | Query id | Subject id | % identity | alignment length | mis-matches | gap openings | q. start | q. end | s. start | s. end | e-value | bit score |
|---|---|---|---|---|---|---|---|---|---|---|---|---|
| 1. | 1_21287 | gi\|10862850\|emb\|AJ250173.2\| LME250173 | 100.00 | 2057 | 0 | 0 | 1 | 2057 | 195 | 6365 | 0 | 4135.5 |
| 310. | 1_21287 | gi\|6899808\|dbj\|AB020020.1\| | 49.53 | 850 | 407 | 19 | 346 | 1173 | 1741 | 4098 | 0 | 703.4 |
| 13. | 1_21287 | gi\|7161824\|emb\|AJ250172.1\| LME250172 | 47.46 | 1258 | 653 | 22 | 238 | 1487 | 1126 | 4656 | 0 | 1052.3 |
| 19. | 1_21287 | gi\|2766611\|gb\|AF030129.1\| AF030129 | 47.38 | 1258 | 654 | 22 | 238 | 1487 | 1107 | 4637 | 0 | 1051.2 |
| 25. | 1_21287 | gi\|11559648\|gb\|AF294469.1\| AF294469 | 47.38 | 1258 | 654 | 22 | 238 | 1487 | 1106 | 4636 | 0 | 1049.7 |
| 31. | 1_21287 | gi\|153644\|gb\|M29296.1\| STRGTFD | 47.22 | 1171 | 600 | 21 | 343 | 1495 | 945 | 4250 | 0 | 961.1 |
| 43. | 1_21287 | gi\|3130075\|dbj\|D88653.1\| | 47.14 | 1171 | 601 | 21 | 343 | 1495 | 751 | 4056 | 0 | 959.1 |
| 50. | 1_21287 | gi\|3218540\|dbj\|D89979.1\| | 47.14 | 1171 | 601 | 21 | 343 | 1495 | 751 | 4056 | 0 | 958.7 |
| 56. | 1_21287 | gi\|3130089\|dbj\|D88659.1\| | 46.97 | 1171 | 603 | 21 | 343 | 1495 | 752 | 4057 | 0 | 958.4 |
| 324. | 1_21287 | gi\|18147720\|dbj\|AB056712.1\| | 46.75 | 338 | 175 | 7 | 301 | 633 | 648 | 1640 | 4.20E−73 | 282.3 |
| 106. | 1_21287 | gi\|11178681\|gb\|U12643.2\| SGU12643 | 46.70 | 1137 | 593 | 22 | 342 | 1465 | 736 | 3930 | 0 | 916 |
| 63. | 1_21287 | gi\|3130096\|dbj\|D88662.1\| | 46.63 | 1171 | 607 | 21 | 343 | 1495 | 751 | 4058 | 0 | 950.3 |
| 91. | 1_21287 | gi\|7684295\|dbj\|AB025228.1\| | 46.32 | 1142 | 600 | 22 | 337 | 1485 | 3428 | 6637 | 0 | 918.7 |
| 298. | 1_21287 | gi\|940396\|dbj\|D63569.1\| | 45.92 | 907 | 509 | 17 | 336 | 1288 | 1462 | 4167 | 0 | 765.4 |
| 157. | 1_21287 | gi\|3130080\|dbj\|D88655.1\| | 45.35 | 1215 | 637 | 28 | 346 | 1533 | 608 | 3982 | 0 | 895.6 |
| 311. | 1_21287 | gi\|6899808\|dbj\|AB020020.1\| | 45.32 | 342 | 179 | 7 | 1154 | 1487 | 4031 | 5017 | 7.10E−73 | 281.6 |
| 119. | 1_21287 | gi\|3130087\|dbj\|D88658.1\| | 45.20 | 1219 | 641 | 28 | 346 | 1537 | 608 | 3994 | 0 | 898.7 |
| 125. | 1_21287 | gi\|3130094\|dbj\|D88661.1\| | 45.20 | 1219 | 641 | 28 | 346 | 1537 | 608 | 3994 | 0 | 897.5 |
| 145. | 1_21287 | gi\|153639\|gb\|M17361.1\| STRGTFBC | 45.07 | 1216 | 644 | 26 | 346 | 1537 | 5890 | 9276 | 0 | 894 |
| 163. | 1_21287 | gi\|153642\|gb\|M22054.1\| STRGTFC | 45.07 | 1216 | 644 | 26 | 346 | 1537 | 757 | 4143 | 0 | 894 |
| 2. | 1_21287 | gi\|21654699\|gb\|AY017384.1\| | 44.76 | 1374 | 735 | 28 | 133 | 1482 | 667 | 4500 | 0 | 1068.1 |
| 8. | 1_21287 | gi\|4205087\|gb\|U81374.1\| LMU01374 | 44.54 | 1374 | 738 | 28 | 133 | 1482 | 397 | 4230 | 0 | 1053.9 |
| 132. | 1_21287 | gi\|3130104\|dbj\|D89978.1\| | 44.18 | 1288 | 688 | 32 | 346 | 1602 | 608 | 4153 | 0 | 897.1 |
| 138. | 1_21287 | gi\|3130073\|dbj\|D88652.1\| | 44.18 | 1288 | 688 | 32 | 346 | 1602 | 608 | 4153 | 0 | 896.3 |

-continued

| No | Query id | Subject id | % identity | alignment length | mismatches | gap openings | q. start | q. end | s. start | s. end | e-value | bit score |
|---|---|---|---|---|---|---|---|---|---|---|---|---|
| 245. | 1_21287 | gi\|662380\|gb\|L35928.1\| STRGTFM | 43.65 | 1157 | 634 | 24 | 344 | 1482 | 904 | 4137 | 0 | 816.6 |
| 231. | 1_21287 | gi\|4691427\|dbj\|AB026123.1\| | 43.48 | 1173 | 634 | 25 | 337 | 1480 | 5784 | 9086 | 0 | 827 |
| 319. | 1_21287 | gi\|18253271\|dbj\|AB078507.1\| | 43.09 | 485 | 261 | 11 | 1068 | 1537 | 3 | 1355 | 2.10E-93 | 349.7 |
| 209. | 1_21287 | gi\|153646\|gb\|M17391.1\| STRGTFI | 42.95 | 1199 | 664 | 25 | 317 | 1495 | 535 | 3885 | 0 | 848.2 |
| 264. | 1_21287 | gi\|47526\|emb\|Z11873.1\| SSGTFJKG | 42.86 | 1155 | 635 | 27 | 351 | 1480 | 5315 | 8578 | 0 | 776.9 |
| 289. | 1_21287 | gi\|47530\|emb\|Z11872.1\| SSGTFKG | 42.86 | 1155 | 635 | 27 | 351 | 1480 | 545 | 3808 | 0 | 776.9 |
| 283. | 1_21287 | gi\|153652\|gb\|M30943.1\| STRGTFS | 42.84 | 1146 | 629 | 33 | 346 | 1465 | 694 | 3846 | 0 | 778.5 |
| 77. | 1_21287 | gi\|3130070\|dbj\|D88651.1\| | 42.73 | 1341 | 744 | 31 | 286 | 1602 | 1378 | 5121 | 0 | 921.8 |
| 171. | 1_21287 | gi\|1163182\|gb\|U38181.1\| LMU38181 | 42.69 | 1225 | 676 | 30 | 343 | 1541 | 928 | 4338 | 0 | 865.9 |
| 84. | 1_21287 | gi\|3130101\|dbj\|D89977.1\| | 42.65 | 1341 | 745 | 31 | 286 | 1602 | 1378 | 5121 | 0 | 920.2 |
| 114. | 1_21287 | gi\|3130084\|dbj\|D88657.1\| | 42.51 | 1341 | 747 | 31 | 286 | 1602 | 1380 | 5123 | 0 | 915.2 |
| 38. | 1_21287 | gi\|3130082\|dbj\|D88656.1\| | 42.30 | 1402 | 745 | 32 | 343 | 1680 | 752 | 4726 | 0 | 960.7 |
| 144. | 1_21287 | gi\|153639\|gb\|M17361.1\| STRGTFBC | 42.10 | 1342 | 752 | 32 | 286 | 1602 | 985 | 4725 | 0 | 895.6 |
| 232. | 1_21287 | gi\|4691427\|dbj\|AB026123.1\| | 42.00 | 1188 | 666 | 31 | 313 | 1477 | 1235 | 4540 | 0 | 778.5 |
| 241. | 1_21287 | gi\|4691427\|dbj\|AB026123.1\| | 41.54 | 65 | 37 | 1 | 156 | 219 | 4742 | 4936 | 0.002 | 50.83 |
| 70. | 1_21287 | gi\|3130077\|dbj\|D88654.1\| | 41.48 | 1420 | 774 | 34 | 286 | 1648 | 1378 | 5382 | 0 | 922.9 |
| 252. | 1_21287 | gi\|662378\|gb\|L35495.1\| STRGTFL | 41.41 | 1287 | 700 | 32 | 309 | 1541 | 633 | 4247 | 0 | 816.2 |
| 258. | 1_21287 | gi\|153548\|gb\|M64111.1\| STRGTFJA | 41.41 | 1292 | 700 | 33 | 343 | 1577 | 540 | 4214 | 0 | 813.9 |
| 263. | 1_21287 | gi\|47526\|emb\|Z11873.1\| SSGTFJKG | 41.41 | 1292 | 700 | 33 | 343 | 1577 | 540 | 4214 | 0 | 813.9 |
| 99. | 1_21287 | gi\|3130091\|dbj\|D88660.1\| | 41.34 | 1420 | 776 | 34 | 286 | 1648 | 1378 | 5382 | 0 | 918.7 |
| 277. | 1_21287 | gi\|2935545\|gb\|AF049609.1\| AF049609 | 41.08 | 1317 | 714 | 34 | 287 | 1541 | 412 | 4116 | 0 | 813.1 |
| 218. | 1_21287 | gi\|22138844\|dbj\|AB009438.1\| | 40.96 | 1377 | 768 | 39 | 210 | 1541 | 127 | 3939 | 0 | 835.9 |

The invention claimed is:

1. An isolated protein encoded by a nucleic acid molecule selected from the group consisting of
   (a) a nucleic acid molecule encoding at least the mature form of a protein comprising the amino acid sequence indicated in SEQ ID NO:2 or the amino acid sequence which is encoded by the insert of plasmid pAlsu-pSK within DSM 12666;
   (b) a nucleic acid molecule comprising the nucleotide sequence indicated in SEQ ID NO:1 or the nucleotide sequence of the insert of plasmid pAlsu-pSK within DSM 12666 or the corresponding ribonucleotide sequence;
   (c) a *Leuconostoc mesenteroides* nucleic acid molecule encoding a protein, the amino acid sequence of which has a homology of at least 90% to the amino acid sequence indicated in SEQ ID NO:2;
   (d) a nucleic acid molecule, the nucleotide sequence of which deviates on account of the degeneracy of the genetic code from the sequence of the nucleic acid molecules as defined in (a), (b) or (c), and
   (e) an enzymatically active fragment of any of the above,
wherein said nucleic acid molecule encodes an alternansucrase protein that catalyzes the conversion of sucrose to alternan and wherein said isolated protein shows no contamination with another *Leuconostoc mesenteroides* protein.

2. The protein of claim 1, wherein the amino acid sequence of (c) has a homology of at least 95% to SEQ ID NO:2.

3. The protein of claim 1, wherein the amino acid sequence of (c) is SEQ ID NO: 2.

4. An isolated protein encoded by a nucleic acid molecule selected from the group consisting of
   (a) a nucleic acid molecule encoding a polypeptide which comprises residues 46 to 2057 of SEQ ID NO: 2 or residues 40 to 2057 of the amino acid sequence which is encoded by the DNA insert of plasmid pAlsu-pSK within DSM 12666;
   (b) a nucleotide sequence comprising bases 795-6848 of SEQ ID NO:1 or bases 813-6848 of the nucleotide sequence of the insert of plasmid pAlsu-pSK within DSM 12666 or the corresponding ribonucleotide sequence;
   (c) a *Leuconostoc mesenteroides* nucleic acid molecule encoding a protein, the amino acid sequence of which has a homology of at least 90% to the amino acid sequence of residues 40 to 2057 of SEQ ID NO:2,
   (d) a nucleic acid molecule, the nucleotide sequence of which deviates on account of the degeneracy of the genetic code from the sequence of the nucleic acid molecules as defined in (a), (b) or (c), and
   (e) an enzymatically active fragment of any one of the above
wherein said nucleic acid molecule encodes an alternansucrase protein that catalyzes the conversion of sucrose to alternan and wherein said isolated protein shows no contamination with another *Leuconostoc mesenteroides* protein.

5. An isolated protein encoded by a nucleic acid molecule selected from the group consisting of
   (a) a nucleic acid molecule encoding a polypeptide which comprises residues 1 to 2057 of SEQ ID NO:2 or residues 1 to 2057 of the amino acid sequence which is encoded by the DNA insert of plasmid pAlsu-pSK within DSM 12666;
   (b) a *Leuconostoc mesenteroides* nucleic acid molecule encoding a protein, the amino acid sequence of which has a homology of at least 90% to the amino acid sequence of residues 1 to 2057 of SEQ ID NO:2;
   (c) a nucleic acid molecule, the nucleotide sequence of which deviates on account of the degeneracy of the genetic code from the sequence of the nucleic acid molecules as defined in (a) or (b), and
   (d) an enzymatically active fragment of any one of the above,
wherein said nucleic acid molecule encodes an alternansucrase protein that catalyzes the conversion of sucrose to alternan and wherein said isolated protein shows no contamination with another *Leuconostoc mesenteroides* protein.

* * * * *